(12) United States Patent
Flygare et al.

(10) Patent No.: US 10,544,215 B2
(45) Date of Patent: Jan. 28, 2020

(54) 1-(CHLOROMETHYL)-2,3-DIHYDRO-1H-BENZO[E]INDOLE DIMER ANTIBODY-DRUG CONJUGATE COMPOUNDS, AND METHODS OF USE AND TREATMENT

(71) Applicant: Genentech, Inc., South San Francisco, CA (US)

(72) Inventors: John A. Flygare, Burlingame, CA (US); Thomas H. Pillow, San Francisco, CA (US); Brian Safina, Redwood City, CA (US); Vishal Verma, San Carlos, CA (US); BinQing Wei, Belmont, CA (US); William Denny, Auckland (NZ); Anna Giddens, Auckland (NZ); Ho Lee, Auckland (NZ); Guo-Liang Lu, Auckland (NZ); Christian Miller, Auckland (NZ); Gordon Rewcastle, Auckland (NZ); Moana Tercel, Auckland (NZ); Muriel Bonnet, Auckland (NZ)

(73) Assignee: Genentech, Inc., South San Francisco, CA (US)

( * ) Notice: Subject to any disclaimer, the term of this patent is extended or adjusted under 35 U.S.C. 154(b) by 408 days.

(21) Appl. No.: 15/182,444

(22) Filed: Jun. 14, 2016

(65) Prior Publication Data
US 2016/0354485 A1 Dec. 8, 2016

Related U.S. Application Data

(63) Continuation of application No. PCT/US2014/070637, filed on Dec. 16, 2014, which is a continuation-in-part of application No. PCT/US2014/042560, filed on Jun. 16, 2014.

(60) Provisional application No. 61/969,499, filed on Mar. 24, 2014, provisional application No. 61/916,388, filed on Dec. 16, 2013.

(51) Int. Cl.
*A61K 47/68* (2017.01)
*C07K 16/28* (2006.01)

(52) U.S. Cl.
CPC .......... *C07K 16/28* (2013.01); *C07K 2317/56* (2013.01)

(58) Field of Classification Search
None
See application file for complete search history.

(56) References Cited

U.S. PATENT DOCUMENTS

| 7,049,311 | B1 | 5/2006 | Thurston et al. |
|---|---|---|---|
| 7,067,511 | B2 | 6/2006 | Thurston et al. |
| 7,265,105 | B2 | 9/2007 | Thurston et al. |
| 7,511,032 | B2 | 3/2009 | Liu et al. |
| 7,528,126 | B2 | 5/2009 | Howard et al. |
| 7,553,816 | B2 | 6/2009 | Senter et al. |
| 7,557,099 | B2 | 7/2009 | Howard et al. |
| 8,226,945 | B2 | 7/2012 | Ebens, Jr. et al. |
| 8,394,607 | B2 | 3/2013 | Ebens, Jr. et al. |
| 8,524,865 | B2 | 9/2013 | Ebens, Jr. et al. |
| 8,697,688 | B2 | 4/2014 | Howard et al. |
| 8,968,741 | B2 | 3/2015 | Ebens et al. |
| 9,242,013 | B2 | 1/2016 | Howard et al. |
| 2008/0050310 | A1 | 2/2008 | Ebens, Jr. et al. |
| 2009/0036431 | A1 | 2/2009 | Gauzy et al. |
| 2009/0304710 | A1 | 12/2009 | Park et al. |
| 2010/0047257 | A1 | 2/2010 | Blanc et al. |
| 2011/0142858 | A1 | 6/2011 | Solomon et al. |
| 2011/0256157 | A1 | 10/2011 | Howard et al. |
| 2012/0329094 | A1 | 12/2012 | Ebens, Jr. et al. |
| 2013/0028919 | A1 | 1/2013 | Howard et al. |
| 2013/0171170 | A1 | 7/2013 | Ebens, Jr. et al. |
| 2014/0030279 | A1 | 1/2014 | Polakis et al. |
| 2014/0030281 | A1 | 1/2014 | Polakis et al. |
| 2014/0127197 | A1 | 5/2014 | Ebens et al. |
| 2015/0010540 | A1 | 1/2015 | Klein et al. |
| 2015/0165063 | A1 | 6/2015 | Flygare et al. |
| 2016/0279261 | A1 | 9/2016 | Lee et al. |

FOREIGN PATENT DOCUMENTS

| DE | 102009051799 A1 | 5/2011 |
|---|---|---|
| WO | 2005/049075 A2 | 6/2005 |
| WO | 2005081711 A2 | 9/2005 |
| WO | 2007/140371 A2 | 12/2007 |
| WO | 2008/083312 A2 | 7/2008 |
| WO | 2009016516 A2 | 2/2009 |
| WO | 2009/099719 A2 | 8/2009 |
| WO | 2010091150 A1 | 8/2010 |
| WO | 2011054837 A2 | 5/2011 |
| WO | 2011/066503 A2 | 6/2011 |
| WO | 2011066503 A2 | 6/2011 |
| WO | 2011/130598 A1 | 10/2011 |

(Continued)

OTHER PUBLICATIONS

Alley et al., "SJG-136 (NSC 694501), a novel rationally designed DNA minor groove interstrand cross-linking agent with potent and broad spectrum antitumor activity: part 2: efficacy evaluations" Cancer Res. 64(18):6700-6 ( 2004).

(Continued)

*Primary Examiner* — Mark Halvorson
*Assistant Examiner* — Kauser M Akhoon
(74) *Attorney, Agent, or Firm* — Viksnins Harris Padys Malen LLP

(57) ABSTRACT

The invention provides antibody-drug conjugates comprising an antibody conjugated to a 1-(chloromethyl)-2,3-dihydro-1H-benzo[e]indole (CBI) dimer drug moiety via a linker, and methods of using the antibody-drug conjugates.

29 Claims, 38 Drawing Sheets

Specification includes a Sequence Listing.

(56) References Cited

FOREIGN PATENT DOCUMENTS

| WO | 2011/130616 A1 | 10/2011 |
|---|---|---|
| WO | 2011133039 A2 | 10/2011 |
| WO | 2011156328 A1 | 12/2011 |
| WO | 2012162482 A1 | 11/2012 |
| WO | 2013055987 A1 | 4/2013 |
| WO | 2014/011518 A1 | 1/2014 |
| WO | 2014/011520 A1 | 1/2014 |
| WO | 2014/177617 A1 | 11/2014 |
| WO | 2015/023355 A1 | 2/2015 |
| WO | 2015/095212 A1 | 6/2015 |
| WO | 2015/095227 A2 | 6/2015 |

OTHER PUBLICATIONS

Atwell et al., "5-Amino-1-(chloromethyl)-1,2-dihydro-3H-benz[e]indoles: relationships between structure and cytotoxicity for analogues bearing different DNA minor groove binding subunits" J Med Chem. 42(17):3400-11 ( 1999).

Bose et al., "Rational design of a highly efficient irreversible DNA interstrand cross-linking agent based on the pyrrolobenzodiazepine ring system" J. Am. Chem. Soc. 114:4939-41 ( 1992).

Doronina et al., "Enhanced activity of monomethylauristatin F through monoclonal antibody delivery: effects of linker technology on efficacy and toxicity" Bioconjug Chem 17(1):114-124 (Jan. 2006).

Doyle et al., "Response of *Staphylococcus aureus* to subinhibitory concentrations of a sequence-selective, DNA minor groove cross-linking pyrrolobenzodiazepine dimer" Journal Antimicrob Chemo 65(5):949-59 ( 2009).

Gregson et al., "Linker length modulates DNA cross-linking reactivity and cytotoxic potency of C8/C8' ether-linked C2-exo-unsaturated pyrrolo[2,1-c][1,4]benzodiazepine (PBD) dimers" J Med Chem. 47(5):1161-74 ( 2004).

Hadjivassileva et al., "Pyrrolobenzodiazepine dimers: novel sequence-selective, DNA-interactive, cross-linking agents with activity against Gram-positive bacteria" J Antimicrob Chemother. 56(3)::513-8 ( 2005).

Hamilton, "Antibody-drug conjugates for cancer therapy: The technological and regulatory challenges of developing drug-biologic hybrids" Biologicals 43(5):318-32 ( 2015).

Hartley et al., "SJG-136 (NSC 694501), a novel rationally designed DNA minor groove interstrand cross-linking agent with potent and broad spectrum antitumor actiVity: part 1: cellular pharmacology, in vitro and initial in vivo antitumor activity" Cancer Res. 64(18):6693-9 (Sep. 15, 2004).

Hay et al., "Structure-activity relationships for 4-nitrobenzyl earbamates of 5-aminobenz[e]indoline minor groove alkylating agents as prodrugs for GDEPT in conjunction with *E. coli* nitroreduetase" J Med Chem. 46(12):2456-66 (2003).

Hochhauser et al., "Phase I study of sequence-selective minor groove DNA binding agent SJG-136 in patients with advanced solid tumors" Clin Cancer Res. 15(6)::2140-7 ( 2009).

ISR and Written Opinion for PCT/US2014/042560.

ISR and Written Opinion for PCT/US2014/070637.

Jeffrey et al., "Design, synthesis, and in vitro evaluation of dipeptide-based antibody minor groove binder conjugates" J Med Chem 48:1344-1358 ( 2005).

Jubala et al., "CD20 expression in normal canine B cells and in canine non-Hodgkin lymphoma". Vet Pathol. 42(4):468-76 ( 2005).

Pepper et al., "The novel sequence-specific DNA cross-linking agent SJG-136 (NSC 694501) has potent and selective in vitro cytotoxicity in human B-cell chronic lymphocytic leukemia cells with evidence of a p53-independent mechanism of cell kill" Cancer Res. 64(18):6750-5 (Sep. 15, 2004).

Polson et al., "Antibody-Drug Conjugates for the Treatment of Non-Hodgkin's Lymphoma: Target and Linker-Drug Selection" Cancer Res 69(6):2358-64 (Mar. 15, 2009).

Rahman et al., "The pyrrolobenzodiazepine dimer SJG-136 forms sequence-dependent intrastrand DNA cross-links and monoalkylated adducts in addition to interstrand cross-links" J Am Chem Soc. 131(38):13756-66 (2009).

Tereel et al., "Selective treatment of hypoxie tumor cells in vivo: phosphate pre-prodrugs of nitro analogues of the duocarmycins" Angew Chem Int Ed Engl. 50(11):2606-9 ( 2011).

Tercel et al., "Unsymmetrical DNA cross-linking agents: Combination of the CBI and PBD Pharmacophores" J. Med. Chem. 46:2132-2151 (Jan. 2003).

Thurston et al., "Synthesis of DNA-Interactive Pyrrolo[2,1-c][1,4]benzodiazepines" Chem Rev 94:433-465 ( 1994).

Sharma, et al., "Novel cyclopropylindole conjugates and dimers: synthesis and anti-cancer evaluation", Curr Med Chem Anticancer Agents 1(1), 27-45 (2001).

Wirth, et al., "The Two Faces of Potent Antitumor Duocarmycin-Based Drugs: A Structural Dissection Reveals Disparate Motifs for DNA versus Aldehyde Dehydrogenase 1 Affinity".

Dorywalska, et al., "Effect of Attachment Site on Stability of Cleavable Antibody Drug Conjugates", Bioconjugate Chem 26, 650-659 (2015).

Junutula, et al., "Site-specific conjugation of a cytotoxic drug to an antibody improves the therapeutic index", Nature Biotechnology 26(8), 925-932 (2008).

Strop, et al., "Location Mailers: Site of Conjugation Modulates Stability and Pharmacokinetics of Antibody Drug Conjugates", Chemistry & Biology 20, 161-167 (2013).

- (1) Vehicle: 20mM Histidine Acetate, pH 5.5, 240mM Sucrose, 0.02% PS 20
- (2) Thio Hu Anti-CD22 10F4v3 HC A118C-MC-MMED-(CBI dimer phos) 110
- (3) Thio Hu Anti-CD22 10F4v3 HC A118C-MC-vc-PAB-(CBI dimer MePip) 108
- (4) Thio Hu Anti-CD22 10F4v3 HC A118C-MC-vc-PAB-(CBI dimer phos) 111
- (5) Thio Hu Anti-Her2 4D5 HC A118C-MC-MMED-(CBI dimer phos) 109
- (6) Thio Hu Anti-Her2 4D5 HC A118C-MC-vc-PAB-(CBI dimer MePip) 107
- (7) Thio Hu Anti-Her2 4D5 HC A118C-MC-vc-PAB-(CBI dimer phos) 112

1-(CHLOROMETHYL)-2,3-DIHYDRO-1H-BENZO[E]INDOLE DIMER ANTIBODY-DRUG CONJUGATE COMPOUNDS, AND METHODS OF USE AND TREATMENT

CROSS REFERENCE TO RELATED APPLICATIONS

This application is a continuation of PCT Application No. PCT/US2014/070637, filed 16 Dec. 2014, which application claims the benefit of priority to U.S. Provisional Application Ser. No. 61/916,388 filed on 16 Dec. 2013 and U.S. Provisional Application Ser. No. 61/969,499 filed on 24 Mar. 2014, and to International Application PCT/US2014/042560 filed on 16 Jun. 2014, all of which applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jun. 14, 2016, is named P05625_US_5_Sequence_Listing.txt and is 43,470 bytes in size.

FIELD OF THE INVENTION

The invention relates generally to antibodies conjugated to 1-(chloromethyl)-2,3-dihydro-1H-benzo[e]indole (CBI) dimer drug moieties to form antibody-drug conjugates with therapeutic or diagnostic applications. The antibodies may be engineered with free cysteine amino acids, reactive for conjugation with CBI dimer drug-linker intermediates. The invention also relates to methods of using the CBI dimer antibody-drug conjugate compounds for in vitro, in situ, and in vivo diagnosis or treatment of mammalian cells, or associated pathological conditions.

BACKGROUND OF THE INVENTION

Antibody drug conjugates (ADC) are targeted chemotherapeutic molecules combining the properties of both antibodies and cytotoxic drugs by targeting potent cytotoxic drugs to antigen-expressing tumor cells, internalization, and release of drug, thereby enhancing their anti-tumor activity (Carter, P. and Senter, P. (2008) The Cancer Jour. 14(3):154-169). Successful ADC development for a given target antigen depends on optimization of antibody selection, linker design and stability, cytotoxic drug potency and mode of drug and linker conjugation to the antibody (Polakis, P. (2005) Current Opinion in Pharmacology 5:382-387).

The 5-amino-1-(chloromethyl)-1,2-dihydro-3H-benz[e]indole (amino CBI) class of DNA minor groove alkylators are potent cytotoxins (Atwell, et al (1999) J. Med. Chem., 42:3400), and have been utilized as effector units in a number of classes of prodrugs designed for cancer therapy. These have included antibody conjugates, (Jeffrey, et al. (2005) J. Med. Chem., 48:1344), prodrugs for gene therapy based on nitrobenzyl carbamates (Hay, et al (2003) J. Med. Chem. 46:2456) and the corresponding nitro-CBI derivatives as hypoxia-activated prodrugs (Tercel, et al (2011) Angew. Chem., Int. Ed., 50:2606-2609). The CBI and pyrrolo[2,1-c][1,4]benzodiazepine (PBD) pharmacophores have been linked together by an alkyl chain (Tercel et al (2003) J. Med. Chem 46:2132-2151). PBD dimers, where two pyrrolo[2,1-c][1,4]benzodiazepine units are tethered by an alkylene or alkylene-arylene chain are highly efficient interstrand crosslinking agents that react with guanine in the DNA minor groove (Rahman et al (2009) Jour. Amer. Chem. Soc. 131(38):13756-13766; Thurston et al (1994) Chem. Rev., 94:433-465; Bose et al (1992) J. Am. Chem. Soc. 114:4939-4941; Gregson et al (2004) Jour. Med. Chem. 47(5):1161-1174; U.S. Pat. Nos. 7,511,032; 7,528,126; 7,557,099; 7,049,311; 7,067,511; 7,265,105) and have activity against gram-positive bacteria (Doyle et al (2009) Jour. Antimicrob. Chemo. 65(5):949-959; Hadjivassileva et al (2005) Jour. Antimicrob. Chemo. 56(3):513-518), human B-cell chronic lymphocytic leukemia (CLL) cells (Pepper et al (2004) Cancer Res. 64(18):6750-6755), and solid tumors (Hochhauser et al (2009) Clin. Cancer Res. 15(6):2140-2147; Alley et al (2004) 64(18):6700-6706; Hartley et al (2004) Cancer Res. 64(18):6693-6699). Dimeric forms of PBD have been linked to antibodies to form ADC (US 2009/304710; US 2010/047257; US 2009/036431; WO 2011/130598, WO 2011/130616; US 2013/0028919).

SUMMARY

The invention includes 1-(chloromethyl)-2,3-dihydro-1H-benzo[e]indole (CBI) dimer drug moieties covalently attached by a linker to form antibody-drug conjugate (ADC) compounds with therapeutic or diagnostic applications.

An aspect of the invention is an antibody-drug conjugate compound having the formula:

wherein:
Ab is an antibody;
L is a linker having the formula:

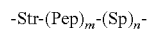

where Str is a stretcher unit covalently attached to the antibody; Pep is an optional peptide unit of two to twelve amino acid residues, Sp is an optional spacer unit covalently attached to a dimer drug moiety, and m and n are independently selected from 0 and 1;
p is an integer from 1 to 8;
D is the dimer drug moiety having the formula:

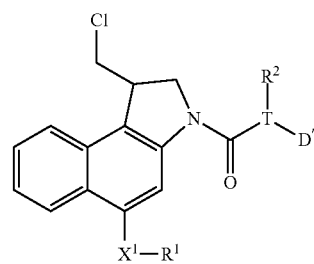

where
$R^1$ is selected from H, $P(O)_3H_2$, $C(O)NR^aR^b$, or a bond to L;
$R^2$ is selected from H, $P(O)_3H_2$, $C(O)NR^aR^b$, or a bond to L;
$R^a$ and $R^b$ are independently selected from H and $C_1$-$C_6$ alkyl optionally substituted with one or more F,
or $R^a$ and $R^b$ form a five or six membered heterocyclyl group;
T is a tether group selected from $C_3$-$C_{12}$ alkylene, Y, $(C_1$-$C_6$ alkylene)-Y—$(C_1$-$C_6$ alkylene), $(C_1$-$C_6$ alkylene)-

Y—($C_1$-$C_6$ alkylene)-Y—($C_1$-$C_6$ alkylene), ($C_2$-$C_6$ alkenylene)-Y—($C_2$-$C_6$ alkenylene), and ($C_2$-$C_6$ alkynylene)-Y—($C_2$-$C_6$ alkynylene);

where Y is independently selected from O, S, $NR^1$, aryl, and heteroaryl;

where alkylene, alkenylene, aryl, and heteroaryl are independently and optionally substituted with F, OH, O($C_1$-$C_6$ alkyl), $NH_2$, $NHCH_3$, $N(CH_3)_2$, $OP(O)_3H_2$, and $C_1$-$C_6$ alkyl, where alkyl is optionally substituted with one or more F;

or alkylene, alkenylene, aryl, and heteroaryl are independently and optionally substituted with a bond to L;

D' is a drug moiety selected from:

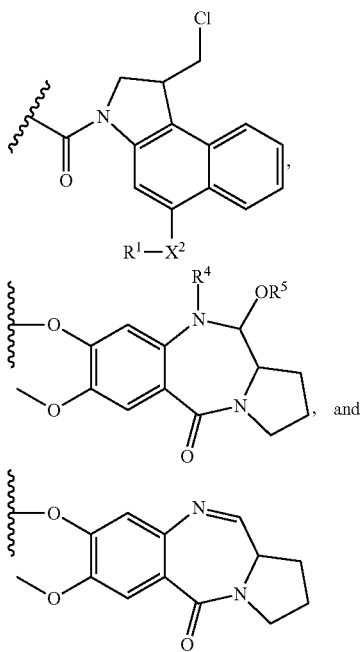

where the wavy line indicates the site of attachment to T;

$X^1$ and $X^2$ are independently selected from O and $NR^3$, where $R^3$ is selected from H and $C_1$-$C_6$ alkyl optionally substituted with one or more F;

$R^4$ is H, $CO_2R$, or a bond to L, where R is $C_1$-$C_6$ alkyl or benzyl; and $R^5$ is H or $C_1$-$C_6$ alkyl.

An aspect of the invention is a pharmaceutical composition of the antibody-drug conjugate compound, and a pharmaceutically acceptable carrier, glidant, diluent, or excipient.

An aspect of the invention is a method of treating cancer comprising administering to a patient a therapeutically-effective amount of the antibody-drug conjugate compound.

An aspect of the invention is a kit for treating cancer, comprising:

a) the pharmaceutical composition; and b) instructions for use.

An aspect of the invention is a linker-drug intermediate selected from:

X-L-D wherein:

X is a reactive functional group selected from maleimide, thiol, amino, bromide, bromoacetamido, iodoacetamido, p-toluenesulfonate, iodide, hydroxyl, carboxyl, pyridyl disulfide, and N-hydroxysuccinimide;

L is a linker having the formula:

-Str-(Pep)$_m$-(Sp)$_n$- where Str is a stretcher unit covalently attached to X; Pep is an optional peptide unit of two to twelve amino acid residues, Sp is an optional spacer unit covalently attached to a dimer drug moiety, and m and n are independently selected from 0 and 1;

D is the dimer drug moiety having the formula:

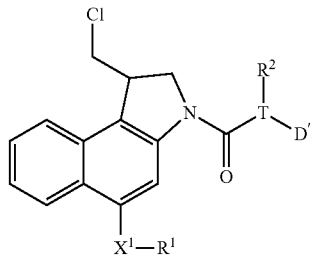

where $R^1$ is selected from H, $P(O)_3H_2$, $C(O)NR^aR^b$, or a bond to L;

$R^2$ is selected from H, $P(O)_3H_2$, $C(O)NR^aR^b$, or a bond to L;

$R^a$ and $R^b$ are independently selected from H and $C_1$-$C_6$ alkyl optionally substituted with one or more F, or $R^a$ and $R^b$ form a five or six membered heterocyclyl group;

T is a tether group selected from $C_3$-$C_{12}$ alkylene, Y, ($C_1$-$C_6$ alkylene)-Y—($C_1$-$C_6$ alkylene), ($C_1$-$C_6$ alkylene)-Y—($C_1$-$C_6$ alkylene)-Y—($C_1$-$C_6$ alkylene), ($C_2$-$C_6$ alkenylene)-Y—($C_2$-$C_6$ alkenylene), and ($C_2$-$C_6$ alkynylene)-Y—($C_2$-$C_6$ alkynylene);

where Y is independently selected from O, S, $NR^1$, aryl, and heteroaryl;

where alkylene, alkenylene, aryl, and heteroaryl are independently and optionally substituted with F, OH, O($C_1$-$C_6$ alkyl), $NH_2$, $NHCH_3$, $N(CH_3)_2$, $OP(O)_3H_2$, and $C_1$-$C_6$ alkyl, where alkyl is optionally substituted with one or more F;

or alkylene, alkenylene, aryl, and heteroaryl are independently and optionally substituted with a bond to L;

D' is a drug moiety selected from:

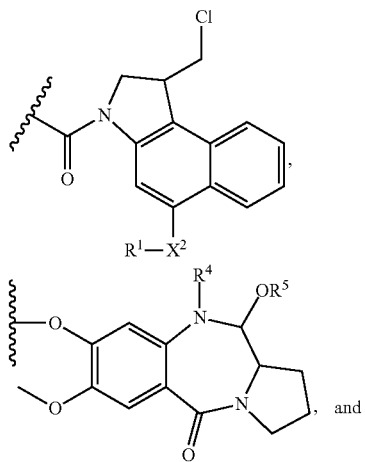

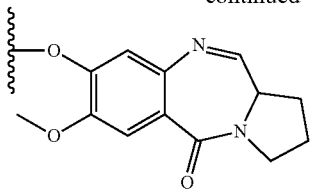

where the wavy line indicates the site of attachment to T;
$X^1$ and $X^2$ are independently selected from O and $NR^3$, where $R^3$ is selected from H and $C_1$-$C_6$ alkyl optionally substituted with one or more F;
$R^4$ is H, $CO_2R$, or a bond to L, where R is $C_1$-$C_6$ alkyl or benzyl; and
$R^5$ is H or $C_1$-$C_6$ alkyl.

An aspect of the invention is a process for making an antibody-drug conjugate by conjugating the antibody to a linker-drug intermediate.

An aspect of the invention is a CBI dimer drug moiety compound having the formula:

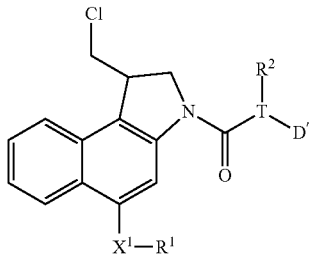

where
$R^1$ is selected from H, $P(O)_3H_2$, $C(O)NR^aR^b$;
$R^2$ is selected from H, $P(O)_3H_2$, $C(O)NR^aR^b$;
$R^a$ and $R^b$ are independently selected from H and $C_1$-$C_6$ alkyl optionally substituted with one or more F, or $R^a$ and $R^b$ form a five or six membered heterocyclyl group;
T is a tether group selected from $C_3$-$C_{12}$ alkylene, Y, ($C_1$-$C_6$ alkylene)-Y—($C_1$-$C_6$ alkylene), ($C_1$-$C_6$ alkylene)-Y—($C_1$-$C_6$ alkylene)-Y—($C_1$-$C_6$ alkylene), ($C_2$-$C_6$ alkenylene)-Y—($C_2$-$C_6$ alkenylene), and ($C_2$-$C_6$ alkynylene)-Y—($C_2$-$C_6$ alkynylene);
where Y is independently selected from O, S, $NR^1$, aryl, and heteroaryl;
where alkylene, alkenylene, aryl, and heteroaryl are independently and optionally substituted with F, OH, $O(C_1$-$C_6$ alkyl), $NH_2$, $NHCH_3$, $N(CH_3)_2$, $OP(O)_3H_2$, and $C_1$-$C_6$ alkyl, where alkyl is optionally substituted with one or more F;
or alkylene, alkenylene, aryl, and heteroaryl are independently and optionally substituted with a bond to L;
D' is a drug moiety selected from:

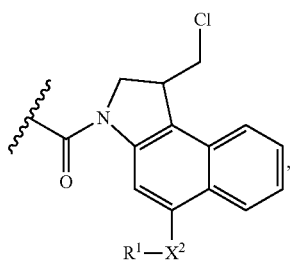

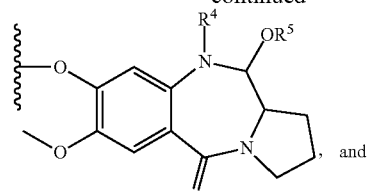

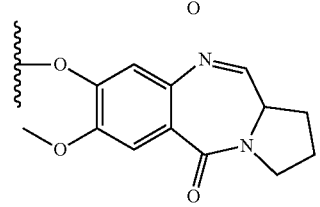

where the wavy line indicates the site of attachment to T;
$X^1$ and $X^2$ are independently selected from O and $NR^3$, where $R^3$ is selected from H and $C_1$-$C_6$ alkyl optionally substituted with one or more F;
$R^4$ is H, $CO_2R$, where R is $C_1$-$C_6$ alkyl or benzyl; and
$R^5$ is H or $C_1$-$C_6$ alkyl.

BRIEF DESCRIPTION OF THE DRAWINGS

FIG. 1 shows the synthesis of (S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yl 2-(2-bromo-N-methylacetamido)ethyl(methyl)carbamate 51 from (S)-tert-Butyl 1-(chloromethyl)-5-hydroxy-1H-benzo[e]indole-3 (2H)-carboxylate 51a.

FIG. 2 shows the synthesis of N—((R)-1-(chloromethyl)-3-(5-((R)-1-(chloromethyl)-5-hydroxy-1H-benzo[e]indol-3 (2H)-yl)-5-oxopentanoyl)-2,3-dihydro-1H-benzo[e]indol-5-yl)-6-(2,5-dioxo-2,5-dihydro-1H-pyrrol-1-yl)hexanamide 53 from (R)-tert-butyl 1-(chloromethyl)-5-(diphenylmethyleneamino)-1H-benzo[e]indole-3(2H)-carboxylate 53a.

FIG. 5 shows the synthesis of N-(4-(((S)-1-(chloromethyl)-3-(6-((S)-7-methoxy-5-oxo-2,3,5,11a-tetrahydro-1H-benzo[e]pyrrolo[1,2-a][1,4]diazepin-8-yloxy)hexanoyl)-2,3-dihydro-1H-benzo[e]indol-5-yloxy)methyl)phenyl)-6-(2,5-dioxo-2,5-dihydro-1H-pyrrol-1-yl)hexanamide 54 from (S)-(2-amino-4-hydroxy-5-methoxyphenyl)(2-(hydroxymethyl)pyrrolidin-1-yl)methanone 54a.

FIG. 6 shows the synthesis of N—((S)-1-((S)-1-(4-(((S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yloxy)methyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide 55 from (S)-tert-butyl 1-(chloromethyl)-5-hydroxy-1H-benzo[e]indole-3(2H)-carboxylate 51a.

FIG. 9 shows the synthesis of (S)-5-(1-(chloromethyl)-5-(di-tert-butoxyphosphoryloxy)-1H-benzo[e]indol-3(2H)-yl)-5-oxopentanoic acid 57d from (S)-tert-Butyl 1-(chloromethyl)-5-hydroxy-1H-benzo[e]indole-3(2H)-carboxylate 51a.

FIG. 12 shows the synthesis of (S)-3-(5-((S)-5-(4-aminobenzyloxy)-1-(chloromethyl)-1H-benzo[e]indol-3(2H)-yl)-5-oxopentanoyl)-1-(chloromethyl)-2,3-dihydro-1H-benzo[e]indol-5-yl 4-methylpiperazine-1-carboxylate 58e from (S)-tert-butyl 1-(chloromethyl)-5-hydroxy-1H-benzo [e]indole-3(2H)-carboxylate 51a.

FIG. 15 shows the synthesis of 2-(pyridin-2-yldisulfanyl) ethyl (S)-1-(chloromethyl)-3-(5-((S)-1-(chloromethyl)-5-(phosphonooxy)-1H-benzo[e]indol-3(2H)-yl)-5-oxopentanoyl)-2,3-dihydro-1H-benzo[e]indol-5-ylcarbamate 61 from (S)-tert-butyl 5-amino-1-(chloromethyl)-1H-benzo[e] indole-3 (2H)-carboxylate 61a.

FIG. 16 shows the synthesis of 2-(pyridin-2-yldisulfanyl) propyl (S)-1-(chloromethyl)-3-(5-((S)-1-(chloromethyl)-5-(phosphonooxy)-1H-benzo[e]indol-3(2H)-yl)-5-oxopentanoyl)-2,3-dihydro-1H-benzo[e]indol-5-ylcarbamate 62 from 51a.

FIG. 21 shows the synthesis of (S)-di-tert-butyl 1-(chloromethyl)-2,3-dihydro-1H-benzo[e]indol-5-yl phosphate 66d from (S)-tert-butyl 5-(benzyloxy)-1-(chloromethyl)-1H-benzo[e]indole-3(2H)-carboxylate 57a, prepared from 51a.

FIG. 35a shows efficacy of ADC138 in SCID mice with HL-60 human acute myeloid leukemia tumors. ADC138 demonstrated dose-dependent inhibition of tumor growth compared with vehicle group. The non-targeting control ADC135 had no effect on tumor growth.

DETAILED DESCRIPTION OF EXEMPLARY EMBODIMENTS

Figure 1:
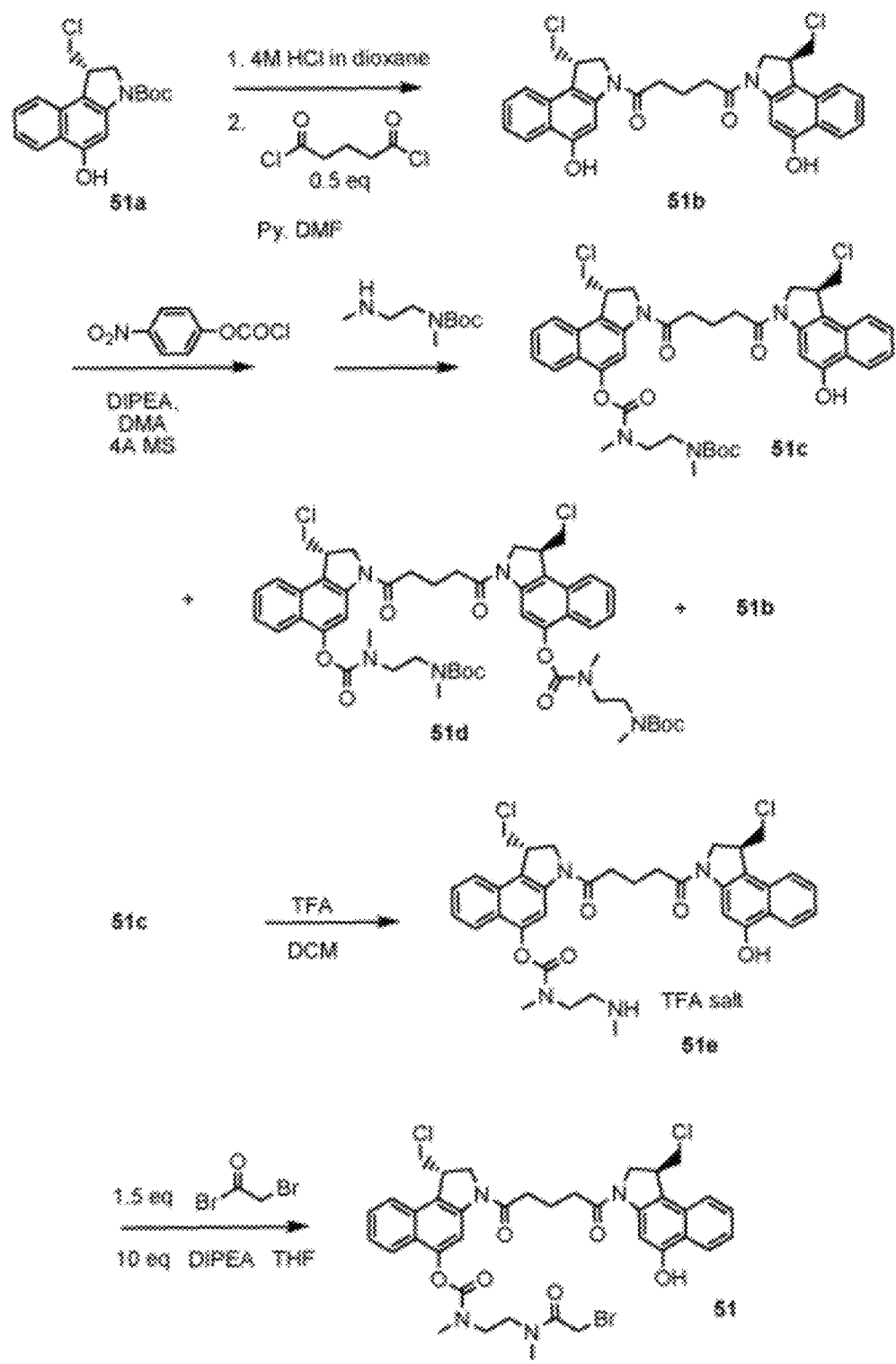

Reference will now be made in detail to certain embodiments of the invention, examples of which are illustrated in the accompanying structures and formulas. While the invention will be described in conjunction with the illustrated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

Unless defined otherwise, technical and scientific terms used herein have the same meaning as commonly understood by one of ordinary skill in the art to which this invention belongs, and are consistent with: Singleton et al (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

Definitions

Unless stated otherwise, the following terms and phrases as used herein are intended to have the following meanings:

When trade names are used herein, applicants intend to independently include the trade name product formulation, the generic drug, and the active pharmaceutical ingredient(s) of the trade name product.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; minibodies (Olafsen et al (2004) Protein Eng. Design & Sel. 17(4):315-323), fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature, 256:495, or may be made by recombinant DNA methods (see for example: U.S. Pat. No. 4,816,567;

5,807,715). The monoclonal antibodies may also be isolated from phage antibody libraries using the techniques described in Clackson et al (1991) Nature, 352:624-628; Marks et al (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape, etc.) and human constant region sequences.

An "intact antibody" herein is one comprising a VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known. Ig forms include hinge-modifications or hingeless forms (Roux et al (1998) J. Immunol. 161:4083-4090; Lund et al (2000) Eur. J. Biochem. 267: 7246-7256; US 2005/0048572; US 2004/0229310).

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J Immunol*. 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

A "free cysteine amino acid" refers to a cysteine amino acid residue which has been engineered into a parent antibody, has a thiol functional group (—SH), and is not paired as an intramolecular or intermolecular disulfide bridge.

"Linker", "Linker Unit", or "link" means a chemical moiety comprising a chain of atoms that covalently attaches an antibody to a drug moiety. In various embodiments, a linker is a divalent radical, specified as L.

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of any length from one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, and the like.

The term "alkylene" as used herein refers to a saturated linear or branched-chain divalent hydrocarbon radical of any length from one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—CH$_2$—), ethylene (—CH$_2$CH$_2$—), propylene (—CH$_2$CH$_2$CH$_2$—), and the like.

The term "alkenyl" refers to linear or branched-chain monovalent hydrocarbon radical of any length from two to eight carbon atoms ($C_2$-$C_8$) with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), and the like.

The term "alkenylene" refers to linear or branched-chain divalent hydrocarbon radical of any length from two to eight carbon atoms ($C_2$-$C_8$) with at least one site of unsaturation, i.e., a carbon-carbon, sp$^2$ double bond, wherein the alkenylene radical may be optionally substituted independently with one or more substituents described herein, and includes radicals having "cis" and "trans" orientations, or alternatively, "E" and "Z" orientations. Examples include, but are not limited to, ethylenylene or vinylene (—CH═CH—), allyl (—CH$_2$CH═CH—), and the like.

The term "alkynyl" refers to a linear or branched monovalent hydrocarbon radical of any length from two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —CH$_2$C≡CH), and the like.

The term "alkynylene" refers to a linear or branched divalent hydrocarbon radical of any length from two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —CH$_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, 1-methyl-1H-benzo[d]imidazole, [1,2,4]triazolo[1,5-a]pyridine, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or 3-carboline.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The phrase "pharmaceutically acceptable salt," as used herein, refers to pharmaceutically acceptable organic or inorganic salts of an antibody-drug conjugate (ADC). Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

The following abbreviations are used herein and have the indicated definitions: BME is beta-mercaptoethanol, Boc is N-(t-butoxycarbonyl), cit is citrulline (2-amino-5-ureido pentanoic acid), DCC is 1,3-dicyclohexylcarbodiimide, DCM is dichloromethane, DEA is diethylamine, DEAD is diethylazodicarboxylate, DEPC is diethylphosphorylcyanidate, DIAD is diisopropylazodicarboxylate, DIEA is N,N-diisopropylethylamine, DMA is dimethylacetamide, DMAP is 4-dimethylaminopyridine, DME is ethyleneglycol dimethyl ether (or 1,2-dimethoxyethane), DMF is N,N-dimethylformamide, DMSO is dimethylsulfoxide, DTT is dithiothreitol, EDCI is 1-(3-dimethylaminopropyl)-3-ethylcarbodiimide hydrochloride, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN ($CH_3CN$) is acetonitrile, MeOH is methanol, Mtr is 4-anisyldiphenylmethyl (or 4-methoxytrityl), NHS is N-hydroxysuccinimide, PBS is phosphate-buffered saline (pH 7), PEG is polyethylene glycol or a unit of ethylene glycol (—$OCH_2CH_2$—), Ph is phenyl, Pnp is p-nitrophenyl, MC is 6-maleimidocaproyl, phe is L-phenylalanine, PyBrop is bromo tris-pyrrolidino phosphonium hexafluorophosphate, SEC is size-exclusion chromatography, Su is succinimide, TFA is trifluoroacetic acid, TLC is thin layer chromatography, UV is ultraviolet, and val is valine.

Cysteine Engineered Antibodies

The compounds of the invention include antibody-drug conjugates comprising cysteine engineered antibodies where one or more amino acids of a wild-type or parent antibody are replaced with a cysteine amino acid. Any form of antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. Mutants with replaced ("engineered") cysteine (Cys) residues are evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies of the invention are in the ranges of 0.6 to 1.0; 0.7 to 1.0; or 0.8 to 1.0.

Cysteine amino acids may be engineered at reactive sites in an antibody and which do not form intrachain or intermolecular disulfide linkages (Junutula, et al., 2008b Nature Biotech., 26(8):925-932; Doman et al (2009) Blood 114(13): 2721-2729; U.S. Pat. No. 7,521,541; 7,723,485; WO2009/052249, Shen et al (2012) Nature Biotech., 30(2):184-191; Junutula et al (2008) Jour of Immun. Methods 332:41-52). The engineered cysteine thiols may react with linker reagents or the linker-drug intermediates of the present invention which have thiol-reactive, electrophilic groups such as maleimide or alpha-halo amides to form ADC with cysteine engineered antibodies (ThioMabs) and the drug (D) moiety. The location of the drug moiety can thus be designed, controlled, and known. The drug loading can be controlled since the engineered cysteine thiol groups typically react with thiol-reactive linker reagents or linker-drug intermediates in high yield. Engineering an antibody to introduce a cysteine amino acid by substitution at a single site on the heavy or light chain gives two new cysteines on the symmetrical antibody. A drug loading near 2 can be achieved and near homogeneity of the conjugation product ADC.

Cysteine engineered antibodies of the invention preferably retain the antigen binding capability of their wild type, parent antibody counterparts. Thus, cysteine engineered antibodies are capable of binding, preferably specifically, to antigens. Such antigens include, for example, tumor-associated antigens (TAA), cell surface receptor proteins and other cell surface molecules, transmembrane proteins, signaling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which a cysteine engineered antibody is capable of binding may be a member of a subset of one of the above-mentioned categories, wherein the other subset(s) of said category comprise other molecules/antigens that have a distinct characteristic (with respect to the antigen of interest).

Cysteine engineered antibodies are prepared for conjugation with linker-drug intermediates by reduction and reoxidation of intrachain disulfide groups (Example 19).

Cysteine engineered antibodies which may be useful in the antibody-drug conjugates of the invention in the treatment of cancer include, but are not limited to, antibodies against cell surface receptors and tumor-associated antigens (TAA). Tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of tumor-associated antigens TAA include, but are not limited to, TAA (1)-(51) listed below. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to TAA (1)-(51) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Figure 2:
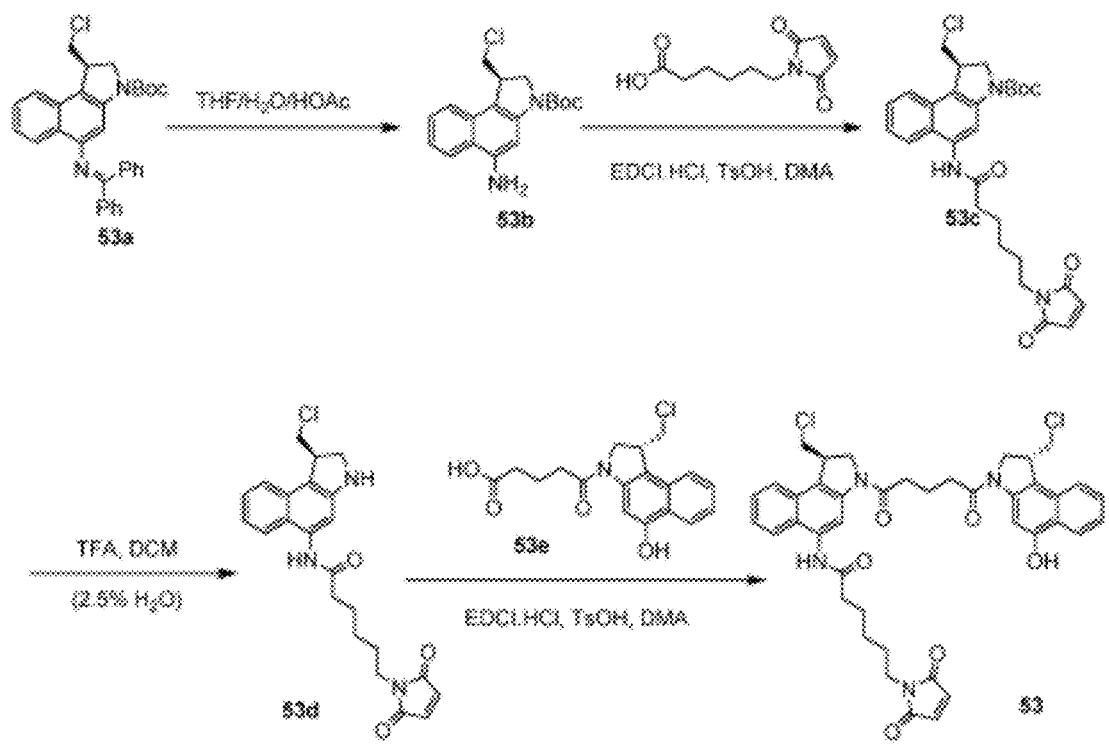
Figure 3:
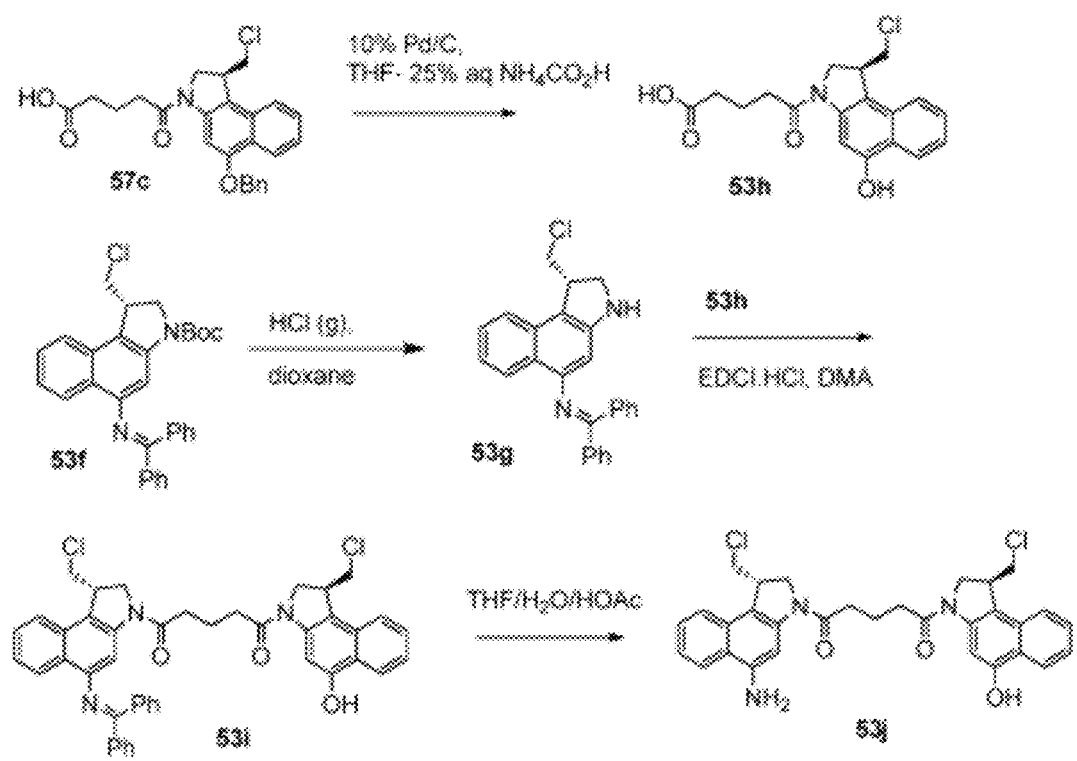
FIG. 3 shows the synthesis of 1-((S)-5-amino-1-(chloromethyl)-1H-benzo[e]indol-3(2H)-yl)-5-((S)-1-(chloromethyl)-5-hydroxy-1H-benzo[e]indol-3(2H)-yl)pentane-1,5-dione 53j from (S)-5-(5-(benzyloxy)-1-(chloromethyl)-1H-benzo[e]indol-3(2H)-yl)-5-oxopentanoic acid 57c.
Figure 4:
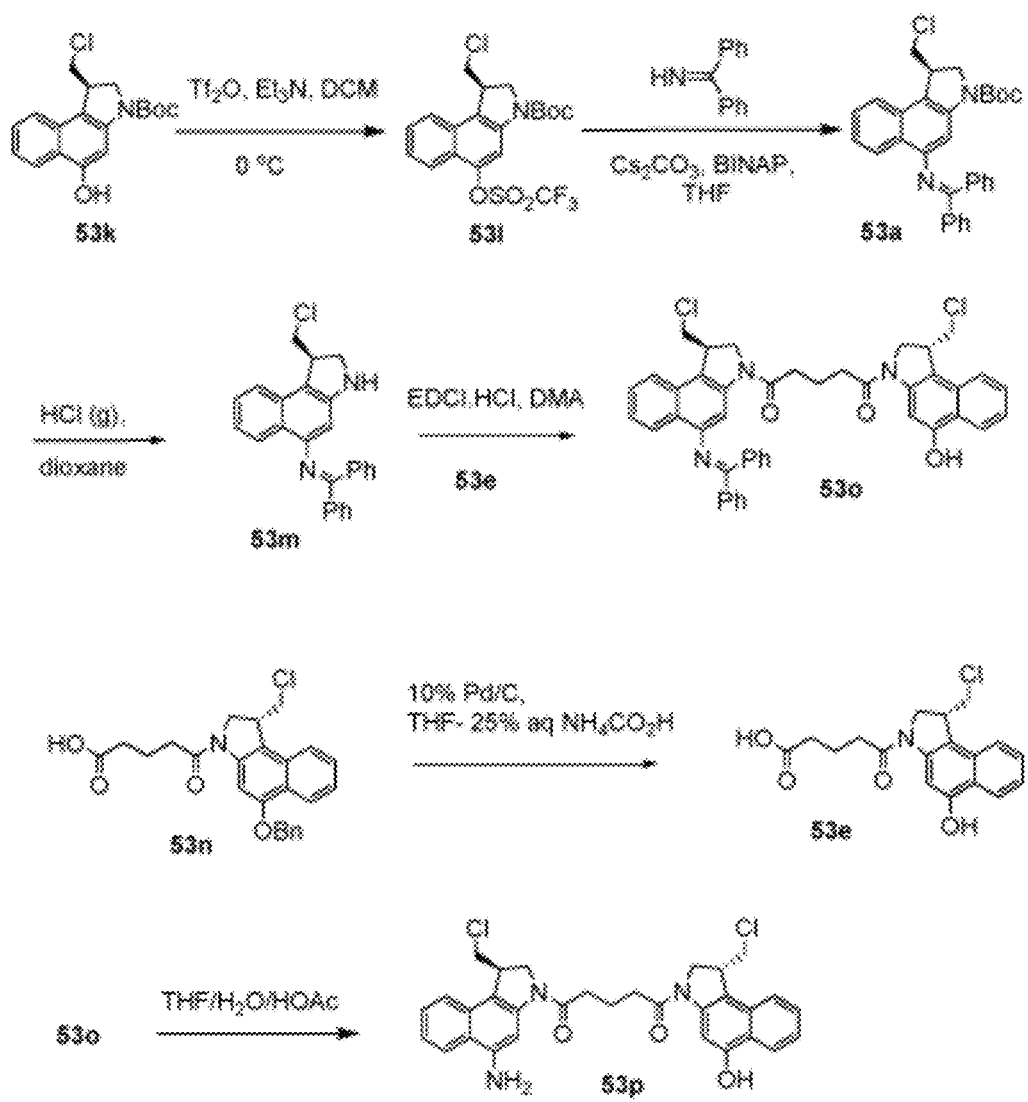
FIG. 4 shows the synthesis of unnatural enantiomer, 1-((R)-5-amino-1-(chloromethyl)-1H-benzo[e]indol-3(2H)-yl)-5-((R)-1-(chloromethyl)-5-hydroxy-1H-benzo[e]indol-3(2H)-yl)pentane-1,5-dione 53p from (R)-tert-butyl 1-(chloromethyl)-5-hydroxy-1H-benzo[e]indole-3(2H)-carboxylate 53k.
Figure 12:
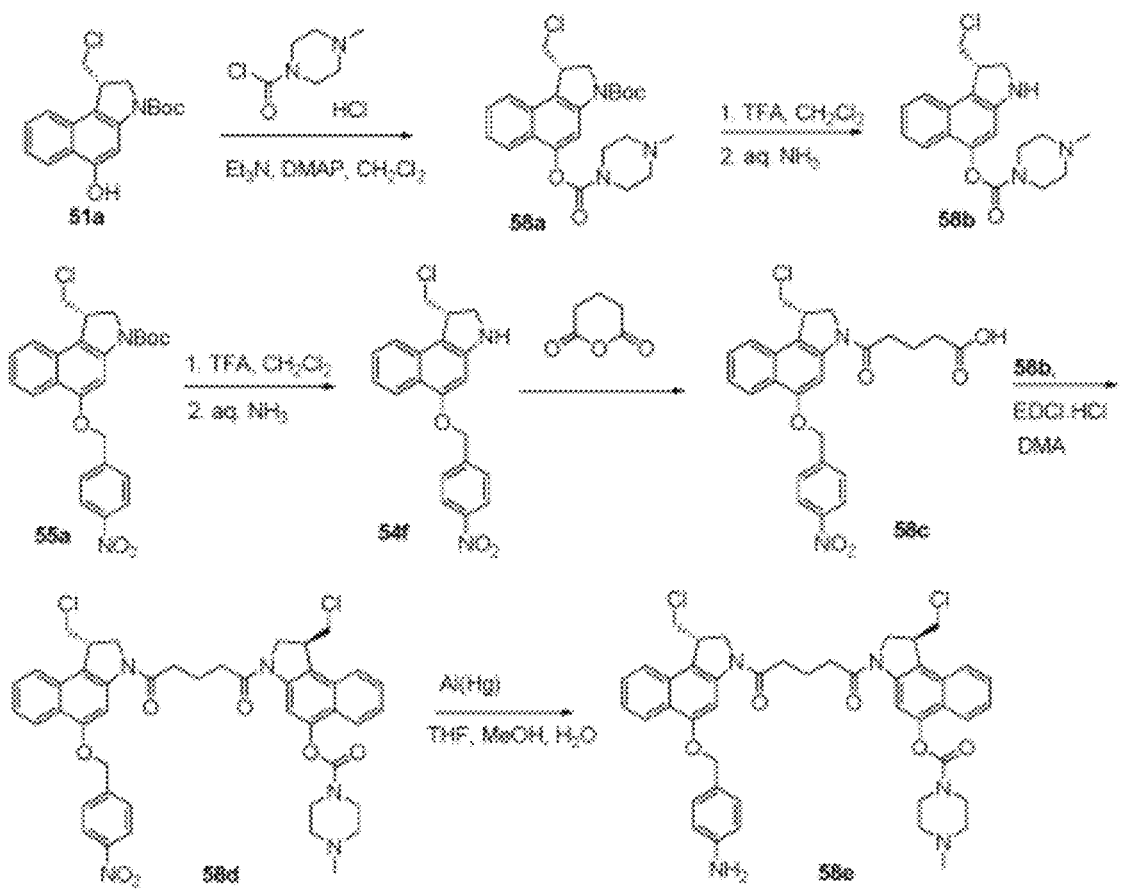
Figure 13:
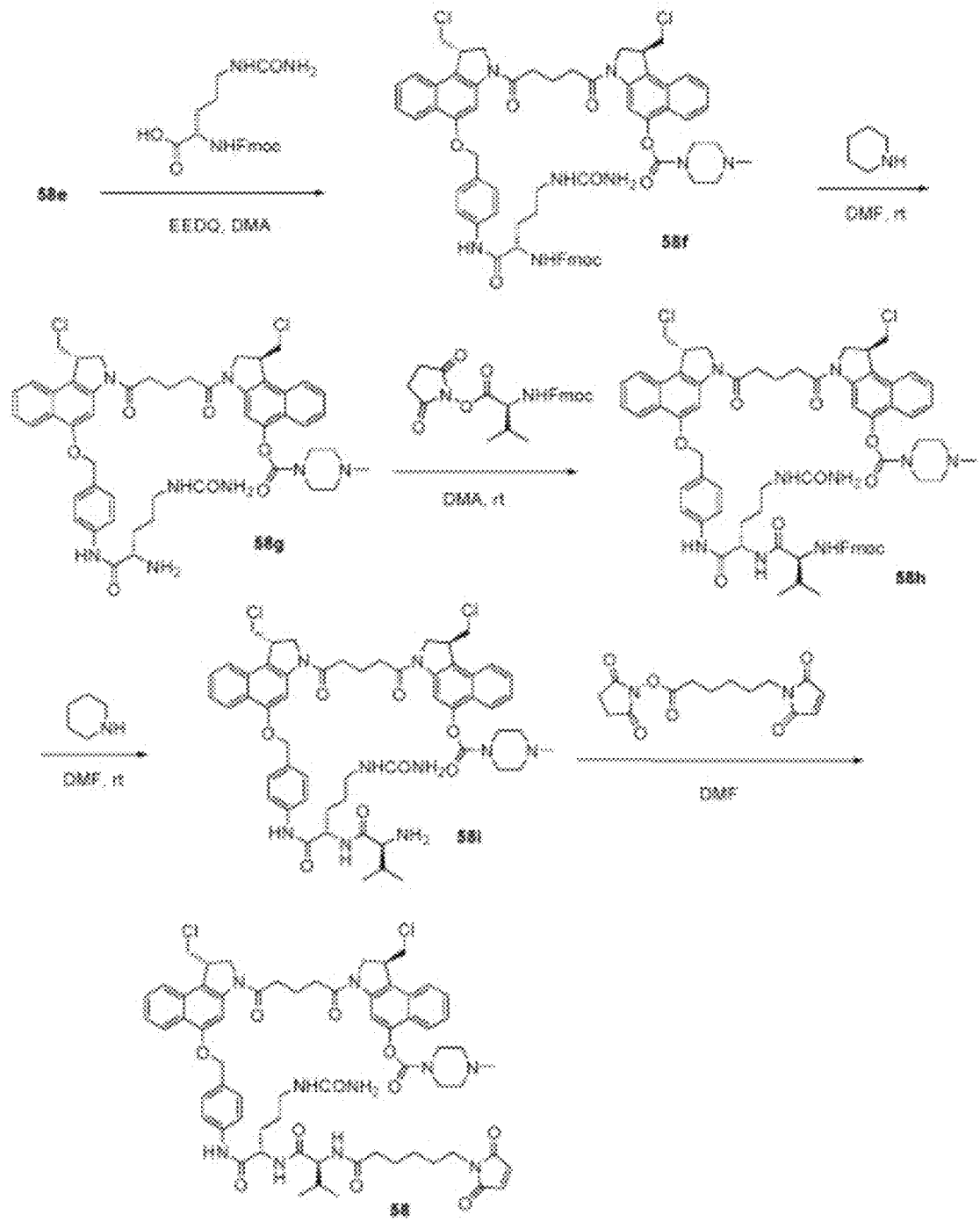
FIG. 13 shows the synthesis of (S)-1-(chloromethyl)-3-(5-((S)-1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-1H-benzo[e]indol-3(2H)-yl)-5-oxopentanoyl)-2,3-dihydro-1H-benzo[e]indol-5-yl 4-methylpiperazine-1-carboxylate 58 from (S)-3-(5-((S)-5-(4-aminobenzyloxy)-1-(chloromethyl)-1H-benzo[e] indol-3(2H)-yl)-5-oxopentanoyl)-1-(chloromethyl)-2,3-dihydro-1H-benzo[e]indol-5-yl 4-methylpiperazine-1-carboxylate 58e.
Figure 14:
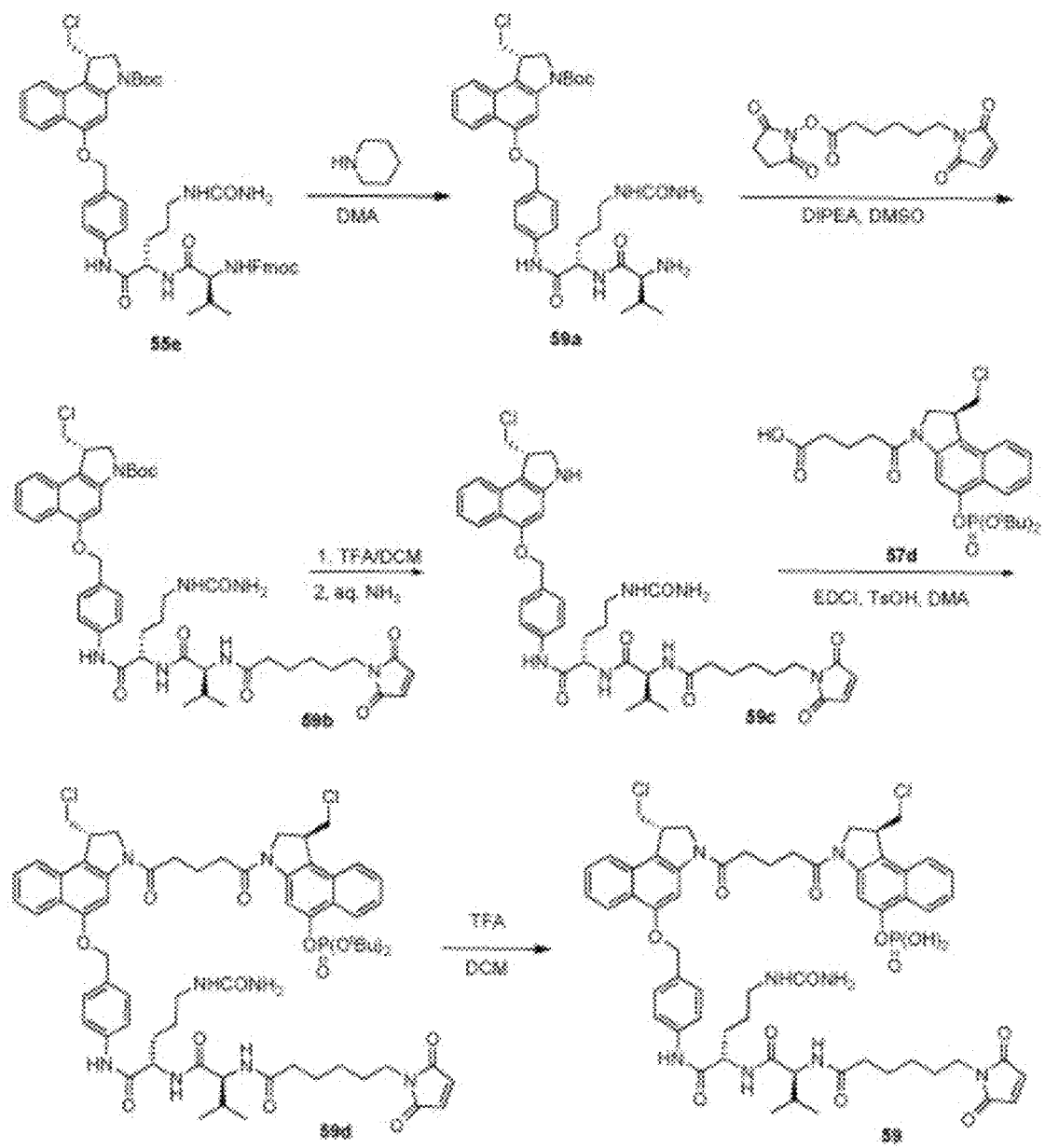
FIG. 14 shows the synthesis of (S)-1-(chloromethyl)-3-(5-((S)-1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-1H-benzo[e]indol-3(2H)-yl)-5-oxopentanoyl)-2,3-dihydro-1H-benzo[e]indol-5-yl dihydrogen phosphate 59 from (S)-tert-butyl 5-(4-((S)-2-((S)-2-(((9H-fluoren-9-yl)methoxy)carbonylamino)-3-methylbutanamido)-5-ureidopentanamido)benzyloxy)-1-(chloromethyl)-1H-benzo[e]indole-3(2H)-carboxylate 55e.

Tumor-Associated Antigens:
(1) BMPR1B (bone morphogenetic protein receptor-type IB, Genbank accession no. NM_001203)
ten Dijke, P., et al Science 264 (5155):101-104 (1994), Oncogene 14 (11):1377-1382 (1997)); WO2004063362 (Claim 2); WO2003042661 (Claim 12); US2003134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358 (Claim 1; Page 183); WO200254940 (Page 100-101); WO200259377 (Page 349-350); WO200230268 (Claim 27; Page 376); WO200148204 (Example; FIG. 4) NP_001194 bone morphogenetic protein receptor, type IB/pid=NP_001194.1—
Cross-references: MIM:603248; NP_001194.1; AY065994
(2) E16 (LAT1, SLC7A5, Genbank accession no. NM_003486)
Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004048938 (Example 2); WO2004032842 (Example IV); WO2003042661 (Claim 12); WO2003016475 (Claim 1); WO200278524 (Example 2); WO200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5; Page 133-136); US2003224454 (FIG. 3); WO2003025138 (Claim 12; Page 150);
NP_003477 solute carrier family 7 (cationic amino acid transporter, y+ system), member 5/pid=NP_003477.3— Homo sapiens
Cross-references: MIM:600182; NP_003477.3; NM_015923; NM_003486_1
(3) STEAP1 (six transmembrane epithelial antigen of prostate, Genbank accession no. NM_012449)
Cancer Res. 61 (15), 5857-5860 (2001), Hubert, R. S., et al (1999) Proc. Natl. Acad. Sci. U.S.A. 96 (25):14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A);
NP_036581 six transmembrane epithelial antigen of the prostate
Cross-references: MIM:604415; NP_036581.1; NM_012449_1
(4) 0772P (CA125, MUC16, Genbank accession no. AF361486)
J. Biol. Chem. 276 (29):27371-27375 (2001)); WO2004045553 (Claim 14); WO200292836 (Claim 6; FIG. 12); WO200283866 (Claim 15; Page 116-121); US2003124140 (Example 16); Cross-references: GI:34501467; AAK74120.3; AF361486_1
(5) MPF (MPF, MSLN, SMR, megakaryocyte potentiating factor, mesothelin, Genbank accession no. NM_005823)
Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (Claim 14); (WO2002102235 (Claim 13; Page 287-288); WO2002101075 (Claim 4; Page 308-309); WO200271928 (Page 320-321); WO9410312 (Page 52-57); Cross-references: MIM:601051; NP_005814.2; NM_005823_1
(6) Napi2b (NAPI-2B, NAPI-3B, NPTIIb, SLC34A2, solute carrier family 34 (sodium phosphate), member 2, type II sodium-dependent phosphate transporter 3b, Genbank accession no. NM_006424)
J. Biol. Chem. 277 (22):19665-19672 (2002), Genomics 62 (2):281-284 (1999), Feild, J. A., et al (1999) Biochem. Biophys. Res. Commun. 258 (3):578-582); WO2004022778 (Claim 2); EP1394274 (Example 11); WO2002102235 (Claim 13; Page 326); EP875569 (Claim 1; Page 17-19);

WO200157188 (Claim 20; Page 329); WO2004032842 (Example IV); WO200175177 (Claim 24; Page 139-140);

Cross-references: MIM:604217; NP_006415.1; NM_006424_1

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878)

Nagase T., et al (2000) DNA Res. 7 (2):143-150); WO2004000997 (Claim 1); WO2003003984 (Claim 1); WO200206339 (Claim 1; Page 50); WO200188133 (Claim 1; Page 41-43, 48-58); WO2003054152 (Claim 20); WO2003101400 (Claim 11); Accession: Q9P283; EMBL; AB040878; BAA95969.1. Genew; HGNC:10737;

(8) PSCA hlg (2700050C12Rik, C530008016Rik, RIKEN cDNA 2700050C12, RIKEN cDNA 2700050C12 gene, Genbank accession no. AY358628); Ross et al (2002) Cancer Res. 62:2546-2553; US2003129192 (Claim 2); US2004044180 (Claim 12); US2004044179 (Claim 11); US2003096961 (Claim 11); US2003232056 (Example 5); WO2003105758 (Claim 12); US2003206918 (Example 5); EP1347046 (Claim 1); WO2003025148 (Claim 20);

Cross-references: GI:37182378; AAQ88991.1; AY358628_1

Figure 6:
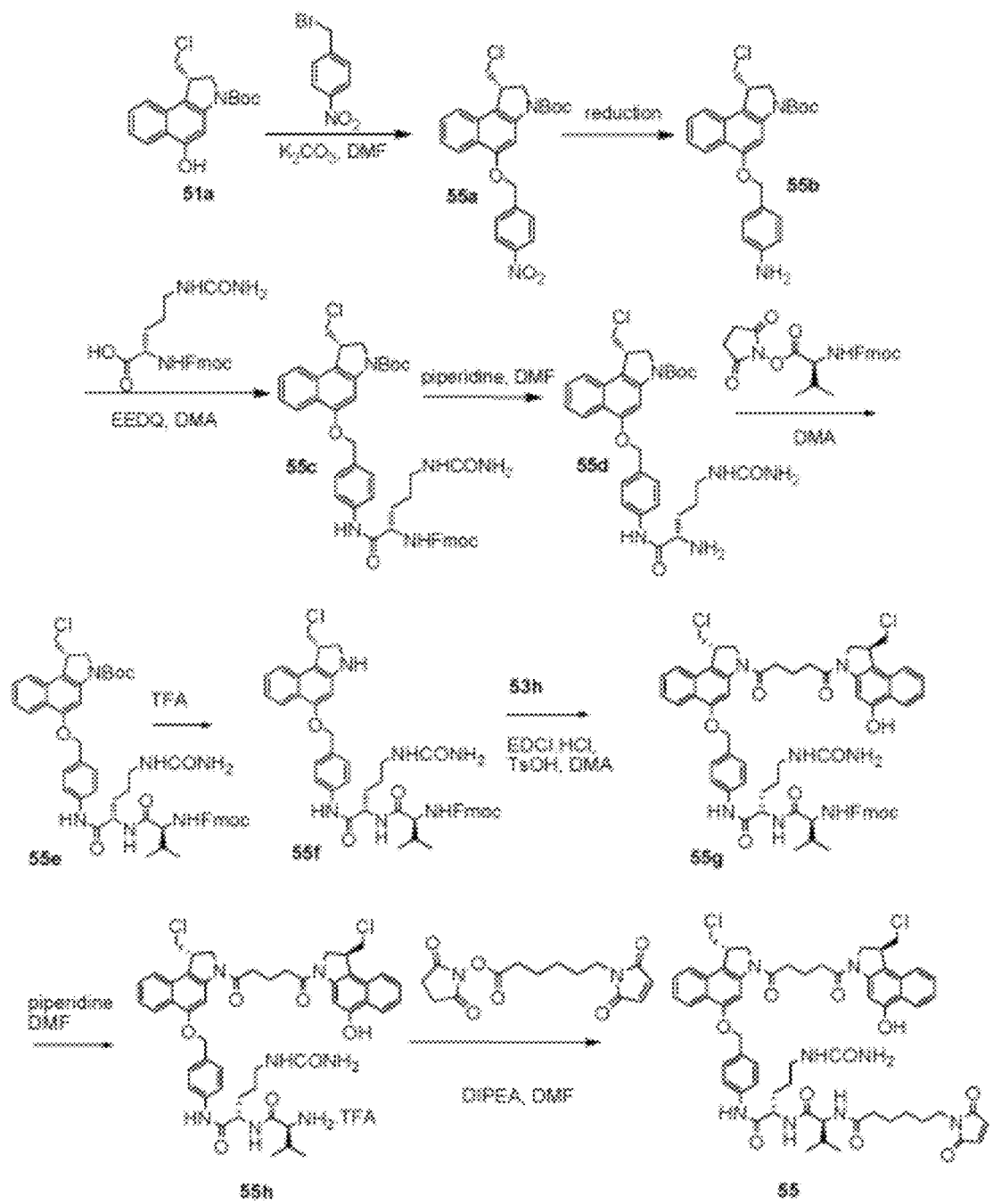

(9) ETBR (Endothelin type B receptor, Genbank accession no. AY275463); Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206); WO2004045516 (Claim 1); WO2004048938 (Example 2); WO2004040000 (Claim 151); WO2003087768 (Claim 1); WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172 (Claim 1; Page 297-299); US2003109676; U.S. Pat. No. 6,518,404 (FIG. 3); U.S. Pat. No. 5,773,223 (Claim 1a; Col 31-34); WO2004001004;

(10) MSG783 (RNF124, hypothetical protein FLJ20315, Genbank accession no. NM_017763); WO2003104275 (Claim 1); WO2004046342 (Example 2); WO2003042661 (Claim 12); WO2003083074 (Claim 14; Page 61); WO2003018621 (Claim 1); WO2003024392 (Claim 2; FIG. 93); WO200166689 (Example 6);

Cross-references: LocusID:54894; NP_060233.2; NM_017763_1

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138)

Figure 10:
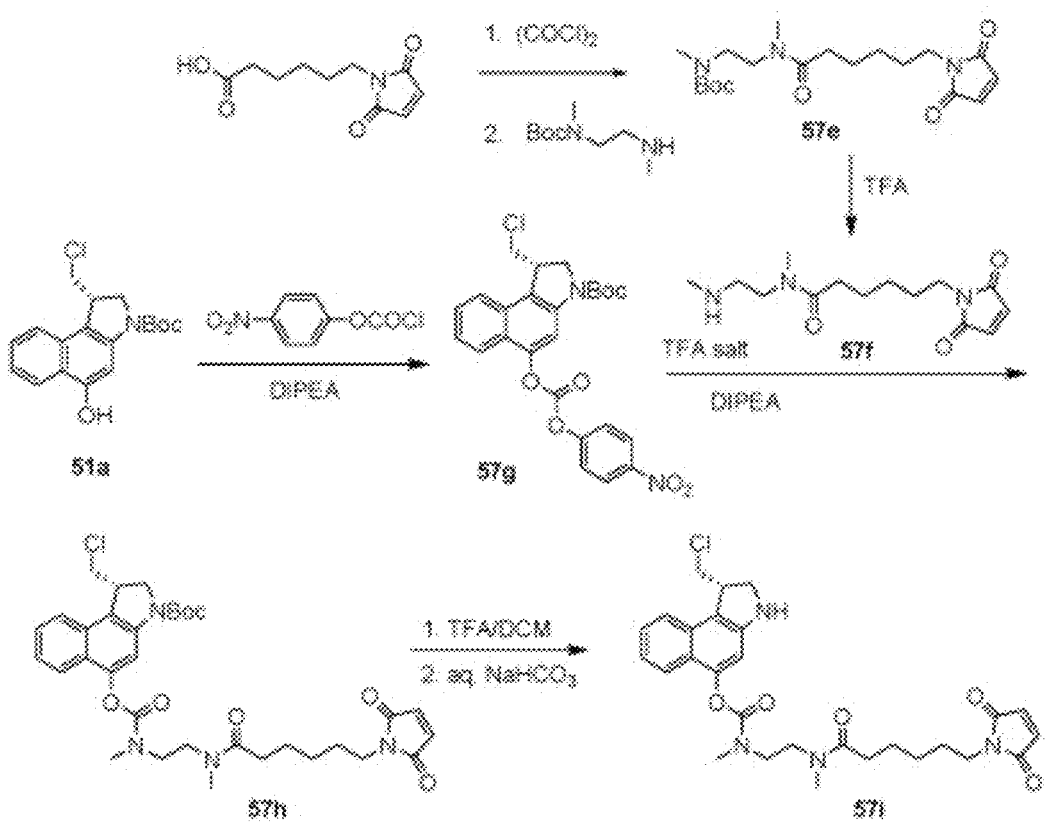
FIG. 10 shows the synthesis of (S)-1-(chloromethyl)-2,3-dihydro-1H-benzo[e]indol-5-yl 2-(6-(2,5-dioxo-2,5-dihydro-1H-pyrrol-1-yl)-N-methylhexanamido)ethyl(methyl) carbamate 57i from 6-(2,5-dioxo-2,5-dihydro-1H-pyrrol-1-yl)hexanoic acid.

Lab. Invest. 82 (11):1573-1582 (2002)); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WO200226822 (Claim 23; FIG. 2); WO200216429 (Claim 12; FIG. 10);

Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636)

Xu, X. Z., et al Proc. Natl. Acad. Sci. U.S.A. 98 (19):10692-10697 (2001), Cell 109 (3):397-407 (2002), J. Biol. Chem. 278 (33):30813-30820 (2003)); US2003143557 (Claim 4); WO200040614 (Claim 14; Page 100-103); WO200210382 (Claim 1; FIG. 9A); WO2003042661 (Claim 12); WO200230268 (Claim 27; Page 391); US2003219806 (Claim 4); WO200162794 (Claim 14; FIG. 1A-D);

Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212)

Ciccodicola, A., et al EMBO J. 8 (7):1987-1991 (1989), Am. J. Hum. Genet. 49 (3):555-565 (1991)); US2003224411 (Claim 1); WO2003083041 (Example 1); WO2003034984 (Claim 12); WO200288170 (Claim 2; Page 52-53); WO2003024392 (Claim 2; FIG. 58); WO200216413 (Claim 1; Page 94-95, 105); WO200222808 (Claim 2; FIG. 1); U.S. Pat. No. 5,854,399 (Example 2; Col 17-18); U.S. Pat. No. 5,792,616 (FIG. 2);

Cross-references: MIM:187395; NP_003203.1; NM_003212_1

(14) CD21 (CR2 (Complement receptor 2) or C3DR (C3d/Epstein Barr virus receptor) or Hs.73792 Genbank accession no. M26004)

Figure 9:
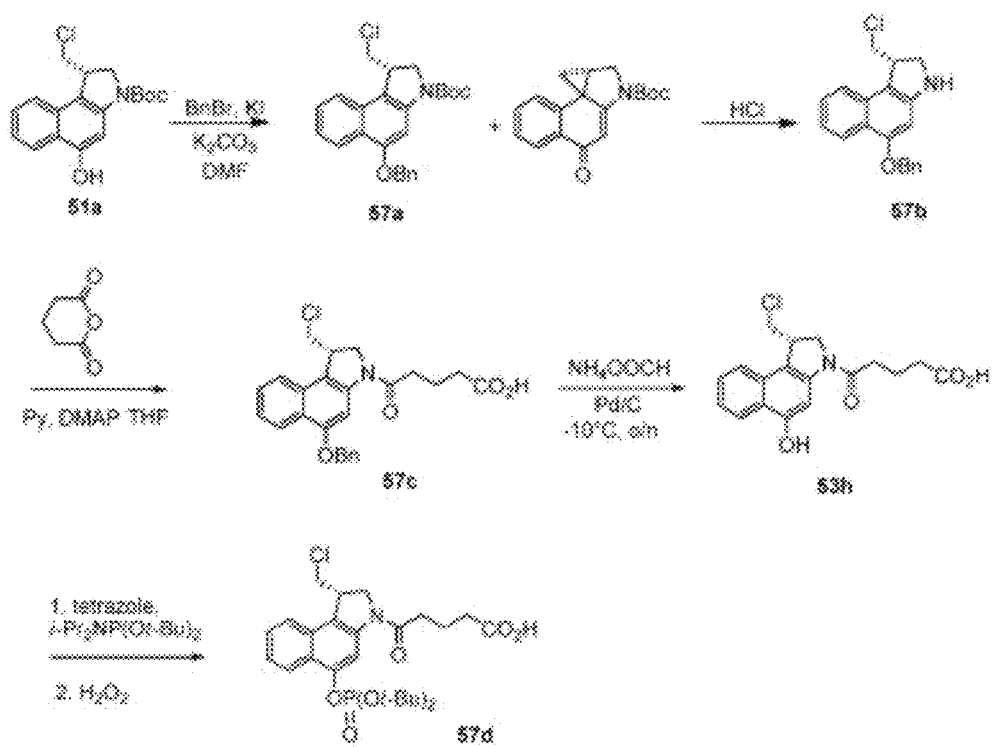

Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (Claim 9); WO2004045520 (Example 4); WO9102536 (FIGS. 9.1-9.9); WO2004020595 (Claim 1);

Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674)

Proc. Natl. Acad. Sci. U.S.A. (2003) 100 (7):4126-4131, Blood (2002) 100 (9):3068-3076, Muller et al (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146);

Cross-references: MIM:147245; NP_000617.1; NM_000626_1

Figure 18:
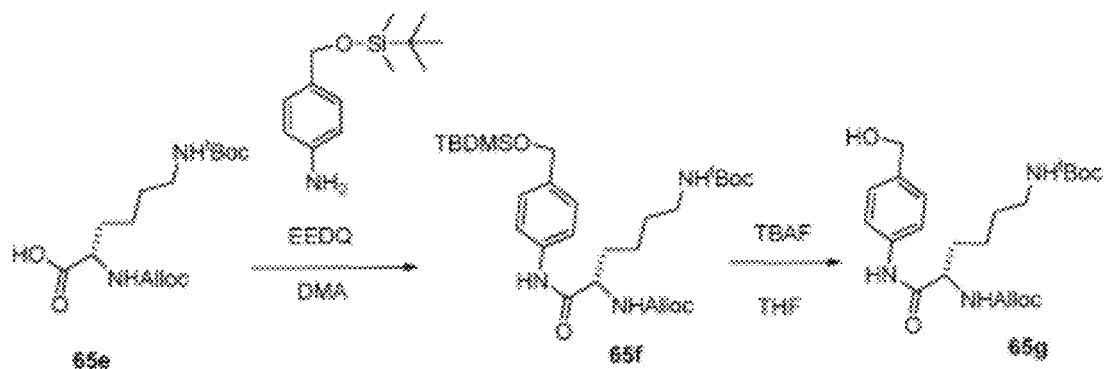
FIG. 18 shows the synthesis of benzyl alcohol lysine 65g from (S)-2-(allyloxycarbonylamino)-6-(tert-butoxycarbonylamino)hexanoic acid 65e.
Figure 19:
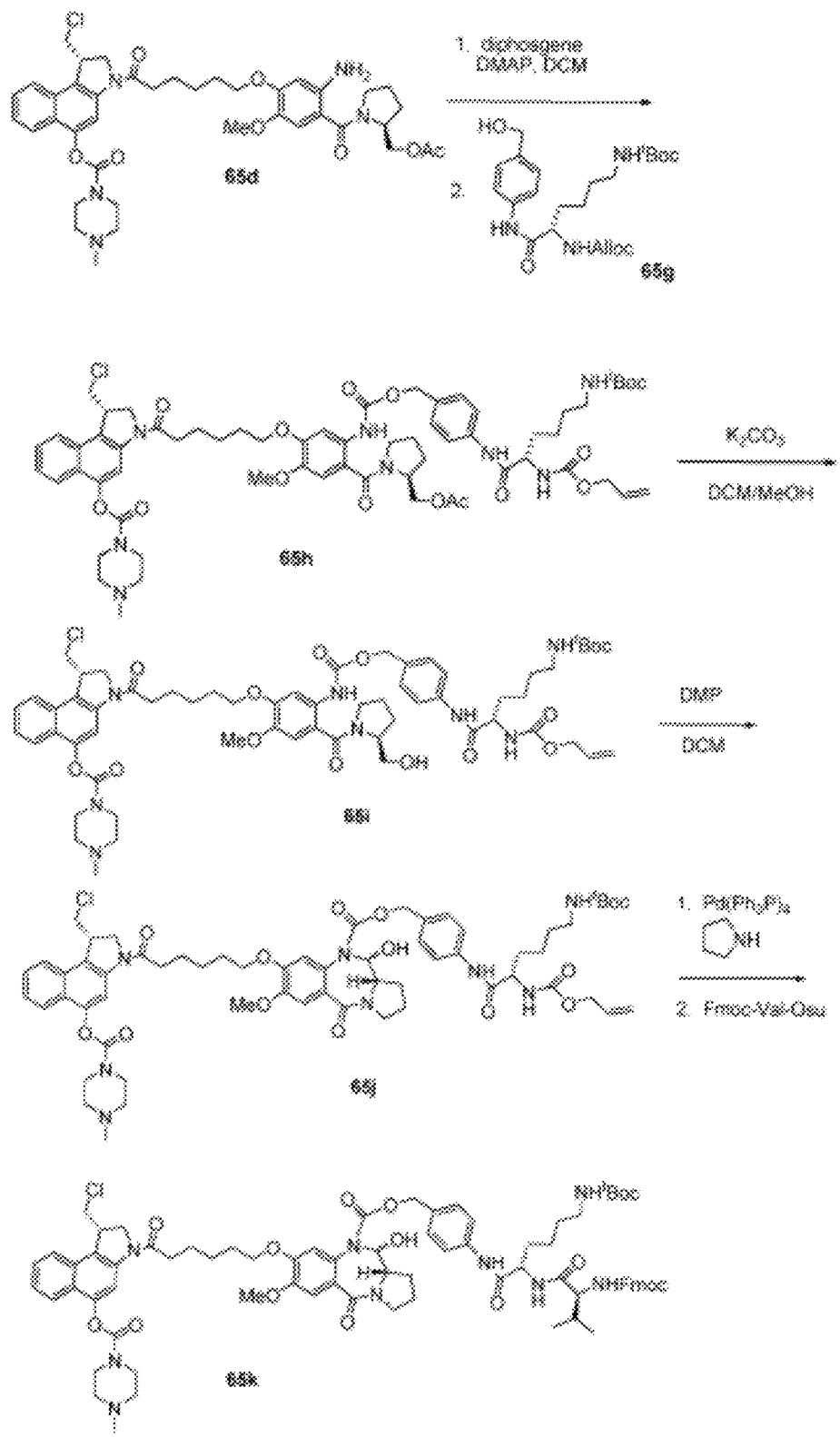
FIG. 19 shows the synthesis of (S)-4-((S)-2-((S)-2-(((9H-fluoren-9-yl)methoxy)carbonylamino)-3-methylbutanamido)-6-(tert-butoxycarbonylamino)hexanamido)benzyl 8-(6-((S)-1-(chloromethyl)-5-(4-methylpiperazine-1-carbonyloxy)-1H-benzo[e]indol-3 (2H)-yl)-6-oxohexyloxy)-11-hydroxy-7-methoxy-5-oxo-2,3,11,11a-tetrahydro-1H-benzo [e]pyrrolo[1,2-a][1,4]diazepine-10(5H)-carboxylate 65k from (S)-3-(6-(4-((S)-2-(acetoxymethyl)pyrrolidine-1-carbonyl)-5-amino-2-methoxyphenoxy)hexanoyl)-1-(chloromethyl)-2,3-dihydro-1H-benzo[e]indol-5-yl 4-methylpiperazine-1-carboxylate 65d.
Figure 20:
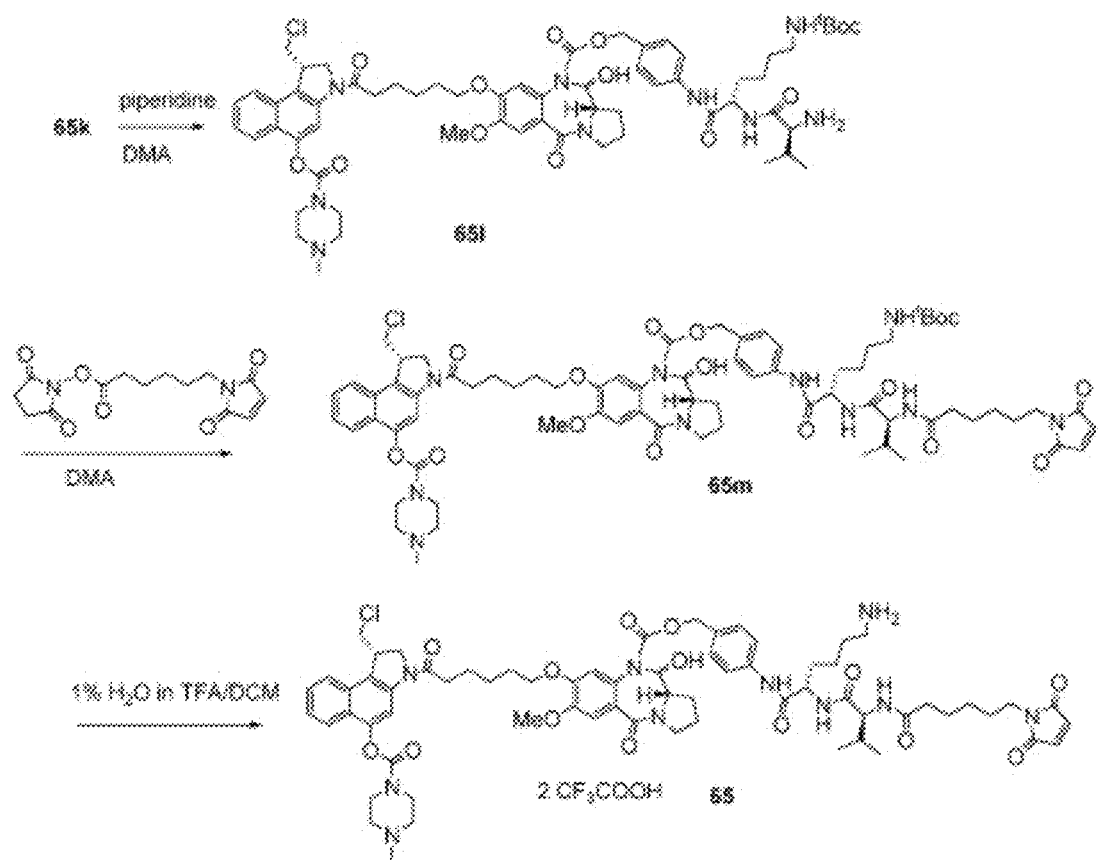
FIG. 20 shows the synthesis of (S)-4-((S)-6-amino-2-((S)-2-(6-(2,5-dioxo-2,5-dihydro-1H-pyrrol-1-yl)hexanamido)-3-methylbutanamido)hexanamido)benzyl 8-(6-((S)-1-(chloromethyl)-5-(4-methylpiperazine-1-carbonyloxy)-1H-benzo[e]indol-3(2H)-yl)-6-oxohexyloxy)-11-hydroxy-7-methoxy-5-oxo-2,3,11,11a-tetrahydro-1H-benzo[e]pyrrolo [1,2-a][1,4]diazepine-10(5H)-carboxylate 65 as the bis-trifluoroacetate salt from 65k.
Figure 21:
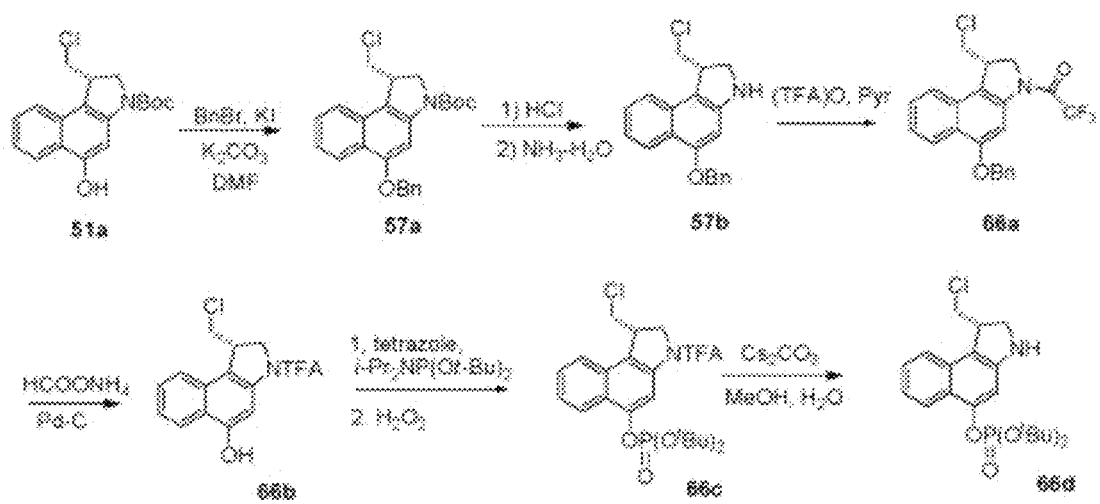
Figure 22:
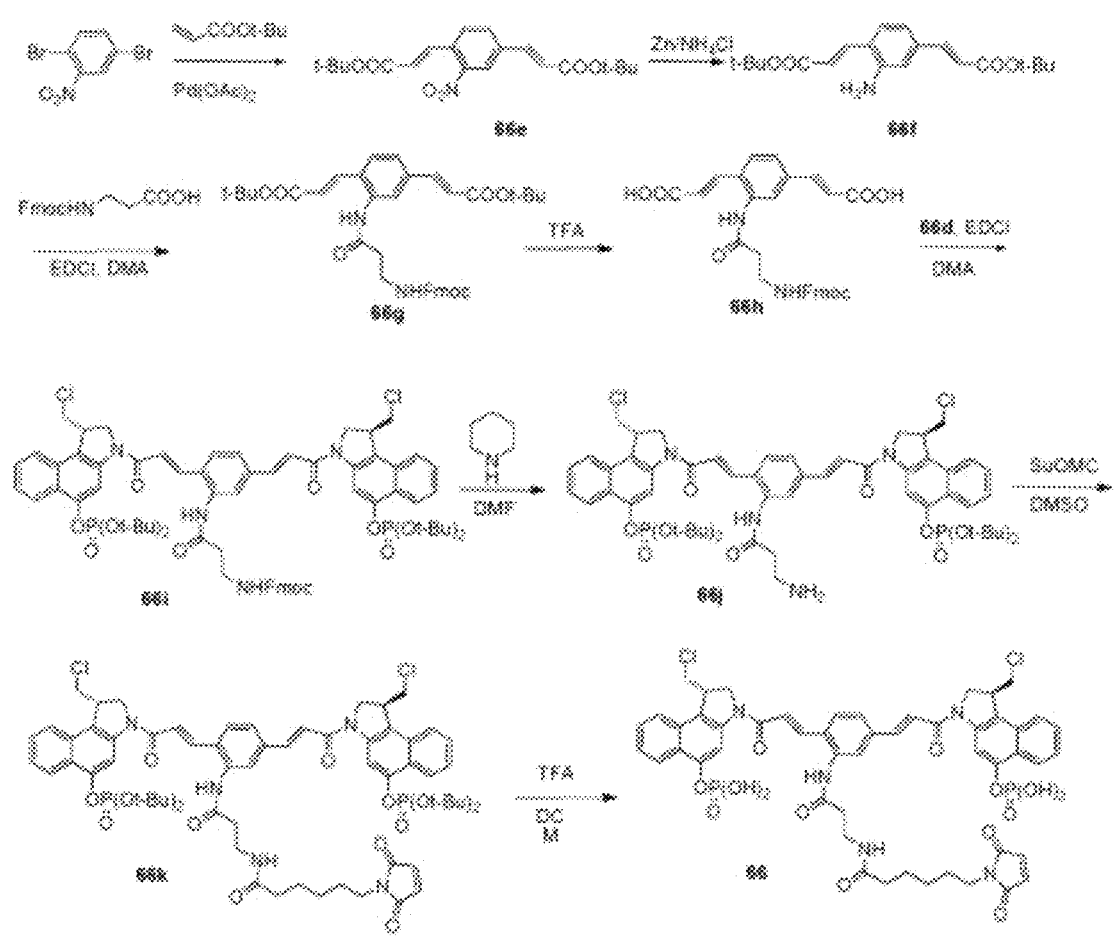
FIG. 22 shows the synthesis of N-(3-(2,5-bis((E)-3-((S)-1-(chloromethyl)-5-phosphonoxy-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide 66 from (2E, 2'E)-tert-butyl 3,3'-(2-nitro-1,4-phenylene)diacrylate 66e.
Figure 23:
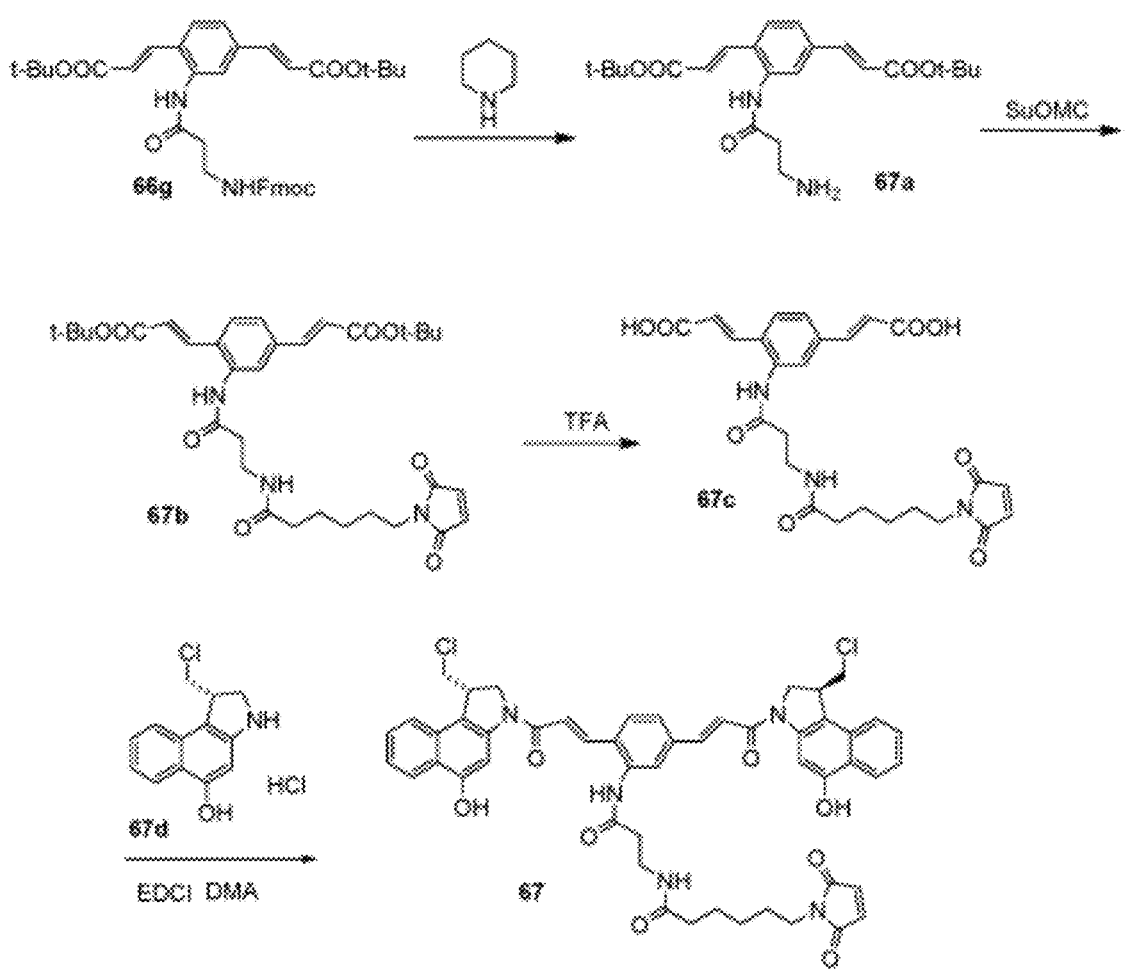
FIG. 23 shows the synthesis of N-(3-(2,5-bis((E)-3-((S)-1-(chloromethyl)-5-hydroxy-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide 67 from (2E, 2'E)-tert-butyl 3,3'-(2-(3-(((9H-fluoren-9-yl)methoxy) carbonylamino)propanamido)-1,4-phenylene)diacrylate 66g.
Figure 24:
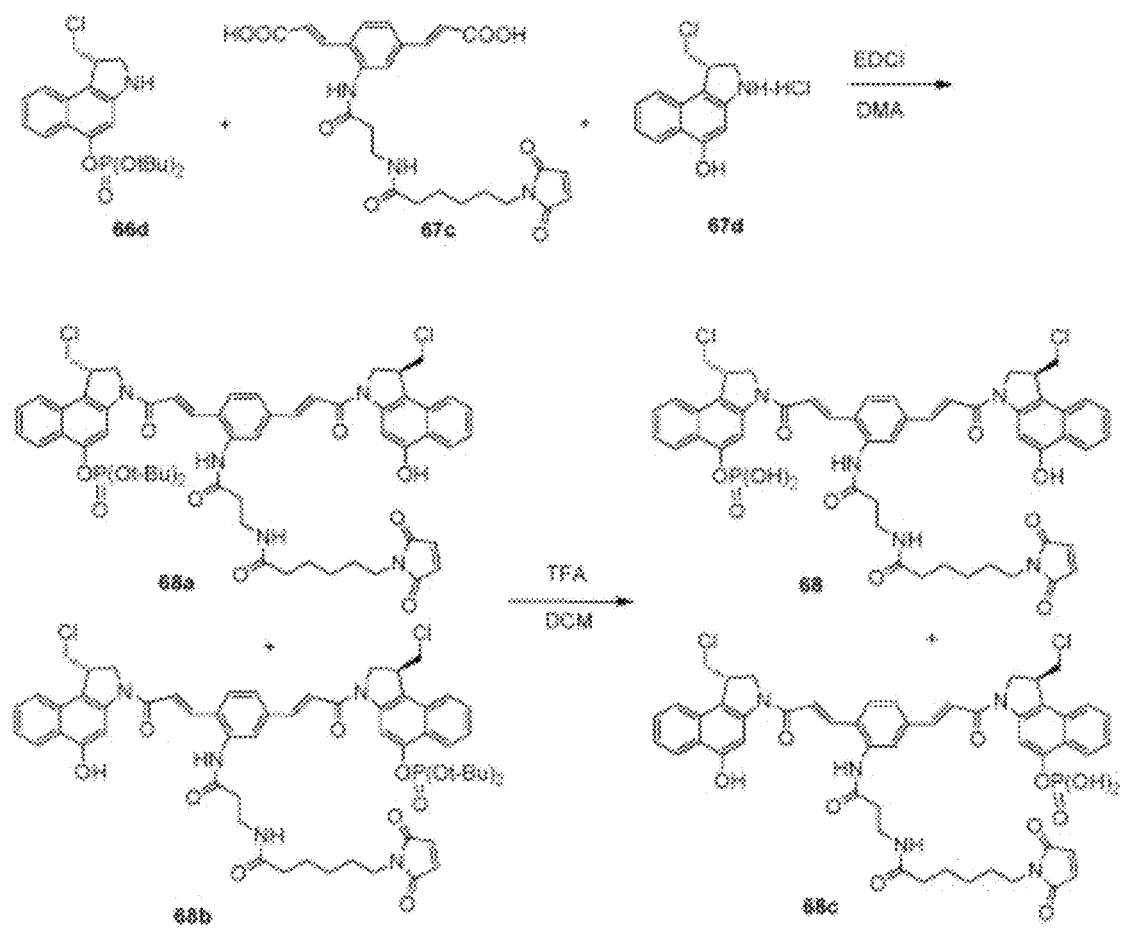
FIG. 24 shows the synthesis of (S)-1-(chloromethyl)-3-((E)-3-(4-((E)-3-((S)-1-(chloromethyl)-5-hydroxy-1H-benzo[e]indol-3(2H)-yl)-3-oxoprop-1-enyl)-2-(3-(6-(2,5-dioxo-2,5-dihydro-1H-pyrrol-1-yl)hexanamido)propanamido) phenyl)acryloyl)-2,3-dihydro-1H-benzo[e]indol-5-yl dihydrogen phosphate 68 from 66d, 67c, 67d.

(16) FcRH2 (IFGP4, IRTA4, SPAP1A (SH2 domain containing phosphatase anchor protein 1a), SPAPIB, SPAPIC, Genbank accession no. NM_030764, AY358130) Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (Claim 2); WO2003077836; WO200138490 (Claim 5; FIG. 18D-1-18D-2); WO2003097803 (Claim 12); WO2003089624 (Claim 25); Cross-references: MIM:606509; NP_110391.2; NM_030764_1

Figure 5:
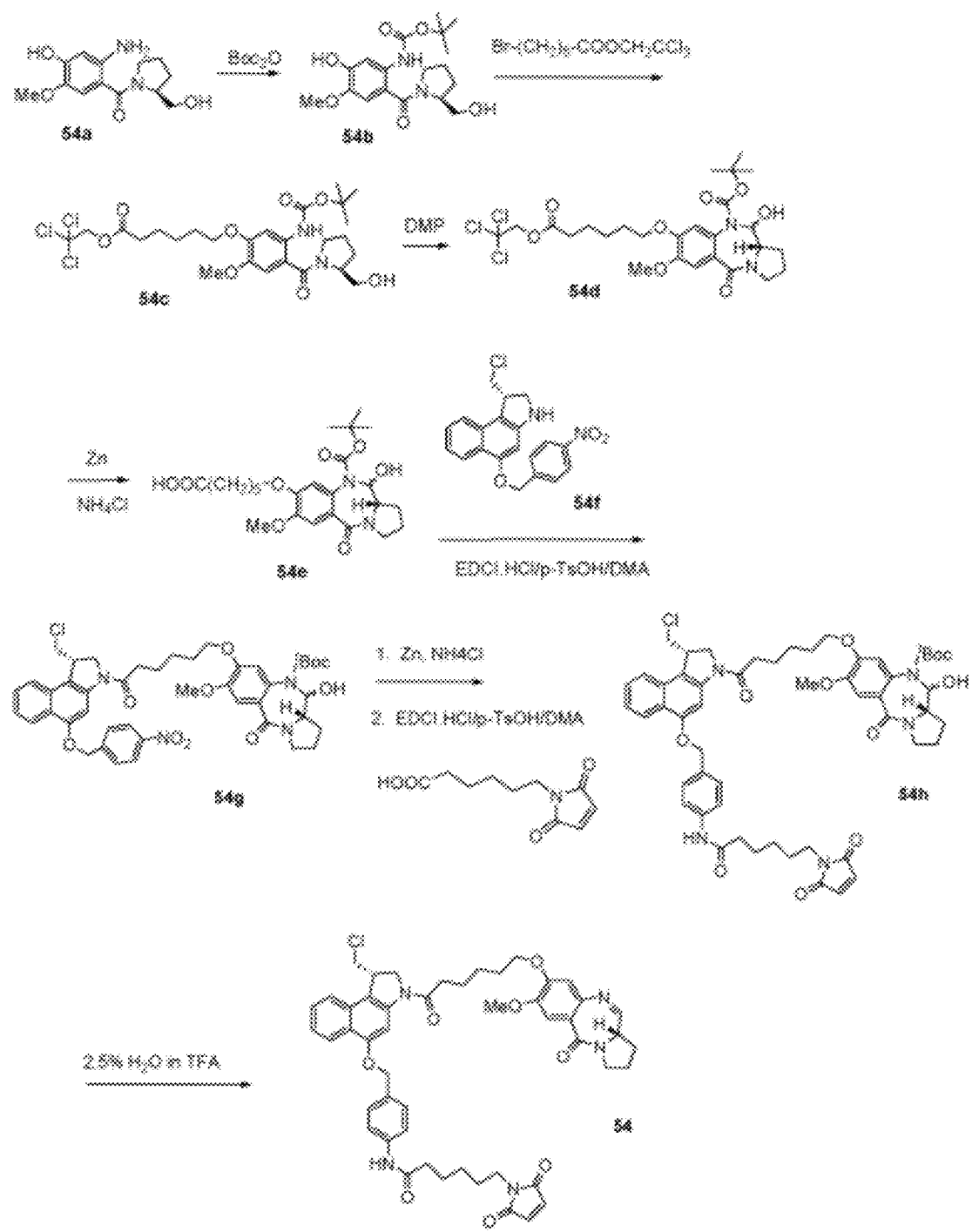
Figure 7:
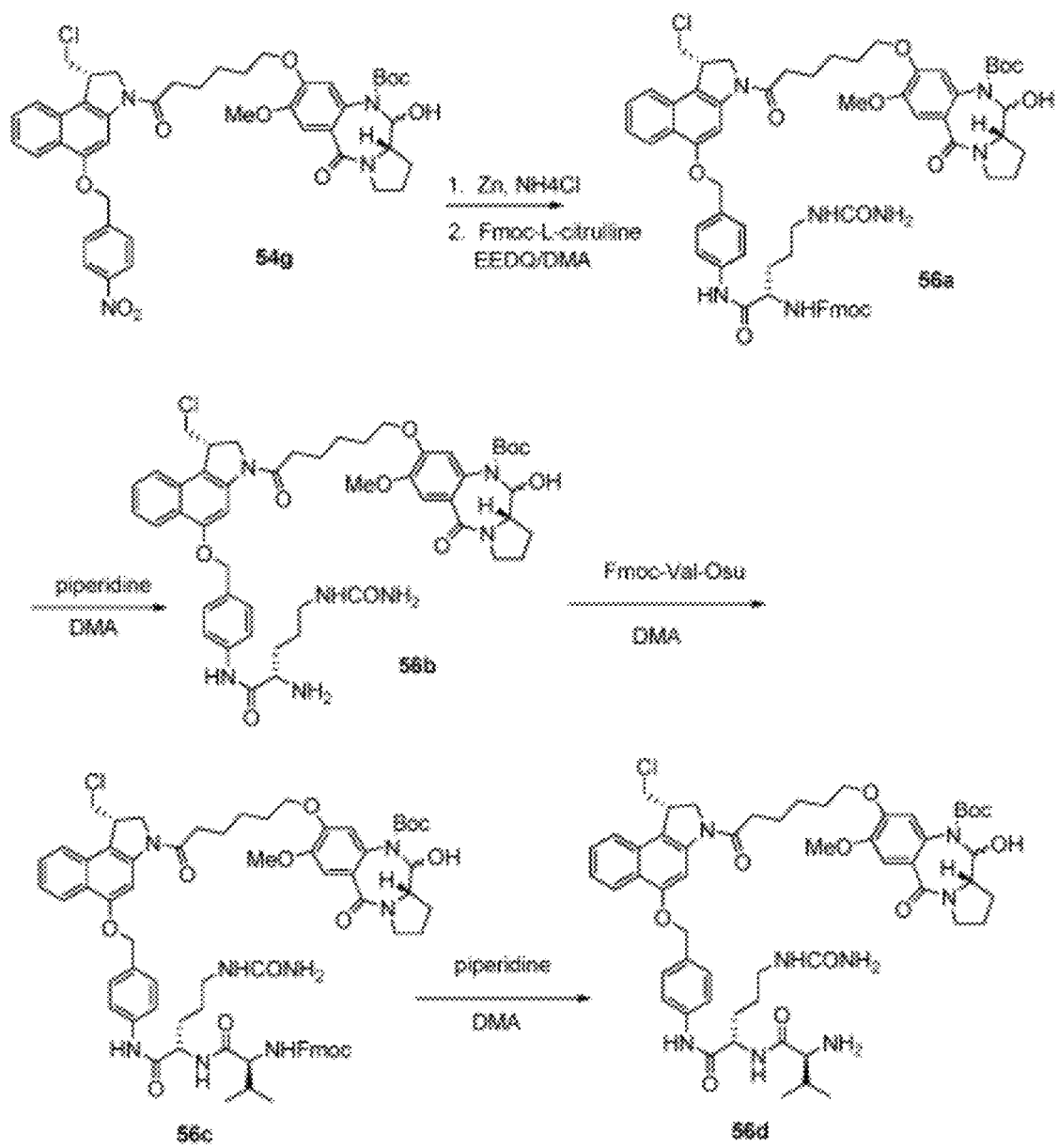
FIG. 7 shows the synthesis of (S)-tert-butyl 8-(6-((S)-5-(4-((S)-2-((S)-2-amino-3-methylbutanamido)-5-ureidopentanamido)benzyloxy)-1-(chloromethyl)-1H-benzo[e]indol-3 (2H)-yl)-6-oxohexyloxy)-11-hydroxy-7-methoxy-5-oxo-2, 3,11,11a-tetrahydro-1H-benzo[e]pyrrolo[1,2-a][1,4] diazepine-10(5H)-carboxylate 56d from (S)-tert-Butyl 8-(6-((S)-1-(chloromethyl)-5-(4-nitrobenzyloxy)-1H-benzo[e] indol-3(2H)-yl)-6-oxohexyloxy)-1-hydroxy-7-methoxy-5-oxo-2,3,11,11a-tetrahydro-1H-benzo[e]pyrrolo[1,2-a][1,4] diazepine-10(5H)-carboxylate 54g.
Figure 11:
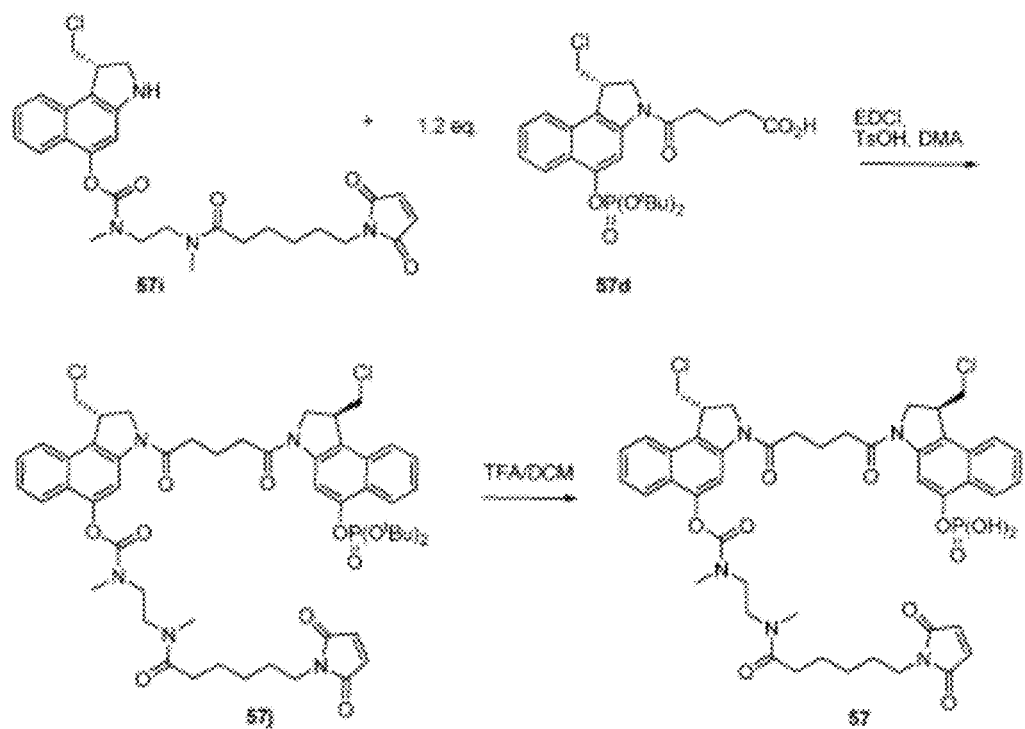
FIG. 11 shows the synthesis of (S)-1-(chloromethyl)-3-(5-((S)-1-(chloromethyl)-5-(phosphonooxy)-1H-benzo[e] indol-3(2H)-yl)-5-oxopentanoyl)-2,3-dihydro-1H-benzo[e] indol-5-yl 2-(6-(2,5-dioxo-2,5-dihydro-1H-pyrrol-1-yl)-N-methylhexanamido)ethyl(methyl)carbamate 57 from (S)-1-(chloromethyl)-2,3-dihydro-1H-benzo[e]indol-5-yl 2-(6-(2, 5-dioxo-2,5-dihydro-1H-pyrrol-1-yl)-N-methylhexanamido)ethyl(methyl)carbamate 57i.

(17) HER2 (ErbB2, Genbank accession no. M11730) Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 11); WO2004009622; WO2003081210; WO2003089904 (Claim 9); WO2003016475 (Claim 1); US2003118592; WO2003008537 (Claim 1); WO2003055439 (Claim 29; FIG. 1A-B); WO2003025228 (Claim 37; FIG. 5C); WO200222636 (Example 13; Page 95-107); WO200212341 (Claim 68; FIG. 7); WO200213847 (Page 71-74); WO200214503 (Page 114-117); WO200153463 (Claim 2; Page 41-46); WO200141787 (Page 15); WO200044899 (Claim 52; FIG. 7); WO200020579 (Claim 3; FIG. 2); U.S. Pat. No. 5,869,445 (Claim 3; Col 31-38); WO9630514 (Claim 2; Page 56-61); EP1439393 (Claim 7); WO2004043361 (Claim 7); WO2004022709; WO200100244 (Example 3; FIG. 4); Accession: P04626; EMBL; M11767; AAA35808.1. EMBL; M11761; AAA35808.1.

Figure 8:
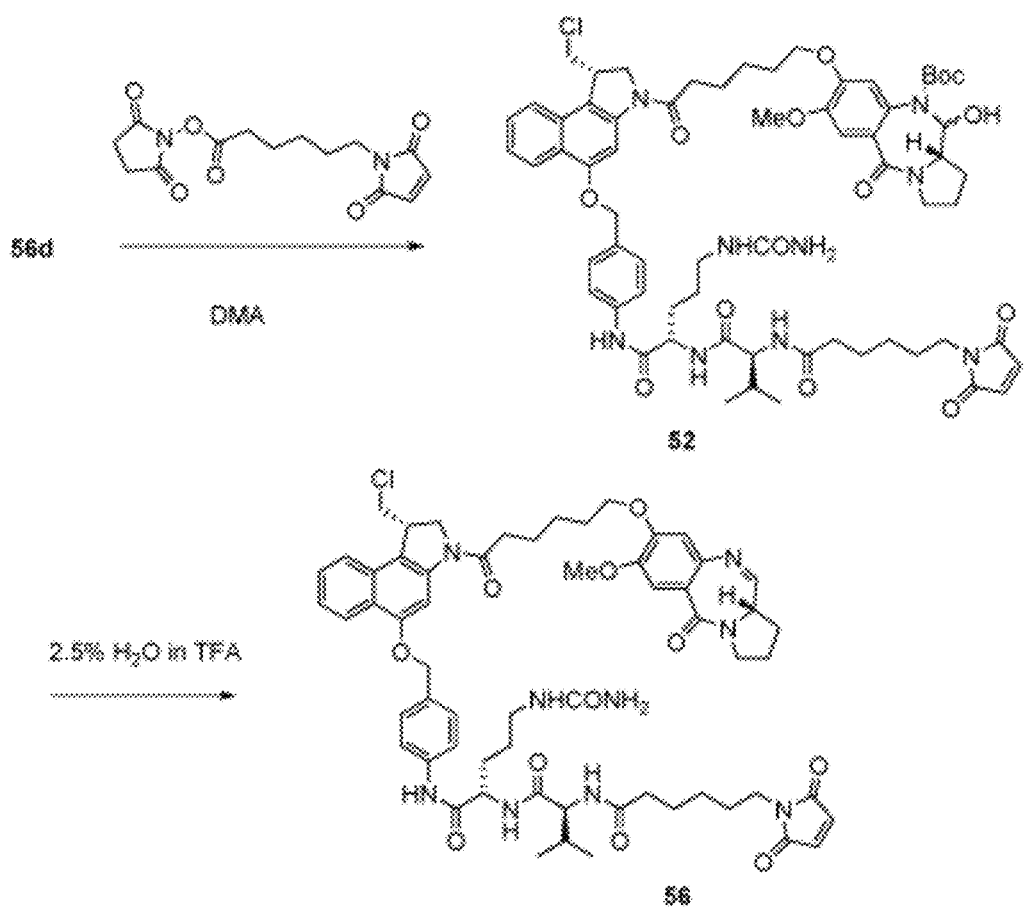
FIG. 8 shows the synthesis of N—((S)-1-((S)-1-(4-(((S)-1-(chloromethyl)-3-(6-((S)-7-methoxy-5-oxo-2, 3,5,11a-tetrahydro-1H-benzo[e]pyrrolo[1,2-a][1,4]diazepin-8-yloxy) hexanoyl)-2,3-dihydro-1H-benzo[e]indol-5-yloxy)methyl) phenylamino)-1-oxo-5-ureidopentan-2-ylamino)-3-methyl-1-oxobutan-2-yl)-6-(2,5-dioxo-2,5-dihydro-1H-pyrrol-1-yl) hexanamide 56 from (S)-tert-butyl 8-(6-((S)-5-(4-((S)-2-((S)-2-amino-3-methylbutanamido)-5-ureidopentanamido) benzyloxy)-1-(chloromethyl)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10 (5H)-carboxylate 56d.

(18) NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (Claim 7); WO2004044178 (Example 4); WO2004031238; WO2003042661 (Claim 12); WO200278524 (Example 2); WO200286443 (Claim 27; Page 427); WO200260317 (Claim 2); Accession: P40199; Q14920; EMBL; M29541; AAA59915.1. EMBL; M18728;

(19) MDP (DPEP1, Genbank accession no. BC017023) Proc. Natl. Acad. Sci. U.S.A. 99 (26):16899-16903 (2002)); WO2003016475 (Claim 1); WO200264798 (Claim 33; Page 85-87); JP05003790 (FIG. 6-8); WO9946284 (FIG. 9); Cross-references: MIM:179780; AAH17023.1; BC017023_1

(20) IL20Rα (IL20Ra, ZCYTOR7, Genbank accession no. AF184971); Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (Claim 2; Page 63); WO200222153 (Page 45-47); US2002042366 (Page 20-21); WO200146261 (Page 57-59); WO200146232 (Page 63-65); WO9837193 (Claim 1; Page 55-59); Accession: Q9UHF4; Q6UWA9; Q96SH8; EMBL; AF184971; AAF01320.1.

(21) Brevican (BCAN, BEHAB, Genbank accession no. AF229053) Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (Claim 11); US2003186373 (Claim 11); US2003119131 (Claim 1; FIG. 52); US2003119122 (Claim 1; FIG. 52); US2003119126 (Claim 1); US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1);

(22) EphB2R (DRT, ERK, Hek5, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42); Cross-references: MIM:600997; NP_004433.2; NM_004442_1

Figure 17:
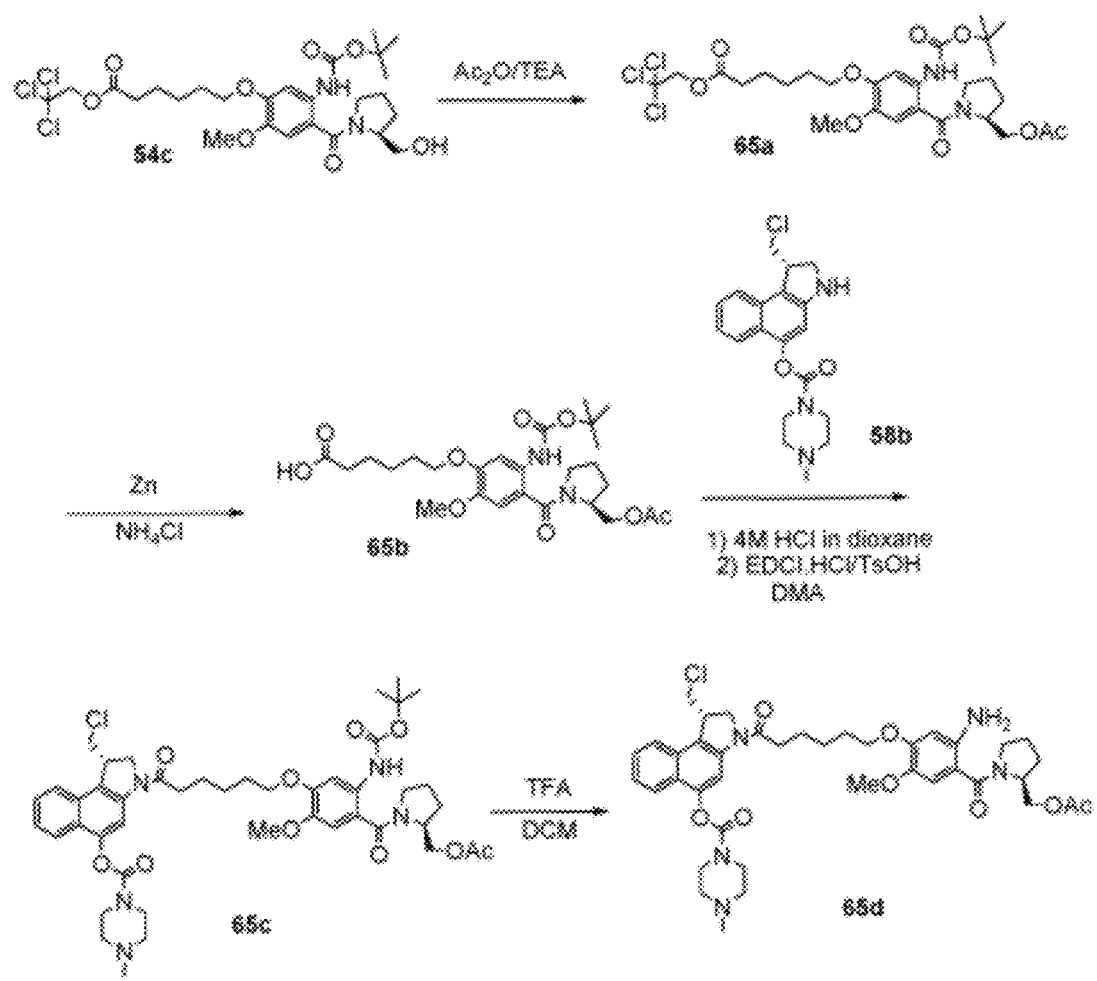
FIG. 17 shows the synthesis of (S)-3-(6-(4-((S)-2-(acetoxymethyl)pyrrolidine-1-carbonyl)-5-amino-2-methoxyphenoxy)hexanoyl)-1-(chloromethyl)-2,3-dihydro-1H-benzo[e]indol-5-yl 4-methylpiperazine-1-carboxylate 65d from (S)-2,2,2-trichloroethyl 6-(5-(tert-butoxycarbonylamino)-4-(2-(hydroxymethyl)pyrrolidine-1-carbonyl)-2-methoxyphenoxy)hexanoate 54c.

(23) ASLG659 (B7h, Genbank accession no. AX092328) US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7b); WO200202624 (Claim 13; FIG. 1A-1B); US2002034749 (Claim 54; Page 45-46); WO200206317 (Example 2; Page 320-321, Claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (Claim 12); WO2003004989 (Claim 1); WO200271928 (Page 233-234, 452-453); WO 0116318;

(24) PSCA (Prostate stem cell antigen precursor, Genbank accession no. AJ297436) Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709; EP1394274 (Example 11); US2004018553 (Claim 17); WO2003008537 (Claim 1); WO200281646 (Claim 1; Page 164); WO2003003906 (Claim 10; Page 288); WO200140309 (Example 1; FIG. 17); US2001055751 (Example 1; FIG. 1b); WO200032752 (Claim 18; FIG. 1); WO9851805 (Claim 17; Page 97); WO9851824 (Claim 10; Page 94); WO9840403 (Claim 2; FIG. 1B); Accession: O43653; EMBL; AF043498; AAC39607.1.

(25) GEDA (Genbank accession No. AY260763); AAP14954 lipoma HMGIC fusion-partner-like protein/pid=AAP14954.1—*Homo sapiens* Species: *Homo sapiens* (human) WO2003054152 (Claim 20); WO2003000842 (Claim 1); WO2003023013 (Example 3, Claim 20); US2003194704 (Claim 45); Cross-references: GI:30102449; AAP14954.1; AY260763_1

(26) BAFF-R (B cell-activating factor receptor, BLyS receptor 3, BR3, Genbank accession No. AF116456); BAFF receptor/pid=NP_443177.1—*Homo sapiens* Thompson, J. S., et al Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616); WO200294852

(Col 136-137); WO200238766 (Claim 3; Page 133); WO200224909 (Example 3; FIG. 3);
Cross-references: MIM:606269; NP_443177.1; NM_052945_1; AF132600

(27) CD22 (B-cell receptor CD22-B isoform, BL-CAM, Lyb-8, Lyb8, SIGLEC-2, FLJ22814, Genbank accession No. AK026467);
Wilson et al (1991) J. Exp. Med. 173:137-146; WO2003072036 (Claim 1; FIG. 1); Cross-references: MIM: 107266; NP_001762.1; NM_001771_1

Figure 15:
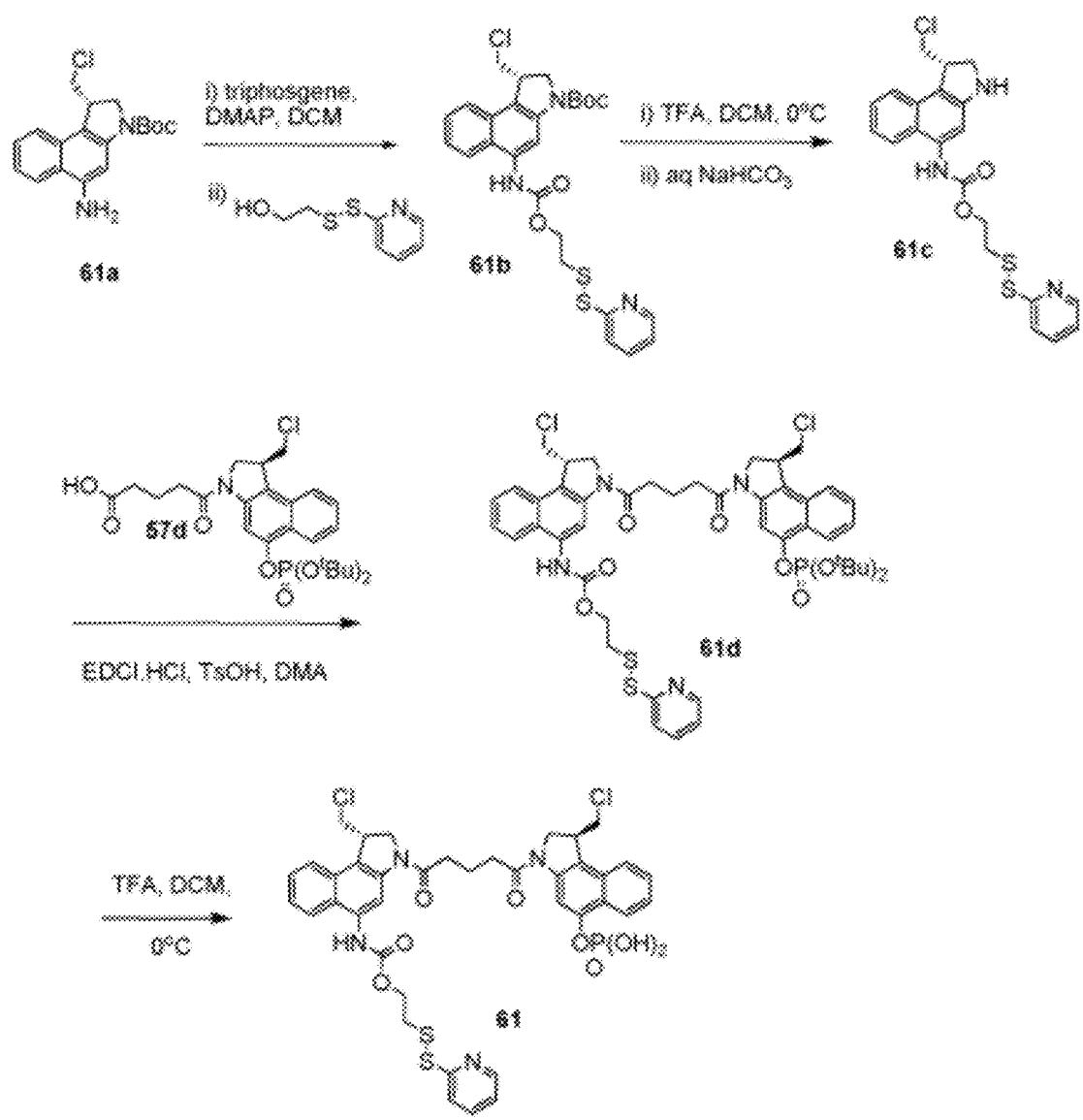
Figure 16:
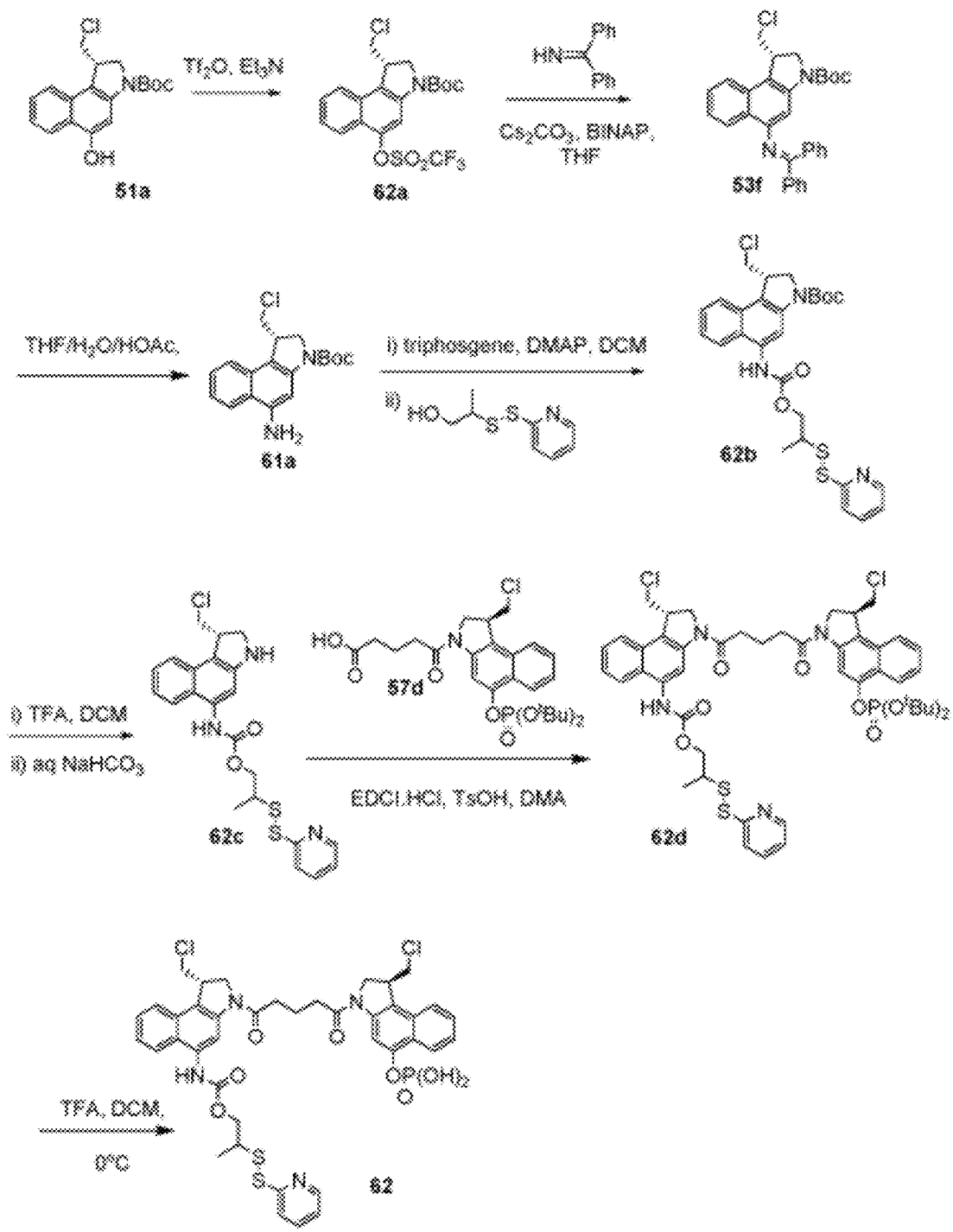

(28) CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10) WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11): 3457-3464;

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1)
WO2004040000; WO2004015426; US2003105292 (Example 2); U.S. Pat. No. 6,555,339 (Example 2); WO200261087 (FIG. 1); WO200157188 (Claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al (1992) Eur. J. Immunol. 22:2795-2799; Barella et al (1995) Biochem. J. 309:773-779;

(30) HLA-DOB (Beta subunit of MHC class II molecule (Ia antigen) that binds peptides and presents them to CD4+ T lymphocytes); 273 aa, pI: 6.56 MW: 30820 TM: 1 [P] Gene Chromosome: 6p21.3, Genbank accession No. NP_002111.1)
Tonnelle et al (1985) EMBO J. 4(11):2839-2847; Jonsson et al (1989) Immunogenetics 29(6):411-413; Beck et al (1992) J. Mol. Biol. 228:433-441; Strausberg et al (2002) Proc. Natl. Acad. Sci USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) Immunogenetics 30(1):66-68; Larhammar et al (1985) J. Biol. Chem. 260(26):14111-14119;

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa, pI: 7.63, MW: 47206 TM: 1 [P] Gene Chromosome: 17p13.3, Genbank accession No. NP_002552.2) Le et al (1997) FEBS Lett. 418(1-2):195-199; WO2004047749; WO2003072035 (claim 10); Touchman et al (2000) Genome Res. 10:165-173; WO200222660 (claim 20); WO2003093444 (claim 1); WO2003087768 (claim 1); WO2003029277 (page 82);

(32) CD72 (B-cell differentiation antigen CD72, Lyb-2) PROTEIN SEQUENCE Full maeaity . . . tafrfpd (1 . . . 359; 359 aa), pI: 8.66, MW: 40225 TM: 1 [P] Gene Chromosome: 9p13.3, Genbank accession No. NP_001773.1)
WO2004042346 (claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci USA 99:16899-16903;

(33) LY64 (Lymphocyte antigen 64 (RP 105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1)
US2002193567; WO9707198 (claim 11, pages 39-42); Miura et al (1996) Genomics 38(3):299-304; Miura et al (1998) Blood 92:2815-2822; WO2003083047; WO9744452 (claim 8, pages 57-61); WO200012130 (pages 24-26);

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1)
WO2003077836; WO200138490 (claim 6, FIG. 18E-1-18-E-2); Davis et al (2001) Proc. Natl. Acad. Sci USA 98(17): 9772-9777; WO2003089624 (claim 8); EP1347046 (claim 1); WO2003089624 (claim 7);

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P] Gene Chromosome: 1q21, Genbank accession No. Human: AF343662, AF343663, AF343664, AF343665, AF369794, AF397453, AK090423, AK090475, AL834187, AY358085; Mouse:AK089756, AY158090, AY506558; NP_112571.1
WO2003024392 (claim 2, FIG. 97); Nakayama et al (2000) Biochem. Biophys. Res. Commun. 277(1):124-127; WO2003077836; WO200138490 (claim 3, FIG. 18B-1-18B-2);

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436
WO2004074320 (SEQ ID NO 810); JP2004113151 (SEQ ID NOS 2, 4, 8); WO2003042661 (SEQ ID NO 580); WO2003009814 (SEQ ID NO 411); EP1295944 (pages 69-70); WO200230268 (page 329); WO200190304 (SEQ ID NO 2706); US2004249130; US2004022727; WO2004063355; US2004197325; US2003232350; US2004005563; US2003124579; Horie et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. October 15; 94(2):178-84;

(37) PMEL17 (silver homolog; SILV; D12S53E; PMEL17; (SI); (SIL); ME20; gp100) BC001414; BT007202; M32295; M77348; NM_006928; McGlinchey, R. P. et al (2009) Proc.

Natl. Acad. Sci. U.S.A. 106 (33), 13731-13736; Kummer, M. P. et al (2009) J. Biol. Chem. 284 (4), 2296-2306;
(38) TMEFF1 (transmembrane protein with EGF-like and two follistatin-like domains 1i Tomoregulin-1; H7365; C9orf2; C9ORF2; U19878; X83961) NM_080655; NM_003692; Harms, P. W. (2003) Genes Dev. 17 (21), 2624-2629; Gery, S. et al (2003) Oncogene 22 (18):2723-2727;
(39) GDNF-Ra1 (GDNF family receptor alpha 1; GFRA1; GDNFR; GDNFRA; RETL1; TRNR1; RET1L; GDNFR-alpha1; GFR-ALPHA-1; U95847; BC014962; NM_145793) NM_005264; Kim, M. H. et al (2009) Mol. Cell. Biol. 29 (8), 2264-2277; Treanor, J. J. et al (1996) Nature 382 (6586):80-83;
(40) Ly6E (lymphocyte antigen 6 complex, locus E; Ly67, RIG-E,SCA-2,TSA-1) NP_002337.1; NM_002346.2; de Nooij-van Dalen, A. G. et al (2003) Int. J. Cancer 103 (6), 768-774; Zammit, D. J. et al (2002) Mol. Cell. Biol. 22 (3):946-952;
(41) TMEM46 (shisa homolog 2 (*Xenopus laevis*); SHISA2) NP_001007539.1; NM_001007538.1; Furushima, K. et al (2007) Dev. Biol. 306 (2), 480-492; Clark, H. F. et al (2003) Genome Res. 13 (10):2265-2270;
(42) Ly6G6D (lymphocyte antigen 6 complex, locus G6D; Ly6-D, MEGT1) NP_067079.2; NM_021246.2; Mallya, M. et al (2002) Genomics 80 (1):113-123; Ribas, G. et al (1999) J. Immunol. 163 (1):278-287;
(43) LGR5 (leucine-rich repeat-containing G protein-coupled receptor 5; GPR49, GPR67) NP_003658.1; NM_003667.2; Salanti, G. et al (2009) Am. J. Epidemiol. 170 (5):537-545; Yamamoto, Y. et al (2003) Hepatology 37 (3):528-533;
(44) RET (ret proto-oncogene; MEN2A; HSCR1; MEN2B; MTC1; (PTC); CDHF12; Hs.168114; RET51; RET-ELE1) NP_066124.1; NM_020975.4; Tsukamoto, H. et al (2009) Cancer Sci. 100 (10):1895-1901; Narita, N. et al (2009) Oncogene 28 (34):3058-3068;
(45) LY6K (lymphocyte antigen 6 complex, locus K; LY6K; HSJ001348; FLJ35226) NP_059997.3; NM_017527.3; Ishikawa, N. et al (2007) Cancer Res. 67 (24):11601-11611; de Nooij-van Dalen, A. G. et al (2003) Int. J. Cancer 103 (6):768-774;
(46) GPR19 (G protein-coupled receptor 19; Mm.4787) NP_006134.1; NM_006143.2; Montpetit, A. and Sinnett, D. (1999) Hum. Genet. 105 (1-2): 162-164; O'Dowd, B. F. et al (1996) FEBS Lett. 394 (3):325-329;
(47) GPR54 (KISS1 receptor; KISS1R; GPR54; HOT7T175; AXOR12) NP_115940.2; NM_032551.4; Navenot, J. M. et al (2009) Mol. Pharmacol. 75 (6):1300-1306; Hata, K. et al (2009) Anticancer Res. 29 (2):617-623;
(48) ASPHD1 (aspartate beta-hydroxylase domain containing 1; LOC253982) NP_859069.2; NM_181718.3; Gerhard, D. S. et al (2004) Genome Res. 14 (10B):2121-2127;
(49) Tyrosinase (TYR; OCAIA; OCA1A; tyrosinase; SHEP3) NP_000363.1; NM_000372.4; Bishop, D. T. et al (2009) Nat. Genet. 41 (8):920-925; Nan, H. et al (2009) Int. J. Cancer 125 (4):909-917;
(50) TMEM118 (ring finger protein, transmembrane 2; RNFT2; FLJ14627) NP_001103373.1; NM_001109903.1; Clark, H. F. et al (2003) Genome Res. 13 (10):2265-2270; Scherer, S. E. et al (2006) Nature 440 (7082):346-351
(51) GPR172A (G protein-coupled receptor 172A; GPCR41; FLJ11856; D15Ertd747e) NP_078807.1; NM_024531.3; Ericsson, T. A. et al (2003) Proc. Natl. Acad. Sci. U.S.A. 100 (11):6759-6764; Takeda, S. et al (2002) FEBS Lett. 520 (1-3):97-101.

The parent antibody may also be a fusion protein comprising an albumin-binding peptide (ABP) sequence (Dennis et al. (2002) "Albumin Binding As A General Strategy For Improving The Pharmacokinetics Of Proteins" J Biol Chem. 277:35035-35043; WO 01/45746). Antibodies of the invention include fusion proteins with ABP sequences taught by: (i) Dennis et al (2002) J Biol Chem. 277:35035-35043 at Tables III and IV, page 35038; (ii) US 20040001827 at [0076]; and (iii) WO 01/45746 at pages 12-13, and all of which are incorporated herein by reference.

To prepare a cysteine engineered antibody by mutagenesis, DNA encoding an amino acid sequence variant of the starting polypeptide is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide. Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies. General guidance can be found in Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993.

Antibodies may be produced using recombinant methods and compositions, e.g., as described in U.S. Pat. No. 4,816, 567. In one embodiment, isolated nucleic acid encodes an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method comprises culturing a host cell comprising a nucleic acid encoding the antibody, as provided above, under conditions suitable for expression of the antibody, and optionally recovering the antibody from the host cell (or host cell culture medium).

For recombinant production, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody). Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B. K. C. Lo, ed., Humana Press, Totowa, N.J., 2003), pp. 245-254, describing expression of antibody fragments in *E. coli.*) After expression, the antibody may be isolated from the bacterial cell paste in a soluble fraction and can be further purified. In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006). Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts, such as those described in U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977); baby hamster kidney cells (BHK); mouse sertoli cells (TM4 cells as described, e.g., in Mather, *Biol. Reprod.* 23:243-251 (1980); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B.K.C. Lo, ed., Humana Press, Totowa, N.J.), pp. 255-268 (2003).

Site-directed mutagenesis is one method for preparing substitution variants, i.e. mutant proteins (Carter (1985) et al Nucleic Acids Res. 13:4431-4443; Ho et al (1989) Gene (Amst.) 77:51-59; and Kunkel et al (1987) Proc. Natl. Acad. Sci. USA 82:488). Starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA. Site-directed mutagenesis may be carried out within the gene expressing the protein to be mutagenized in an expression plasmid and the resulting plasmid may be sequenced to confirm the introduction of the desired cysteine replacement mutations (Liu et al (1998) J. Biol. Chem. 273:20252-20260). Site-directed mutagenesis protocols and formats are widely available, e.g. QuikChange® Multi Site-Directed Mutagenesis Kit (Stratagene, La Jolla, Calif.).

PCR mutagenesis is also suitable for making amino acid sequence variants of the starting polypeptide. See Higuchi, (1990) in PCR Protocols, pp. 177-183, Academic Press; Ito et al (1991) Gene 102:67-70; Bernhard et al (1994) Bioconjugate Chem., 5:126-132; and Vallette et al (1989) Nuc. Acids Res., 17:723-733. Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al (1985) Gene, 34:315-323. The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence. Mutant DNA containing the encoded cysteine replacements can be confirmed by DNA sequencing.

Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition; Zoller et al (1983) Methods Enzymol. 100:468-500; Zoller, M. J. and Smith, M. (1982) Nucl. Acids Res. 10:6487-6500).

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability.

CBI Dimer Drug Moiety

An antibody-drug conjugate compound of the invention comprises a CBI dimer drug moiety D. A CBI dimer drug moiety may be comprised of two CBI drug units or one CBI drug unit and one PBD drug unit.

The CBI dimer drug moiety D has the formula:

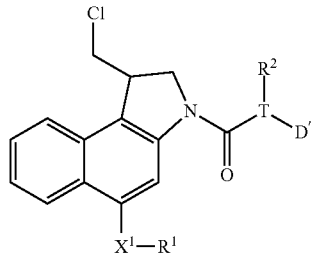

where

R[1] is selected from H, $P(O)_3H_2$, $C(O)NR^aR^b$;

R[2] is selected from H, $P(O)_3H_2$, $C(O)NR^aR^b$;

$R^a$ and $R^b$ are independently selected from H and $C_1$-$C_6$ alkyl optionally substituted with one or more F, or $R^a$ and $R^b$ form a five or six membered heterocyclyl group;

T is a tether group selected from $C_3$-$C_{12}$ alkylene, Y, ($C_1$-$C_6$ alkylene)-Y—($C_1$-$C_6$ alkylene), ($C_1$-$C_6$ alkylene)-Y—($C_1$-$C_6$ alkylene)-Y—($C_1$-$C_6$ alkylene), ($C_2$-$C_6$ alkenylene)-Y—($C_2$-$C_6$ alkenylene), and ($C_2$-$C_6$ alkynylene)-Y—($C_2$-$C_6$ alkynylene);

where Y is independently selected from O, S, $NR^1$, aryl, and heteroaryl;

where alkylene, alkenylene, aryl, and heteroaryl are independently and optionally substituted with F, OH, $O(C_1$-$C_6$ alkyl), $NH_2$, $NHCH_3$, $N(CH_3)_2$, $OP(O)_3H_2$, and $C_1$-$C_6$ alkyl, where alkyl is optionally substituted with one or more F;

or alkylene, alkenylene, aryl, and heteroaryl are independently and optionally substituted with a bond to L;

D' is a drug moiety selected from:

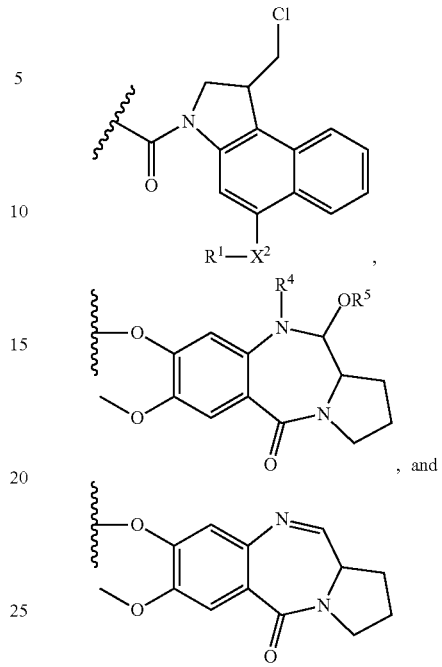

, and where the wavy line indicates the site of attachment to T;

$X^1$ and $X^2$ are independently selected from O and $NR^3$, where $R^3$ is selected from H and $C_1$-$C_6$ alkyl optionally substituted with one or more F;

$R^4$ is H, $CO_2R$, where R is $C_1$-$C_6$ alkyl or benzyl; and $R^5$ is H or $C_1$-$C_6$ alkyl.

In certain embodiments, Y is phenyl, pyridyl, 1-methyl-1H-benzo[d]imidazole, or [1,2,4]triazolo[1,5-a]pyridine.

CBI dimer drug moiety D compounds include those in Table 1 which are useful for preparing Linker-CBI drug intermediates of Table 3.

TABLE 1

CBI dimer drug moiety compounds

| No. | Structure | Name | MW |
|---|---|---|---|
| 51b | 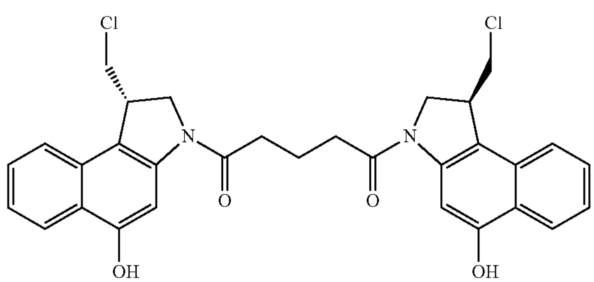 [SMILES: O=C(CCCC(=O)N1C[C@@H](CCl)c2c1cc(O)c1ccccc21)N1C[C@@H](CCl)c2c1cc(O)c1ccccc21] | 1,5-bis((S)-1-(chloromethyl)-5-hydroxy-1H-benzo[e]indol-3(2H)-yl)pentane-1,5-dione | 563.47 |
| 53j | 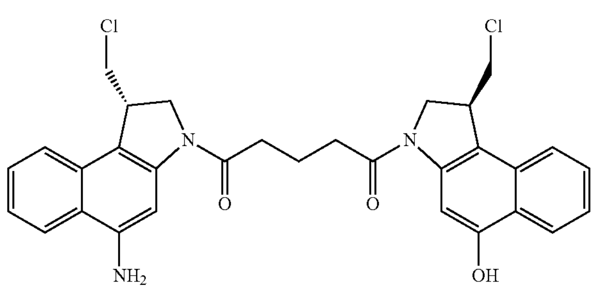 [SMILES: Nc1cc2c(c3ccccc13)[C@H](CCl)CN2C(=O)CCCC(=O)N1C[C@@H](CCl)c2c1cc(O)c1ccccc21] | 1-((S)-5-amino-1-(chloromethyl)-1H-benzo[e]indol-3(2H)-yl)-5-((S)-1-(chloromethyl)-5-hydroxy-1H-benzo[e]indol-3(2H)-yl)pentane-1,5-dione | 562.49 |

TABLE 1-continued

CBI dimer drug moiety compounds

| No. | Structure | Name | MW |
|---|---|---|---|
| 53p | 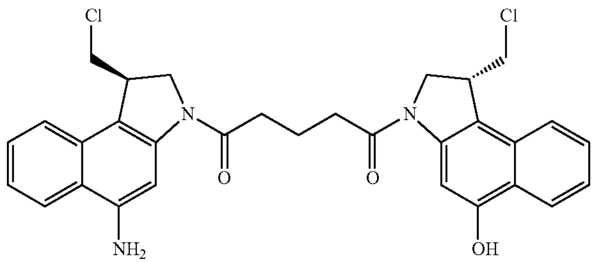 [SMILES: Nc1cc2c(c3ccccc13)[C@@H](CCl)CN2C(=O)CCCC(=O)N1C[C@H](CCl)c2c1cc(O)c1ccccc21] | 1-((R)-5-amino-1-(chloromethyl)-1H-benzo[e]indol-3(2H)-yl)-5-((R)-1-(chloromethyl)-5-hydroxy-1H-benzo[e]indol-3(2H)-yl)pentane-1,5-dione | 562.49 |
| 11 | (racemic) | 2,2'-azanediylbis(1-(1-(chloromethyl)-5-hydroxy-1H-benzo[e]indol-3(2H)-yl)ethanone)hydrochloride | 600.92 |
| 12 | (racemic) | 1,5-bis(1-(chloromethyl)-5-hydroxy-1H-benzo[e]indol-3(2H)-yl)pentane-1,5-dione | 563.47 |
| 13 | (racemic) | 1,7-bis(1-(chloromethyl)-5-hydroxy-1H-benzo[e]indol-3(2H)-yl)heptane-1,7-dione | 591.52 |
| 14 | 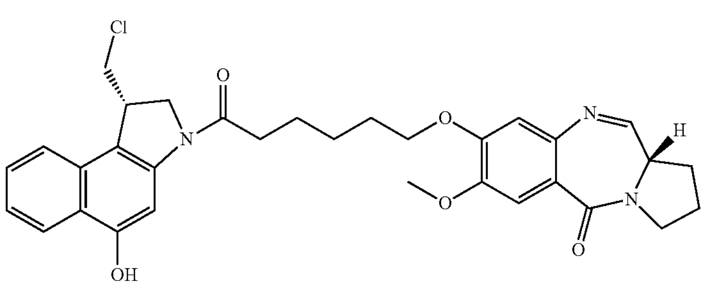 [SMILES: COc1cc2c(cc1OCCCCCC(=O)N1C[C@@H](CCl)c3c1cc(O)c1ccccc31)N=C[C@@H]1CCCN1C2=O] | (S)-8-(6-((S)-1-(chloromethyl)-5-hydroxy-1H-benzo[e]indol-3(2H)-yl)-6-oxohexyloxy)-7-methoxy-2,3-dihydro-1H-benzo[e]pyrrolo[1,2-a][1,4]diazepin-5(11aH)-one | 576.08 |

TABLE 1-continued

CBI dimer drug moiety compounds

| No. | Structure | Name | MW |
|---|---|---|---|
| 15 | 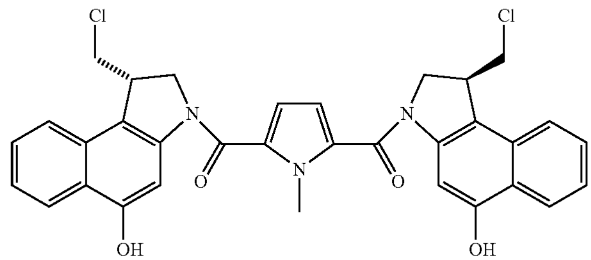 | (S)-(1-methyl-1H-pyrrole-2,5-diyl)bis(((S)-1-(chloromethyl)-5-hydroxy-1H-benzo[e]indol-3(2H)-yl)methanone) | 622.13 |
| 16 | 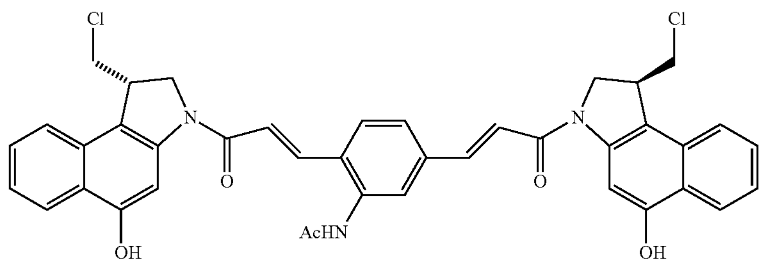 | N-(2,5-bis((E)-3-((S)-1-(chloromethyl)-5-hydroxy-1H-benzo[e]indol-3(2H)-yl)-3-oxoprop-1-enyl)phenyl)acetamide | 728.17 |
| 17 | 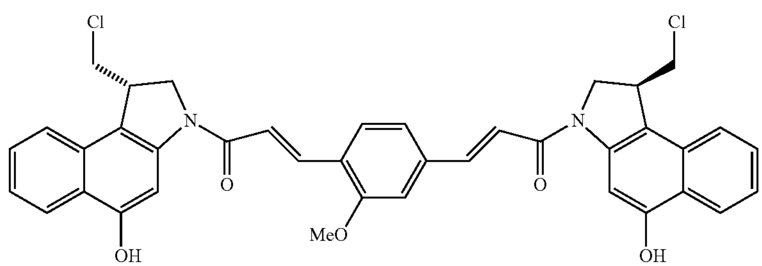 | (S,2E,2'E)-3,3'-(2-methoxy-1,4-phenylene)bis(1-((S)-1-(chloromethyl)-5-hydroxy-1H-benzo[e]indol-3(2H)-yl)prop-2-en-1-one) | 701.16 |
| 18 | 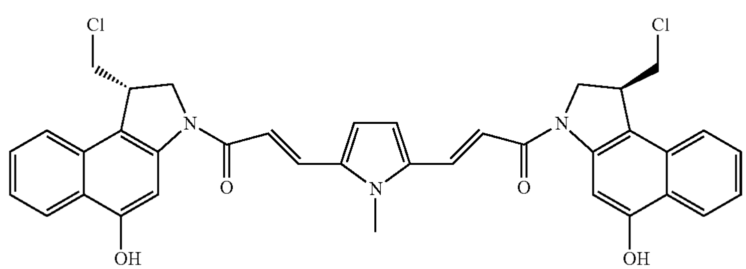 [SMILES: Cn1c(/C=C/C(=O)N2C[C@@H](CCl)c3c2cc(O)c2ccccc32)ccc1/C=C/C(=O)N1C[C@@H](CCl)c2c1cc(O)c1ccccc21] | (S,2E,2'E)-3,3'-(1-methyl-1H-pyrrole-2,5-diyl)bis(1-((S)-1-(chloromethyl)-5-hydroxy-1H-benzo[e]indol-3(2H)-yl)prop-2-en-1-one) | 650.16 |
| 19 | 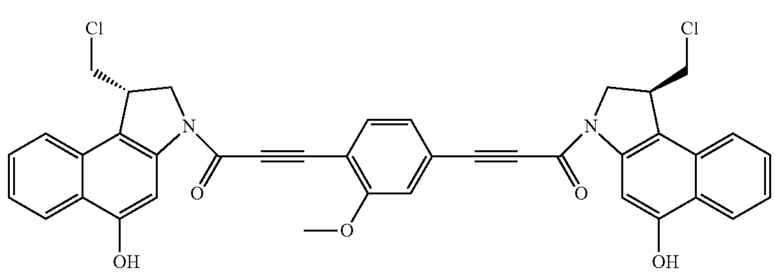 [SMILES: COc1cc(C#CC(=O)N2C[C@@H](CCl)c3c2cc(O)c2ccccc32)ccc1C#CC(=O)N1C[C@@H](CCl)c2c1cc(O)c1ccccc21] | (S)-3,3'-(2-methoxy-1,4-phenylene)bis(1-((S)-1-(chloromethyl)-5-hydroxy-1H-benzo[e]indol-3(2H)-yl)prop-2-yn-1-one) | 697.13 |

Tether reagents useful for preparing CBI dimer drug moiety D compounds include those in Table 2

TABLE 2

Tether reagents

| No. | Structure | Name | MW |
|---|---|---|---|
| 21 | 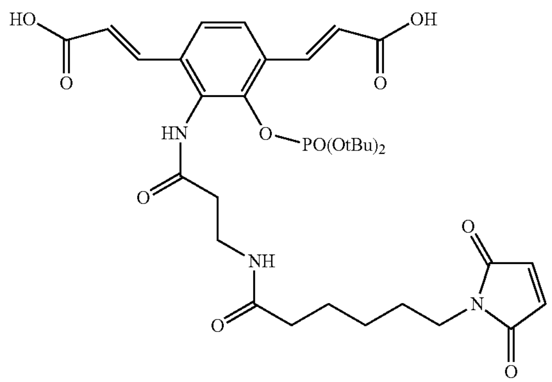 | (2E,2'E)-3,3'-(2-(di-tert-butoxyphosphoryloxy)-3-(3-(6-(2,5-dioxo-2,5-dihydro-1H-pyrrol-1-yl)hexanamido)propanamido)-1,4-phenylene)diacrylic acid | 705.69 |
| 22 | 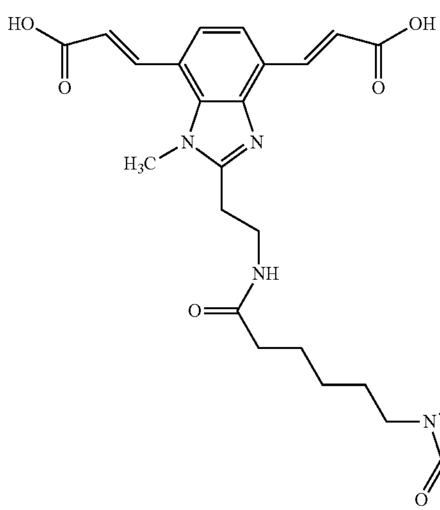 | (2E,2'E)-3,3'-(2-(2-(6-(2,5-dioxo-2,5-dihydro-1H-pyrrol-1-yl)hexanamido)ethyl)-1-methyl-1H-benzo[d]imidazole-4,7-diyl)diacrylic acid | 508.52 |
| 23 | 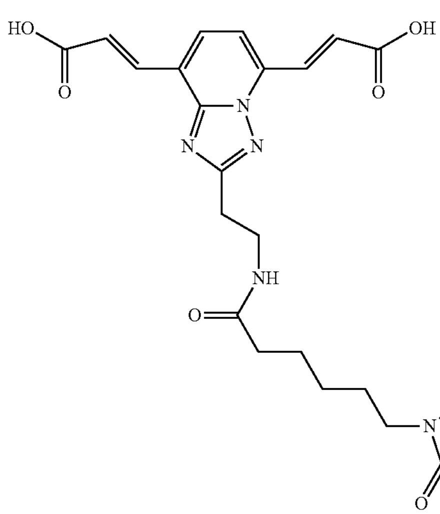 | (2E,2'E)-3,3'-(2-(2-(6-(2,5-dioxo-2,5-dihydro-1H-pyrrol-1-yl)hexanamido)ethyl)-[1,2,4]triazolo[1,5-a]pyridine-5,8-diyl)diacrylic acid | 495.48 |

TABLE 2-continued

Tether reagents

| No. | Structure | Name | MW |
|---|---|---|---|
| 24 | 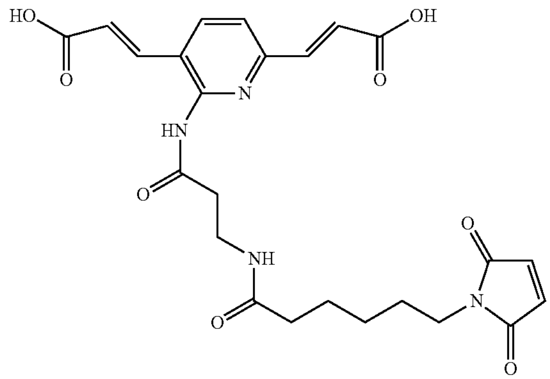 [SMILES: O=C(O)/C=C/c1ccc(/C=C/C(=O)O)c(NC(=O)CCNC(=O)CCCCCN2C(=O)C=CC2=O)n1] | (2E,2'E)-3,3'-(6-(3-(6-(2,5-dioxo-2,5-dihydro-1H-pyrrol-1-yl)hexanamido)propanamido)pyridine-2,5-diyl)diacrylic acid | 498.49 |
| 25 | 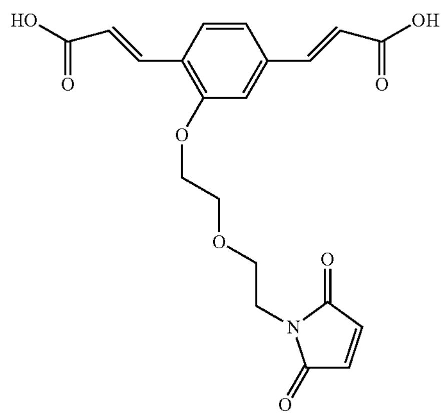 [SMILES: O=C(O)/C=C/c1ccc(/C=C/C(=O)O)c(OCCOCCN2C(=O)C=CC2=O)c1] | (2E,2'E)-3,3'-(2-(2-(2-(2,5-dioxo-2,5-dihydro-1H-pyrrol-1-yl)ethoxy)ethoxy)-1,4-phenylene)diacrylic acid | 401.37 |
| 26 | 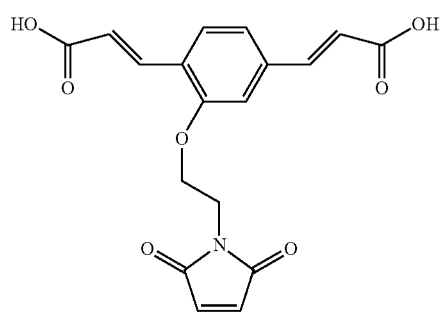 [SMILES: O=C(O)/C=C/c1ccc(/C=C/C(=O)O)c(OCCN2C(=O)C=CC2=O)c1] | (2E,2'E)-3,3'-(2-(2-(2,5-dioxo-2,5-dihydro-1H-pyrrol-1-yl)ethoxy)-1,4-phenylene)diacrylic acid | 357.08 |
| 27 | 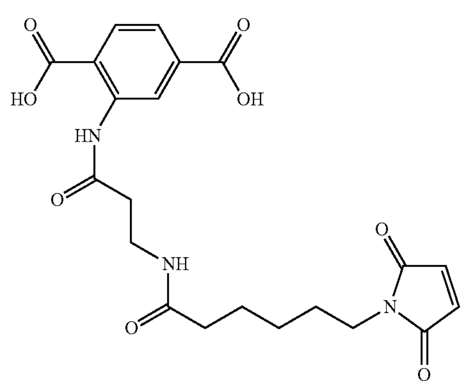 [SMILES: O=C(CCCCCN1C(=O)C=CC1=O)NCCC(=O)Nc1cc(C(=O)O)ccc1C(=O)O] | 2-(3-(6-(2,5-dioxo-2,5-dihydro-1H-pyrrol-1-yl)hexanamido)propanamido)terephthalic acid | 445.42 |

TABLE 2-continued

Tether reagents

| No. | Structure | Name | MW |
|---|---|---|---|
| 28 | 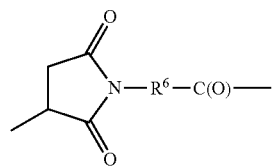 | 3,3'-(2-(3-(6-(2,5-dioxo-2,5-dihydro-1H-pyrrol-1-yl)hexanamido)propanamido)-1,4-phenylene)dipropiolic acid | 493.47 |

Linkers

An antibody-drug conjugate (ADC) compound of the invention comprises a linker L having the formula:

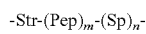

-Str-(Pep)$_m$-(Sp)$_n$- where Str is a stretcher unit covalently attached to the antibody; Pep is an optional peptide unit of two to twelve amino acid residues, Sp is an optional spacer unit covalently attached to a dimer drug moiety, and m and n are independently selected from 0 and 1.

In an exemplary embodiment, Str has the 1,3-disubstituted, pyrrolidine-2,5-dione (succinimide) formula:

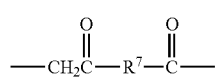

wherein $R^6$ is selected from the group consisting of $C_1$-$C_{10}$ alkylene, $C_3$-$C_8$ carbocyclyl, O—($C_1$-$C_8$ alkyl), arylene, $C_1$-$C_{10}$ alkylene-arylene, arylene-$C_1$-$C_{10}$ alkylene, $C_1$-$C_{10}$ alkylene-($C_3$-$C_8$ carbocyclyl), ($C_3$-$C_8$ carbocyclyl)-$C_1$-$C_{10}$ alkylene, $C_3$-$C_8$ heterocyclyl, $C_1$-$C_{10}$ alkylene-($C_3$-$C_8$ heterocyclyl), ($C_3$-$C_8$ heterocyclyl)-$C_1$-$C_{10}$ alkylene, $C_1$-$C_{10}$ alkylene-C(O)N($R^8$)—$C_2$-$C_6$ alkylene-N($R^8$), N($R^8$)—($C_2$-$C_6$ alkylene), and $(CH_2CH_2O)_r$—$CH_2$; where $R^8$ is H or $C_1$-$C_6$ alkyl, and r is an integer ranging from 1 to 10.

The 1,3-disubstituted, pyrrolidine-2,5-dione embodiments of the Str stretcher unit may be formed from conjugation of cysteine thiols of antibodies with the maleimide group of linker-drug intermediates, such as those in Table 4.

In another exemplary embodiment, Str has the formula:

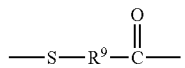

wherein $R^7$ is selected from $C_1$-$C_{10}$ alkylene, $C_1$-$C_{10}$ alkylene-O, N($R^8$)—($C_2$-$C_6$ alkylene)-N($R^8$), N($R^8$)—($C_2$-$C_6$ alkylene), and $(CH_2CH_2O)_r$—$CH_2$; where $R^8$ is H or $C_1$-$C_6$ alkyl, and r is an integer ranging from 1 to 10.

In another exemplary embodiment, Str has the formula:

—S—$R^9$—C(O)— wherein $R^9$ is selected from $C_1$-$C_{10}$ alkylene, $C_1$-$C_{10}$ alkylene-O, ($C_2$-$C_6$ alkylene)-N($R^8$), and $(CH_2CH_2O)_r$—$CH_2$; where $R^8$ is H or $C_1$-$C_6$ alkyl, and r is an integer ranging from 1 to 10.

In another exemplary embodiment, L forms a disulfide bond with a cysteine amino acid of the antibody, and $R^9$ is $C_2$-$C_6$ alkylene-O where alkylene is optionally substituted with F, OH, O($C_1$-$C_6$ alkyl), $NH_2$, $NHCH_3$, $N(CH_3)_2$, OP(O)$_3H_2$, and $C_1$-$C_6$ alkyl, where alkyl is optionally substituted with one or more F.

Linker reagents and linker-drug intermediates may have a peptide unit of two to twelve or more amino acid residues.

In an exemplary embodiment, m is 1 and Pep comprises two to twelve amino acid residues independently selected from glycine, alanine, phenylalanine, lysine, arginine, valine, and citrulline.

In an exemplary embodiment, Pep is valine-citrulline.

Peptide-linker reagents were prepared as described (WO 2012113847; U.S. Pat. Nos. 7,659,241; 7,498,298; US 2009/0111756; US 2009/0018086; U.S. Pat. No. 6,214,345; Dubowchik et al (2002) Bioconjugate Chem. 13(4):855-869).

In an exemplary embodiment, Sp comprises para-aminobenzyl or para-aminobenzyloxycarbonyl.

Table 3 shows exemplary Linker reagents useful for preparing Linker-CBI drug intermediates of Table 4.

45
46

TABLE 3

Peptide-linker reagents

| No. | Structure | Name |
|---|---|---|
| 41 | 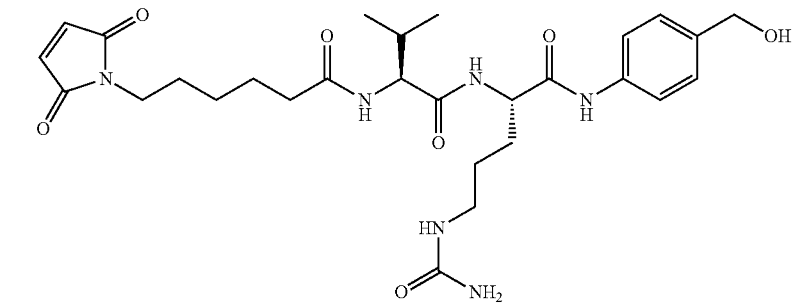 [SMILES: CC(C)[C@H](NC(=O)CCCCCN1C(=O)C=CC1=O)C(=O)N[C@@H](CCCNC(N)=O)C(=O)Nc1ccc(CO)cc1] | 6-(2,5-dioxo-2,5-dihydro-1H-pyrrol-1-yl)-N-((S)-1-((S)-1-(4-(hydroxymethyl)phenylamino)-1-oxo-5-ureidopentan-2-ylamino)-3-methyl-1-oxobutan-2-yl)hexanamide |
| 42 | 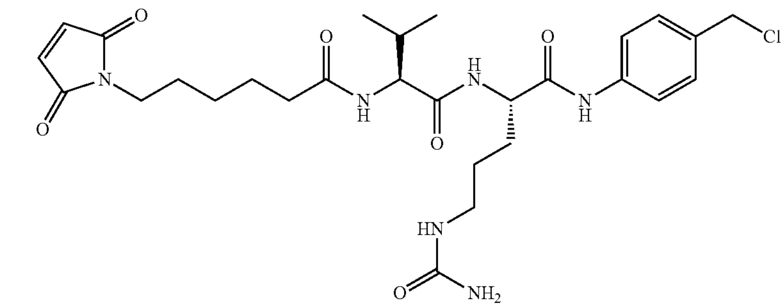 [SMILES: CC(C)[C@H](NC(=O)CCCCCN1C(=O)C=CC1=O)C(=O)N[C@@H](CCCNC(N)=O)C(=O)Nc1ccc(CCl)cc1] | N-((S)-1-((S)-1-(4-(chloromethyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide |
| 43 | 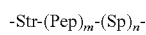 | 4-((S)-2-((S)-2-(6-(2,5-dioxo-2,5-dihydro-1H-pyrrol-1-yl)hexanamido)-3-methylbutanamido)-5-ureidopentanamido)benzyl 4-nitrophenyl carbonate |

Linker-Drug Intermediates Useful for ADC

Linker-drug intermediates useful for conjugation to antibodies to prepare antibody-drug conjugates have the formula:

X-L-D wherein:

X is a reactive functional group selected from maleimide, thiol, amino, bromide, bromoacetamido, iodoacetamido, p-toluenesulfonate, iodide, hydroxyl, carboxyl, pyridyl disulfide, and N-hydroxysuccinimide;

L is a linker having the formula:

-Str-(Pep)$_m$-(Sp)$_n$- where Str is a stretcher unit covalently attached to reactive functional group X; Pep is an optional peptide unit of two to twelve amino acid residues, Sp is an optional spacer unit covalently attached to a dimer drug moiety, and m and n are independently selected from 0 and 1;

D is the dimer drug moiety having the formula:

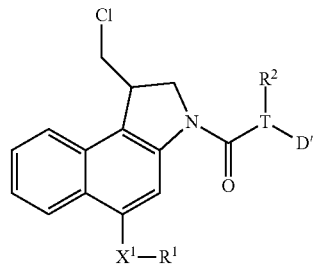

where $R^1$ is selected from H, $P(O)_3H_2$, $C(O)NR^aR^b$, or a bond to L;

$R^2$ is selected from H, $P(O)_3H_2$, $C(O)NR^aR^b$, or a bond to L;

$R^a$ and $R^b$ are independently selected from H and $C_1$-$C_6$ alkyl optionally substituted with one or more F, or $R^a$ and $R^b$ form a five or six membered heterocyclyl group;

T is a tether group selected from $C_3$-$C_{12}$ alkylene, Y, ($C_1$-$C_6$ alkylene)-Y—($C_1$-$C_6$ alkylene), ($C_1$-$C_6$ alkylene)-

Y—($C_1$-$C_6$ alkylene)-Y—($C_1$-$C_6$ alkylene), ($C_2$-$C_6$ alkenylene)-Y—($C_2$-$C_6$ alkenylene), and ($C_2$-$C_6$ alkynylene)-Y—($C_2$-$C_6$ alkynylene);

where Y is independently selected from O, S, $NR^1$, aryl, and heteroaryl;

where alkylene, alkenylene, aryl, and heteroaryl are independently and optionally substituted with F, OH, O($C_1$-$C_6$ alkyl), $NH_2$, $NHCH_3$, $N(CH_3)_2$, $OP(O)_3H_2$, and $C_1$-$C_6$ alkyl, where alkyl is optionally substituted with one or more F;

or alkylene, alkenylene, aryl, and heteroaryl are independently and optionally substituted with a bond to L;

D' is a drug moiety selected from:

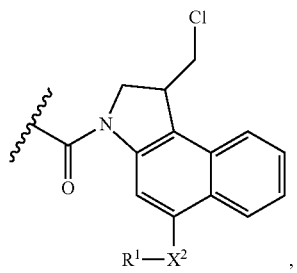

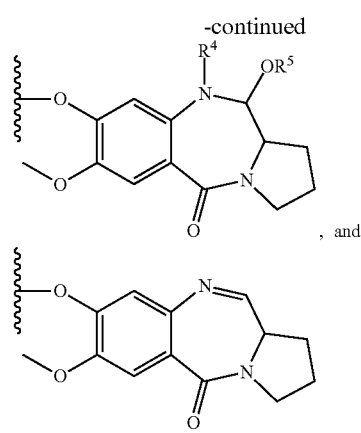

where the wavy line indicates the site of attachment to T;
$X^1$ and $X^2$ are independently selected from O and $NR^3$, where $R^3$ is selected from H and $C_1$-$C_6$ alkyl optionally substituted with one or more F;
$R^4$ is H, $CO_2R$, or a bond to L, where R is $C_1$-$C_6$ alkyl or benzyl; and
$R^5$ is H or $C_1$-$C_6$ alkyl.

Linker-drug intermediates of Table 4 were prepared by coupling a CBI dimer drug moiety with a linker reagent, as exemplified in Examples 1-18 and FIGS. 1-24.

TABLE 4

Linker-CBI drug intermediates

| No. | Structure | Name |
|---|---|---|
| 51 | 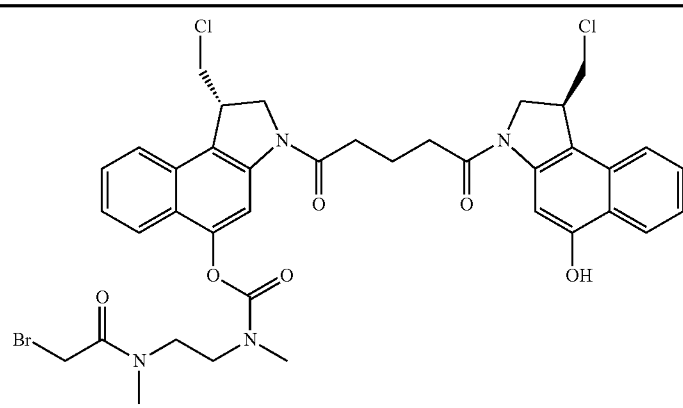 | (S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yl 2-(2-bromo-N-methylacetamido)ethyl(methyl)carbamate |
| 52 | 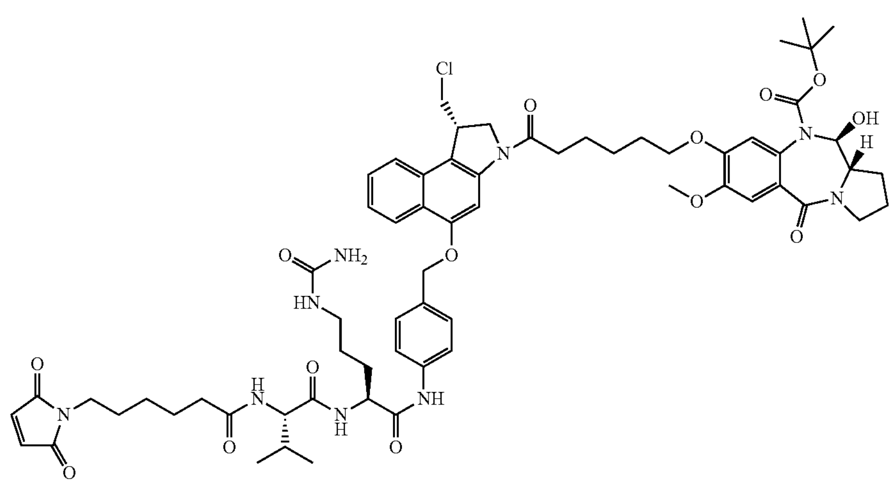 [SMILES: COc1cc2c(cc1OCCCCCC(=O)N1C[C@@H](CCl)c3c1cc(OCc1ccc(NC(=O)[C@H](CCCNC(N)=O)NC(=O)[C@@H](NC(=O)CCCCCN4C(=O)C=CC4=O)C(C)C)cc1)c1ccccc31)N(C(=O)OC(C)(C)C)[C@@H](O)[C@@H]1CCCN1C2=O] | (11S,11aS)-tert-butyl 8-(6-((S)-1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate |

TABLE 4-continued

Linker-CBI drug intermediates

| No. | Structure | Name |
| --- | --- | --- |
| 53 | 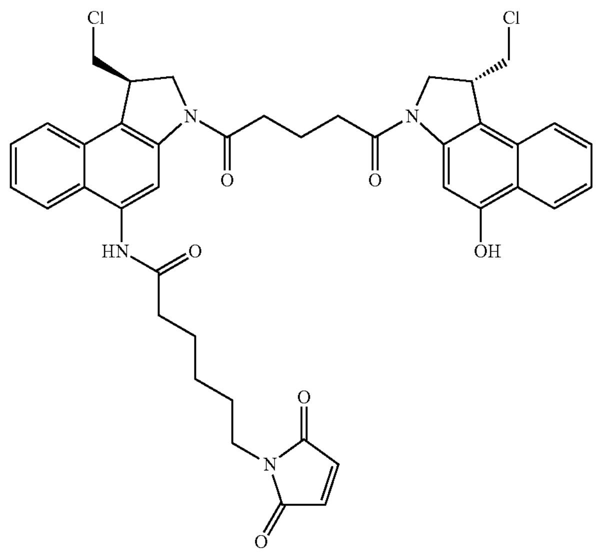 [SMILES: O=C(CCCCCN1C(=O)C=CC1=O)Nc1cc2c(c3ccccc13)[C@@H](CCl)CN2C(=O)CCCC(=O)N1C[C@H](CCl)c2c1cc(O)c1ccccc21] | N-((R)-1-(chloromethyl)-3-(5-((R)-1-(chloromethyl)-5-hydroxy-1H-benzo[e]indol-3(2H)-yl)-5-oxopentanoyl)-2,3-dihydro-1H-benzo[e]indol-5-yl)-6-(2,5-dioxo-2,5-dihydro-1H-pyrrol-1-yl)hexanamide |
| 54 | 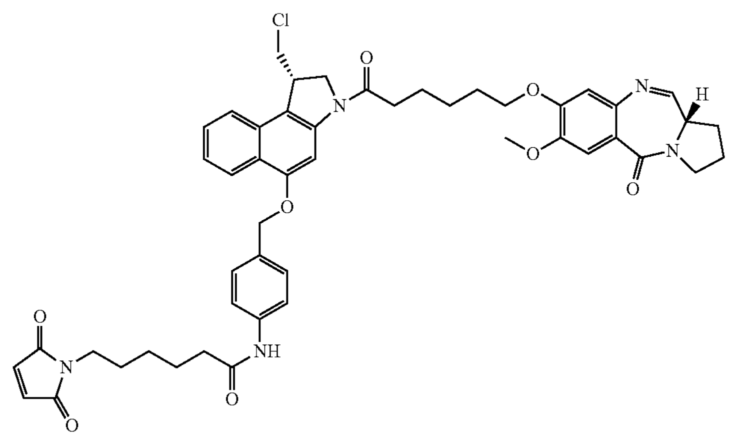 [SMILES: COc1cc2c(cc1OCCCCCC(=O)N1C[C@@H](CCl)c3c1cc(OCc1ccc(NC(=O)CCCCCN4C(=O)C=CC4=O)cc1)c1ccccc31)N=C[C@@H]1CCCN1C2=O] | N-(4-(((S)-1-(chloromethyl)-3-(6-((S)-7-methoxy-5-oxo-2,3,5,11a-tetrahydro-1H-benzo[e]pyrrolo[1,2-a][1,4]diazepin-8-yloxy)hexanoyl)-2,3-dihydro-1H-benzo[e]indol-5-yloxy)methyl)phenyl)-6-(2,5-dioxo-2,5-dihydro-1H-pyrrol-1-yl)hexanamide |
| 55 | 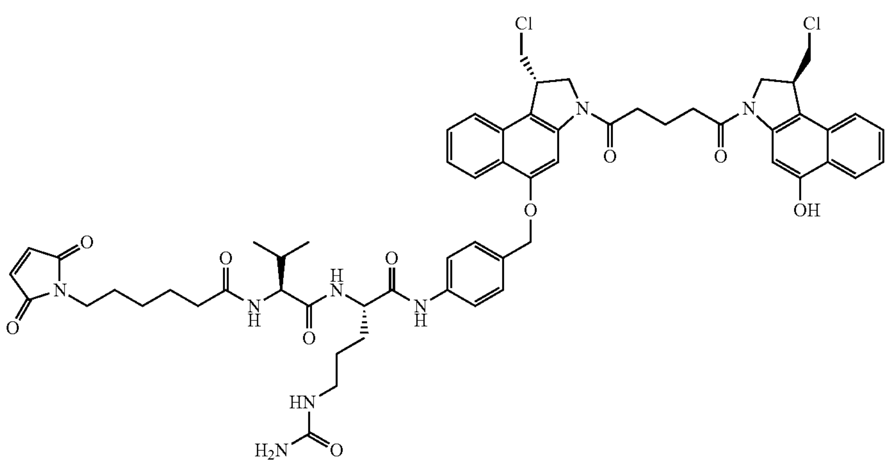 [SMILES: CC(C)[C@H](NC(=O)CCCCCN1C(=O)C=CC1=O)C(=O)N[C@@H](CCCNC(N)=O)C(=O)Nc1ccc(COc2cc3c(c4ccccc24)[C@H](CCl)CN3C(=O)CCCC(=O)N2C[C@@H](CCl)c3c2cc(O)c2ccccc32)cc1] | N-((S)-1-((S)-1-(4-(((S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yloxy)methyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide |

TABLE 4-continued

Linker-CBI drug intermediates

| No. | Structure | Name |
|---|---|---|
| 56 | 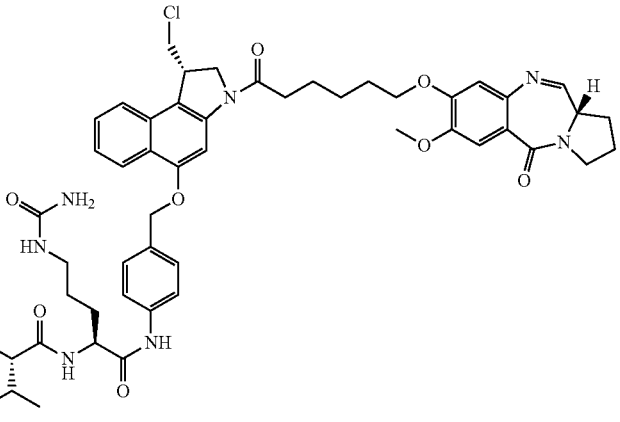 | N-((S)-1-((S)-1-(4-(((S)-1-(chloromethyl)-3-(6-((S)-7-methoxy-5-oxo-2,3,5,11a-tetrahydro-1H-benzo[e]pyrrolo[1,2-a][1,4]diazepin-8-yloxy)hexanoyl)-2,3-dihydro-1H-benzo[e]indol-5-yloxy)methyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide |
| 57 | 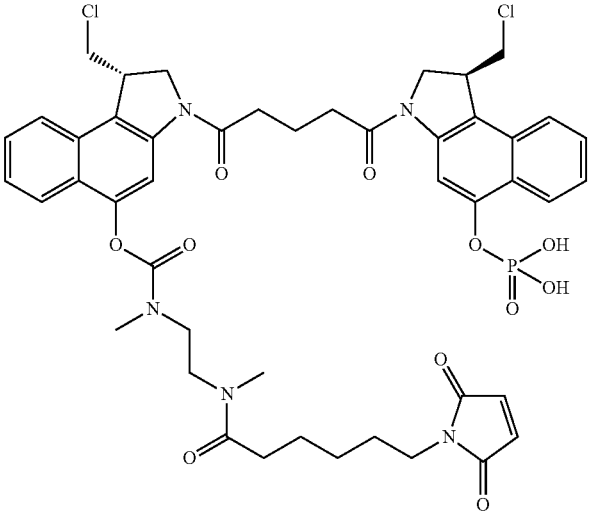 [SMILES: CN(CCN(C)C(=O)Oc1cc2c(c3ccccc13)[C@H](CCl)CN2C(=O)CCCC(=O)N1C[C@@H](CCl)c2c1cc(OP(=O)(O)O)c1ccccc21)C(=O)CCCCCN1C(=O)C=CC1=O] | (S)-1-(chloromethyl)-3-(5-((S)-1-(chloromethyl)-5-(phosphonooxy)-1H-benzo[e]indol-3(2H)-yl)-5-oxopentanoyl)-2,3-dihydro-1H-benzo[e]indol-5-yl 2-(6-(2,5-dioxo-2,5-dihydro-1H-pyrrol-1-yl)-N-methylhexanamido)ethyl(methyl)carbamate |
| 58 | 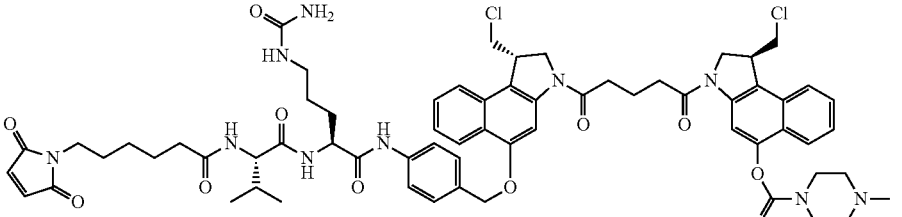 | (S)-1-(chloromethyl)-3-(5-((S)-1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-1H-benzo[e]indol-3(2H)-yl)-5-oxopentanoyl)-2,3-dihydro-1H-benzo[e]indol-5-yl 4-methylpiperazine-1-carboxylate |

TABLE 4-continued

Linker-CBI drug intermediates

| No. | Structure | Name |
|---|---|---|
| 59 | 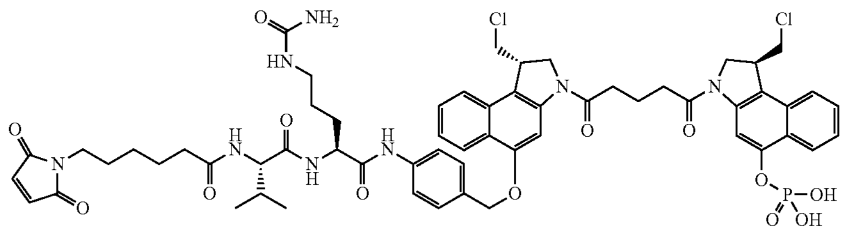 [SMILES: CC(C)[C@H](NC(=O)CCCCCN1C(=O)C=CC1=O)C(=O)N[C@@H](CCCNC(N)=O)C(=O)Nc1ccc(COc2cc3c(c4ccccc24)[C@H](CCl)CN3C(=O)CCCC(=O)N2C[C@@H](CCl)c3c2cc(OP(=O)(O)O)c2ccccc32)cc1] | (S)-1-(chloromethyl)-3-(5-((S)-1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-1H-benzo[e]indol-3(2H)-yl)-5-oxopentanoyl)-2,3-dihydro-1H-benzo[e]indol-5-yl dihydrogen phosphate |
| 60 | 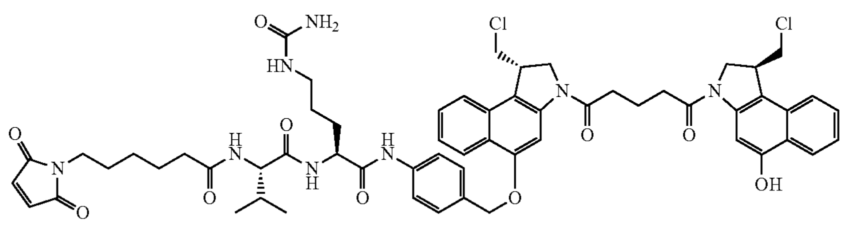 [SMILES: CC(C)[C@H](NC(=O)CCCCCN1C(=O)C=CC1=O)C(=O)N[C@@H](CCCNC(N)=O)C(=O)Nc1ccc(COc2cc3c(c4ccccc24)[C@H](CCl)CN3C(=O)CCCC(=O)N2C[C@@H](CCl)c3c2cc(O)c2ccccc32)cc1] | N-((S)-1-((S)-1-(4-(((S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yloxy)methyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide |
| 61 | 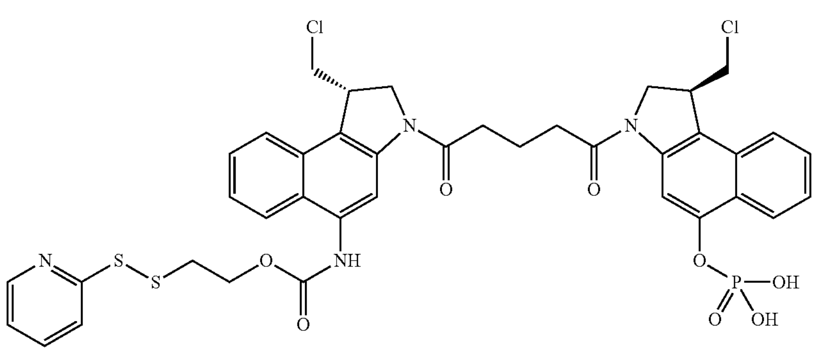 [SMILES: O=C(Nc1cc2c(c3ccccc13)[C@H](CCl)CN2C(=O)CCCC(=O)N1C[C@@H](CCl)c2c1cc(OP(=O)(O)O)c1ccccc21)OCCSSc1ccccn1] | 2-(pyridin-2-yldisulfanyl)ethyl (S)-1-(chloromethyl)-3-(5-((S)-1-(chloromethyl)-5-(phosphonooxy)-1H-benzo[e]indol-3(2H)-yl)-5-oxopentanoyl)-2,3-dihydro-1H-benzo[e]indol-5-ylcarbamate |

TABLE 4-continued

Linker-CBI drug intermediates

| No. | Structure | Name |
|---|---|---|
| 62 | 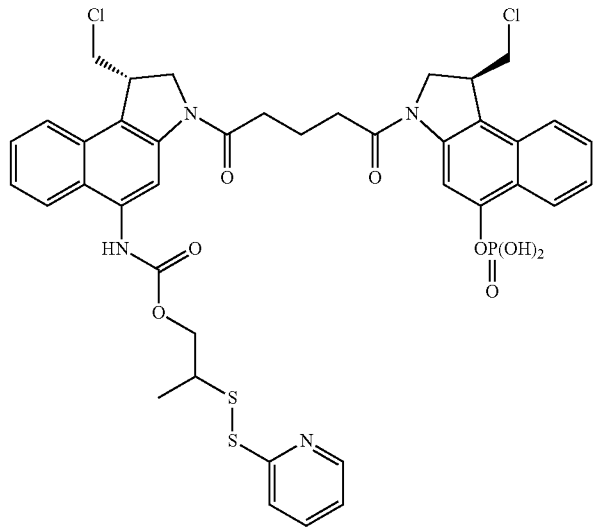 | 2-(pyridin-2-yldisulfanyl)propyl (S)-1-(chloromethyl)-3-(5-((S)-1-(chloromethyl)-5-(phosphonooxy)-1H-benzo[e]indol-3(2H)-yl)-5-oxopentanoyl)-2,3-dihydro-1H-benzo[e]indol-5-ylcarbamate |
| 63 | 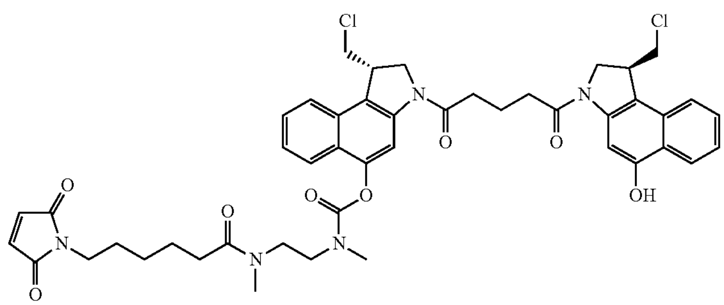 [SMILES: CN(CCN(C)C(=O)Oc1cc2c(c3ccccc13)[C@H](CCl)CN2C(=O)CCCC(=O)N1C[C@@H](CCl)c2c1cc(O)c1ccccc21)C(=O)CCCCCN1C(=O)C=CC1=O] | (S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yl 2-(6-(2,5-dioxo-2,5-dihydro-1H-pyrrol-1-yl)-N-methylhexanamido)ethyl(methyl)carbamate |
| 64 | 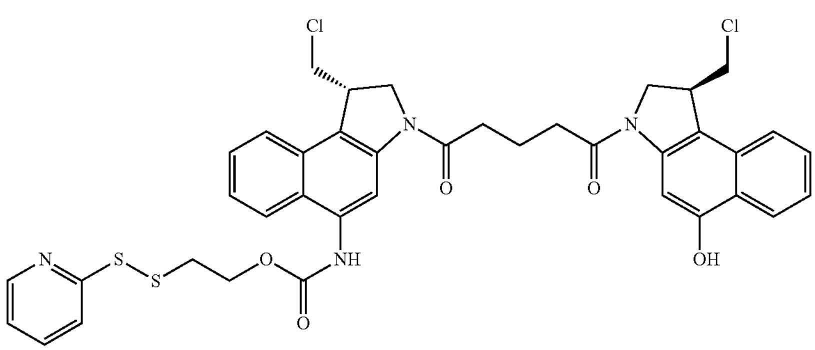 [SMILES: O=C(Nc1cc2c(c3ccccc13)[C@H](CCl)CN2C(=O)CCCC(=O)N1C[C@@H](CCl)c2c1cc(O)c1ccccc21)OCCSSc1ccccn1] | 2-(pyridin-2-yldisulfanyl)ethyl (S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-ylcarbamate |

TABLE 4-continued

Linker-CBI drug intermediates

| No. | Structure | Name |
|---|---|---|
| 65 | 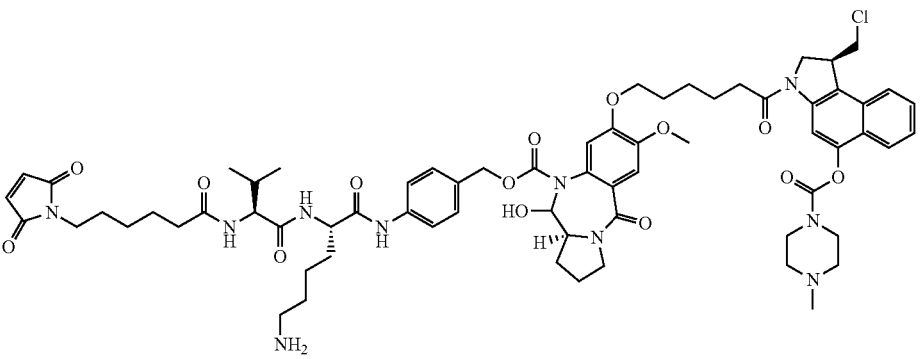 [SMILES: COc1cc2c(cc1OCCCCCC(=O)N1C[C@@H](CCl)c3c1cc(OC(=O)N1CCN(C)CC1)c1ccccc31)N(C(=O)OCc1ccc(NC(=O)[C@H](CCCCN)NC(=O)[C@@H](NC(=O)CCCCCN3C(=O)C=CC3=O)C(C)C)cc1)C(O)[C@@H]1CCCN1C2=O] | (11aS)-4-((S)-6-amino-2-((S)-2-(6-(2,5-dioxo-2,5-dihydro-1H-pyrrol-1-yl)hexanamido)-3-methylbutanamido)hexanamido)benzyl 8-(6-((S)-1-(chloromethyl)-5-(4-methylpiperazine-1-carbonyloxy)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate |
| 66 | 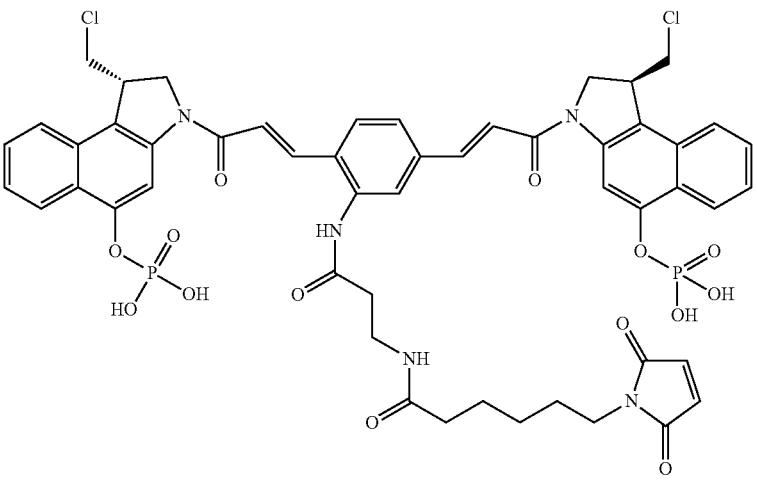 [SMILES: O=C(CCCCCN1C(=O)C=CC1=O)NCCC(=O)Nc1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21] | N-(3-(2,5-bis((E)-3-((S)-1-(chloromethyl)-5-phosphonoxy-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide |
| 67 | 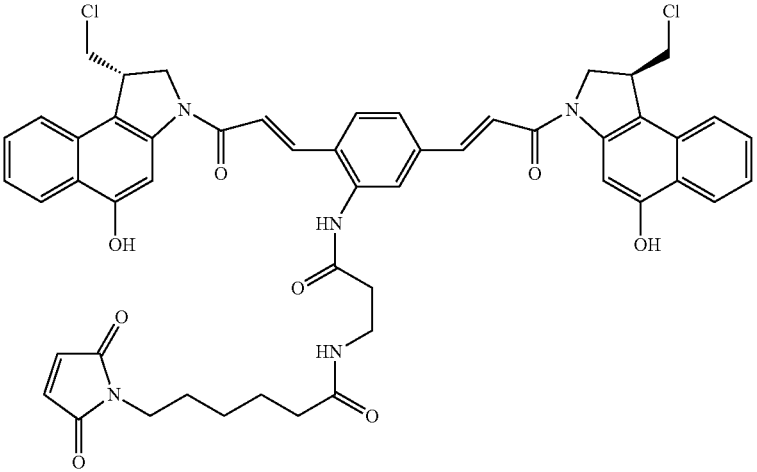 [SMILES: O=C(CCCCCN1C(=O)C=CC1=O)NCCC(=O)Nc1cc(/C=C/C(=O)N2C[C@@H](CCl)c3c2cc(O)c2ccccc32)ccc1/C=C/C(=O)N1C[C@@H](CCl)c2c1cc(O)c1ccccc21] | N-(3-(2,5-bis((E)-3-((S)-1-(chloromethyl)-5-hydroxy-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide |

TABLE 4-continued

Linker-CBI drug intermediates

| No. | Structure | Name |
|---|---|---|
| 68 | 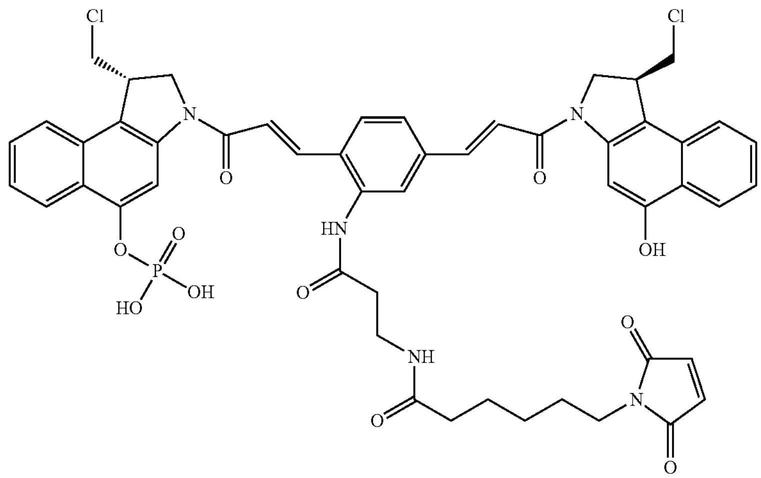 [SMILES: O=C(CCCCCN1C(=O)C=CC1=O)NCCC(=O)Nc1cc(/C=C/C(=O)N2C[C@@H](CCl)c3c2cc(O)c2ccccc32)ccc1/C=C/C(=O)N1C[C@@H](CCl)c2c1cc(OP(=O)(O)O)c1ccccc21] | (S)-1-(chloromethyl)-3-((E)-3-(4-((E)-3-((S)-1-(chloromethyl)-5-hydroxy-1H-benzo[e]indol-3(2H)-yl)-3-oxoprop-1-enyl)-2-(3-(6-(2,5-dioxo-2,5-dihydro-1H-pyrrol-1-yl)hexanamido)propanamido)phenyl)acryloyl)-2,3-dihydro-1H-benzo[e]indol-5-yl dihydrogen phosphate |
| 69 | 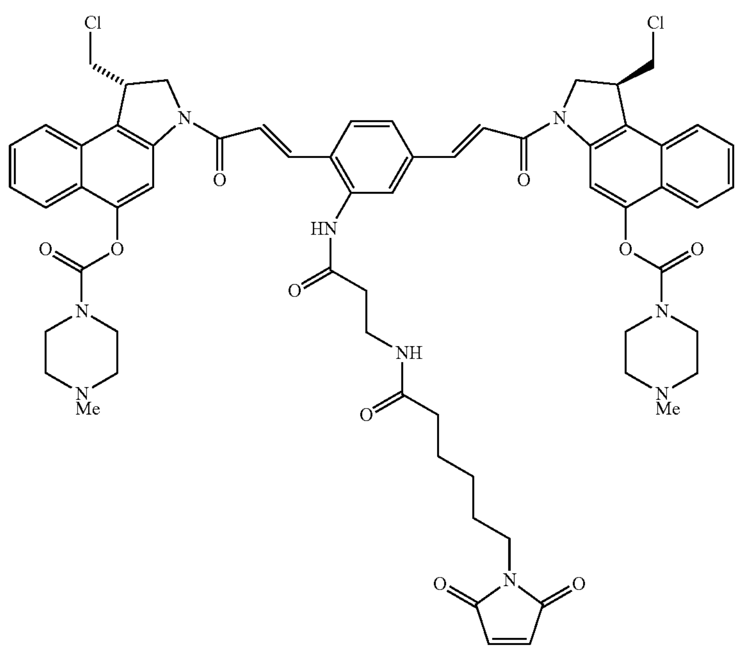 | N-(3-(2,5-bis((E)-3-((S)-1-(chloromethyl)-5-(4-methylpiperazine-1-carbonyloxy)-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide |

TABLE 4-continued

Linker-CBI drug intermediates

| No. | Structure | Name |
|---|---|---|
| 70 | 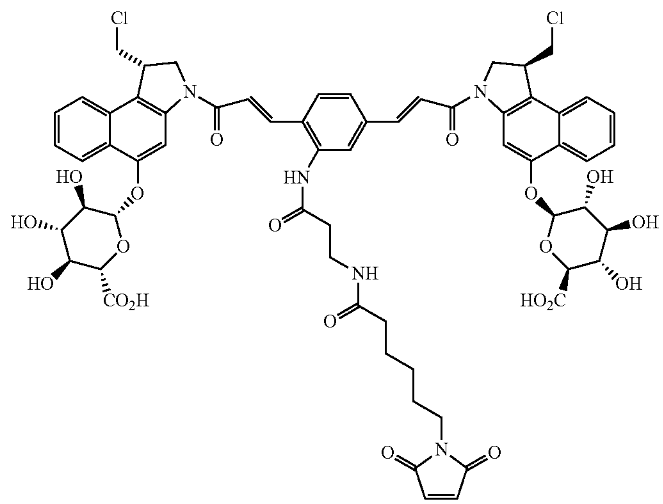 | N-(3-(2,5-bis((E)-3-((S)-1-(chloromethyl)-5-((2S,3S,4S,5R,6S)-3,4,5-trihydroxy-tetrahydro-2H-pyran-2-carboxyl-6-oxy)-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide |
| 71 | 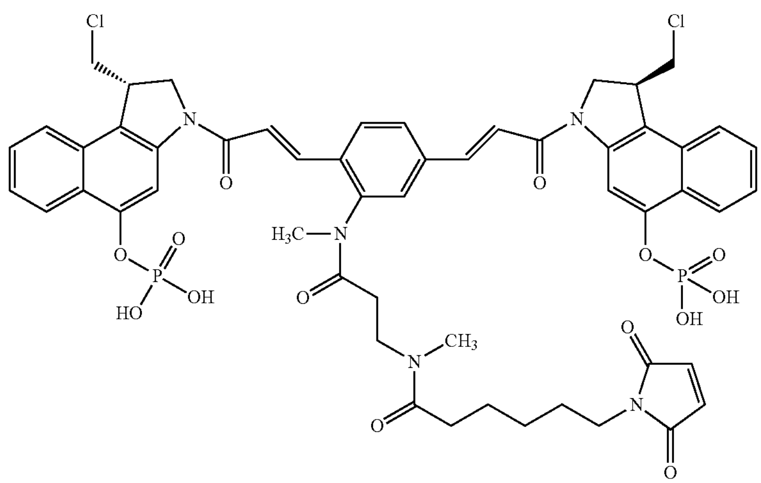 [SMILES: CN(CCC(=O)N(C)c1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21)C(=O)CCCCCN1C(=O)C=CC1=O] | N-(3-(2,5-bis((E)-3-((S)-1-(chloromethyl)-5-phosphonoxy-1H-benzo[e]indol-3(2H)-yl)-3-oxoprop-1-enyl)phenylamino)-6-(2,5-dioxo-2,5-dihydro-1H-pyrrol-1-yl)-N-methyl-N-(3-(methylamino)-3-oxopropyl)hexanamide |
| 72 | 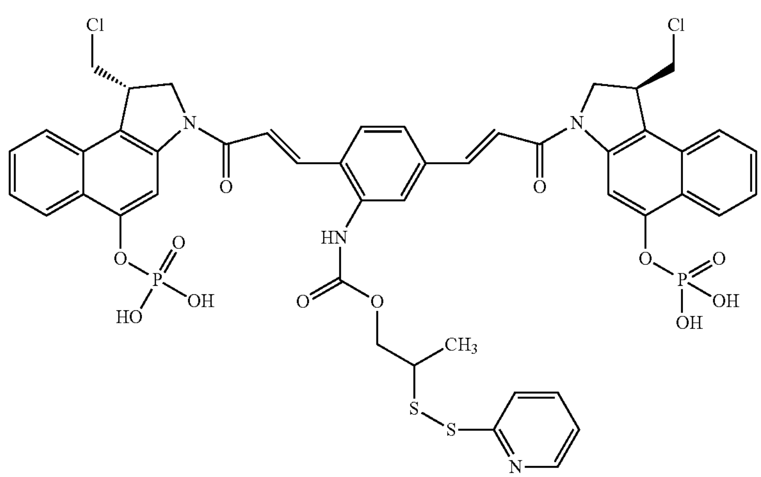 [SMILES: CC(COC(=O)Nc1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21)SSc1ccccn1] | 2-(pyridin-2-yldisulfanyl)propyl2,5-bis((E)-3-((S)-1-(chloromethyl)-5-(phosphonooxy)-1H-benzo[e]indol-3(2H)-yl)-3-oxoprop-1-enyl)phenylcarbamate |

TABLE 4-continued

Linker-CBI drug intermediates

| No. | Structure | Name |
|---|---|---|
| 73 | 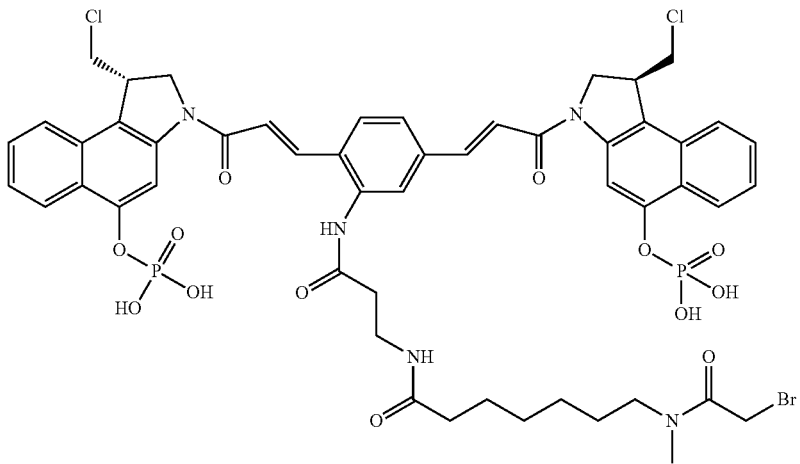 [SMILES: CN(CCCCCCC(=O)NCCC(=O)Nc1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21)C(=O)CBr] | N-(3-(2,5-bis((E)-3-((S)-1-(chloromethyl)-5-phosphonoxy-1H-benzo[e]indol-3(2H)-yl)-3-oxoprop-1-enyl)phenylamino)-7-(2-bromo-N-methylacetamido)-N-(3-oxopropyl)heptanamide |
| 74 | 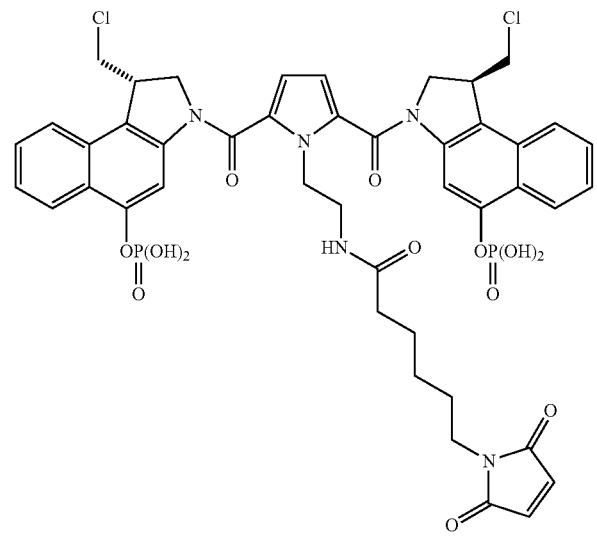 | N-(2-(2,5-bis((S)-1-(chloromethyl)-5-phosphonoxy-2,3-dihydro-1H-benzo[e]indole-3-carbonyl)-1H-pyrrol-1-yl)ethyl)-6-(2,5-dioxo-2,5-dihydro-1H-pyrrol-1-yl)hexanamide |
| 75 | 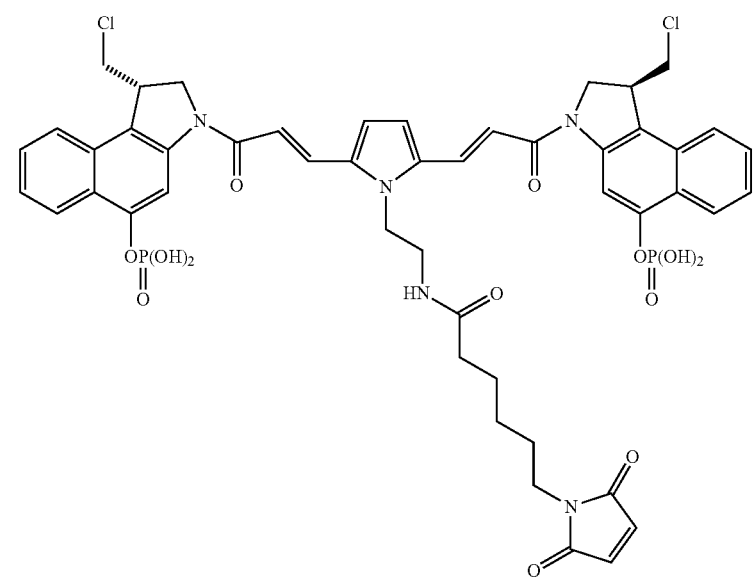 | N-(2-(2,5-bis((E)-3-((S)-1-(chloromethyl)-5-phosphonoxy-1H-benzo[e]indol-3(2H)-yl)-3-oxoprop-1-enyl)-1H-pyrrol-1-yl)ethyl)-6-(2,5-dioxo-2,5-dihydro-1H-pyrrol-1-yl)hexanamide |

TABLE 4-continued

Linker-CBI drug intermediates

| No. | Structure | Name |
|---|---|---|
| 76 | 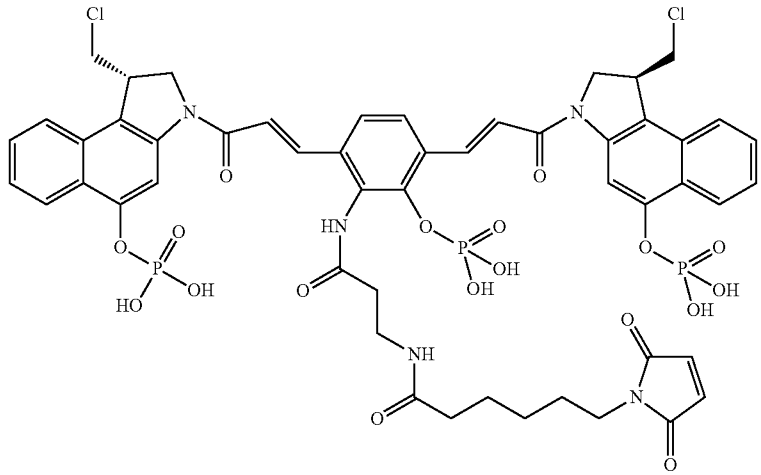 [SMILES: O=C(CCCCCN1C(=O)C=CC1=O)NCCC(=O)Nc1c(/C=C/C(=O)N2C[C@@H](CCl)c3c2cc(OP(=O)(O)O)c2ccccc32)ccc(/C=C/C(=O)N2C[C@@H](CCl)c3c2cc(OP(=O)(O)O)c2ccccc32)c1OP(=O)(O)O] | N-(3-(2,5-bis((E)-3-((S)-1-(chloromethyl)-5-phosphonoxy-1H-benzo[e]indol-3(2H)-yl)-3-oxoprop-1-enyl)phenylamino,2-phosphonoxy)-3-oxopropyl)-6-(2,5-dioxo-2,5-dihydro-1H-pyrrol-1-yl)hexanamide |
| 77 | 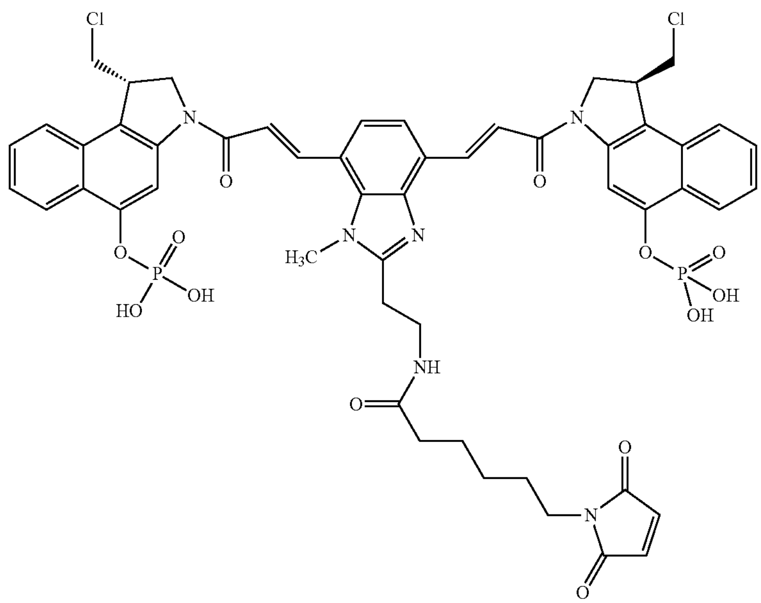 [SMILES: Cn1c(CCNC(=O)CCCCCN2C(=O)C=CC2=O)nc2c(/C=C/C(=O)N3C[C@@H](CCl)c4c3cc(OP(=O)(O)O)c3ccccc43)ccc(/C=C/C(=O)N3C[C@@H](CCl)c4c3cc(OP(=O)(O)O)c3ccccc43)c21] | N-(3-(2,5-bis((E)-3-((S)-1-(chloromethyl)-5-phosphonoxy-1H-benzo[e]indol-3(2H)-yl)-3-oxoprop-1-enyl)-1-methyl-1H-benzo[d]imidazol-2-yl)ethyl)-6-(2,5-dioxo-2,5-dihydro-1H-pyrrol-1-yl)hexanamide |
| 78 | 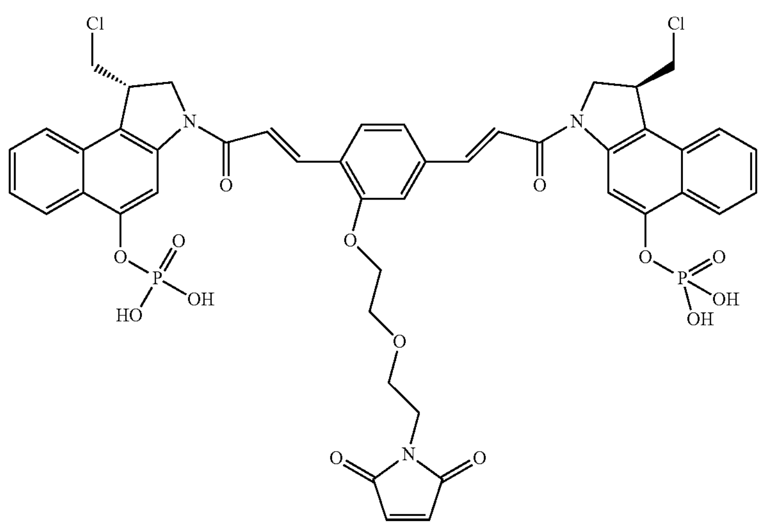 [SMILES: O=C1C=CC(=O)N1CCOCCOc1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21] | [(1S)-1-(chloromethyl)-3-[(E)-3-[4-[(E)-3-[(1S)-1-(chloromethyl)-5-phosphonooxy-1,2-dihydrobenzo[e]indol-3-yl]-3-oxo-prop-1-enyl]-2-[2-[2-(2,5-dioxopyrrol-1-yl)ethoxy]ethoxy]phenyl]prop-2-enoyl]-1,2-dihydrobenzo[e]indol-5-yl] dihydrogen phosphate |

TABLE 4-continued

Linker-CBI drug intermediates

| No. | Structure | Name |
|---|---|---|
| 79 | 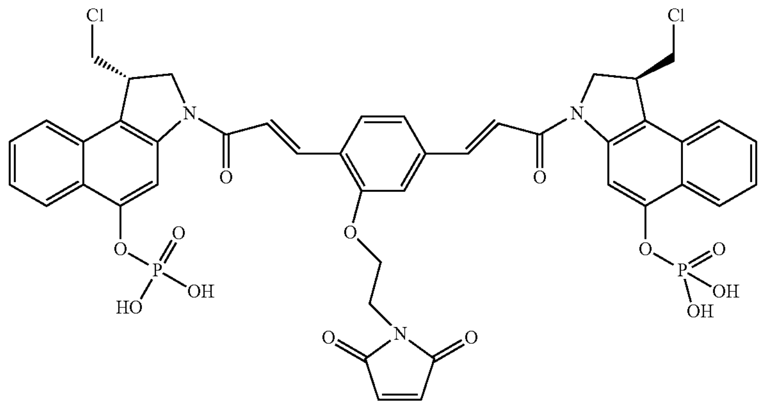 [SMILES: O=C1C=CC(=O)N1CCOc1cc(/C=C/C(=O)N2C[C@@H](CCl)c3c2cc(OP(=O)(O)O)c2ccccc32)ccc1/C=C/C(=O)N1C[C@@H](CCl)c2c1cc(OP(=O)(O)O)c1ccccc21] | [(1S)-1-(chloromethyl)-3-[(E)-3-[4-[(E)-3-[(1S)-1-(chloromethyl)-5-phosphonooxy-1,2-dihydrobenzo[e]indol-3-yl]-3-oxo-prop-1-enyl]-2-[2-(2,5-dioxopyrrol-1-yl)ethoxy]phenyl]prop-2-enoyl]-1,2-dihydrobenzo[e]indol-5-yl] dihydrogen phosphate |
| 80 | 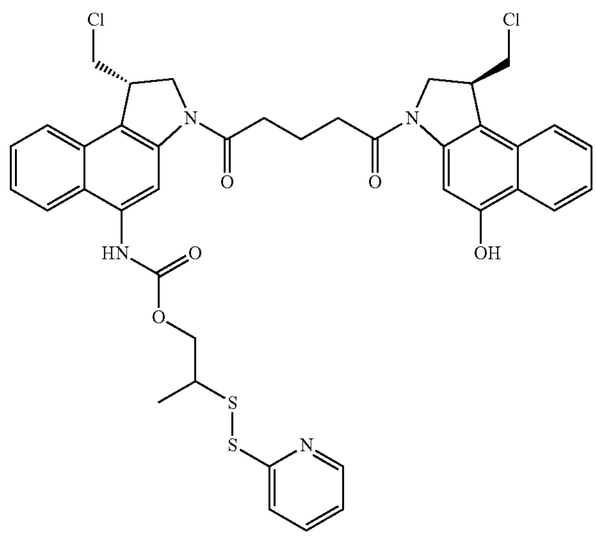 [SMILES: CC(COC(=O)Nc1cc2c(c3ccccc13)[C@H](CCl)CN2C(=O)CCCC(=O)N1C[C@@H](CCl)c2c1cc(O)c1ccccc21)SSc1ccccn1] | 2-(2-pyridyldisulfanyl)propyl N-[1-(chloromethyl)-3-[5-[1-(chloromethyl)-5-hydroxy-1,2-dihydrobenzo[e]indol-3-yl]-5-oxo-pentanoyl]-1,2-dihydrobenzo[e]indol-5-yl]carbamate |
| 81 | 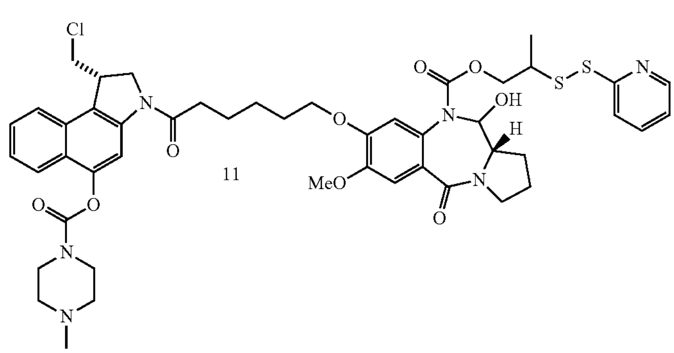 | 2-(2-pyridyldisulfanyl)propyl 3-[6-[1-(chloromethyl)-5-(4-methylpiperazine-1-carbonyl)oxy-1,2-dihydrobenzo[e]indol-3-yl]-6-oxo-hexoxy]-6-hydroxy-2-methoxy-11-oxo-6a,7,8,9-tetrahydro-6H-pyrrolo[2,1-c][1,4]benzodiazepine-5-carboxylate |

TABLE 4-continued

Linker-CBI drug intermediates

| No. | Structure | Name |
|---|---|---|
| 82 | 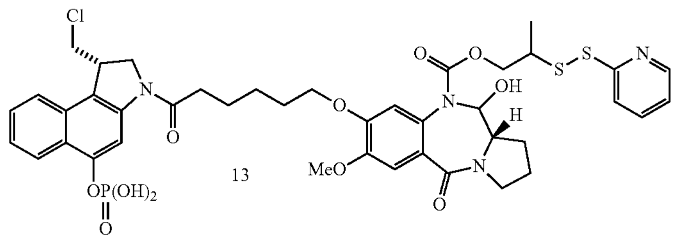 | 2-(2-pyridyldisulfanyl)propyl 3-[6-[1-(chloromethyl)-5-phosphonooxy-1,2-dihydrobenzo[e]indol-3-yl]-6-oxo-hexoxy]-6-hydroxy-2-methoxy-11-oxo-6a,7,8,9-tetrahydro-6H-pyrrolo[2,1-c][1,4]benzodiazepine-5-carboxylate |
| 83 | 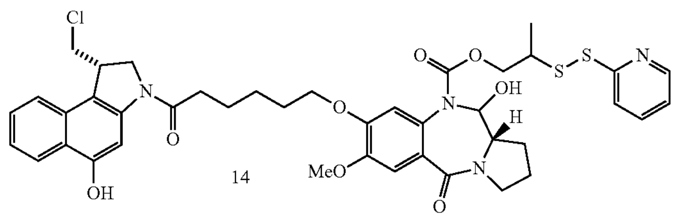 | 2-(2-pyridyldisulfanyl)propyl 3-[6-[1-(chloromethyl)-5-hydroxy-1,2-dihydrobenzo[e]indol-3-yl]-6-oxo-hexoxy]-6-hydroxy-2-methoxy-11-oxo-6a,7,8,9-tetrahydro-6H-pyrrolo[2,1-c][1,4]benzodiazepine-5-carboxylate |
| 84 | 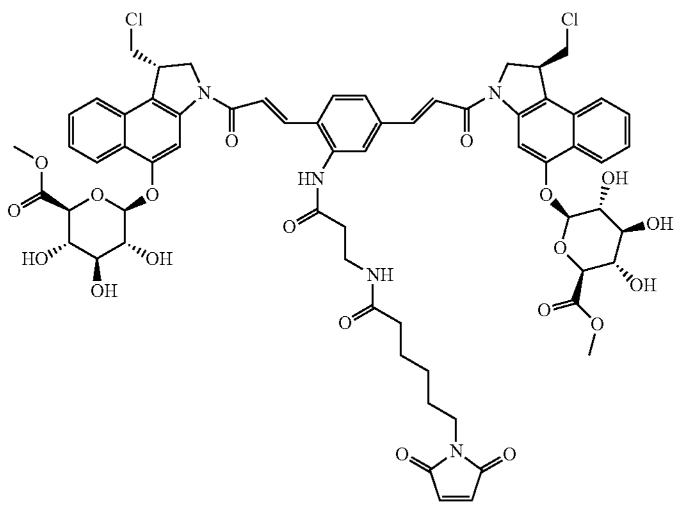 [SMILES: COC(=O)[C@H]1O[C@@H](Oc2cc3c(c4ccccc24)[C@H](CCl)CN3C(=O)/C=C/c2ccc(/C=C/C(=O)N3C[C@@H](CCl)c4c3cc(O[C@@H]3O[C@H](C(=O)OC)[C@@H](O)[C@H](O)[C@H]3O)c3ccccc43)c(NC(=O)CCNC(=O)CCCCCN3C(=O)C=CC3=O)c2)[C@H](O)[C@@H](O)[C@@H]1O] | (1S)-1-(chloromethyl)-3-((2E)-3-{4-((1E)-3-{(1S)-1-(chloromethyl)-5-[(6-methyl-β-D-glucopyranuronosyl)oxy]-1,2-dihydro-3H-benzo[e]indol-3-yl}-3-oxo-1-propenyl)-2-[(3-{[6-(2,5-dioxo-2,5-dihydro-1H-pyrrol-1-yl)hexanoyl]amino}propanoyl)amino]phenyl}-2-propenoyl)-1,2-dihydro-3H-benzo[e]indol-5-yl methyl β-D-glucopyranosiduronate |

Antibody-Drug Conjugates (ADC)

The antibody-drug conjugate (ADC) compounds of the invention comprise an antibody specific for a tumor-associated antigen linked to a potent CBI dimer drug moiety, and include those with therapeutic activity, effective against a number of hyperproliferative disorders, including cancer. The biological activity of the drug moiety is modulated by conjugation to an antibody. The ADC of the invention selectively deliver an effective dose of the CBI dimer drug, or toxin, to tumor cell or site whereby greater selectivity, i.e. a lower efficacious dose, may be achieved while increasing the therapeutic index ("therapeutic window"). In an exemplary embodiment, the ADC compounds include a cysteine-engineered antibody conjugated, i.e. covalently attached by a linker, to the CBI dimer drug moiety.

An antibody-drug conjugate compound of the invention has the formula:

wherein:
Ab is an antibody;
L is a linker having the formula:

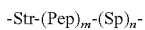

where Str is a stretcher unit covalently attached to the antibody; Pep is an optional peptide unit of two to twelve amino acid residues, Sp is an optional spacer unit covalently attached to a dimer drug moiety, and m and n are independently selected from 0 and 1;
p is an integer from 1 to 8;

D is the dimer drug moiety having the formula:

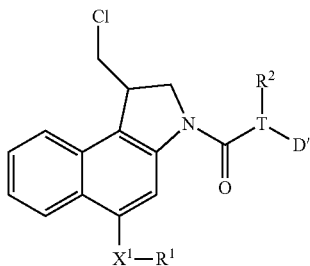

where $R^1$ is selected from H, $P(O)_3H_2$, $C(O)NR^aR^b$, or a bond to L;

$R^2$ is selected from H, $P(O)_3H_2$, $C(O)NR^aR^b$, or a bond to L;

$R^a$ and $R^b$ are independently selected from H and $C_1$-$C_6$ alkyl optionally substituted with one or more F, or $R^a$ and $R^b$ form a five or six membered heterocyclyl group;

T is a tether group selected from $C_3$-$C_{12}$ alkylene, Y, ($C_1$-$C_6$ alkylene)-Y—($C_1$-$C_6$ alkylene), ($C_1$-$C_6$ alkylene)-Y—($C_1$-$C_6$ alkylene)-Y—($C_1$-$C_6$ alkylene), ($C_2$-$C_6$ alkenylene)-Y—($C_2$-$C_6$ alkenylene), and ($C_2$-$C_6$ alkynylene)-Y—($C_2$-$C_6$ alkynylene);

where Y is independently selected from O, S, $NR^1$, aryl, and heteroaryl;

where alkylene, alkenylene, aryl, and heteroaryl are independently and optionally substituted with F, OH, $O(C_1$-$C_6$ alkyl), $NH_2$, $NHCH_3$, $N(CH_3)_2$, $OP(O)_3H_2$, and $C_1$-$C_6$ alkyl, where alkyl is optionally substituted with one or more F;

or alkylene, alkenylene, aryl, and heteroaryl are independently and optionally substituted with a bond to L;

D' is a drug moiety selected from:

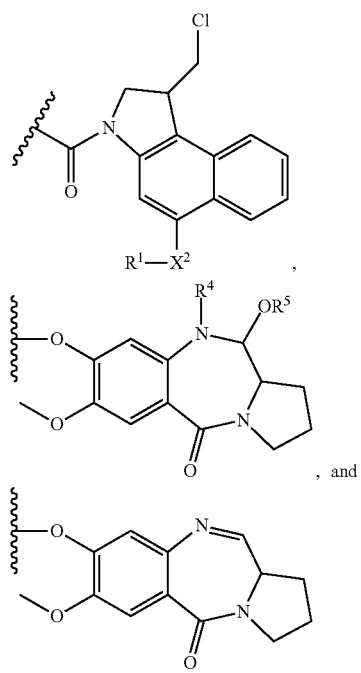

, and where the wavy line indicates the site of attachment to T;

$X^1$ and $X^2$ are independently selected from O and $NR^3$, where $R^3$ is selected from H and $C_1$-$C_6$ alkyl optionally substituted with one or more F;

$R^4$ is H, $CO_2R$ where R is $C_1$-$C_6$ alkyl or benzyl; and $R^5$ is H.

In one embodiment, $R^a$ and $R^b$ form a five or six membered heterocyclyl group selected from N-methylpiperazinyl, morpholinyl, piperidyl, and pyrrolidinyl.

In one embodiment, the drug moiety may is joined to the antibody via a protease cleavable, peptide linker cleavable by cathepsin B, a lysosomal protease found in most mammalian cell types (U.S. Pat. No. 6,214,345; Dubowchik et al (2002) Bioconj. Chem. 13:855-869). While the invention is not limited or defined by any particular mechanism of action, the ADC may act as a pro-drug in that the drug is inactive until the linker is cleaved. The ADC is able to concentrate the active drug specifically in a tumor cell location where disease may be poorly treated by conventional chemotherapy. In other embodiments, the drug moiety is attached to the antibody via a non-peptide, non-protease cleavable linker, which may include functionality such as disulfide or succinimidyl groups.

The number of drug moieties which may be conjugated via a reactive linker moiety to an antibody molecule may be limited by the number of free cysteine residues, which are introduced by the methods described herein. Exemplary ADC therefore comprise antibodies which have 1, 2, 3, or 4 engineered cysteine amino acids (Lyon, R. et al (2012) *Methods in Enzym.* 502:123-138).

In one embodiment, the antibody-drug conjugate compound has the formula:

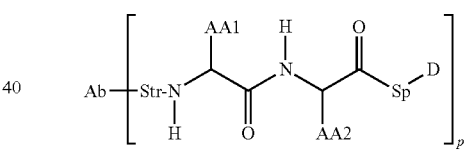

where AA1 and AA2 are independently selected from an amino acid side chain. The amino acid side chain is independently selected from H, —$CH_3$, —$CH_2(C_6H_5)$, —$CH_2CH_2CH_2CH_2NH_2$, —$CH_2CH_2CH_2NHC(NH)NH_2$, —$CHCH(CH_3)CH_3$, and —$CH_2CH_2CH_2NHC(O)NH_2$.

In one embodiment, the antibody-drug conjugate compound has the formula:

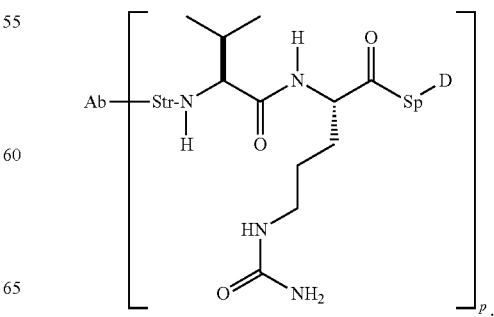

In one embodiment, the antibody-drug conjugate compound has the formula:

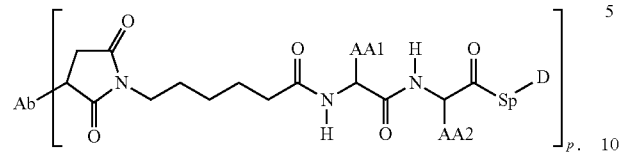

In one embodiment, the antibody-drug conjugate compound has the formula:

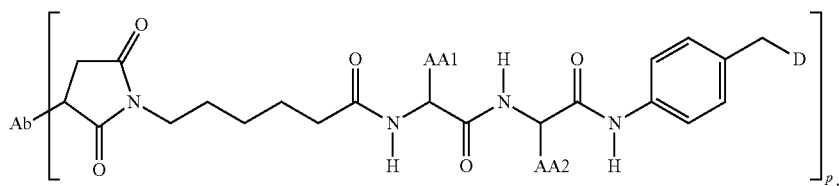

In one embodiment, the antibody-drug conjugate compound has the formula:

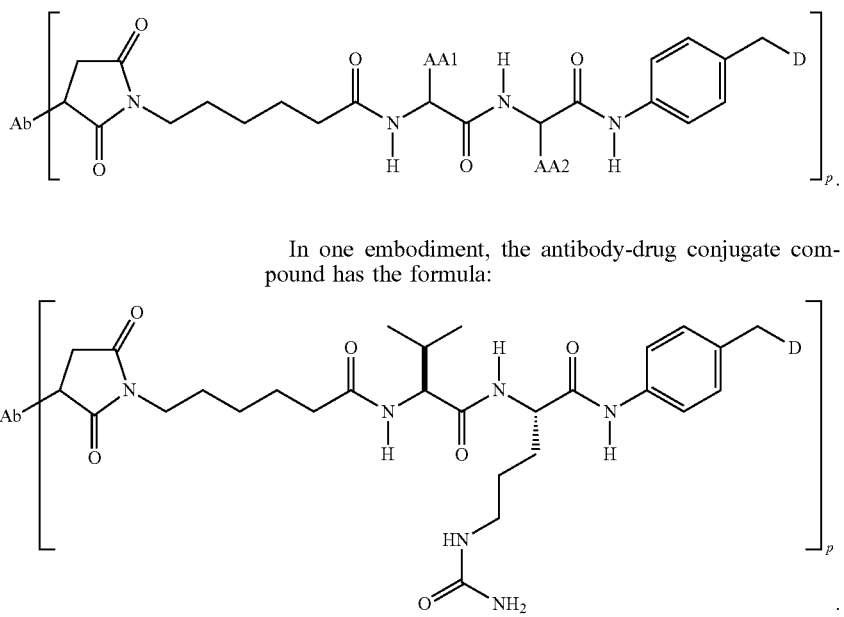

In one embodiment, the antibody-drug conjugate compound has the formula:

In one embodiment, the antibody-drug conjugate compound has the formula:

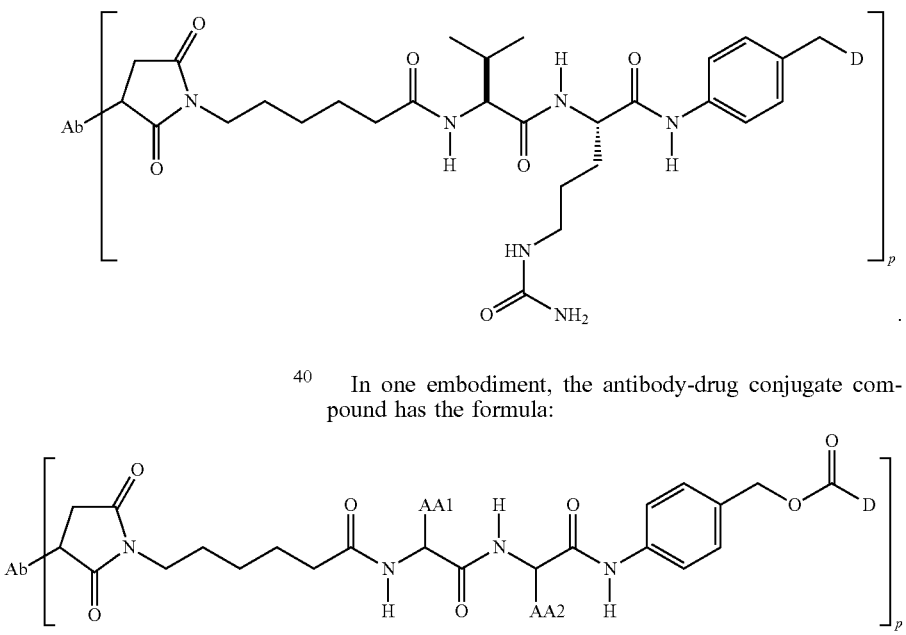

In one embodiment, the antibody-drug conjugate compound has the formula:

In one embodiment, the antibody-drug conjugate compound has the formula:

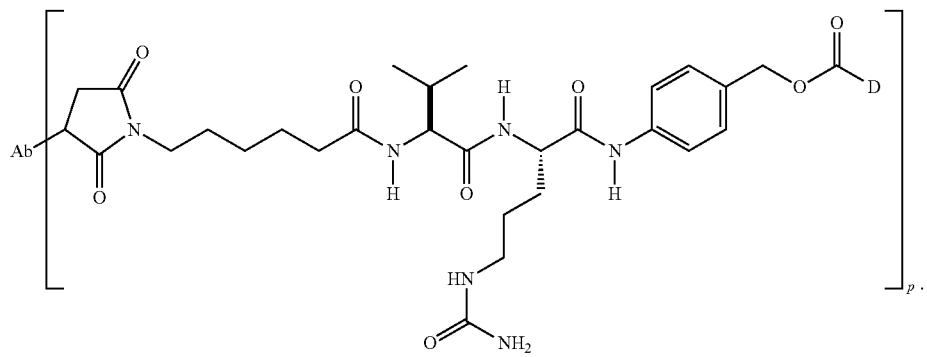

In one embodiment, the antibody-drug conjugate compound has the formula:

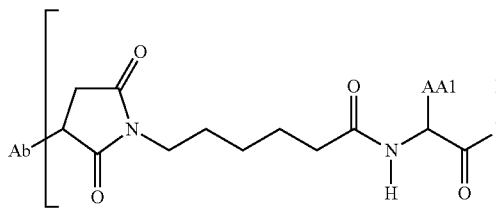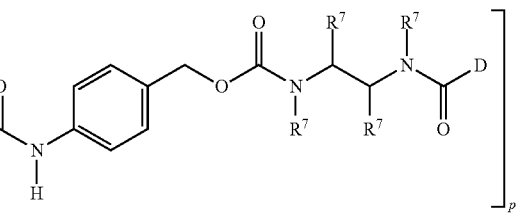

where $R^7$ is independently selected from H and $C_1$-$C_{12}$ alkyl.

In one embodiment, p is 1, 2, 3 or 4.

In one embodiment, p is 2.

In one embodiment, D is a moiety selected from the compounds listed in Table 1 or a derivative thereof.

In one embodiment, L-D is a moiety selected from the compounds listed in Table 4 or a derivative thereof.

In one embodiment, the present invention relates to a conjugate selected from the molecules listed in Table 5.

Drug Loading of ADC

The drug loading is the average number of CBI drug moieties per antibody. Drug loading may range from 1 to 8 drugs (D) per antibody (Ab), i.e. where 1, 2, 3, 4, 5, 6, 7, and 8 drug moieties are covalently attached to the antibody. Compositions of ADC include collections of antibodies conjugated with a range of drugs, from 1 to 8. The average number of drugs per antibody in preparations of ADC from conjugation reactions may be characterized by conventional means such as mass spectroscopy, ELISA assay, electrophoresis, and HPLC. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody-drug conjugates.

Typically, fewer than the theoretical maximum of drug moieties is conjugated to an antibody during a conjugation reaction. An antibody may contain, for example, many lysine residues that do not react with the linker-drug intermediate (X-L-D) or linker reagent. Only the most reactive lysine groups may react with an amine-reactive linker reagent. Also, only the most reactive cysteine thiol groups may react with a thiol-reactive linker reagent or linker-drug intermediate. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio, "DAR") of an ADC may be controlled in several different manners, including: (i) limiting the molar excess of linker-drug intermediate or linker reagent relative to antibody, (ii) limiting the conjugation reaction time or temperature, and (iii) partial or limiting reductive conditions for cysteine thiol modification.

Where more than one nucleophilic or electrophilic group of the antibody reacts with a linker-drug intermediate, or linker reagent followed by CBI dimer drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody. Thus the antibody-drug conjugate compositions of the invention include mixtures of antibody-drug conjugate compounds where the antibody has one or more drug moieties and where the drug moieties may be attached to the antibody at various amino acid residues.

Methods of Preparing Antibody-Drug Conjugates

Exemplary antibody-drug conjugates (ADC) compounds 101-139 of the invention were prepared from linker-drug intermediates 51-68 according to Example 20 and as shown in Table 4.

TABLE 5

Antibody-drug conjugates (ADC)

| No. | ADC formula | linker-CBI intermediate (Table 4) | DAR* |
|---|---|---|---|
| 101 | Thio hu anti-CD22 HC A121C-MC-vc-PAB-(CBI dimer) | 55 | 1.7 |
| 102 | Thio hu anti-Her2 HC A121C-MC-vc-PAB-(CBI dimer) | 55 | 1.8 |
| 103 | Thio Hu Anti-Her2 4D5 HC A118C-MC-vc-PAB-(CBI-PBD) | 56 | 1.6 |
| 104 | Thio Hu Anti-CD22 10F4v3 HC A118C-MC-vc-PAB-(CBI-PBD) | 56 | 1.6 |
| 105 | Thio Hu Anti-Her2 4D5 HC A118C-MC-vc-PAB-(CBI dimer MePip) | 58 | 1.7 |
| 106 | Thio Hu Anti-Her2 4D5 HC A118C-MC-MMED-(CBI dimer phos) | 57 | 2.0 |
| 107 | Thio Hu Anti-Her2 4D5 HC A118C-MC-vc-PAB-(CBI dimer MePip) | 58 | 1.6 |
| 108 | Thio Hu Anti-CD22 10F4v3 HC A118C-MC-vc-PAB-(CBI dimer MePip) | 58 | 1.8 |

TABLE 5-continued

Antibody-drug conjugates (ADC)

| No. | ADC formula | linker-CBI intermediate (Table 4) | DAR* |
|---|---|---|---|
| 109 | Thio Hu Anti-Her2 4D5 HC A118C-MC-MMED-(CBI dimer phos) | 57 | 1.9 |
| 110 | Thio Hu Anti-CD22 10F4v3 HC A118C-MC-MMED-(CBI dimer phos) | 57 | 1.9 |
| 111 | Thio Hu Anti-CD22 10F4v3 HC A118C-MC-vc-PAB-(CBI dimer phos) | 59 | 1.8 |
| 112 | Thio Hu Anti-Her2 4D5 HC A118C-MC-vc-PAB-(CBI dimer phos) | 59 | 1.9 |
| 113 | Thio Hu Anti-Her2 4D5 HC A118C-DSE-(CBI dimer phos) | 61 | 2.0 |
| 114 | Thio Hu Anti-Her2 4D5 HC A118C-MC-MMED-(CBI dimer phos) Phosphatase treated | 57 | 1.9 |
| 115 | Thio Hu Anti-CD22 10F4v3 HC A118C-MC-MMED-(CBI dimer) Phosphatase treated | 63 | 1.9 |
| 116 | Thio Hu Anti-CD22 10F4v3 HC A118C-MC-vc-PAB-(CBI dimer) Phosphatase treated | 60 | 1.8 |
| 117 | Thio Hu Anti-Her2 4D5 HC A118C-MC-vc-PAB-(CBI dimer) Phosphatase treated | 60 | 1.9 |
| 118 | Thio Hu Anti-Her2 4D5 HC A118C-DSE-(CBI dimer) Phosphatase treated | 64 | 2.0 |
| 119 | Thio Hu Anti-Her2 4D5 HC A118C-DSE-(CBI dimer phos) | 61 | 1.9 |
| 120 | Thio Hu Anti-CD22 10F4v3 HC A118C-DSE-(CBI dimer phos) | 61 | 1.8 |
| 121 | Thio Hu Anti-Her2 4D5 HC A118C-DSP-(CBI dimer phos) | 62 | 1.8 |
| 122 | Thio Hu Anti-CD22 10F4v3 HC A118C-DSE-(CBI dimer phos) | 62 | 1.6 |
| 123 | Thio Hu Anti-Her2 4D5 HC A118C-MC-vc-PAB-(N10, PBD-CBI MePip) | 65 | 1.9 |
| 124 | Thio Hu Anti-CD22 10F4v3 HC A118C-MC-vc-PAB-(N10,PBD-CBI MePip) | 65 | 1.7 |
| 125 | Thio Hu Anti-CD33 15G15.33 HC A118C-MC-MMED-(CBI dimer phos) | 57 | 1.6 |
| 126 | Thio Hu Anti-MUC16 3A5 HC A118C-MC-ED-(CBI dimer DVB diphos) | 66 | 1.8 |
| 127 | Thio Hu Anti-CD33 15G15.33 HC A118C-MC-ED-(CBI dimer DVB diphos) | 66 | 1.5 |
| 128 | Thio Hu Anti-MUC16 3A5 HC A118C-MC-MMED-(CBI dimer phos) | 57 | 1.95 |
| 129 | Thio Hu Anti-CD33 15G15.33 HC A118C-MC-ED-(CBI dimer DVB phos) | 68 | 2.0 |
| 130 | Thio Hu Anti-MUC16 3A5 HC A118C-MC-ED-(CBI dimer DVB phos) | 68 | 2.0 |
| 131 | Thio Hu Anti-CD33 15G15.33 HC A118C-DSP-(CBI dimer phos) | 62 | 1.55 |
| 132 | Thio Hu Anti-MUC16 3A5 HC A118C-DSP-(CBI dimer phos) | 62 | |
| 133 | Thio Hu Anti-CD33 15G15.33 LC V205C-DSP-(CBI dimer phos) | 62 | 1.9 |
| 134 | Thio Hu Anti-NaPi2b 10H1.11.4B HC A118C-(Compound 81) | 81 | 1.8 |
| 135 | Thio Hu Anti-NaPi2b 10H1.11.4B HC A118C-(Compound 78) | 78 | 1.8 |
| 136 | Thio Hu Anti-NaPi2b 10H1.11.4B HC A118C-(Compound 72) | 72 | 2 |
| 137 | Thio HC anti-CD33 (GM15.33)-(Compound 81) | 81 | 1.8 |
| 138 | Thio Hu Anti-CD33 (GM15.33)-(Compound 78) | 78 | 1.9 |
| 139 | Thio Hu Anti-CD33 (GM15.33)-(Compound 72) | 72 | 1.57 |

*DAR = drug/antibody ratio average
** A118C (EU numbering) = A121C (Sequential numbering) = A114C (Kabat numbering)

Anti-NaPi2b Antibodies

The anti-NaPi2b antibodies of ADC in Table 5 comprise three light chain hypervariable regions (HVR-L1, HVR-L2 and HVR-L3) and three heavy chain hypervariable regions (HVR-H1, HVR-H2 and HVR-H3), according to U.S. Pat. No. 8,535,675:

| HVR-L1 | RSSETLVHSSGNTYLE | (SEQ ID NO: 75) |
|---|---|---|
| HVR-L2 | RVSNRFS | (SEQ ID NO: 76) |
| HVR-L3 | FQGSFNPLT | (SEQ ID NO: 77) |
| HVR-H1 | GFSFSDFAMS | (SEQ ID NO: 78) |
| HVR-H2 | ATIGRVAFHTYYPDSMKG | (SEQ ID NO: 79) |
| HVR-H3 | ARHRGFDVGHFDF | (SEQ ID NO: 80) |

The anti-NaPi2b antibodies of ADC in Table 5 comprise the light chain variable region (VL) shown in SEQ ID NO: 81 and the heavy chain variable region (VH) shown in SEQ ID NO: 82.

(SEQ ID NO: 81)
DIQMTQSPSSLSASVGDRVTITCRSSETLVHSSGNTYLEWYQQKPGKAPK

LLIYRVSNRFSGVPSRFSGSGSGTDFTLTISSLQPEDFATYYCFQGSFNP

LTFGQGTKVEIKR (SEQ ID NO: 82)
EVQLVESGGGLVQPGGSLRLSCAASGFSFSDFAMSWVRQAPGKGLEWVAT

IGRVAFHTYYPDSMKGRFTISRDNSKNTLYLQMNSLRAEDTAVYYCARHR

GFDVGHFDFWGQGTLVTVSS

In some embodiments, the invention provides an anti-NaPi2b antibody comprising at least one, two, three, four, five, or six HVRs selected from (a) HVR-H1 comprising the amino acid sequence of SEQ ID NO:78; (b) HVR-H2 comprising the amino acid sequence of SEQ ID NO:79; (c) HVR-H3 comprising the amino acid sequence of SEQ ID NO:80; (d) HVR-L1 comprising the amino acid sequence of SEQ ID NO:75; (e) HVR-L2 comprising the amino acid sequence of SEQ ID NO:76; and (f) HVR-L3 comprising the amino acid sequence of SEQ ID NO:77.

In one aspect, the invention provides an anti-NaPi2b antibody comprising at least one, at least two, or all three VH HVR sequences selected from (a) HVR-H1 comprising the amino acid sequence of SEQ ID NO:78; (b) HVR-H2 comprising the amino acid sequence of SEQ ID NO:79; and (c) HVR-H3 comprising the amino acid sequence of SEQ ID NO:80. In one embodiment, the antibody comprises HVR-H3 comprising the amino acid sequence of SEQ ID NO:80. In another embodiment, the antibody comprises HVR-H3 comprising the amino acid sequence of SEQ ID NO:80 and HVR-L3 comprising the amino acid sequence of SEQ ID NO:77. In a further embodiment, the antibody comprises HVR-H3 comprising the amino acid sequence of SEQ ID NO:80, HVR-L3 comprising the amino acid sequence of SEQ ID NO:77, and HVR-H2 comprising the amino acid sequence of SEQ ID NO:79. In a further embodiment, the antibody comprises (a) HVR-H1 comprising the amino acid sequence of SEQ ID NO:78; (b) HVR-H2 comprising the amino acid sequence of SEQ ID NO:79; and (c) HVR-H3 comprising the amino acid sequence of SEQ ID NO:80.

In another aspect, the invention provides an antibody comprising at least one, at least two, or all three VL HVR sequences selected from (a) HVR-L1 comprising the amino acid sequence of SEQ ID NO:75; (b) HVR-L2 comprising the amino acid sequence of SEQ ID NO:76; and (c) HVR-L3 comprising the amino acid sequence of SEQ ID NO:77. In one embodiment, the antibody comprises (a) HVR-L1 comprising the amino acid sequence of SEQ ID NO:75; (b) HVR-L2 comprising the amino acid sequence of SEQ ID NO:76; and (c) HVR-L3 comprising the amino acid sequence of SEQ ID NO:77.

In another aspect, an antibody of the invention comprises (a) a VH domain comprising at least one, at least two, or all three VH HVR sequences selected from (i) HVR-H1 comprising the amino acid sequence of SEQ ID NO:78, (ii) HVR-H2 comprising the amino acid sequence of SEQ ID NO:79, and (iii) HVR-H3 comprising an amino acid sequence selected from SEQ ID NO:80; and (b) a VL domain comprising at least one, at least two, or all three VL HVR sequences selected from (i) HVR-L1 comprising the amino acid sequence of SEQ ID NO:75, (ii) HVR-L2 comprising the amino acid sequence of SEQ ID NO:76, and (c) HVR-L3 comprising the amino acid sequence of SEQ ID NO:77.

In another aspect, the invention provides an antibody comprising (a) HVR-H1 comprising the amino acid sequence of SEQ ID NO:78; (b) HVR-H2 comprising the amino acid sequence of SEQ ID NO:79; (c) HVR-H3 comprising the amino acid sequence of SEQ ID NO:80; (d) HVR-L1 comprising the amino acid sequence of SEQ ID NO:75; (e) HVR-L2 comprising the amino acid sequence of SEQ ID NO:76; and (f) HVR-L3 comprising the amino acid sequence of SEQ ID NO:77.

In any of the above embodiments, an anti-NaPi2b antibody is humanized. In one embodiment, an anti-NaPi2b antibody comprises HVRs as in any of the above embodiments, and further comprises a human acceptor framework, e.g. a human immunoglobulin framework or a human consensus framework. In certain embodiments, the human acceptor framework is the human VL kappa I consensus (VL$_{KI}$) framework and/or the VH framework VH$_1$. In certain embodiments, the human acceptor framework is the human VL kappa I consensus (VL$_{KI}$) framework and/or the VH framework VH$_1$ comprising any one of the following mutations.

In another aspect, an anti-NaPi2b antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:82. In certain embodiments, a VH sequence having at least 90%, 91%, 92%, 93%, 94%, 95%, 96%, 97%, 98%, or 99% identity to the amino acid sequence of SEQ ID NO:82 contains substitutions (e.g., conservative substitutions), insertions, or deletions relative to the reference sequence, but an anti-NaPi2b antibody comprising that sequence retains the ability to bind to NaPi2b. In certain embodiments, a total of 1 to 10 amino acids have been substituted, inserted and/or deleted in SEQ ID NO:82. In certain embodiments, a total of 1 to 5 amino acids have been substituted, inserted and/or deleted in SEQ ID NO:82. In certain embodiments, substitutions, insertions, or deletions occur in regions outside the HVRs (i.e., in the FRs). Optionally, the anti-NaPi2b antibody comprises the VH sequence of SEQ ID NO:82, including post-translational modifications of that sequence. In a particular embodiment, the VH comprises one, two or three HVRs selected from: (a) HVR-H1 comprising the amino acid sequence of SEQ ID NO:78, (b) HVR-H2 comprising the amino acid sequence of SEQ ID NO:79, and (c) HVR-H3 comprising the amino acid sequence of SEQ ID NO:80.

In another aspect, an anti-NaPi2b antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:81. In certain embodiments, a VL sequence having at least 90%, 91%, 92%, 93%, 94%, 95%, 96%, 97%, 98%, or 99% identity to the amino acid sequence of SEQ ID NO:81 contains substitutions (e.g., conservative substitutions), insertions, or deletions relative to the reference sequence, but an anti-NaPi2b antibody comprising that sequence retains the ability to bind to NaPi2b. In certain embodiments, a total of 1 to 10 amino acids have been substituted, inserted and/or deleted in SEQ ID NO:81. In certain embodiments, a total of 1 to 5 amino acids have been substituted, inserted and/or deleted in SEQ ID NO:81. In certain embodiments, the substitutions, insertions, or deletions occur in regions outside the HVRs (i.e., in the FRs). Optionally, the anti-NaPi2b antibody comprises the VL sequence of SEQ ID NO:81 including post-translational modifications of that sequence. In a particular embodiment, the VL comprises one, two or three HVRs selected from (a) HVR-L1 comprising the amino acid sequence of SEQ ID NO:75; (b) HVR-L2 comprising the amino acid sequence of SEQ ID NO:76; and (c) HVR-L3 comprising the amino acid sequence of SEQ ID NO:77.

In another aspect, an anti-NaPi2b antibody is provided, wherein the antibody comprises a VH as in any of the embodiments provided above, and a VL as in any of the embodiments provided above.

In one embodiment, the antibody comprises the VH and VL sequences in SEQ ID NO:82 and SEQ ID NO:81, respectively, including post-translational modifications of those sequences.

In a further aspect, provided are herein are antibodies that bind to the same epitope as an anti-NaPi2b antibody provided herein. For example, in certain embodiments, an antibody is provided that binds to the same epitope as an anti-NaPi2b antibody comprising a VH sequence of SEQ ID NO:82 and a VL sequence of SEQ ID NO:81.

In a further aspect of the invention, an anti-NaPi2b antibody according to any of the above embodiments is a monoclonal antibody, including a human antibody. In one embodiment, an anti-NaPi2b antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

In a further aspect, an anti-NaPi2b antibody according to any of the above embodiments may incorporate any of the features, singly or in combination, as described below.

Anti-CD22 Antibodies

The anti-CD22 antibodies of ADC in Table 5 comprise three light chain hypervariable regions (HVR-L1, HVR-L2 and HVR-L3) and three heavy chain hypervariable regions (HVR-H1, HVR-H2 and HVR-H3), according to U.S. Pat. No. 8,226,945:

| | | |
|---|---|---|
| HVR-L1 | RSSQSIVHSVGNTFLE | (SEQ ID NO: 1) |
| HVR-L2 | KVSNRFS | (SEQ ID NO: 2) |
| HVR-L3 | FQGSQFPYT | (SEQ ID NO: 3) |
| HVR-H1 | GYEFSRSWMN | (SEQ ID NO: 4) |
| HVR-H2 | GRIYPGDGDTNYSGKFKG | (SEQ ID NO: 5) |
| HVR-H3 | DGSSWDWYFDV | (SEQ ID NO: 6) |

Anti-MUC16 Antibodies

The anti-MUC16 antibodies of ADC in Table 5 comprise three light chain hypervariable regions (HVR-L1, HVR-L2 and HVR-L3) and three heavy chain hypervariable regions (HVR-H1, HVR-H2 and HVR-H3), according to U.S. Pat. No. 7,989,595:

```
HVR-L1    KASDLIHNWLA       (SEQ ID NO: 7)
HVR-L2    YGATSLET          (SEQ ID NO: 8)
HVR-L3    QQYWTTPFT         (SEQ ID NO: 9)
HVR-H1    GYSITNDYAWN       (SEQ ID NO: 10)
HVR-H2    GYISYSGYTTYNPSLKS (SEQ ID NO: 11)
HVR-H3    ARWTSGLDY         (SEQ ID NO: 12)
```

The anti-MUC16 antibodies of ADC in Table 5 comprise the variable heavy chain sequence of SEQ ID NO: 13 and the variable light chain sequence of SEQ ID NO: 14.

```
                                    (SEQ ID NO: 13)
E V Q L V E S G G G L V Q P G G S L R L S C A A S
G Y S I T N D Y A W N W V R Q A P G K G L E W V G
Y I S Y S G Y T T Y N P S L K S R F T I S R D T S
K N T L Y L Q M N S L R A E D T A V Y Y C A R W T
S G L D Y W G Q G T L V T V S S (SEQ ID NO: 14)
D I Q M T Q S P S S L S A S V G D R V T I T C K A
S D L I H N W L A W Y Q Q K P G K A P K L L I Y G
A T S L E T G V P S R F S G S G S G T D F T L T I
S S L Q P E D F A T Y Y C Q Q Y W T T P F T F G Q
G T K V E I K R
```

In one embodiment, the anti-MUC16 antibody of an ADC of the invention is a cysteine-engineered, ThioMab comprising one or more free cysteine amino acid residues located in a light chain sequence selected from SEQ ID NOs: 15-32, or in a heavy chain sequence selected from SEQ ID NOs: 33-46:

```
EVQLCESGGG       SEQ ID NO: 15
LRLSCCASGYS      SEQ ID NO: 16
MNSLRCEDTAV      SEQ ID NO: 17
TLVTVCSASTK      SEQ ID NO: 18
VTVSSCSTKGP      SEQ ID NO: 19
VSAASCKGPSV      SEQ ID NO: 20
WYVDGCEVHNA      SEQ ID NO: 21
KGFVPCDIAVE      SEQ ID NO: 22
PPVLDCGDSFF      SEQ ID NO: 23
DVQLCESGPG       SEQ ID NO: 24
LSLTCCVTGYS      SEQ ID NO: 25
LNSVTCEDTAT      SEQ ID NO: 26
TLVTVCSASTK      SEQ ID NO: 27
VTVSSCSTKGP      SEQ ID NO: 28
VSAASCKGPSV      SEQ ID NO: 29
WYVDGCEVHNA      SEQ ID NO: 30
KGFVPCDIAVE      SEQ ID NO: 31
PPVLDCDGSFF      SEQ ID NO: 32
SLSASCGDRVT      SEQ ID NO: 33
EIKRTCAAPSV      SEQ ID NO: 34
TVAAPCVFIFP      SEQ ID NO: 35
FIFPPCDEQLK      SEQ ID NO: 36
DEQLKCGTASV      SEQ ID NO: 37
VTEQDCKDSTY      SEQ ID NO: 38
GLSSPCTKSFN      SEQ ID NO: 39
FLSVSCGGRVT      SEQ ID NO: 40
EIKRTCAAPSV      SEQ ID NO: 41
TVAAPCVFIFP      SEQ ID NO: 42
FIFPPCDEQLK      SEQ ID NO: 43
DEQLKCGTASV      SEQ ID NO: 44
VTEQDCKDSTY      SEQ ID NO: 45
GLSSPCTKSFN      SEQ ID NO: 46
```

In one embodiment, the anti-MUC16 cysteine-engineered, ThioMab is a humanized antibody comprising the heavy chain sequence of SEQ ID NO:47.

```
                                                    (SEQ ID NO: 47)
EVQLVESGGGLVQPGGSLRLSCAASGYSITNDYAWNWVRQAPGKGLEWVG
YISYSGYTTYNPSLKSRFTISRDISKNTLYLQMNSLRAEDTAVYYCARWT
SGLDYWGQGTLVTVSSCSTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK
```

In one embodiment, the anti-MUC16 cysteine-engineered, ThioMab is a humanized antibody comprising the light chain sequence of SEQ ID NO:48.

```
                                                    (SEQ ID NO: 48)
DIQMTQSPSSLSASVGDRVTITCKASDLIHNWLAWYQQKPGKAPKLLIYG
ATSLETGVPSRFSGSGSGTDFTLTISSLQPEDFATYYCQQYWTTPFTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC
```

In one embodiment, the anti-MUC16 cysteine-engineered, ThioMab is a chimeric antibody comprising the heavy chain sequence of SEQ ID NO:49.

(SEQ ID NO: 49)
DVQLQESGPGLVNPSQSLSLICTVTGYSITNDYAWNWIRQFPGNKLEWMG

YINYSGYTTYNPSLKSRISITRDTSKNQFFLHLNSVTTEDTATYYCARWD

GGLTYWGQGTLVTVSACSTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK

In one embodiment, the anti-MUC16 cysteine-engineered, ThioMab is a chimeric antibody comprising the light chain sequence of SEQ ID NO:50.

(SEQ ID NO: 50)
DIQMTQSSSFLSVSLGGRVTITCKASDLIHNWLAWYQQKPGNAPRLLISG

ATSLETGVPSRFSGSGSGNDYTLSIASLQTEDAATYYCQQYWTTPFTFGS

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Anti-HER2 Antibodies

In certain embodiments, ADC of Table 5 comprise anti-HER2 antibodies. In one embodiment of the invention, an anti-HER2 antibody of an ADC of the invention comprises a humanized anti-HER2 antibody, e.g., huMAb4D5-1, huMAb4D5-2, huMAb4D5-3, huMAb4D5-4, huMAb4D5-5, huMAb4D5-6, huMAb4D5-7 and huMAb4D5-8, as described in Table 3 of U.S. Pat. No. 5,821,337. Those antibodies contain human framework regions with the complementarity-determining regions of a murine antibody (4D5) that binds to HER2. The humanized antibody huMAb4D5-8 is also referred to as trastuzumab, commercially available under the tradename HERCEPTIN®. In another embodiment of the invention, an anti-HER2 antibody of an ADC of the invention comprises a humanized anti-HER2 antibody, e.g., humanized 2C4, as described in U.S. Pat. No. 7,862,817. An exemplary humanized 2C4 antibody is pertuzumab, commercially available under the tradename PERJETA®.

The cysteine-engineered Thiomab antibodies used to prepare the ADC of Table 5 have a cysteine residue introduced at the 118-alanine site (EU numbering) of the heavy chain. This site is numbered 121 by Sequential numbering or 114 by Kabat numbering.

Anti-CD33 Antibodies

The anti-CD33 antibody 15G15.33 of ADC in Table 5 comprises three light chain hypervariable regions (HVR-L1, HVR-L2 and HVR-L3) and three heavy chain hypervariable regions (HVR-H1, HVR-H2 and HVR-H3)

| HVR-L1 | RSSQSLLHSNGYNYLD | (SEQ ID NO: 51) |
| HVR-L2 | LGVNSVS | (SEQ ID NO: 52) |
| HVR-L3 | MQALQTPWT | (SEQ ID NO: 53) |
| HVR-H1 | NHAIS | (SEQ ID NO: 54) |
| HVR-H2 | GIIPIFGTANYAQKFQG | (SEQ ID NO: 55) |
| HVR-H3 | EWADVFD | (SEQ ID NO: 56) |

The anti-CD33 antibody 15G15.33 of ADC in Table 5 comprises the light chain variable region of SEQ ID NO:57 and/or the heavy chain variable region of SEQ ID NO:58.

(SEQ ID NO: 57)
EIVLTQSPLSLPVTPGEPASISCRSSQSLLHSNGYNYLDWYLQKPGQSPQ

LLIYLGVNSVSGVPDRFSGSGSGTDFTLKISRVEAEDVGVYYCMQALQTP

WTFGQGTKVEIK (SEQ ID NO: 58)
QVQLVQSGAEVKKPGSSVKVSCKASGGIFSNHAISWVRQAPGQGLEWMGG

IIPIFGTANYAQKFQGRVTITADESTSTAFMELSSLRSEDTAVYYCAREW

ADVFDIWGQGTMVTVSS

Anti-CD33 Antibody 9C3 and Other Embodiments

| 9C3-HVR L1 | RASQGIRNDLG | (SEQ ID NO: 59) |
| 9C3-HVR L2 | AASSLQS | (SEQ ID NO: 60) |
| 9C3-HVR L3 | LQHNSYPWT | (SEQ ID NO: 61) |
| 9C3-HVR H1 | GNYMS | (SEQ ID NO: 62) |
| 9C3-HVR H2 | LIYSGDSTYYADSVKG | (SEQ ID NO: 63) |
| 9C3-HVR H3 | DGYYVSDMVV | (SEQ ID NO: 64) |

9C3 $V_L$
(SEQ ID NO: 65)
DIQMTQSPSSLSASVGDRVTITCRASQGIRNDLGWYQQKPGKAPKRLIYA

ASSLQSGVPSRFSGSGSGTEFTLTISSLQPEDFATYYCLQHNSYPWTFGQ

GTKLEIK

9C3 $V_H$
(SEQ ID NO: 66)
EVQLVESGGALIQPGGSLRLSCVASGFTISGNYMSWVRQAPGKGLEWVSL

IYSGDSTYYADSVKGRFNISRDISKNTVYLQMNSLRVEDTAVYYCVRDGY

YVSDMVVWGKGTTVTVSS

9C3.2 $V_L$
(SEQ ID NO: 67)
DIQMTQSPSSLSASVGDRVTITCRASQGIRNDLGWYQQKPGKAPKRLIYA

ASSLQSGVPSRFSGSGSGTEFTLTISSLQPEDFATYYCLQHNSYPWTFGQ

GTKLEIK

9C3.2 $V_H$
(SEQ ID NO: 68)
EVQLVESGGALIQPGGSLRLSCVASGFTISGNYMSWVRQAPGKGLEWVSL

IYSGDSTYYADSVKGRFTISRDISKNTVYLQMNSLRVEDTAVYYCVRDGY

YVSDMVVWGKGTTVTVSS

-continued

9C3.3 V<sub>L</sub>

(SEQ ID NO: 69)
DIQMTQSPSSLSASVGDRVTITCRASQGIRNDLGWYQQKPGKAPKRLIYA

ASSLQSGVPSRFSGSGSGTEFTLTISSLQPEDFATYYCLQHNSYPWTFGQ

GTKLEIK

9C3.3 V<sub>H</sub>

(SEQ ID NO: 70)
EVQLVESGGALIQPGGSLRLSCVASGFTISGNYMSWVRQAPGKGLEWVSL

IYSGDSTYYADSVKGRFSISRDISKNTVYLQMNSLRVEDTAVYYCVRDGY

YVSDMVVWGKGTTVTVSS

9C3.4 V<sub>L</sub>

(SEQ ID NO: 71)
DIQMTQSPSSLSASVGDRVTITCRASQGIRNDLGWYQQKPGKAPKRLIYA

ASSLQSGVPSRFSGSGSGTEFTLTISSLQPEDFATYYCLQHNSYPWTFGQ

GTKLEIK

9C3.4 V<sub>H</sub>

(SEQ ID NO: 72)
EVQLVESGGALIQPGGSLRLSCVASGFTISGNYMSWVRQAPGKGLEWVSL

IYSGDSTYYADSVKGRFAISRDISKNTVYLQMNSLRVEDTAVYYCVRDGY

YVSDMVVWGKGTTVTVSS

In some embodiments, the invention provides an anti-CD33 antibody comprising at least one, two, three, four, five, or six HVRs selected from (a) HVR-H1 comprising the amino acid sequence of SEQ ID NO:62; (b) HVR-H2 comprising the amino acid sequence of SEQ ID NO:63; (c) HVR-H3 comprising the amino acid sequence of SEQ ID NO:64; (d) HVR-L1 comprising the amino acid sequence of SEQ ID NO:59; (e) HVR-L2 comprising the amino acid sequence of SEQ ID NO:60; and (f) HVR-L3 comprising the amino acid sequence of SEQ ID NO:61.

In one aspect, the invention provides an antibody comprising at least one, at least two, or all three VH HVR sequences selected from (a) HVR-H1 comprising the amino acid sequence of SEQ ID NO:62; (b) HVR-H2 comprising the amino acid sequence of SEQ ID NO:63; and (c) HVR-H3 comprising the amino acid sequence of SEQ ID NO:64. In one embodiment, the antibody comprises HVR-H3 comprising the amino acid sequence of SEQ ID NO:64. In another embodiment, the antibody comprises HVR-H3 comprising the amino acid sequence of SEQ ID NO:64 and HVR-L3 comprising the amino acid sequence of SEQ ID NO:61. In a further embodiment, the antibody comprises HVR-H3 comprising the amino acid sequence of SEQ ID NO:64, HVR-L3 comprising the amino acid sequence of SEQ ID NO:61, and HVR-H2 comprising the amino acid sequence of SEQ ID NO:63. In a further embodiment, the antibody comprises (a) HVR-H1 comprising the amino acid sequence of SEQ ID NO:62; (b) HVR-H2 comprising the amino acid sequence of SEQ ID NO:63; and (c) HVR-H3 comprising the amino acid sequence of SEQ ID NO:64.

In another aspect, the invention provides an antibody comprising at least one, at least two, or all three VL HVR sequences selected from (a) HVR-L1 comprising the amino acid sequence of SEQ ID NO:59; (b) HVR-L2 comprising the amino acid sequence of SEQ ID NO:60; and (c) HVR-L3 comprising the amino acid sequence of SEQ ID NO:61. In one embodiment, the antibody comprises (a) HVR-L1 comprising the amino acid sequence of SEQ ID NO:59; (b) HVR-L2 comprising the amino acid sequence of SEQ ID NO:60; and (c) HVR-L3 comprising the amino acid sequence of SEQ ID NO:61.

In another aspect, an antibody of the invention comprises (a) a VH domain comprising at least one, at least two, or all three VH HVR sequences selected from (i) HVR-H1 comprising the amino acid sequence of SEQ ID NO:62, (ii) HVR-H2 comprising the amino acid sequence of SEQ ID NO:63, and (iii) HVR-H3 comprising an amino acid sequence selected from SEQ ID NO:64; and (b) a VL domain comprising at least one, at least two, or all three VL HVR sequences selected from (i) HVR-L1 comprising the amino acid sequence of SEQ ID NO:59, (ii) HVR-L2 comprising the amino acid sequence of SEQ ID NO:60, and (c) HVR-L3 comprising the amino acid sequence of SEQ ID NO:61.

In another aspect, the invention provides an antibody comprising (a) HVR-H1 comprising the amino acid sequence of SEQ ID NO:62; (b) HVR-H2 comprising the amino acid sequence of SEQ ID NO:63; (c) HVR-H3 comprising the amino acid sequence of SEQ ID NO:64; (d) HVR-L1 comprising the amino acid sequence of SEQ ID NO:59; (e) HVR-L2 comprising the amino acid sequence of SEQ ID NO:60; and (f) HVR-L3 comprising the amino acid sequence of SEQ ID NO:61.

In any of the above embodiments, an anti-CD33 antibody is humanized. In one embodiment, an anti-CD33 antibody comprises HVRs as in any of the above embodiments, and further comprises a human acceptor framework, e.g. a human immunoglobulin framework or a human consensus framework. In certain embodiments, the human acceptor framework is the human VL kappa I consensus (VL$_{KI}$) framework and/or the VH framework VH$_1$. In certain embodiments, the human acceptor framework is the human VL kappa I consensus (VL$_{KI}$) framework and/or the VH framework VH$_1$ comprising any one of the following mutations.

In another aspect, an anti-CD33 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:66, SEQ ID NO:68, SEQ ID NO:70, and/or SEQ ID NO:72. In certain embodiments, a VH sequence having at least 90%, 91%, 92%, 93%, 94%, 95%, 96%, 97%, 98%, or 99% identity to the amino acid sequence of SEQ ID NO:66, SEQ ID NO:68, SEQ ID NO:70, and/or SEQ ID NO:72 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO:66, SEQ ID NO:68, SEQ ID NO:70, and/or SEQ ID NO:72. In certain embodiments, a total of 1 to 5 amino acids have been substituted, inserted and/or deleted in SEQ ID NO:66, SEQ ID NO:68, SEQ ID NO:70, and/or SEQ ID NO:72. In certain embodiments, substitutions, insertions, or deletions occur in regions outside the HVRs (i.e., in the FRs). Optionally, the anti-CD33 antibody comprises the VH sequence of SEQ ID NO:66, SEQ ID NO:68, SEQ ID NO:70, and/or SEQ ID NO:72, including post-translational modifications of that sequence. In a particular embodiment, the VH comprises one, two or three HVRs selected from: (a) HVR-H1 comprising the amino acid sequence of SEQ ID NO:62, (b) HVR-H2 comprising the amino acid sequence of SEQ ID NO:63, and (c) HVR-H3 comprising the amino acid sequence of SEQ ID NO:64.

In another aspect, an anti-CD33 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:65, SEQ ID NO:67, SEQ ID NO:69, and/or SEQ ID NO:71. In certain embodiments, a VL sequence having at least 90%, 91%, 92%, 93%, 94%, 95%, 96%, 97%, 98%, or 99% identity to the amino acid sequence of SEQ ID NO:65, SEQ ID NO:67, SEQ ID NO:69, and/or SEQ ID NO:71 contains substitutions (e.g., conservative substitutions), insertions, or deletions relative to the reference sequence, but an anti-CD33 antibody comprising that sequence retains the ability to bind to CD33. In certain embodiments, a total of 1 to 10 amino acids have been substituted, inserted and/or deleted in SEQ ID NO:65, SEQ ID NO:67, SEQ ID NO:69, and/or SEQ ID NO:71. In certain embodiments, a total of 1 to 5 amino acids have been substituted, inserted and/or deleted in SEQ ID NO:65, SEQ ID NO:67, SEQ ID NO:69, and/or SEQ ID NO:71. In certain embodiments, the substitutions, insertions, or deletions occur in regions outside the HVRs (i.e., in the FRs). Optionally, the anti-CD33 antibody comprises the VL sequence of SEQ ID NO:65, SEQ ID NO:67, SEQ ID NO:69, and/or SEQ ID NO:71, including post-translational modifications of that sequence. In a particular embodiment, the VL comprises one, two or three HVRs selected from (a) HVR-L1 comprising the amino acid sequence of SEQ ID NO:59; (b) HVR-L2 comprising the amino acid sequence of SEQ ID NO:60; and (c) HVR-L3 comprising the amino acid sequence of SEQ ID NO:61.

In another aspect, an anti-CD33 antibody is provided, wherein the antibody comprises a VH as in any of the embodiments provided above, and a VL as in any of the embodiments provided above.

In one embodiment, the antibody comprises the VH and VL sequences in SEQ ID NO:66 and SEQ ID NO:65, respectively, including post-translational modifications of those sequences. In one embodiment, the antibody comprises the VH and VL sequences in SEQ ID NO:68 and SEQ ID NO:67, respectively, including post-translational modifications of those sequences. In one embodiment, the antibody comprises the VH and VL sequences in SEQ ID NO:70 and SEQ ID NO:69, respectively, including post-translational modifications of those sequences. In one embodiment, the antibody comprises the VH and VL sequences in SEQ ID NO:72 and SEQ ID NO:71, respectively, including post-translational modifications of those sequences.

In a further aspect, provided are herein are antibodies that bind to the same epitope as an anti-CD33 antibody provided herein. For example, in certain embodiments, an antibody is provided that binds to the same epitope as an anti-CD33 antibody comprising a VH sequence of SEQ ID NO:66, SEQ ID NO:68, SEQ ID NO:70, and/or SEQ ID NO:72 and a VL sequence of SEQ ID NO:65, SEQ ID NO:67, SEQ ID NO:69, and/or SEQ ID NO:71, respectively.

In a further aspect of the invention, an anti-CD33 antibody according to any of the above embodiments is a monoclonal antibody, including a human antibody. In one embodiment, an anti-CD33 antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

In a further aspect, an anti-CD33 antibody according to any of the above embodiments may incorporate any of the features, singly or in combination, as described below.

In Vitro Cell Proliferation Assays

Generally, the cytotoxic or cytostatic activity of an antibody-drug conjugate (ADC) is measured by: exposing mammalian cells having receptor proteins, e.g. HER2, to the antibody of the ADC in a cell culture medium; culturing the cells for a period from about 6 hours to about 5 days; and measuring cell viability. Cell-based in vitro assays were used to measure viability (proliferation), cytotoxicity, and induction of apoptosis (caspase activation) of the ADC of the invention.

The in vitro potency of antibody-drug conjugates (ADC) was measured by a cell proliferation assay (Example 21). The ADC showed surprising and unexpected potency in inhibition of tumor cell proliferation. Potency of the ADC was correlated with target antigen expression of the cells. The data of FIGS. 25-30 demonstrate the tested conjugates are capable of binding to the specific antigen expressed on the surface of cells and causing the death of those cells in vitro.

The CellTiter-Glo® Luminescent Cell Viability Assay is a commercially available (Promega Corp., Madison, Wis.), homogeneous assay method based on the recombinant expression of *Coleoptera* luciferase (U.S. Pat. Nos. 5,583, 024; 5,674,713; 5,700,670). This cell proliferation assay determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons.

Cell-based in vitro assays are used to measure viability (proliferation), cytotoxicity, and induction of apoptosis (caspase activation) of the ADC of the invention. Generally, the cytotoxic or cytostatic activity of an antibody-drug conjugate (ADC) is measured by: exposing mammalian cells expressing antigen such as Her2 or MUC16 polypeptide to ADC in a cell culture medium; culturing the cells for a period from about 6 hours to about 5 days; and measuring cell viability. Mammalian cells useful for cell proliferation assays for anti-MUC16 ADC include: (1) a MUC16 polypeptide-expressing cell line OVCAR-3; (2) a PC3-derived cell line engineered to stably express a portion of the MUC16 polypeptide on its cell surface (PC3/MUC16); (3) the parental PC3 cell line that does not express the MUC16 polypeptide; and (4) a PC3 cell line that does not express MUC16 polypeptide but carries the vector used to drive exogenous MUC16 expression (PC3/neo).

Figure 25:
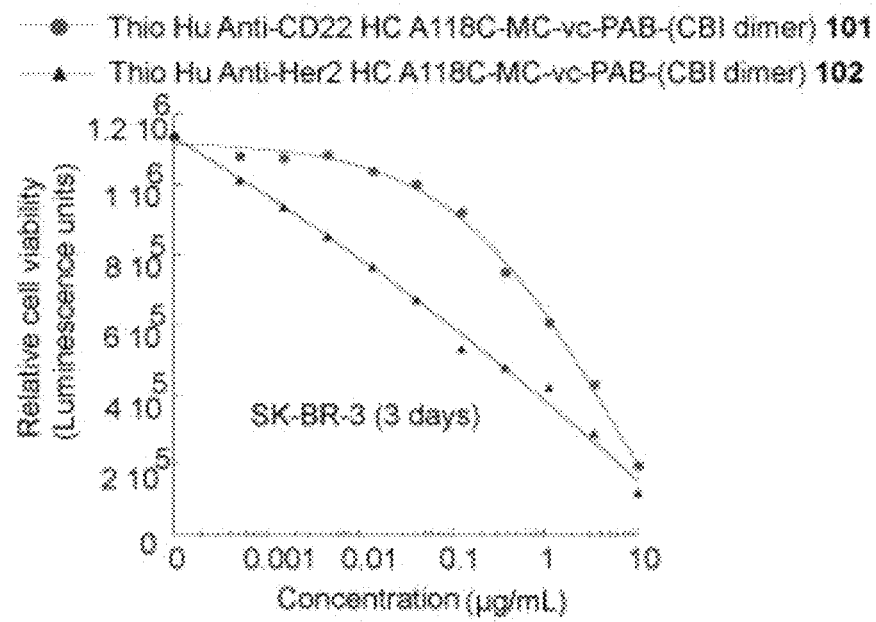
FIG. 25 shows the efficacy of antibody-drug conjugates in a plot of SK-BR-3 in vitro cell viability at 3 days versus concentrations (μg/ml) of Thio hu anti-CD22 HC A121C-MC-vc-PAB-(CBI dimer) 101 and Thio hu anti-Her2 HC A121C-MC-vc-PAB-(CBI dimer) 102.

FIG. 25 shows the efficacy of antibody-drug conjugates in a plot of SK-BR-3 in vitro cell viability at 3 days versus concentrations (μg/ml) of Thio hu anti-CD22 HC A121C-MC-vc-PAB-(CBI dimer) 101 and Thio hu anti-Her2 HC A121C-MC-vc-PAB-(CBI dimer) 102. The Her2 antigen is highly expressed in SK-BR-3 cells. The anti-Her2 ADC 102 shows linear, non-dose response cell-killing activity whereas control, off-target anti-CD22 ADC 101 shows less activity.

Figure 26:
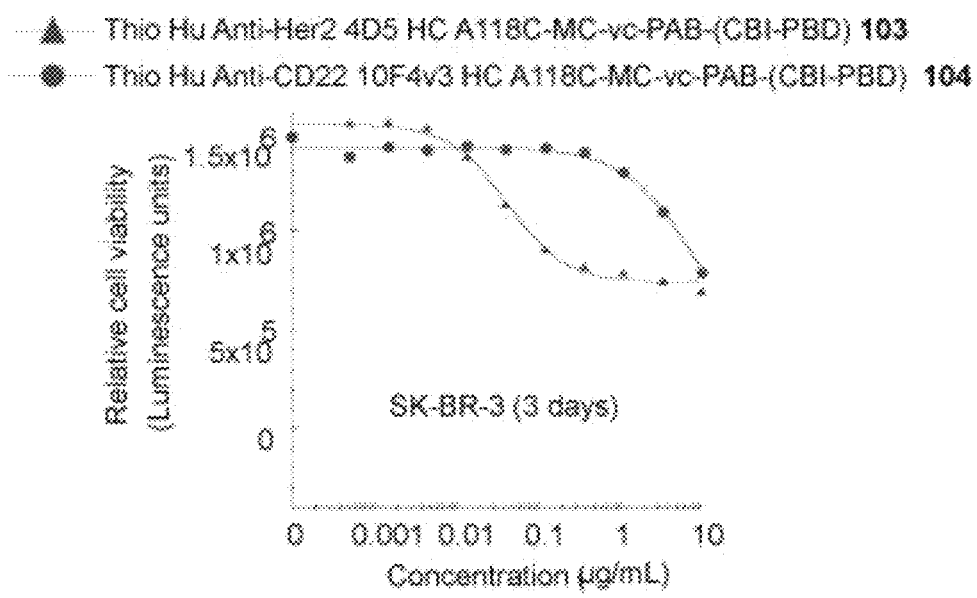
FIG. 26 shows the efficacy of antibody-drug conjugates in a plot of SK-BR-3 in vitro cell viability at 3 days versus concentrations (μg/ml) of Thio Hu Anti-Her2 4D5 HC A118C-MC-vc-PAB-(CBI-PBD) 103 and Thio Hu Anti-CD22 10F4v3 HC A118C-MC-vc-PAB-(CBI-PBD) 104

FIG. 26 shows the efficacy of antibody-drug conjugates in a plot of SK-BR-3 in vitro cell viability at 3 days versus concentrations (μg/ml) of Thio Hu Anti-Her2 4D5 HC A118C-MC-vc-PAB-(CBI-PBD) 103 and Thio Hu Anti-CD22 10F4v3 HC A118C-MC-vc-PAB-(CBI-PBD) 104. The anti-Her2 ADC 103 shows linear, non-dose response cell-killing activity whereas control, off-target anti-CD22 ADC 104 shows less activity.

Figure 27:
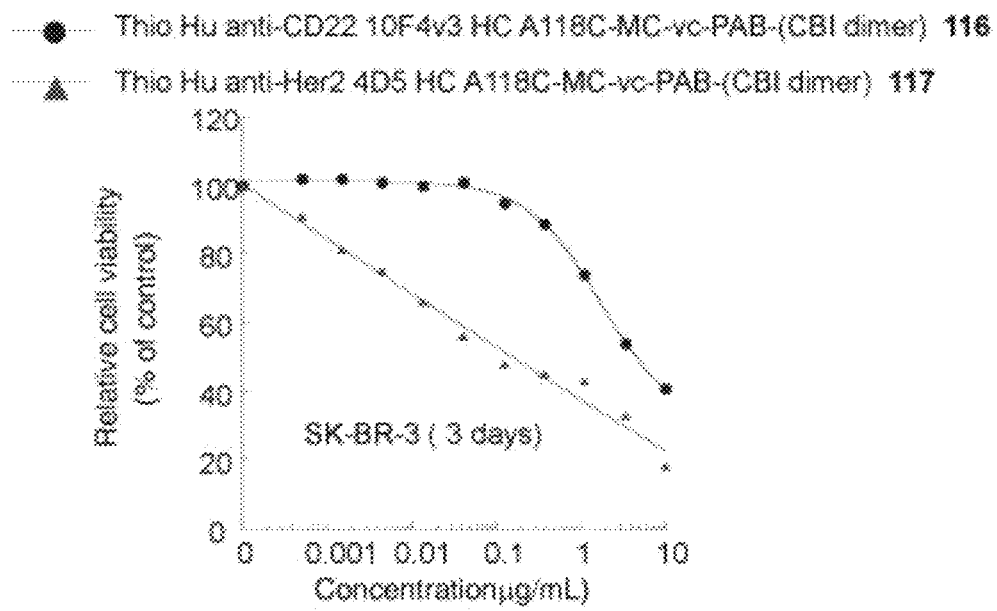
FIG. 27 shows the efficacy of antibody-drug conjugates in a plot of SK-BR-3 in vitro cell viability at 3 days versus concentrations (μg/ml) of Thio Hu Anti-CD22 10F4v3 HC A118C-MC-vc-PAB-(CBI dimer) 116 and Thio Hu Anti-Her2 4D5 HC A118C-MC-vc-PAB-(CBI dimer) 117.

FIG. 27 shows the efficacy of antibody-drug conjugates in a plot of SK-BR-3 in vitro cell viability at 3 days versus concentrations (μg/ml) of Thio Hu Anti-CD22 10F4v3 HC A118C-MC-vc-PAB-(CBI dimer) 116 and Thio Hu Anti-Her2 4D5 HC A118C-MC-vc-PAB-(CBI dimer) 117. The anti-Her2 ADC 117 shows linear, non-dose response cell-killing activity whereas control, off-target anti-CD22 ADC 116 shows less activity.

Figure 28:
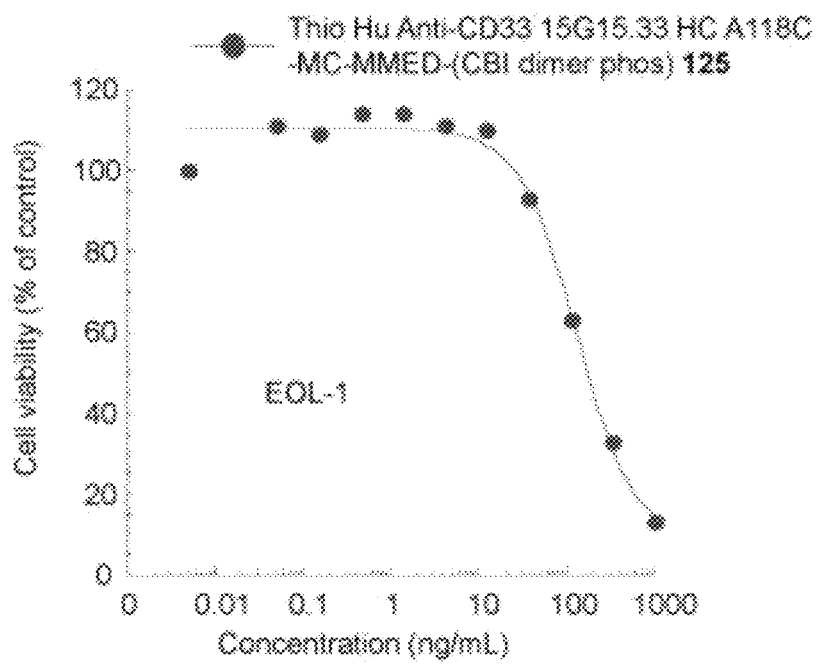
FIG. 28 shows the efficacy of antibody-drug conjugates in a plot of EOL-1 in vitro cell viability at 3 days versus concentrations (μg/ml) of Thio Hu Anti-CD33 15G15.33 HC A118C-MC-MMED-(CBI dimer phos) 125.

FIG. 28 shows the efficacy of antibody-drug conjugates in a plot of EOL-1 in vitro cell viability at 3 days versus concentrations (μg/ml) of Thio Hu Anti-CD33 15G15.33 HC A118C-MC-MMED-(CBI dimer phos) 125 which shows modest dose response cell-killing activity.

Figure 29:
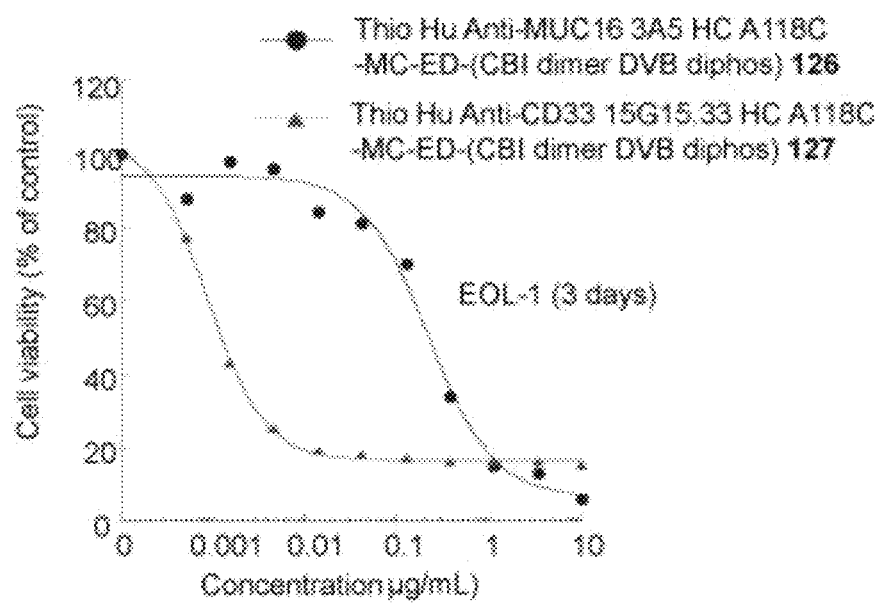
FIG. 29 shows the efficacy of antibody-drug conjugates in a plot of EOL-1 in vitro cell viability at 3 days versus concentrations (μg/ml) of Thio Hu Anti-MUC16 3A5 HC A118C-MC-ED-(CBI dimer DVB diphos) 126 and Thio Hu Anti-CD33 15G15.33 HC A118C-MC-ED-(CBI dimer DVB diphos) 127.

FIG. 29 shows the efficacy of antibody-drug conjugates in a plot of EOL-1 in vitro cell viability at 3 days versus concentrations (μg/ml) of Thio Hu Anti-MUC16 3A5 HC A118C-MC-ED-(CBI dimer DVB diphos) 126 and Thio Hu Anti-CD33 15G15.33 HC A118C-MC-ED-(CBI dimer DVB diphos) 127. The anti-CD33 ADC 127 shows potent, dose responsive cell-killing activity whereas control, off-target anti-MUC16 ADC 126 shows less activity.

Figure 30:
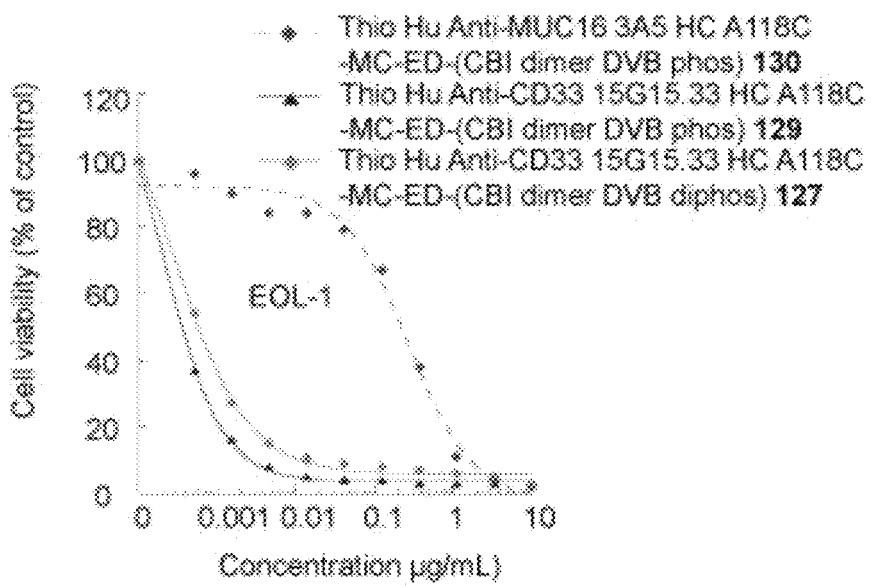
FIG. 30 shows the efficacy of antibody-drug conjugates in a plot of EOL-1 in vitro cell viability at 3 days versus concentrations (μg/ml) of Thio Hu Anti-CD33 15G15.33 HC A118C-MC-ED-(CBI dimer DVB diphos) 127, Thio Hu Anti-CD33 15G15.33 HC A118C-MC-ED-(CBI dimer DVB phos) 129, and Thio Hu Anti-MUC16 3A5 HC A118C-MC-ED-(CBI dimer DVB phos) 130.

FIG. 30 shows the efficacy of antibody-drug conjugates in a plot of EOL-1 in vitro cell viability at 3 days versus concentrations (μg/ml) of Thio Hu Anti-CD33 15G15.33 HC A118C-MC-ED-(CBI dimer DVB diphos) 127, Thio Hu Anti-CD33 15G15.33 HC A118C-MC-ED-(CBI dimer DVB phos) 129, and Thio Hu Anti-MUC16 3A5 HC A118C-MC-ED-(CBI dimer DVB phos) 130. The anti-CD33 ADC 127 and 129 shows potent, dose responsive cell-killing activity whereas control, off-target anti-MUC16 ADC 130 shows less activity.

In Vivo Efficacy

The in vivo efficacy of antibody-drug conjugates (ADC) of the invention can be measured by tumor xenograft studies in mice (Example 22). The in vivo efficacy of antibody-drug conjugates (ADC) was measured tumor growth inhibition in mice (Example 21). The ADC showed surprising and unexpected potency in inhibition of tumor growth. Efficacy of the ADC was correlated with target antigen expression of the tumor cells.

The efficacy of antibody-drug conjugates were measured in vivo by implanting allografts or xenografts of cancer cells in rodents and treating the tumors with ADC. Variable results are to be expected depending on the cell line, the specificity of antibody binding of the ADC to receptors present on the cancer cells, dosing regimen, and other factors. The in vivo efficacy of the ADC was measured using a transgenic explant mouse model expressing moderate to high levels of a tumor-associated antigen, such as Her2, MUC16, and CD33. Subjects were treated once with ADC and monitored over 3-6 weeks to measure the time to tumor doubling, log cell kill, and tumor shrinkage. Follow up dose-response and multi-dose experiments were conducted.

For example, the in vivo efficacy of an anti-HER2 ADC of the invention can be measured by a high expressing HER2 transgenic explant mouse model (Phillips et al (2008) Cancer Res. 68:9280-90). An allograft is propagated from the Fo5 mmtv transgenic mouse which does not respond to, or responds poorly to, HERCEPTIN® therapy. Subjects were treated once with ADC at certain dose levels (mg/kg) and placebo buffer control (Vehicle) and monitored over two weeks or more to measure the time to tumor doubling, log cell kill, and tumor shrinkage.

Figure 31:
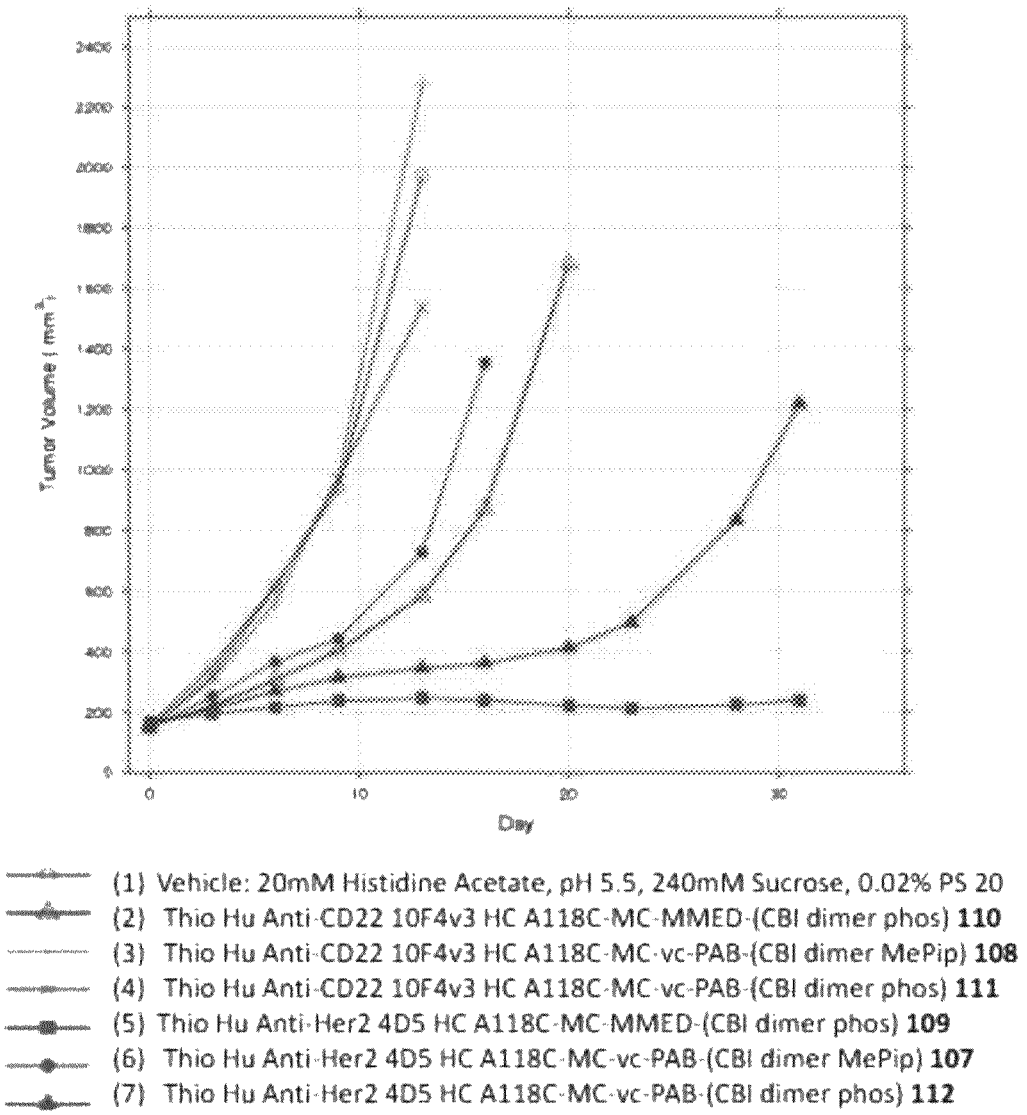
FIG. 31 shows the efficacy of antibody-drug conjugates in a plot of the in vivo fitted tumor volume change over time in MMTV-HER2 Fo5 transgenic mammary tumors inoculated into the mammary fat pad of CRL nu/nu mice after dosing once IV with: (1) Vehicle: Histidine Buffer #8: 20 mM Histidine Acetate, pH 5.5, 240 mM Sucrose, 0.02% PS 20, (2) Thio Hu Anti-CD22 10F4v3 HC A118C-MC-MMED-(CBI dimer phos) 110, (3) Thio Hu Anti-CD22 10F4v3 HC A118C-MC-vc-PAB-(CBI dimer MePip) 108, (4) Thio Hu Anti-CD22 10F4v3 HC A118C-MC-vc-PAB-(CBI dimer phos) 111, (5) Thio Hu Anti-Her2 4D5 HC A118C-MC-MMED-(CBI dimer phos) 109, (6) Thio Hu Anti-Her2 4D5 HC A118C-MC-vc-PAB-(CBI dimer MePip) 107, (7) Thio Hu Anti-Her2 4D5 HC A118C-MC-vc-PAB-(CBI dimer phos) 112. ADC were dosed at 10 mg/kg.

FIG. 31 shows the efficacy of antibody-drug conjugates in a plot of the in vivo fitted tumor volume change over time in MMTV-HER2 Fo5 transgenic mammary tumors inoculated into the mammary fat pad of CRL nu/nu mice after dosing once IV with: (1) Vehicle: Histidine Buffer #8: 20 mM Histidine Acetate, pH 5.5, 240 mM Sucrose, 0.02% PS 20, (2) Thio Hu Anti-CD22 10F4v3 HC A118C-MC-MMED-(CBI dimer phos) 110, (3) Thio Hu Anti-CD22 10F4v3 HC A118C-MC-vc-PAB-(CBI dimer MePip) 108, (4) Thio Hu Anti-CD22 10F4v3 HC A118C-MC-vc-PAB-(CBI dimer phos) 111, (5) Thio Hu Anti-Her2 4D5 HC A118C-MC-MMED-(CBI dimer phos) 109, (6) Thio Hu Anti-Her2 4D5 HC A118C-MC-vc-PAB-(CBI dimer MePip) 107, (7) Thio Hu Anti-Her2 4D5 HC A118C-MC-vc-PAB-(CBI dimer phos) 112. ADC were dosed at 10 mg/kg.

Figure 32:
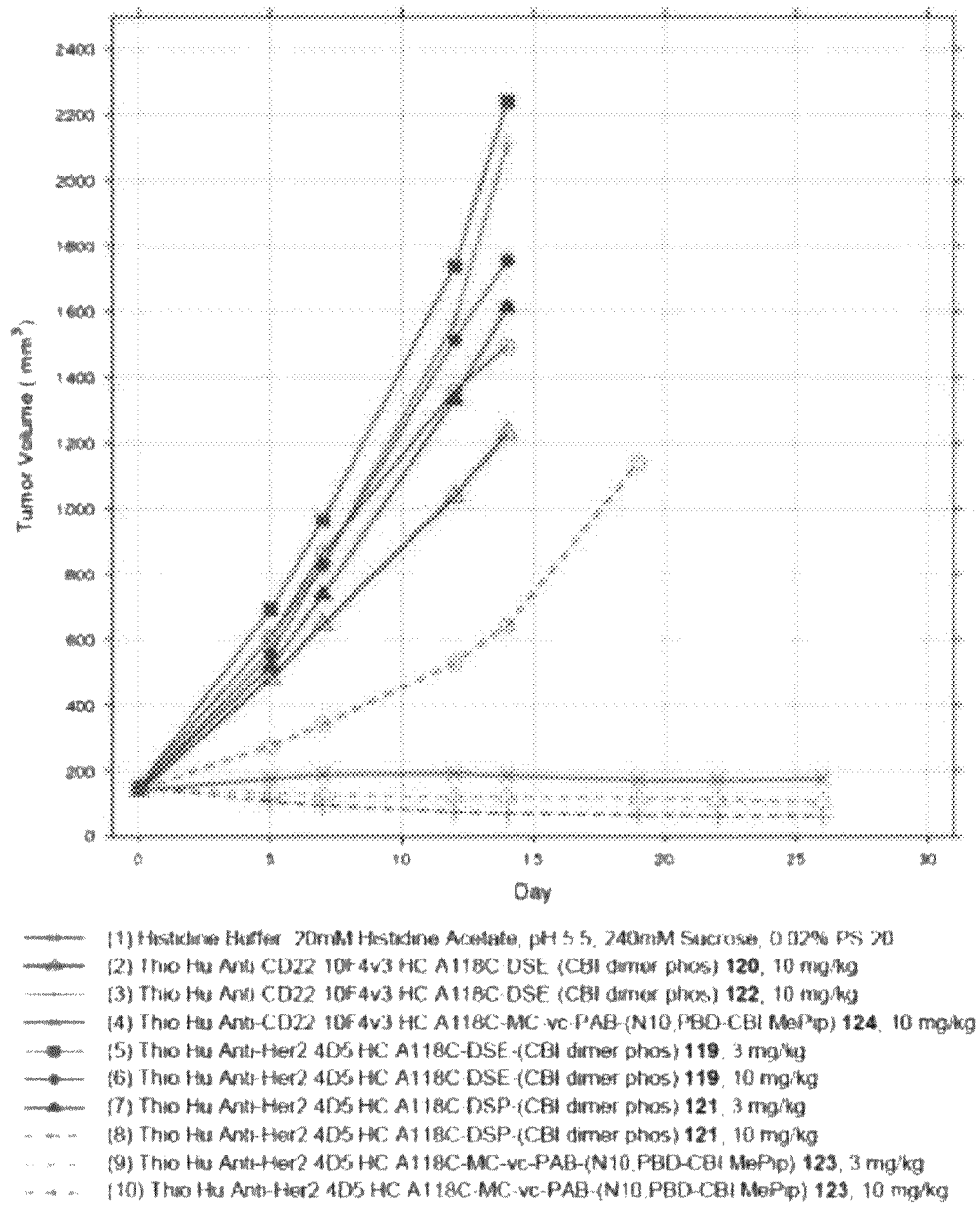
FIG. 32 shows the efficacy of antibody-drug conjugates in a plot of the in vivo fitted tumor volume change over time in MMTV-HER2 Fo5 transgenic mammary tumors inoculated into the mammary fat pad of CRL nu/nu mice after dosing once IV with: (1) Vehicle: Histidine Buffer #8: 20 mM Histidine Acetate, pH 5.5, 240 mM Sucrose, 0.02% PS 20, (2) Thio Hu Anti-CD22 10F4v3 HC A118C-DSE-(CBI dimer phos) 120, 10 mg/kg, (3) Thio Hu Anti-CD22 10F4v3 HC A118C-DSE-(CBI dimer phos) 122, 10 mg/kg, (4) Thio Hu Anti-CD22 10F4v3 HC A118C-MC-vc-PAB-(N10,PBD-CBI MePip) 124, 10 mg/kg, (5) Thio Hu Anti-Her2 4D5 HC A118C-DSE-(CBI dimer phos) 119, 3 mg/kg, (6) Thio Hu Anti-Her2 4D5 HC A118C-DSE-(CBI dimer phos) 119, 10 mg/kg, (7) Thio Hu Anti-Her2 4D5 HC A118C-DSP-(CBI dimer phos) 121, 3 mg/kg, (8) Thio Hu Anti-Her2 4D5 HC A118C-DSP-(CBI dimer phos) 121, 10 mg/kg (9) Thio Hu Anti-Her2 4D5 HC A118C-MC-vc-PAB-(N10,PBD-CBI MePip) 123, 3 mg/kg, (10) Thio Hu Anti-Her2 4D5 HC A118C-MC-vc-PAB-(N10,PBD-CBI MePip) 123, 10 mg/kg.

FIG. 32 shows the efficacy of antibody-drug conjugates in a plot of the in vivo fitted tumor volume change over time in MMTV-HER2 Fo5 transgenic mammary tumors inoculated into the mammary fat pad of CRL nu/nu mice after dosing once IV with: (1) Vehicle: Histidine Buffer #8: 20 mM Histidine Acetate, pH 5.5, 240 mM Sucrose, 0.02% PS 20, (2) Thio Hu Anti-CD22 10F4v3 HC A118C-DSE-(CBI dimer phos) 120, 10 mg/kg, (3) Thio Hu Anti-CD22 10F4v3 HC A118C-DSE-(CBI dimer phos) 122, 10 mg/kg, (4) Thio Hu Anti-CD22 10F4v3 HC A118C-MC-vc-PAB-(N10, PBD-CBI MePip) 124, 10 mg/kg, (5) Thio Hu Anti-Her2 4D5 HC A118C-DSE-(CBI dimer phos) 119, 3 mg/kg, (6) Thio Hu Anti-Her2 4D5 HC A118C-DSE-(CBI dimer phos) 119, 10 mg/kg, (7) Thio Hu Anti-Her2 4D5 HC A118C-DSP-(CBI dimer phos) 121, 3 mg/kg, (8) Thio Hu Anti-Her2 4D5 HC A118C-DSP-(CBI dimer phos) 121, 10 mg/kg (9) Thio Hu Anti-Her2 4D5 HC A118C-MC-vc-PAB-(N10, PBD-CBI MePip) 123, 3 mg/kg, (10) Thio Hu Anti-Her2 4D5 HC A118C-MC-vc-PAB-(N10,PBD-CBI MePip) 123, 10 mg/kg.

Figure 33:
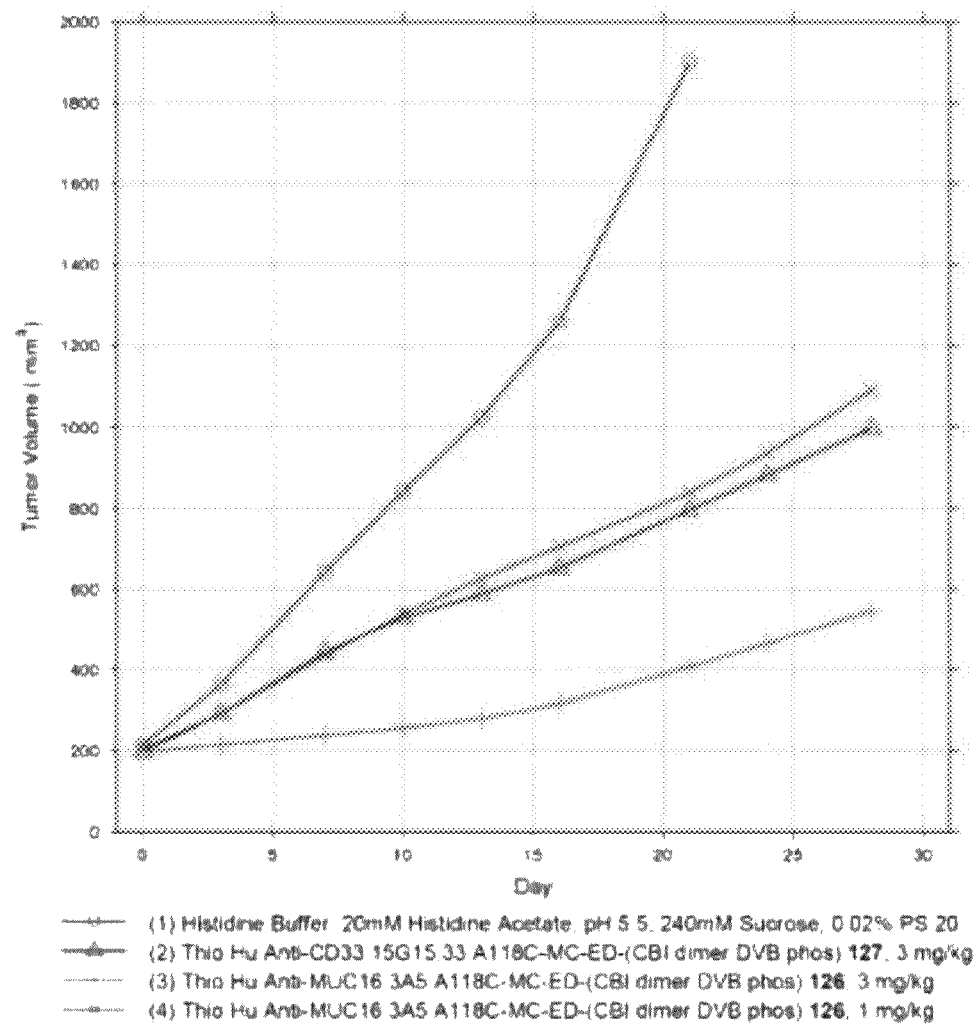
FIG. 33 shows the efficacy of antibody-drug conjugates in a plot of the in vivo fitted tumor volume change over time in OVCAR3X2.1 human ovarian tumors inoculated into C.B-17 SCID mice after dosing once IV with: (1) Vehicle: Histidine Buffer #8: 20 mM Histidine Acetate, pH 5.5, 240 mM Sucrose, 0.02% PS 20, (2) Thio Hu Anti-CD33 15G15.33 HC A118C-MC-ED-(CBI dimer DVB diphos) 127, 3 mg/kg, (3) Thio Hu Anti-MUC16 3A5 HC A118C-MC-ED-(CBI dimer DVB diphos) 126, 3 mg/kg, (4) Thio Hu Anti-MUC16 3A5 HC A118C-MC-ED-(CBI dimer DVB diphos) 126, 1 mg/kg.

FIG. 33 shows the efficacy of antibody-drug conjugates in a plot of the in vivo fitted tumor volume change over time in OVCAR3X2.1 human ovarian tumors inoculated into C.B-17 SCID mice after dosing once IV with: (1) Vehicle: Histidine Buffer #8: 20 mM Histidine Acetate, pH 5.5, 240 mM Sucrose, 0.02% PS 20, (2) Thio Hu Anti-CD33 15G15.33 HC A118C-MC-ED-(CBI dimer DVB diphos) 127, 3 mg/kg, (3) Thio Hu Anti-MUC16 3A5 HC A118C-MC-ED-(CBI dimer DVB diphos) 126, 3 mg/kg, (4) Thio Hu Anti-MUC16 3A5 HC A118C-MC-ED-(CBI dimer DVB diphos) 126, 1 mg/kg.

The anti-MUC16 antibody of ADC 126, and including 3A5 and 11D10 variants, have been described in WO 2007/001851; U.S. Pat. No. 7,989,595; 8,449,883, the contents of which are incorporated by reference. The 3A5 monoclonal antibody binds multiple sites of the MUC16 polypeptide with 433 pM affinity by OVCAR-3 Scatchard analysis (Chen et al (2007) Cancer Res. 67(10): 4924-4932)

Figure 34:
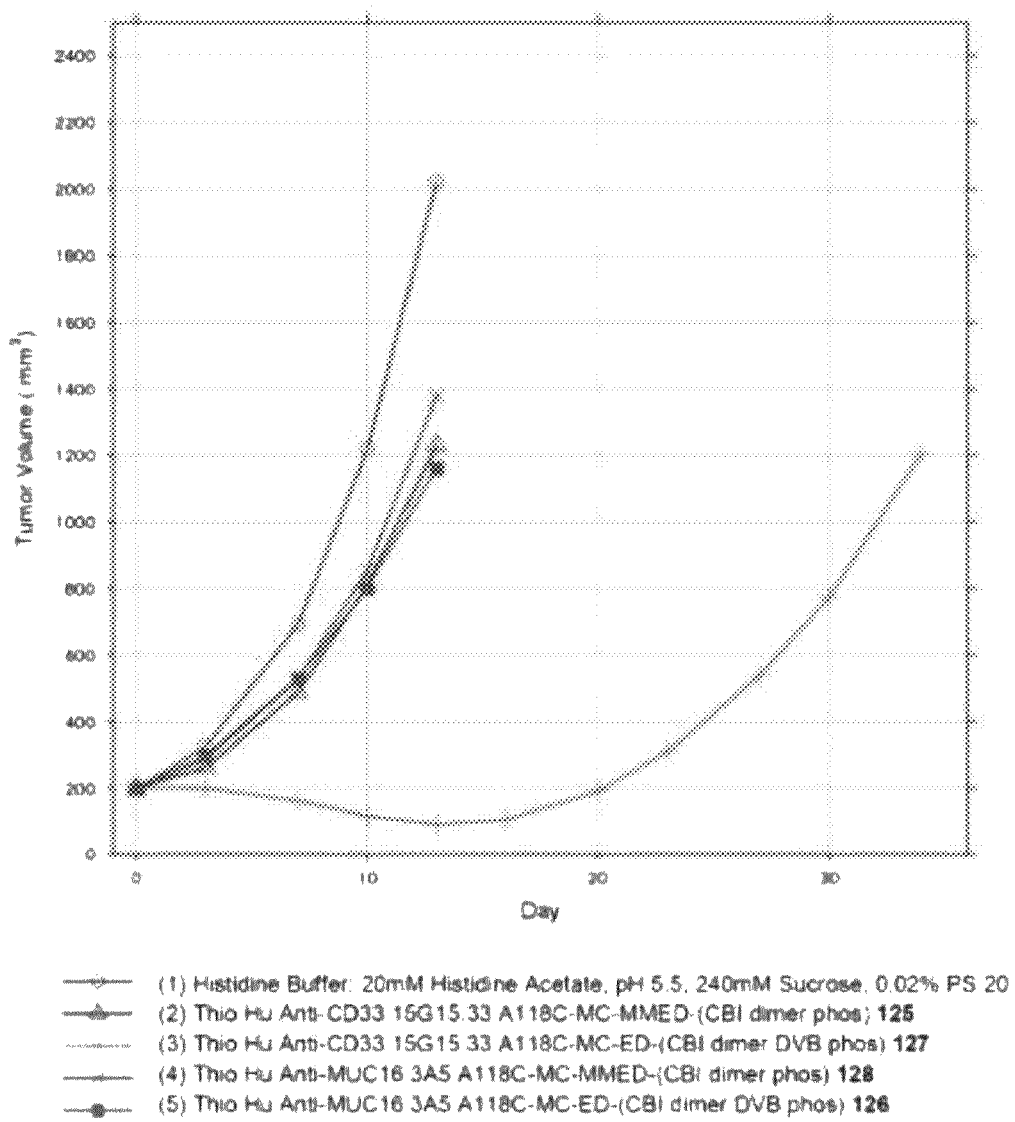
FIG. 34 shows the efficacy of antibody-drug conjugates in a plot of the in vivo fitted tumor volume change over time in HL-60 human acute myeloid leukemia inoculated into C.B-17 SCID mice after dosing once IV at 20 μg/m2 with: (1) Vehicle: Histidine Buffer #8: 20 mM Histidine Acetate, pH 5.5, 240 mM Sucrose, 0.02% PS 20, (2) Thio Hu Anti-CD33 15G15.33 HC A118C-MC-MMED-(CBI dimer phos) 125, (3) Thio Hu Anti-CD33 15G15.33 HC A118C-MC-ED-(CBI dimer DVB diphos) 127, (4) Thio Hu Anti-MUC16 3A5 HC A118C-MC-MMED-(CBI dimer phos) 128, (5) Thio Hu Anti-MUC16 3A5 HC A118C-MC-ED-(CBI dimer DVB diphos) 126.
Figure 38A:
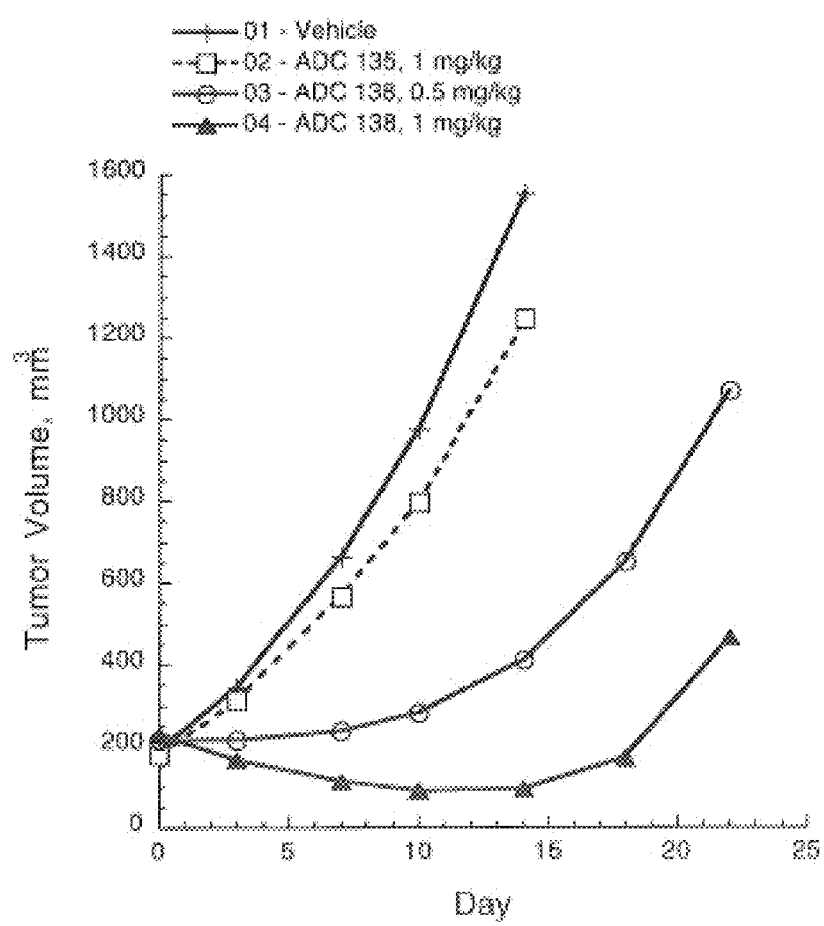
FIG. 38 shows the synthesis of 2-(pyridin-2-yldisulfanyl)propyl 2,5-bis((E)-3-((S)-1-(chloromethyl)-5-(phosphonooxy)-1H-benzo[e]indol-3(2H)-yl)-3-oxoprop-1-enyl)phenylcarbamate (Table 4, Compound No. 72, FIG. 38).
Figure 35B:
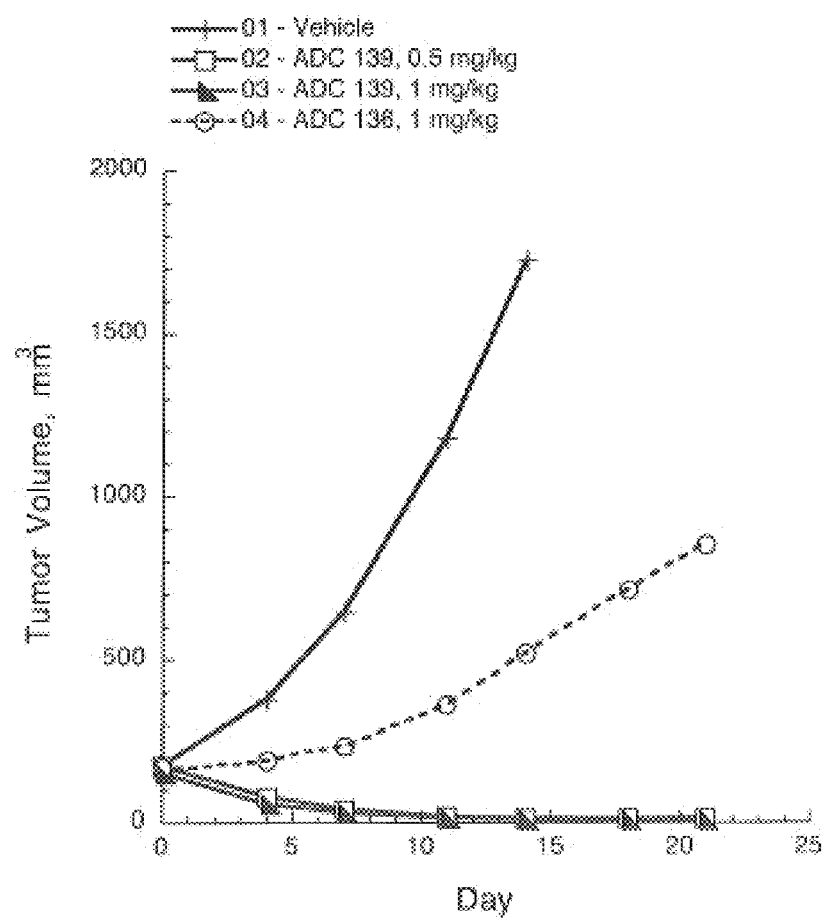
FIG. 35b shows efficacy of ADC139 in SCID mice with HL-60 human acute myeloid leukemia tumors. ADC139 demonstrated clear inhibition of tumor growth compared with vehicle group. The non-targeting control ADC136 at 1 mg/kg had a modest effect on tumor growth; however, ADC139 at the matching dose was substantially more effective, resulting in complete tumor remission.

FIG. 34 shows the efficacy of antibody-drug conjugates in a plot of the in vivo fitted tumor volume change over time in HL-60 human acute myeloid leukemia inoculated into C.B-17 SCID mice after dosing once IV at 20 µg/m2 with: (1) Vehicle: Histidine Buffer #8: 20 mM Histidine Acetate, pH 5.5, 240 mM Sucrose, 0.02% PS 20, (2) Thio Hu Anti-CD33 15G15.33 HC A118C-MC-MMED-(CBI dimer phos) 125, (3) Thio Hu Anti-CD33 15G15.33 HC A118C-MC-ED-(CBI dimer DVB diphos) 127, (4) Thio Hu Anti-MUC16 3A5 HC A118C-MC-MMED-(CBI dimer phos) 128, (5) Thio Hu Anti-MUC16 3A5 HC A118C-MC-ED-(CBI dimer DVB diphos) 126.

Administration of Antibody-Drug Conjugates

The antibody-drug conjugates (ADC) of the invention may be administered by any route appropriate to the condition to be treated. The ADC will typically be administered parenterally, i.e. infusion, subcutaneous, intramuscular, intravenous, intradermal, intrathecal and epidural.

Pharmaceutical Formulations

Pharmaceutical formulations of therapeutic antibody-drug conjugates (ADC) of the invention are typically prepared for parenteral administration, i.e. bolus, intravenous, intratumor injection with a pharmaceutically acceptable parenteral vehicle and in a unit dosage injectable form. An antibody-drug conjugate (ADC) having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation or an aqueous solution.

Antibody-Drug Conjugate Treatments

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant solid tumors and hematological disorders such as leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis, Sjögren's syndrome, scleroderma, lupus such as systemic lupus erythematosus (SLE) and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight Articles of Manufacture In another embodiment of the invention, an article of manufacture, or "kit", containing materials useful for the treatment of the disorders described above is provided. The article of manufacture comprises a container and a label or package insert on or associated with the container. Suitable containers include, for example, bottles, vials, syringes, blister pack, etc. The containers may be formed from a variety of materials such as glass or plastic. The container holds an antibody-drug conjugate (ADC) composition which is effective for treating the condition and may have a sterile access port (for example the container may be an intravenous solution bag or a vial having a stopper pierceable by a hypodermic injection needle). At least one active agent in the composition is an ADC. The label or package insert indicates that the composition is used for treating the condition of choice, such as cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

Example 1 (S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yl 2-(2-bromo-N-methylacetamido)ethyl(methyl)carbamate 51

Following the procedure of L. F. Tietze, J. M. von Hof, M. Müller, B. Krewer, I. Schuberth, *Angew. Chem. Int. Ed.* (2010) 49:7336-7339, (S)-tert-Butyl 1-(chloromethyl)-5-hydroxy-1H-benzo[e]indole-3(2H)-carboxylate 51a was deprotected with HCl and acylated with glutaroyl dichloride (FIG. 1). Instead of preparative HPLC, reaction solvent was removed under vacuum and the resultant residue was triturated with methanol to give 1,5-bis((S)-1-(Chloromethyl)-5-hydroxy-1H-benzo[e]indol-3(2H)-yl)pentane-1,5-dione 51b as an off-white solid (yield 51%). $R_f$=0.50 (ethyl acetate/petroleum ether=2:1). NMR and MS data are identical to the reported value. $[\alpha]_D^{26}$=−46.3° (c=0.41, DMA).

To a solution of 51b (650 mg, 1.15 mmol) in DMA (5 mL) cooled in an ice bath was added DIPEA (0.40 mL, 2.31 mmol) and 4-nitrophenyl chloroformate (302 mg, 1.50 mmol). After the mixture was allowed to warm up to room temperature and stirred overnight, tert-butyl methyl(2-(methylamino)ethyl)carbamate (652 mg, 3.00 mmol) was added. The mixture was stirred at room temperature for 7 h and then redistributed between ethyl acetate and cold dilute aqueous NaHCO$_3$. The aqueous phase was extracted with ethyl acetate three times. The combined organic extracts were washed with water followed by brine, dried over anhydrous Na$_2$SO$_4$, and filtered through celite. The solvent was removed and the residue was further purified by column chromatography using gradient mixtures of ethyl acetate and petroleum ether (v/v 1:1 to 4:1) and then ethyl acetate only as eluents to give Boc (S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yl methyl (2-(methylamino)ethyl)carbamate 51c as an off-white solid (359 mg, 40%); mp 157° C. (dec.). $[\alpha]_D^{26}$=−45.4° (c=1.08, ethyl acetate). $^1$H NMR (DMSO) (mixture of rotamers) δ 10.35 (s, 1H), 8.25 (s, 1H), 8.08 (d, J=8.2 Hz, 1H), 8.02 (s, 1H), 7.87-7.77 (m, 2H), 7.58 (t, J=7.6 Hz, 1H), 7.50-7.42 (m, 2H), 7.31 (t, J=7.9 Hz, 1H), 4.42 (t, J=9.7 Hz, 1H), 4.36-4.31 (m, 2H), 4.25 (d, J=10.3 Hz, 1H), 4.19-4.13 (m, 2H), 4.05 (dd, J=2.9, 11.0 Hz, 1H), 3.98 (dd, J=2.6, 10.9 Hz, 1H), 3.92 (dd, J=7.2, 10.9 Hz, 1H), 3.79 (dd, J=8.5, 10.2 Hz, 1H), 3.69 (br s, 1H), 3.52-3.42 (m, 3H), 3.21-2.79 (m, 6H, 2NMe), 2.75-2.67 (m, 2H), 2.64-2.58 (m, 2H), 2.00-1.93 (m, 2H), 1.44-1.35 (m, 9H, Bu$^t$) ppm. HRMS (ESI) found m/z 777.2801 (M+H). C$_{41}$H$_{47}$Cl$_2$N$_4$O$_7$ requires 777.2816.

Also obtained from the same chromatographic separation were bis-Boc protected 51d and unprotected recovered starting material 51b as a white solid (15 mg, 2%). 51d (429 mg, 37%) was obtained as an off-white solid. $[\alpha]_D^{26}$=−32.0° (c=1.00, ethyl acetate). $^1$H NMR (DMSO) (mixture of rotamers) δ 8.25 (s, 2H), 7.95 (d, J=8.4 Hz, 2H), 7.87-7.76 (m, 2H), 7.58 (t, J=7.6 Hz, 2H), 7.44 (t, J=7.6 Hz, 2H), 4.41 (t, J=9.8 Hz, 2H), 4.32 (br s, 2H), 4.24 (d, J=10.6 Hz, 2H), 4.06-4.03 (m, 2H), 3.98 (dd, J=7.3, 10.8 Hz, 2H), 3.69 (br s, 2H), 3.52-3.43 (m, 2H), 3.21-2.79 (m, 12H, 4NMe), 2.75-2.69 (m, 2H), 2.66-2.58 (m, 2H), 1.99-1.95 (m, 2H), 1.44-1.35 (m, 18H, 2Bu$^t$) ppm. HRMS (ESI) found m/z 1013.3991 (M+Na). C$_{51}$H$_{64}$Cl$_2$N$_6$NaO$_{10}$ requires 1013.3991.

To a solution of 51c (200 mg, 0.26 mmol) in DCM (3 mL) cooled in an ice bath was added trifluoroacetic acid, TFA (1.5 mL) dropwise. The mixture was allowed to warm to room temperature and stirred for 2 h. All volatile components were removed to give crude trifluoroacetate salt of (S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yl methyl(2-(methylamino)ethyl)carbamate 51e as an off-white solid, which was used directly. $^1$H NMR (DMSO) (mixture of rotamers) δ 10.36 (s, 1H), 8.64 (br s, 1H), 8.48 (br s, 1H), 8.35 (s, 1H), 8.08 (d, J=8.1 Hz, 1H), 8.01 (s, 1H), 7.97 (d, J=8.4 Hz, 1H), 7.94-7.88 (m, 1H), 7.78 (d, J=8.4 Hz, 1H), 7.61-7.57 (m, 2H), 7.51-7.45 (m, 2H), 7.34-7.30 (m, 1H), 4.43 (t, J=9.8 Hz, 1H), 4.36-4.31 (m, 2H), 4.26 (d, J=10.4 Hz, 1H), 4.18-4.14 (m, 2H), 4.06 (dd, J=2.9, 11.0 Hz, 1H), 4.00 (dd, J=2.7, 10.8 Hz, 1H), 3.94 (dd, J=7.5, 11.0 Hz, 1H), 3.89-3.84 (m, 1H), 3.79 (dd, J=8.1, 10.8 Hz, 1H), 3.63 (t, J=5.7 Hz, 1H), 3.33-3.30 (m, 6H, 2NMe), 2.78-2.55 (m, 6H), 2.00-1.94 (m, 2H) ppm. HRMS (ESI) found m/z 677.2306 (M+H). C$_{36}$H$_{39}$Cl$_2$N$_4$O$_5$ requires 677.2292.

At −5° C., to a solution of 51e in THF (4 mL), was added a drop of DIPEA followed by bromoacetyl bromide (34 μL, 0.39 mmol) slowly and then the rest of DIPEA (448 μL, 2.57 mmol in total). The mixture was allowed to warm up to room temperature and stirred for 1 h. All volatile components were removed by rotary evaporator and then high vacuum pump. The resultant residue was stirred with ethyl acetate and the insoluble solid was filtered off before the filtrate was loaded on a chromatography column. Gradient mixtures of ethyl acetate and petroleum ether (v/v 1:4 to 1:1) were used as eluents to give (S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yl 2-(2-bromo-N-methylacetamido)ethyl(methyl)carbamate 51 as an off-white solid (80 mg, 39%); mp 167-170° C. $[\alpha]_D^{26}$=−64.0° (c=0.25, ethyl acetate). $^1$H NMR (DMSO) (mixture of rotamers) δ 10.39 (s, 1H), 8.25-8.20 (m, 1H), 8.08 (d, J=8.3 Hz, 1H), 8.01 (s, 1H), 7.96 (d, J=8.3 Hz, 1H), 7.89 (d, J=7.4 Hz, 0.34H), 7.82 (d, J=7.4 Hz, 0.66H), 7.78 (d, J=8.4 Hz, 1H), 7.58 (t, J=7.6 Hz, 1H), 7.51-7.45 (m, 2H), 7.31 (t, J=7.6 Hz, 1H), 4.42 (t, J=9.6 Hz, 1H), 4.36-4.31 (m, 1H), 4.24 (d, J=10.7 Hz, 1H), 4.18-4.09 (m, 3H including CH$_2$Br), 4.07-4.03 (dd, J=2.8, 10.9 Hz, 1H), 4.00-3.97 (dd, J=2.6, 10.8 Hz, 1H), 3.96-3.91 (m, 1H), 3.82-3.75 (m, 1H), 3.70-3.68 (m, 1H), 3.58-3.43 (m, 3H), 3.26-2.89 (m, 6H, 2NMe), 2.78-2.67 (m, 2H), 2.65-2.55 (m, 2H), 1.99-1.92 (m, 2H) ppm. HRMS (ESI) found m/z 819.1316 (M+Na). C$_{38}$H$_{38}$BrCl$_2$N$_4$O$_6$ requires 819.1322.

Example 2 (11S,11aS)-tert-butyl 8-(6-((S)-1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate 52

Following the experimental procedures of Example 6, linker-drug intermediate 52 was prepared (FIGS. 7 and 8). HPLC: 96.7% pure; mp 210° C. (dec.); $^1$H NMR [(CD$_3$)$_2$SO] δ 10.03 (s, exchangeable with D$_2$O, 1H), 8.23-8.11 (m, 2H), 8.09 (d, J=7.3 Hz, exchangeable with D$_2$O, 1H), 7.85 (d, J=8.5 Hz, 1H), 7.80 (d, J=8.3 Hz, exchangeable with D$_2$O, 1H), 7.66 (d, J=8.6 Hz, 2H), 7.59-7.44 (m, 3H), 7.38 (br t, J=7.6 Hz, 1H), 7.04 (s, 1H), 6.99 (s, 2H), 6.69 (s, 1H), 6.38 (br s, exchangeable with D$_2$O, 1H), 5.99 (t, J=5.5 Hz, exchangeable with D$_2$O, 1H), 5.49-5.34 (m, 3H, reduced to 1H as d after D$_2$O, J=9.5 Hz), 5.20 (s, 2H), 4.44-4.30 (m, 2H), 4.26-4.13 (m, 3H), 4.10-3.91 (m, 3H), 3.88-3.76 (m, 1H), 3.79 (s, 3H), 3.53-3.44 (m, 1H), 3.41-3.20 (m, partially obscured by water peak, 4H), 3.09-2.88 (m, 2H), 2.66-2.42 (m, partially obscured by DMSO peak, 2H), 2.25-1.24 (m, 21H), 1.31 (s, 9H), 1.24-1.11 (m, 2H), 0.86 (d, J=6.8 Hz, 3H), 0.82 (d, J=6.7 Hz, 3H). Anal. (C$_{55}$H$_{71}$ClN$_8$O$_{11}$.H$_2$O) Calc: C, 61.53; H, 6.85; N, 10.44. Found: C, 61.39; H, 7.11; N, 10.15.

Example 3 N—((R)-1-(chloromethyl)-3-(5-((R)-1-(chloromethyl)-5-hydroxy-1H-benzo[e]indol-3(2H)-yl)-5-oxopentanoyl)-2,3-dihydro-1H-benzo[e]indol-5-yl)-6-(2,5-dioxo-2,5-dihydro-1H-pyrrol-1-yl) hexanamide 53

Acetic acid (50 mL) was added to a stirred solution of (R)-tert-butyl 1-(chloromethyl)-5-(diphenylmethyleneamino)-1H-benzo[e]indole-3(2H)-carboxylate 53a (1.00 g, 2.01 mmol) in THF-H$_2$O (150 mL/75 mL) at room temperature (r.t.) and the mixture stirred overnight (FIG. 2). After 19.5 h the THF was removed under vacuum, the mixture diluted with EtOAc, the layers well shaken and then separated. The organic layer was washed with saturated aqueous NaHCO$_3$ (4×), dried (Na$_2$SO$_4$) and solvent removed under vacuum. Purification by column chromatography on silica gel using hexanes:EtOAc 100:0 to 90:10 gave (R)-tert-butyl 5-amino-1-(chloromethyl)-1H-benzo[e]indole-3 (2H)-carboxylate 53b (382 mg, 57%) as an orange gel-like solid. $^1$H NMR δ (400 MHz, DMSO-d$_6$) 8.01 (d, J=8.4 Hz, 1H), 7.64 (d, J=8.0 Hz, 1H), 7.42-7.38 (m, 1H), 7.37 (br s, 1H), 7.22-7.18 (m, 1H), 5.91 (s, 2H), 4.08-3.91 (m, 4H), 3.66 (dd, J=10.6, 8.2 Hz, 1H), 1.53 (s, 9H).

A mixture of 53b (380 mg, 1.14 mmol), 6-(2,5-dioxo-2,5-dihydro-1H-pyrrol-1-yl)hexanoic acid (361 mg, 1.71 mmol), 1-(3-dimethylaminopropyl)-3-ethylcarbodiimide hydrochloride (EDCI.HCl, 765 mg, 3.99 mmol) and para-toluenesulfonic acid (TsOH, 49 mg, 0.285 mmol) in dry DMA (10 mL) was stirred at r.t. overnight, under nitrogen. After 17 h the solvent was removed under vacuum. The crude product was purified by column chromatography on silica gel using DCM:hexanes 75:25 to 100:0, then DCM:MeOH 99:1 to 97:3 and the product-containing fractions evaporated to dryness. The resulting material was then dissolved in EtOAc and the organic layer washed with H$_2$O (2×), dried (Na$_2$SO$_4$) and solvent removed to give (R)-tert-butyl 1-(chloromethyl)-5-(6-(2,5-dioxo-2,5-dihydro-1H-pyrrol-1-yl)hexanamido)-1H-benzo[e]indole-3(2H)-carboxylate 53c (282 mg, 47%) as a yellow solid. $^1$H NMR δ (400 MHz, DMSO-d$_6$) 9.86 (s, 1H), 8.24 (br s, 1H), 7.99 (d, J=8.4 Hz, 1H), 7.88 (d, J=8.3 Hz, 1H), 7.55-7.51 (m, 1H), 7.43-7.39 (m, 1H), 7.01 (s, 2H), 4.21-4.11 (m, 2H), 4.08-4.00 (m, 2H), 3.87 (dd, J=10.9, 6.9 Hz, 1H), 3.42 (t, J=7.0 Hz, 2H), 2.45 (t, J=7.1 Hz, 2H), 1.69-1.62 (m, 2H), 1.56-1.54 (m, 2H), 1.54 (s, 9H), 1.35-1.28 (m, 2H).

Trifluoroacetic acid (3.9 mL) and H$_2$O (0.1 mL) were added to a solution of 53c (66 mg, 0.125 mmol) in DCM (4 mL) at 0° C. The mixture was stirred at 0° C. for 1 h 20 min, then ice and H$_2$O were added. The mixture was basified to pH 8 with saturated aqueous NaHCO$_3$ at 0° C. The organic and aqueous layers were separated, the organic layer washed with H$_2$O (1×), dried (Na$_2$SO$_4$) and solvent removed under vacuum to give (R)—N-(1-(chloromethyl)-2,3-dihydro-1H-benzo[e]indol-5-yl)-6-(2,5-dioxo-2,5-dihydro-1H-pyrrol-1-yl)hexanamide 53d (50 mg, 94%) as a yellow solid which was used in the next step without purification. $^1$H NMR δ (400 MHz, DMSO-d$_6$) 9.70 (s, 1H), 7.87 (d, J=8.5 Hz, 1H), 7.64 (d, J=8.2 Hz, 1H), 7.39 (ddd, J=8.1, 6.9, 1.0 Hz, 1H), 7.21-7.15 (m, 2H), 7.01 (s, 2H), 5.92 (s, 1H), 4.02-3.96 (m, 1H), 3.85 (dd, J=10.8, 3.5 Hz, 1H), 3.69 (t, J=9.3 Hz, 1H), 3.63-3.55 (m, 2H), 3.42 (t, J=7.0 Hz, 2H), 2.42 (t, J=7.1 Hz, 2H), 1.64 (td, J=15.2, 7.6 Hz, 2H), 1.55 (td, J=14.5, 7.2 Hz, 2H), 1.35-1.26 (m, 2H).

A mixture of 53d (50 mg, 0.117 mmol), (R)-5-(1-(chloromethyl)-5-hydroxy-1H-benzo[e]indol-3(2H)-yl)-5-oxopentanoic acid 53e (56 mg, 0.161 mmol), 1-(3-dimethylaminopropyl)-3-ethylcarbodiimide hydrochloride EDCI.HCl (58 mg, 0.303 mmol) and TsOH (8 mg, 0.0465 mmol) in dry DMA (2 mL) was stirred at r.t. overnight, under nitrogen. After 19 h the mixture was diluted with H$_2$O and a solid precipitated out of solution. The aqueous suspension was extracted with EtOAc (1×), DCM (1×), DCM:MeOH 95:5 (1×) and the combined organics dried (Na$_2$SO$_4$) and solvents removed under vacuum. The crude product was purified by column chromatography on silica gel using DCM:MeOH 100:0 to 94:6 to give N—((S)-1-(chloromethyl)-3-(5-((S)-1-(chloromethyl)-5-hydroxy-1H-benzo[e]indol-3 (2H)-yl)-5-oxopentanoyl)-2,3-dihydro-1H-benzo[e]indol-5-yl)-6-(2,5-dioxo-2,5-dihydro-1H-pyrrol-1-yl)hexanamide 53 (15 mg, 17%, HPLC purity: 82.3%) as a yellow solid. $^1$H NMR δ (400 MHz, DMSO-d$_6$) 10.35 (s, 1H), 9.88 (s, 1H), 8.58 (s, 1H), 8.08 (d, J=8.2 Hz, 1H), 8.02 (s, 1H), 7.96 (d, J=8.3 Hz, 1H), 7.92 (d, J=8.4 Hz, 1H), 7.78 (d, J=8.3 Hz, 1H), 7.55 (t, J=7.4 Hz, 1H), 7.51-7.47 (m, 1H), 7.46-7.42 (m, 1H), 7.33-7.30 (m, 1H), 7.01 (s, 2H), 4.42-4.28 (m, 3H), 4.25-4.13 (m, 3H), 4.01 (ddd, J=19.6, 10.9, 2.6 Hz, 2H), 3.90 (dd, J=10.9, 7.5 Hz, 1H), 3.79 (dd, J=10.8, 8.1 Hz, 1H), 3.43 (t, J=6.7 Hz, 2H), 2.77-2.57 (m, 4H), 2.46-2.43 (m, 2H), 2.01-1.96 (m, 2H), 1.70-1.62 (m, 2H), 1.60-1.53 (m, 2H), 1.36-1.28 (m, 2H). HRMS m/z 777.2186 [(M+Na)$^+$ calcd. for C$_{41}$H$_{40}$Cl$_2$N$_4$NaO$_6$ 777.2217].

Example 3a 1-((S)-5-amino-1-(chloromethyl)-1H-benzo[e]indol-3(2H)-yl)-5-((S)-1-(chloromethyl)-5-hydroxy-1H-benzo[e]indol-3(2H)-yl)pentane-1,5-dione 53j 10% Pd/C (1.5 g) was added to a stirred solution of (S)-5-(5-(benzyloxy)-1-(chloromethyl)-1H-benzo[e]indol-3 (2H)-yl)-5-oxopentanoic acid 57c (2.00 g, 4.57 mmol) in THF-25% aqueous NH$_4$HCO$_2$ (60 mL/23 mL) at −20° C., under nitrogen (FIG. 3). The reaction mixture was stirred at −15 to −10° C. for 3.5 hrs. The reaction mixture was then kept at −20° C. overnight. After 17.5 h the mixture was warmed to −10° C. and stirred at −10 to −5° C. for 5 h. The mixture was then allowed to warm to 0° C. and stirred at this temperature for 30 mins, then diluted with MeOH, filtered through celite, the celite plug washed with MeOH (3×) and the solvents concentrated under vacuum until a solid precipitated out of solution. This was then diluted with H$_2$O (150 mL) and hexanes (150 mL) and stirred at r.t. while being acidified to pH 1 with concentrated HCl. The mixture was stirred for a further 30 min and the solid then collected by filtration and washed with H$_2$O and hexanes and dried to give (S)-5-(1-(chloromethyl)-5-hydroxy-1H-benzo[e]indol-3(2H)-yl)-5-oxopentanoic acid 53h (1.43 g, 90%) as a beige solid. $^1$H NMR δ (400 MHz, DMSO-d$_6$) 12.07 (br s, 1H), 10.35 (s, 1H), 8.08 (d, J=8.0 Hz, 1H), 7.98 (s, 1H), 7.77 (d, J=8.3 Hz, 1H), 7.50-7.46 (m, 1H), 7.33-7.29 (m, 1H), 4.30 (t, J=10.4 Hz, 1H), 4.14-4.12 (m, 2H), 3.98 (dd, J=10.9, 2.8

Hz, 1H), 3.78 (dd, J=10.8, 7.8 Hz, 1H), 2.63-2.45 (m, 2H), 2.35 (t, J=7.4 Hz, 2H), 1.89-1.78 (m, 2H).

Hydrogen chloride gas (HCl) was bubbled through a solution of (S)-tert-butyl 1-(chloromethyl)-5-(diphenylmethyleneamino)-1H-benzo[e]indole-3(2H)-carboxylate 53f (425 mg, 0.855 mmol) in dry dioxane (12 mL) (over 3 A molecular sieves), at r.t. (FIG. 3). A solid precipitated out of solution and the solvent was removed under vacuum after 15 min. The crude solid, (S)-1-(chloromethyl)-N-(diphenylmethylene)-2,3-dihydro-1H-benzo[e]indol-5-amine 53g was used in the next step without purification. Dry DMA (10 mL) was added to a mixture of 53g, (S)-5-(1-(chloromethyl)-5-hydroxy-1H-benzo[e]indol-3(2H)-yl)-5-oxopentanoic acid 53h (327 mg, 0.941 mmol), EDCI.HCl (573 mg, 2.99 mmol) and 3A (angstrom) molecular sieves at r.t., under nitrogen. After 2 days and 19.5 h the solvent was removed under vacuum. The crude material was purified by column chromatography on silica gel using DCM:MeOH 100:0 to 90:10, and the material then chromatographed again using hexanes: DCM 100:0 to 50:50 to 0:100, then DCM:MeOH 99:1 to 98:2 to give 1-((S)-1-(chloromethyl)-5-(diphenylmethyleneamino)-1H-benzo[e]indol-3(2H)-yl)-5-((S)-1-(chloromethyl)-5-hydroxy-1H-benzo[e]indol-3(2H)-yl)pentane-1,5-dione 53i (193 mg, 31% over 2 steps from 53f). $^1$H NMR δ (400 MHz, DMSO-$d_6$) 10.35 (s, 1H), 8.08 (d, J=8.1 Hz, 1H), 8.00 (s, 1H), 7.84 (t, J=9.0 Hz, 2H), 7.79-7.74 (m, 3H), 7.62-7.57 (m, 2H), 7.54-7.46 (m, 4H), 7.40-7.36 (m, 1H), 7.33-7.29 (m, 1H), 7.27-7.22 (m, 3H), 7.09-7.08 (m, 2H), 4.34-4.26 (m, 2H), 4.22-4.12 (m, 4H), 4.01-3.97 (m, 2H), 3.83-3.76 (m, 2H), 2.69-2.50 (m, 4H), 1.93-1.86 (m, 2H). HRMS m/z 726.2264 [(M+H)$^+$ calcd for $C_{44}H_{38}Cl_2N_3O_3$ 726.2285].

Acetic acid (HOAc, 8 mL) was added to a stirred solution of 53i (190 mg, 0.261 mmol) in THF-H$_2$O (24 mL/12 mL) at r.t. and the mixture stirred overnight. After 19 h the mixture was diluted with H$_2$O and a solid precipitated out. The THF was removed under vacuum and the aqueous suspension treated with DIPEA until neutral. The solid was collected by filtration, washed with H$_2$O and dried. The solid was dissolved in DMF (1.5 mL) and diluted with MeOH causing a solid to precipitate. The solvents were decanted and hexanes:DCM 90:10 were added to the solid, the suspension was shaken and the solvents decanted. This process was repeated using hexanes:EtOAc 90:10, followed by hexanes alone. The solid was then dissolved in DMF/THF, absorbed onto silica gel and the product eluted using DCM:MeOH 100:0 to 90:10. The material was further purified by preparative HPLC (column: Synergi-MAX RP 4µ, 21.20×250 mm; flow rate: 13 mL/min; mobile phase: solvent A: H$_2$O/TFA pH 2.5, solvent B: MeCN/H$_2$O 90:10; method: isocratic, solvent A:solvent B 20:80, 15 min; wavelength: 254 nm, 330 nm) to give 1-((S)-5-amino-1-(chloromethyl)-1H-benzo[e]indol-3(2H)-yl)-5-((S)-1-(chloromethyl)-5-hydroxy-1H-benzo[e]indol-3(2H)-yl)pentane-1,5-dione 53j, 30 mg, 22%, HPLC purity: 87.9%) as a white solid. $^1$H NMR δ (400 MHz, DMSO-$d_6$) 10.36 (s, 1H), 8.08 (d, J=8.1 Hz, 1H), 8.04-8.02 (m, 2H), 7.79-7.77 (m, 2H), 7.69 (d, J=8.3 Hz, 1H), 7.51-7.47 (m, 1H), 7.42 (t, J=7.5 Hz, 1H), 7.34-7.30 (m, 1H), 7.23 (t, J=7.6 Hz, 1H), 5.91 (s, 2H), 4.36-4.26 (m, 2H), 4.19-4.13 (m, 3H), 4.08-4.04 (m, 1H), 4.01-3.93 (m, 2H), 3.79 (dd, J=10.7, 8.2 Hz, 1H), 3.70 (dd, J=10.5, 8.9 Hz, 1H), 2.75-2.66 (m, 2H), 2.63-2.54 (m, 2H), 2.00-1.93 (m, 2H). HRMS m/z 584.1456 [(M+Na)$^+$ calcd for $C_{31}H_{29}Cl_2N_3NaO_3$ 584.1478]. [t]D$^{28}$=−37.6° (c=0.559, DMSO).

Example 3b 1-((R)-5-amino-1-(chloromethyl)-1H-benzo[e]indol-3 (2H)-yl)-5-((R)-1-(chloromethyl)-5-hydroxy-1H-benzo[e]indol-3(2H)-yl)pentane-1,5-dione 53p Triethylamine (Et$_3$N, 0.54 mL, 3.89 mmol) and triflic anhydride (0.60 mL, 3.60 mmol) were added to a stirred solution of (R)-tert-butyl 1-(chloromethyl)-5-hydroxy-1H-benzo[e]indole-3(2H)-carboxylate 53k (1.00 g, 3.00 mmol) in DCM (100 mL) at 0° C. (FIG. 4). The reaction was stirred at 0° C. for 20 min, then diluted with H$_2$O, the layers were separated and the aqueous layer was extracted with DCM (1×). The combined organic layers were dried (Na$_2$SO$_4$) and solvent was removed under vacuum. Purification by column chromatography on silica gel using hexanes:EtOAc 100:0 to 96:4 gave (R)-tert-butyl 1-(chloromethyl)-5-(trifluoromethylsulfonyloxy)-1H-benzo[e]indole-3(2H)-carboxylate 53l (1.30 g, 93%) as an orange foamy solid. $^1$H NMR δ (400 MHz, CDCl$_3$) 8.30 (br s, 1H), 8.03 (d, J=8.5 Hz, 1H), 7.76 (d, J=8.4 Hz, 1H), 7.62-7.58 (m, 1H), 7.53-7.49 (m, 1H), 4.32 (br s, 1H), 4.20-4.15 (m, 1H), 4.09-4.03 (m, 1H), 3.92 (dd, J=11.2, 2.8 Hz, 1H), 3.54-3.49 (m, 1H), 1.61 (s, 9H).

A solution of 53l (1.30 g, 2.79 mmol) in dry THF (60 mL, degassed) was added to a mixture of Cs$_2$CO$_3$ (1.27 g, 3.91 mmol), BINAP (209 mg, 0.336 mmol) and Pd(OAc)$_2$ (63 mg, 0.281 mmol), under nitrogen. Diphenylmethanimine (0.56 mL, 3.34 mmol) was then added and the mixture refluxed overnight, under nitrogen. After 20 h the reaction temperature was reduced to 60-65° C. and the reaction was stirred at this temperature under nitrogen for 1 day. Additional THF (10 mL) was added and the mixture stirred at the same temperature for another day before more THF (25 mL) was again added to the mixture. After another day additional portions of Pd(OAc)$_2$ (19 mg, 0.0846 mmol), BINAP (52 mg, 0.0835 mmol) and THF (30 mL) were added and the mixture heated at 70° C. overnight, under nitrogen. After a further 28 h additional portions of Pd(OAc)$_2$ (31 mg, 0.138 mmol), BINAP (104 mg, 0.167 mmol) were again added and the reaction continued for 22 h. The reaction mixture was then cooled to r.t., diluted with DCM, filtered through celite, the celite plug washed with DCM until there was no more color in the washings and the filtrate evaporated under vacuum. Purification by column chromatography on silica gel using hexanes:DCM 100:0 to 50:50 gave (R)-tert-butyl 1-(chloromethyl)-5-(diphenylmethyleneamino)-1H-benzo[e]indole-3(2H)-carboxylate 53a (1.19 g, 85%) as a yellow, foamy solid. $^1$H NMR δ (400 MHz, DMSO-$d_6$) 7.85 (d, J=8.3 Hz, 1H), 7.80 (d, J=8.4 Hz, 1H), 7.75 (d, J=7.2 Hz, 2H), 7.61-7.57 (m, 1H), 7.54-7.49 (m, 3H), 7.37-7.33 (m, 1H), 7.30-7.23 (m, 3H), 7.06 (d, J=6.8 Hz, 2H), 4.13-4.02 (m, 2H), 4.00-3.94 (m, 2H), 3.77 (dd, J=10.9, 7.5 Hz, 1H), 1.46 (s, 9H), 1H not observed. [α]$_D^{27}$=+101° (c=1.04, DCM).

Hydrogen chloride gas (HCl (g)) was bubbled through a solution of 53a (300 mg, 0.604 mmol) in dry dioxane (10 mL) (over 3 A molecular sieves) at r.t. After 10 min a solid had precipitated out of solution and the solvent was removed under vacuum after 20 mins. The crude solid, (R)-1-(chloromethyl)-N-(diphenylmethylene)-2,3-dihydro-1H-benzo[e]indol-5-amine 53m was used in the next step without purification.

Palladium on carbon, 10% Pd/C (690 mg) was added to a stirred solution of (R)-5-(5-(benzyloxy)-1-(chloromethyl)-1H-benzo[e]indol-3(2H)-yl)-5-oxopentanoic acid 53n (1.38 g, 3.15 mmol) in THF-25% aqueous NH$_4$HCO$_2$ (40 mL/16 mL) at −10° C., under nitrogen. The reaction mixture was stirred at −10 to −5° C. for 3 h. The reaction mixture was then kept at −20° C. overnight. After 15 h at −20° C. the mixture was diluted with MeOH, filtered through celite, the celite plug washed with MeOH and the solvents concentrated under vacuum until a solid precipitated out of solution. The suspension was then diluted with $H_2O$ (130 mL) and hexanes (100 mL) and stirred at r.t. while being acidified to pH 1 with concentrated HCl. The mixture was stirred for 30 mins, let settle and the hexanes decanted. Additional hexanes (120 mL) was added and the mixture stirred for another 30 mins, the hexanes decanted again and the solid then collected by filtration and washed with $H_2O$ and hexanes and dried to give (R)-5-(1-(chloromethyl)-5-hydroxy-1H-benzo[e]indol-3(2H)-yl)-5-oxopentanoic acid 53e (925 mg, 84%) as a beige solid. $^1$H NMR δ (400 MHz, DMSO-$d_6$) 12.06 (br s, 1H), 10.35 (s, 1H), 8.08 (d, J=8.0 Hz, 1H), 7.98 (s, 1H), 7.77 (d, J=8.3 Hz, 1H), 7.50-7.46 (m, 1H), 7.33-7.29 (m, 1H), 4.30 (t, J=10.5 Hz, 1H), 4.14-4.12 (m, 2H), 3.98 (dd, J=10.9, 2.8 Hz, 1H), 3.78 (dd, J=10.8, 7.9 Hz, 1H), 2.63-2.45 (m, 2H), 2.35 (t, J=7.4 Hz, 2H), 1.89-1.78 (m, 2H).

Dry DMA (8 mL) was added to a mixture of 53m from the previous reaction, 53e (241 mg, 0.693 mmol), EDCI.HCl (404 mg, 2.11 mmol) and 3A molecular sieves at r.t., under nitrogen. The reaction mixture was stirred overnight. After 19.5 h the mixture was diluted with $H_2O$ and the resulting suspension filtered. The aqueous filtrate was extracted with EtOAc (3×) and the filtered solid dissolved in EtOAc/MeOH and combined with the EtOAc extracts. The combined organic solution was absorbed onto silica gel and the product eluted using hexanes:DCM 50:50 to 0:100, then DCM:MeOH 99.5:0.5 to 97:3 to give 1-((R)-1-(chloromethyl)-5-(diphenylmethyleneamino)-1H-benzo[e]indol-3(2H)-yl)-5-((R)-1-(chloromethyl)-5-hydroxy-1H-benzo[e]indol-3(2H)-yl)pentane-1,5-dione 53o (155 mg, 35% over 2 steps from 53a) as a dark yellow solid. $^1$H NMR δ (400 MHz, DMSO-$d_6$) 10.35 (s, 1H), 8.08 (d, J=8.0 Hz, 1H), 8.00 (s, 1H), 7.85 (t, J=8.9 Hz, 2H), 7.79-7.74 (m, 3H), 7.62-7.57 (m, 2H), 7.54-7.46 (m, 4H), 7.40-7.36 (m, 1H), 7.33-7.29 (m, 1H), 7.27-7.22 (m, 3H), 7.09-7.08 (m, 2H), 4.34-4.27 (m, 2H), 4.22-4.11 (m, 4H), 4.02-3.97 (m, 2H), 3.83-3.76 (m, 2H), 2.69-2.51 (m, 4H), 1.93-1.85 (m, 2H), NMR spectrum matches that of 53i. HRMS m/z 748.2077 [(M+Na)$^+$ calcd for $C_{44}H_{37}Cl_2N_3NaO_3$ 748.2104].

Acetic acid (HOAc, 4 mL) was added to a stirred solution of 53o (80 mg, 0.110 mmol) in THF-$H_2O$ (12 mL/6 mL) at r.t. and the mixture stirred overnight. After 18 h the mixture was diluted with $H_2O$ and a solid precipitated out. The THF was removed under vacuum and the aqueous suspension treated with DIPEA until pH 8, resulting in the precipitation of more solid. The solid was collected by filtration, dried, and purified by column chromatography on silica gel using DCM:MeOH 100:0 to 97:3 to give 1-((R)-5-amino-1-(chloromethyl)-1H-benzo[e]indol-3(2H)-yl)-5-((R)-1-(chloromethyl)-5-hydroxy-1H-benzo[e]indol-3(2H)-yl)pentane-1,5-dione 53p (20 mg, 32%) as a tan solid. $^1$H NMR δ (400 MHz, DMSO-$d_6$) 10.36 (s, 1H), 8.08 (d, J=8.2 Hz, 1H), 8.04-8.02 (m, 2H), 7.79-7.77 (m, 2H), 7.69 (d, J=8.3 Hz, 1H), 7.51-7.47 (m, 1H), 7.42 (t, J=7.5 Hz, 1H), 7.34-7.30 (m, 1H), 7.23 (t, J=7.6 Hz, 1H), 5.91 (s, 2H), 4.36-4.26 (m, 2H), 4.19-4.13 (m, 3H), 4.08-4.04 (m, 1H), 4.01-3.93 (m, 2H), 3.79 (dd, J=10.7, 8.3 Hz, 1H), 3.71 (dd, J=10.5, 8.9 Hz, 1H), 2.75-2.66 (m, 2H), 2.63-2.53 (m, 2H), 2.00-1.93 (m, 2H), NMR spectrum matches that of 53j.

Example 4 N-(4-(((S)-1-(chloromethyl)-3-(6-((S)-7-methoxy-5-oxo-2,3,5,11a-tetrahydro-1H-benzo[e]pyrrolo[1,2-a][1,4]diazepin-8-yloxy)hexanoyl)-2,3-dihydro-1H-benzo[e]indol-5-yloxy)methyl)phenyl)-6-(2,5-dioxo-2,5-dihydro-1H-pyrrol-1-yl) hexanamide 54

A mixture of (S)-(2-amino-4-hydroxy-5-methoxyphenyl)(2-(hydroxymethyl)pyrrolidin-1-yl)methanone 54a (7.6 g, 28.6 mmol), prepared by the procedures of Tercel et al (2003) J. Med. Chem 46:2132-2151, and di-t-butyl dicarbonate (12.48 g, 57.2 mmol) in anhydrous THF (140 mL) was stirred under reflux in a nitrogen atmosphere for 18 h. The reaction mixture was cooled to r.t. and 2N NaOH (57.2 mL, 114 mmol) and MeOH (70 mL) were added. The mixture was stirred at r.t. for 6 h. Volatiles were evaporated under reduced pressure at 35-40° C. (bath temperature). Ice water (250 mL) was added and the pH was adjusted to 8-9 at 0° C. The mixture was stirred with petroleum ether-ethyl acetate (20:1) (2×400 mL) at r.t. for 15 min. The organic layer was separated and discarded. The aqueous layer was extracted with DCM (4×300 mL) and the combined extracts were dried (MgSO$_4$) and evaporated under reduced pressure to give (S)-tert-butyl 5-hydroxy-2-(2-(hydroxymethyl)pyrrolidine-1-carbonyl)-4-methoxyphenylcarbamate 54b as a pink-white solid (9.36 g, 89%); mp 154-156° C.; $^1$H NMR [(CD$_3$)$_2$SO] δ 9.51 (s, 1H), 8.90 (s, 1H), 7.27 (s, 1H), 6.91 (s, 1H), 4.73 (t, J=5.8 Hz, 1H), 4.16-4.02 (m, 1H), 3.73 (s, 3H), 3.64-3.34 (m, 4H), 1.99-1.60 (m, 4H), 1.43 (s, 9H). Anal. ($C_{18}H_{26}N_2O_6$) Calc: C, 59.00; H, 7.15; N, 7.65. Found: C, 58.94; H, 7.31; N, 7.39.

To a solution of 54b (2.88 g, 7.87 mmol) and 2,2,2-trichloroethyl 6-bromohexanoate (3.86 g, 11.8 mmol), prepared by the procedures in Tercel et al (2003) J. Med. Chem 46:2132-2151, in dry DMA (7 mL) was added anhydrous K$_2$CO$_3$ (2.61 g, 18.9 mmol). The resulting mixture was stirred at r.t. for 68 h. It was poured into ice-water (600 mL) and the product was extracted into ethyl acetate (600 mL). The extracts were washed successively with cold (0° C.) aqueous 2N Na$_2$CO$_3$ solution (2×400 mL) and water (400 mL) and then dried (MgSO$_4$). Evaporation of the solvent gave a brown oil which was purified by SiO$_2$ column chromatography (DCM-ethyl acetate=2:1) to give pure (S)-2,2,2-trichloroethyl 6-(5-(tert-butoxycarbonylamino)-4-(2-(hydroxymethyl)pyrrolidine-1-carbonyl)-2-methoxyphenoxy)hexanoate 54c (3.62 g, 76%) as a pale yellow foam; mp 36-39° C.; $^1$H NMR [(CD$_3$)$_2$SO] δ 9.90 (s, 1H), 7.33 (s, 1H), 6.93 (s, 1H), 4.89 (s, 2H), 4.74 (t, J=5.8 Hz, 1H), 4.17-4.02 (m, 1H), 3.94 (t, J=6.4 Hz, 2H), 3.73 (s, 3H), 3.63-3.26 (m, 4H), 2.55-2.46 (m, 2H, partially obscured by DMSO peak), 2.00-1.55 (m, 8H), 1.53-1.36 (m, 11H). Anal. ($C_{26}H_{37}N_2O_8$) Calc: C, 51.03; H, 6.09; N, 4.58. Found: C, 51.33; H, 6.21; N, 4.35.

To a solution of 54c (3.62 g, 5.92 mmol) in dry DCM (12 mL) was added Dess-Martin periodinane (DMP, 1,1,1-triacetoxy-1,1-dihydro-1,2-benziodoxol-3(1H)-one, CAS Reg. No. 87413-09-0) (3.27 g, 7.70 mmol) portionwise over 15 min at r.t. The reaction mixture was stirred at r.t. for 45 min. It was diluted with DCM (800 mL) and washed successively with 10% Na$_2$S$_2$O$_3$ (100 mL), cold (0° C.) NaHCO$_3$ solution (400 mL), and water (300 mL) and then dried (MgSO$_4$). Evaporation of the solvent gave an amber solid which was purified by SiO$_2$ column chromatography (petroleum ether-ethyl acetate=3:4) to give (S)-tert-butyl 11-hydroxy-7-methoxy-5-oxo-8-(6-oxo-6-(2,2,2-trichloroethoxy)hexyloxy)-2,3,11,11a-tetrahydro-1H-benzo[e]pyrrolo[1,2-a][1,4]diazepine-10(5H)-carboxylate 54d (2.61g, 72%) as a sticky foam; ¹H NMR [(CD₃)₂SO] δ 7.03 (s, 1H), 6.67 (s, 1H), 6.38 (s, 1H), 5.41 (s, 1H), 4.89 (s, 2H), 4.06-3.87 (m, 2H), 3.79 (s, 3H), 3.52-3.43 (m, 1H), 3.42-3.28 (m, 1H, partially obscured by water peak), 3.27-3.20 (m, 1H), 2.08-1.82 (m, 5H), 1.81-1.71 (m, 2H), 1.71-1.61 (m, 2H), 1.53-1.40 (m, 3H), 1.31 (s, 9H). HRMS (ESI) m/z calc. for $C_{26}H_{35}Cl_3N_2NaO_8$: 631.1351. found: 631.1361 [MNa⁺].

To a stirred solution of 54d (1.80 g, 2.95 mmol) in acetone-water (3:2) (100 mL) under nitrogen was added Zn (7.72 g, 118 mmol) and NH₄Cl (6.32 g, 118 mmol). The mixture was stirred at r.t. for 28 h. The supernatant was decanted and the Zn residue was washed with aqueous NaHCO₃ (3×100 mL). The washes and the supernatant were combined and stirred with DCM (300 mL then 2×100 mL). The DCM layers were separated and discarded. The aqueous layer was acidified with conc. HCl to pH<1 at 0° C. The product was extracted into DCM (400 mL; 2×200 mL) which was dried (MgSO₄) and evaporated to give (S)-tert-butyl 8-(5-hydroperoxyhex-5-enyloxy)-11-hydroxy-7-methoxy-5-oxo-2,3,11,11a-tetrahydro-1H-benzo[e]pyrrolo[1,2-a][1,4]diazepine-10(5H)-carboxylate 54e (1.34 g, 95%) as a colorless foam; mp 65-67° C.; ¹H NMR [(CD₃)₂SO] δ 11.99 (br s, 1H), 7.04 (s, 1H), 6.67 (s, 1H), 6.37 (br s, 1H), 5.41 (d, J=9.4 Hz, 1H), 4.06-3.87 (m, 2H), 3.79 (s, 3H), 3.53-3.19 (m, 3H, partially obscured by water peak), 2.22 (t, J=7.2 Hz, 2H), 2.09-1.81 (m, 4H), 1.80-1.67 (m, 2H), 1.62-1.49 (m, 2H), 1.49-1.37 (m, 2H), 1.31 (s, 9H). Anal. ($C_{24}H_{34}N_2O_8$. ¼H₂O) Calc: C, 59.68; H, 7.20; N, 5.80. Found: C, 59.37; H, 7.20; N, 5.62.

A mixture of 54e (1.16 g, 2.42 mmol), (S)-1-(chloromethyl)-5-(4-nitrobenzyloxy)-2,3-dihydro-1H-benzo[e]indole 54f (893 mg, 2.42 mmol), EDCI.HCl (1.39 g, 7.26 mmol), and anhydrous TsOH (83 mg, 0.48 mmol) in DMA (7 mL) was stirred at room temperature under a nitrogen atmosphere for 4 h. Water (120 mL) was added and the mixture was stirred at r.t. for 15 min. The precipitated solid was filtered off, washed successively with water (4×40 mL), 0.01% NH₄OH (4×40 mL), and petroleum ether (4×40 mL) and then dried to give N-Boc-(S)-8-(6-((S)-1-(chloromethyl)-5-(4-nitrobenzyloxy)-1H-benzo[e]indol-3(2H)-yl)-6-oxohexyloxy)-11-hydroxy-7-methoxy-2,3,11,11a-tetrahydro-1H-benzo[e]pyrrolo[1,2-a][1,4]diazepin-5(10H)-one 54g (1.71 g, 85%) as a pale yellow solid; mp 130-133° C.; ¹H NMR [(CD₃)₂SO] δ 8.30 (d, J=8.8 Hz, 2H), 8.23 (d, J=8.1 Hz, 1H), 8.18 (s, 1H), 7.92-7.82 (m, 3H), 7.57 (td, J=8.2, 1.1 Hz, 1H), 7.43 (t, J=8.0 Hz, 1H), 7.03 (s, 1H), 6.69 (s, 1H), 6.39 (br s, 1H), 5.51-5.35 (m, 3H), 4.36 (t, J=9.5 Hz, 1H), 4.28-4.15 (m, 2H), 4.10-3.90 (m, 3H), 3.85 (dd, J=11.1, 7.8 Hz, 1H), 3.79 (s, 3H), 3.52-3.42 (m, 1H), 3.42-3.20 (m, 2H, partially obscured by water peak), 2.68-2.50 (m, 2H, partially obscured by DMSO peak), 2.11-1.95 (m, 1H), 1.95-1.75 (m, 5H), 1.75-1.61 (m, 2H), 1.59-1.45 (m, 2H), 1.31 (s, 9H). Anal. ($C_{44}H_{49}ClN_4O_{10}$) Calc: C, 63.72; H, 5.96; N, 6.76. Found: C, 63.33; H, 5.97; N, 6.92.

To a stirred solution 54g (1.70 g, 2.05 mmol) in a mixture of THF (90 mL), acetone (70 mL), and water (40 mL) under nitrogen was added Zn (2.68 g, 41.0 mmol) and NH₄Cl (4.39 g, 82.0 mmol). The mixture was stirred at r.t. for 45 min, then filtered through celite, washing with THF several times. The filtrate was concentrated under reduced pressure at r.t. to ca. 60 mL. A solution of 0.01% NH₄OH (400 mL) was added and the mixture was stirred at r.t. for 15 min. The solid was collected and washed successively with 0.01% NH₄OH (3×100 mL), water (3×100 mL), and petroleum ether (3×100 mL). The solid was dried to give the anilino derivative of 54g (1.16 g, 100%) which was treated with 6-(2,5-dioxo-2,5-dihydro-1H-pyrrol-1-yl)hexanoic acid (253 mg, 1.20 mmol), EDCI.HCl (576 mg, 3.00 mmol) and anhydrous TsOH (34.4 mg, 0.20 mmol) in dry DMA (2 mL). The mixture was stirred at r.t. and under nitrogen for 17 h. NaHCO₃ solution (50 mL) was added and the mixture was stirred at r.t. for 30 min. The solid was collected, washed with water, dried, and purified by a silica column chromatography (DCM-ethyl acetate=1:1) to give pure (S)-tert-butyl 8-(6-((S)-1-(chloromethyl)-5-(4-(6-(2,5-dioxo-2,5-dihydro-1H-pyrrol-1-yl)hexanamido)benzyloxy)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate 54h (194 mg, 33%) as a yellow solid, mp 128-132° C.; ¹H NMR [(CD₃)₂SO] δ 9.91 (s, 1H), 8.20-8.11 (m, 2H), 7.84 (d, J=8.3 Hz, 1H), 7.62 (d, J=8.5 Hz, 2H), 7.54 (br t, J=8.1 Hz, 1H), 7.47 (d, J=8.5 Hz, 2H), 7.38 (br t, J=8.0 Hz, 1H), 7.04 (s, 1H), 7.00 (s, 2H), 6.69 (s, 1H), 6.38 (br s, 1H), 5.45-5.37 (m, 1H), 5.20 (s, 2H), 4.36 (t, J=10.2 Hz, 1H), 4.26-4.13 (m, 2H), 4.10-3.92 (m, 3H), 3.88-3.79 (m, 1H), 3.79 (s, 3H), 3.52-3.30 (m, 4H), 3.24 (br t, J=8.9 Hz, 1H), 2.66-2.50 (m, 2H, partially obscured by DMSO peak), 2.28 (t, J=7.3 Hz, 2H), 2.08-1.95 (m, 1H), 1.95-1.76 (m, 5H), 1.76-1.64 (m, 2H), 1.64-1.20 (m, 8H), 1.31 (s, 9H). Anal. ($C_{54}H_{62}ClN_5O_{11}$) Calc: C, 65.35; H, 6.30; N, 7.06. Found: C, 65.08; H, 6.39; N, 6.67.

To a solution of N-(4-(((S)-1-(chloromethyl)-3-(6-((S)-7-methoxy-5-oxo-2,3,5,11a-tetrahydro-1H-benzo[e]pyrrolo[1,2-a][1,4]diazepin-8-yloxy)hexanoyl)-2,3-dihydro-1H-benzo[e]indol-5-yloxy)methyl)phenyl)-6-(2,5-dioxo-2,5-dihydro-1H-pyrrol-1-yl)hexanamide 54h (204 mg, 0.21 mmol) in DCM (15 mL) stirred at −10 to −11° C. under a nitrogen atmosphere was added dropwise (over 30 min) TFA containing 2.5% water (15 mL). After addition, the mixture was stirred further at this temperature for 4 h. The mixture was poured into a mixture of ice, DCM, and sufficient saturated NaHCO₃ solution to give a pH 7-8 at 0° C. The mixture was stirred at r.t. for 15 min. The DCM layer was separated and washed with more aqueous NaHCO₃ and water and then dried (MgSO₄). The solvent was evaporated at 25° C. (bath temperature) to give a yellow solid (172 mg, 94% material recovered). This crude product was purified by preparative HPLC (Synergi-Max RP column) (eluted with 30% ammonium formate buffer pH=3.5; 70% aqueous (10%) acetonitrile; flow rate: 13 mL/min) to give 54 (30 mg, 16%), HPLC: 98.8% pure; mp 190° C. (dec.); $[\alpha^{20}_D$+320° (c 0.100, DCM); ¹H NMR [CDCl₃] δ 8.29 (d, J=8.3 Hz, 1H), 8.18 (s, 1H), 7.69-7.63 (m, 2H), 7.61-7.44 (m, 6H), 7.37 (br t, J=7.3 Hz, 2H), 6.82 (s, 1H), 6.66 (s, 2H), 5.24 (s, 2H), 4.34-4.19 (m, 2H), 4.19-4.00 (m, 3H), 3.99-3.92 (m, 1H), 3.89 (s, 3H), 3.86-3.78 (m, 1H), 3.76-3.70 (m, 1H), 3.63-3.49 (m, 3H), 3.42 (t, J=10.8 Hz, 1H), 2.68-2.47 (m, 2H), 2.40-2.27 (m, 3H), 2.12-1.92 (m, 5H), 1.92-1.82 (m, 2H), 1.82-1.71 (m, 2H), 1.71-1.54 (m, 4H, partially obscured by water peak), 1.43-1.32 (m, 2H). HRMS (ESI) m/z calc. for $C_{49}H_{52}ClN_5NaO_8$: 896.3397. found: 896.3375 [MNa⁺].

Example 5 N—((S)-1-((S)-1-(4-(((S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yloxy)methyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide 55

Potassium carbonate, K₂CO₃ (2.50 g, 18.1 mmol) was added to a mixture of (S)-tert-butyl 1-(chloromethyl)-5-hydroxy-1H-benzo[e]indole-3(2H)-carboxylate 51a (2.01 g, 6.02 mmol) and 1-(bromomethyl)-4-nitrobenzene (5.20 g, 24.1 mmol) in DMF (12 mL) at room temperature (FIG. 6). The reaction mixture was stirred at r.t. for 2 h, then diluted with EtOAc and H$_2$O and the layers separated. The organic layer was washed with H$_2$O (3×), brine (1×), dried (Na$_2$SO$_4$) and solvent removed under vacuum. Purification by column chromatography on silica gel twice using hexanes:EtOAc 100:0 to 96:4 gave (S)-tert-butyl 1-(chloromethyl)-5-(4-nitrobenzyloxy)-1H-benzo[e]indole-3(2H)-carboxylate 55a (2.17 g, 77%) as a bright yellow solid. $^1$H NMR δ (400 MHz, CDCl$_3$) 8.31-8.27 (m, 3H), 7.85 (br s, 1H), 7.72 (d, J=8.4 Hz, 2H), 7.67 (d, J=8.3 Hz, 1H), 7.54 (ddd, J=8.2, 6.8, 1.2 Hz, 1H), 7.38 (ddd, J=8.2, 6.8, 1.1 Hz, 1H), 4.28-4.25 (m, 1H), 4.16-4.10 (m, 1H), 4.02-3.92 (m, 2H), 3.45 (t, J=10.6 Hz, 1H), 1.60 (s, 9H). HRMS m/z 491.1338 [(M+Na)$^+$ calcd for C$_{25}$H$_{25}$ClN$_2$NaO$_5$ 491.1344].

Reduction Method A: 55a (1.53 g, 3.26 mmol) was dissolved in THF-acetone (75 mL/60 mL). H$_2$O (30 mL) was added once 55a had dissolved. NH$_4$Cl (10.5 g, 196 mmol) and Zn powder (6.40 g, 97.9 mmol) were added and the resulting mixture stirred at r.t., under nitrogen for 1 h. The reaction mixture was then filtered through celite, the celite plug washed with DCM and the combined filtrates washed with H$_2$O (1×), dried (Na$_2$SO$_4$) and solvent removed under vacuum to give compound 55b as an orange solid. The crude product was used in the next step without purification.

Reduction Method B: Mercury-aluminium amalgam was added to a solution of 55a in THF-MeOH—H$_2$O (150 mL/50 mL/20 mL). After 15 min the reaction mixture was diluted with DCM, filtered through celite and the celite plug washed with DCM. The organics were washed with H$_2$O, dried (Na$_2$SO$_4$) and solvents removed under vacuum to give (S)-tert-butyl 5-(4-aminobenzyloxy)-1-(chloromethyl)-1H-benzo[e]indole-3(2H)-carboxylate 55b as an orange solid. The product was used in the next step without purification. $^1$H NMR δ (400 MHz, DMSO-d$_6$) 8.06 (d, J=8.6 Hz, 1H), 7.80 (d, J=8.3 Hz, 1H), 7.53-7.49 (m, 1H), 7.34-7.30 (m, 1H), 7.19 (d, J=8.2 Hz, 2H), 6.60 (d, J=8.4 Hz, 2H), 5.16 (s, 2H), 5.04 (d, J=1.3 Hz, 2H), 4.18-4.05 (m, 3H), 4.00-3.97 (m, 1H), 3.81 (dd, J=10.9, 6.9 Hz, 1H), 1.56 (s, 9H), 1H not observed.

A mixture of (S)-2-(((9H-fluoren-9-yl)methoxy)carbonylamino)-5-ureidopentanoic acid (Fmoc-L-citrulline, 3.26 g, 8.20 mmol) and 2-ethoxy-1-ethoxycarbonyl-1,2-dihydroquinoline (EEDQ, CAS Reg. No. 16357-59-8, 3.12 g, 12.6 mmol) in DMA (15 mL) was stirred at r.t., under nitrogen for 20 min. A solution of 55b (2.77 g, 6.31 mmol) in DMA (15 mL) was then added, the resulting mixture flushed with nitrogen and left stirring overnight. After 16 h the reaction mixture was poured over ice and diluted with H$_2$O. The resulting precipitate was filtered off, washed with H$_2$O, dissolved in DCM/MeOH, dried (Na$_2$SO$_4$) and solvents removed under vacuum. The crude product was purified by trituration where the product was precipitated with hexanes:EtOAc 94:6, the solvents decanted and the process repeated using hexanes:EtOAc 90:10 and then hexanes:EtOAc 95:5. The material was then columned on silica gel using DCM:MeOH 100:0 to 95:5 to give (S)-tert-butyl 5-(4-((S)-2-(((9H-fluoren-9-yl)methoxy)carbonylamino)-5-ureidopentanamido)benzyloxy)-1-(chloromethyl)-1H-benzo[e]indole-3(2H)-carboxylate 55c (4.23 g, 79% over two steps from 55a, HPLC purity: 95.3%) as a yellow solid. $^1$H NMR δ (400 MHz, DMSO-d$_6$) 10.12 (s, 1H), 8.12 (d, J=8.4 Hz, 1H), 7.89 (d, J=7.5 Hz, 2H), 7.82 (d, J=8.3 Hz, 1H), 7.77-7.74 (m, 2H), 7.70-7.67 (m, 3H), 7.55-7.49 (m, 3H), 7.42 (t, J=7.4 Hz, 2H), 7.37-7.31 (m, 3H), 6.00 (t, J=5.7 Hz, 1H), 5.43 (s, 2H), 5.22 (s, 2H), 4.29-4.27 (m, 2H), 4.24-4.05 (m, 6H), 4.01- 3.98 (m, 1H), 3.82 (dd, J=10.9, 7.0 Hz, 1H), 3.09-2.92 (m, 2H), 1.74-1.35 (m, 4H), 1.55 (s, 9H). HRMS m/z 840.3101 [(M+Na)$^+$ calcd for C$_{46}$H$_{48}$ClN$_5$NaO$_7$ 840.3134].

Piperidine (1.5 mL, 10% v/v) was added to a stirred solution of 55c (4.18 g, 5.11 mmol) in DMF (15 mL) at r.t. The reaction mixture was stirred for 1 h. The resulting suspension was diluted with hexanes:EtOAc 90:10 (100 mL) and stirred for 10 min. Two layers formed and the top layer was decanted off. The solvent in the retained bottom layer was removed under vacuum. Purification by column chromatography on silica gel using DCM:MeOH 100:0 to 85:15 gave (S)-tert-butyl 5-(4-((S)-2-amino-5-ureidopentanamido)benzyloxy)-1-(chloromethyl)-1H-benzo[e]indole-3(2H)-carboxylate 55d (2.97 g, 97%, HPLC purity: 99.1%) as a yellow powder. $^1$H NMR δ (400 MHz, DMSO-d$_6$) 9.93 (br s, 1H), 8.12 (d, J=8.3 Hz, 1H), 7.82 (d, J=8.3 Hz, 1H), 7.70 (d, J=8.6 Hz, 2H), 7.55-7.48 (m, 3H), 7.37-7.33 (m, 1H), 5.94 (t, J=5.7 Hz, 1H), 5.37 (s, 2H), 5.22 (s, 2H), 4.19-4.05 (m, 4H), 4.01-3.98 (m, 1H), 3.82 (dd, J=10.9, 7.0 Hz, 1H), 3.04-2.91 (m, 2H), 1.71-1.36 (m, 4H), 1.55 (s, 9H), 3H not observed. HRMS m/z 596.2627 [(M+H)$^+$ calcd for C$_{31}$H$_{39}$ClN$_5$O$_5$ 596.2634].

A mixture of (S)-2,5-dioxopyrrolidin-1-yl 2-(((9H-fluoren-9-yl)methoxy)carbonylamino)-3-methylbutanoate (Fmoc-Val-OSu, 3.19 g, 7.31 mmol) and 55d (2.91 g, 4.87 mmol) in DMA (15 mL) was stirred overnight at r.t., under nitrogen. After 20 h hexanes:EtOAc 80:20 (150 mL) were added and the suspension stirred for 30 min. The solvents were then decanted leaving behind a solid. This was repeated using hexanes:EtOAc 75:25 several times. The solid was then suspended in DCM:MeOH 75:25 and the suspension sonicated. The suspension was diluted with hexanes (200 mL) and the solid filtered off and washed with hexanes:EtOAc 65:35 and dried to give (S)-tert-butyl 5-(4-((S)-2-((S)-2-(((9H-fluoren-9-yl)methoxy)carbonylamino)-3-methylbutanamido)-5-ureidopentanamido)benzyloxy)-1-(chloromethyl)-1H-benzo[e]indole-3(2H)-carboxylate 55e (3.79 g, 85%, HPLC purity: 92.4%) as an orange powder. $^1$H NMR δ (400 MHz, DMSO-d$_6$) 10.12 (s, 1H), 8.14-8.12 (m, 2H), 7.89 (d, J=7.5 Hz, 2H), 7.82 (d, J=8.4 Hz, 1H), 7.75 (t, J=7.6 Hz, 2H), 7.66 (d, J=8.5 Hz, 2H), 7.55-7.48 (m, 3H), 7.45-7.30 (m, 6H), 5.98 (t, J=5.7 Hz, 1H), 5.41 (s, 2H), 5.22 (s, 2H), 4.45 (dd, J=13.6, 7.7 Hz, 1H), 4.36-4.04 (m, 6H), 4.02-3.90 (m, 2H), 3.82 (dd, J=10.8, 6.9 Hz, 1H), 3.08-2.91 (m, 2H), 2.05-1.96 (m, 1H), 1.76-1.34 (m, 4H), 1.55 (s, 9H), 0.89 (d, J=6.8 Hz, 3H), 0.86 (d, J=6.8 Hz, 3H). HRMS m/z 939.3808 [(M+Na)$^+$ calcd for C$_{51}$H$_{57}$ClN$_6$NaO$_8$ 939.3819].

Boc removal Method A: TFA (9.5 mL) was added portion wise to a suspension of 55e (685 mg, 0.747 mmol) in DCM (19 mL) at 0° C. The reaction mixture was stirred at 0° C. for 1 h 45 min. Aqueous NH$_3$ (0.25%, 100 mL) was then added portion wise to the mixture at 0° C., followed by the addition of concentrated aqueous NH$_3$ until pH 9-10. Hexanes:EtOAc 90:10 were then added and the mixture stirred at 0° C. for 40 mins, the suspension sonicated and the precipitate collected by filtration, washed with H$_2$O, H$_2$O:MeOH 80:20, hexanes:EtOAc 60:40, hexanes:Et$_2$O 50:50, hexanes and dried to give (9H-fluoren-9-yl)methyl (S)-1-((S)-1-(4-(((S)-1-(chloromethyl)-2,3-dihydro-1H-benzo[e]indol-5-yloxy)methyl)phenyl amino)-1-oxo-5-ureidopentan-2-ylamino)-3-methyl-1-oxobutan-2-ylcarbamate 55f as a brown solid (364 mg, 60%).

Boc removal Method B: BF$_3$.Et$_2$O (0.07 mL, 0.552 mmol) was added to a suspension of 55e (0.106 g, 0.116 mmol) in DCM (40 mL), at 0° C. After 1 h 50 mins the suspension was concentrated under vacuum at r.t. until only a little DCM remained. A little MeOH was added until the precipitate dissolved and the solution was then diluted with H$_2$O. A solid precipitated out and the H$_2$O was decanted. Hexanes:EtOAc 90:10 (20 mL) were added and the suspension sonicated before the solid was collected by filtration. The solid was washed with H$_2$O and hexanes and dried to give (9H-fluoren-9-yl)methyl (S)-1-((S)-1-(4-(((S)-1-(chloromethyl)-2,3-dihydro-1H-benzo[e]indol-5-yloxy)methyl)phenylamino)-1-oxo-5-ureidopentan-2-ylamino)-3-methyl-1-oxobutan-2-ylcarbamate 55f (66 mg, 70%) as a brown solid. $^1$H NMR δ (400 MHz, DMSO-d$_6$) 10.10 (s, 1H), 8.12 (d, J=7.6 Hz, 1H), 8.00 (d, J=8.3 Hz, 1H), 7.89 (d, J=7.4 Hz, 2H), 7.74 (t, J=7.7 Hz, 2H), 7.64 (d, J=8.5 Hz, 2H), 7.58 (d, J=8.3 Hz, 1H), 7.46-7.37 (m, 5H), 7.34-7.30 (m, 2H), 7.13-7.09 (m, 1H), 6.55 (s, 1H), 5.97 (t, J=5.7 Hz, 1H), 5.41 (s, 2H), 5.17 (s, 2H), 4.43 (dd, J=13.0, 7.5 Hz, 1H), 4.34-4.21 (m, 3H), 3.95-3.90 (m, 2H), 3.83 (dd, J=10.7, 3.4 Hz, 1H), 3.70-3.66 (m, 1H), 3.61-3.51 (m, 2H), 3.08-2.90 (m, 2H), 2.04-1.96 (m, 1H), 1.76-1.33 (m, 4H), 0.89 (d, J=6.8 Hz, 3H), 0.86 (d, J=6.8 Hz, 3H), 2H not observed. HRMS m/z 839.3266 [(M+Na)$^+$ calcd for C$_{46}$H$_{49}$ClN$_6$NaO$_6$ 839.3294].

A mixture of 55f (485 mg, 0.593 mmol), 53h (206 mg, 0.593 mmol), EDCI.HCl (293 mg, 1.48 mmol) and TsOH (26 mg, 0.151 mmol) in DMA (10 mL) was flushed with nitrogen and stirred at r.t. overnight. After 19.5 h the reaction mixture was diluted with H$_2$O and the resulting solid collected by filtration, washed with H$_2$O and hexanes:EtOAc 50:50. Filtration column chromatography on a plug of silica gel using DCM: MeOH 100:0 to 90:10 gave (9H-fluoren-9-yl)methyl (S)-1-((S)-1-(4-(((S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yloxy)methyl)phenylamino)-1-oxo-5-ureidopentan-2-ylamino)-3-methyl-1-oxobutan-2-ylcarbamate 55g (391 mg) used crude in the next step. HRMS m/z 1144.4169 [(M−H)$^+$ calcd for C$_{64}$H$_{64}$Cl$_2$N$_7$O$_9$ 1144.4148].

Piperidine (0.39 mL, 3.95 mmol) was added to a suspension of 55g (910 mg, 0.793 mmol) in DMF (6 mL) at r.t. After 10 min the mixture was concentrated under vacuum. Purification by column chromatography on silica gel using DCM:MeOH 95:5 to 85:15 followed by further purification by preparative HPLC (column: Synergi-MAX RP 4µ, 21.20×250 mm; flow rate: 12 mL/min; mobile phase: solvent A: H$_2$O/TFA pH 2.47, solvent B: MeCN/H$_2$O 90:10; method: gradient, solvent A:solvent B 60:40 to 22:78 in 60:40, 24 min; wavelength: 254 nm, 330 nm) gave (S)-2-((S)-2-amino-3-methylbutanamido)-N-(4-(((S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yloxy)methyl)phenyl)-5-ureidopentanamide trifluoroacetate 55h (75 mg, 9%) as a cream solid. $^1$H NMR δ (400 MHz, DMSO-d$_6$) 10.35 (s, 1H), 10.24 (s, 1H), 8.69 (d, J=7.7 Hz, 1H), 8.20 (s, 1H), 8.15 (d, J=8.4 Hz, 1H), 8.09-8.02 (m, 4H), 7.86 (d, J=8.4 Hz, 1H), 7.78 (d, J=8.4 Hz, 1H), 7.65 (d, J=8.5 Hz, 2H), 7.57-7.47 (m, 3H), 7.40-7.37 (m, 1H), 7.34-7.30 (m, 1H), 6.04 (t, J=5.8 Hz, 1H), 5.48 (br s, 2H), 5.22 (s, 2H), 4.57-4.51 (m, 1H), 4.40-4.33 (m, 2H), 4.25-4.14 (m, 4H), 4.03-3.98 (m, 2H), 3.85 (dd, J=10.7, 7.6 Hz, 1H), 3.79 (dd, J=10.3, 8.6 Hz, 1H), 3.66 (t, J=5.2 Hz, 2H), 3.09-2.97 (m, 2H), 2.75-2.57 (m, 4H), 2.11-2.06 (m, 1H), 2.01-1.96 (m, 2H), 1.78-1.70 (m, 1H), 1.68-1.58 (m, 1H), 1.53-1.40 (m, 2H), 0.95 (d, J=6.8 Hz, 3H), 0.94 (d, J=6.8 Hz, 3H). HRMS m/z 924.3672 [(M+H)$^+$ calcd for C$_{49}$H$_{56}$Cl$_2$N$_7$O$_7$ 924.3613].

Diisopropylethylamine, DIPEA (10 mg, 0.0774 mmol) in DMF (3 mL) was added to 55h (74 mg, 0.0712 mmol) and 2,5-dioxopyrrolidin-1-yl 6-(2,5-dioxo-2,5-dihydro-1H-pyrrol-1-yl)hexanoate (33 mg, 0.107 mmol), and the resulting mixture stirred at r.t., under nitrogen. After 5.5 h additional portions of DIPEA (0.9 mg, 0.00693 mmol) and 2,5-dioxopyrrolidin-1-yl 6-(2,5-dioxo-2,5-dihydro-1H-pyrrol-1-yl)hexanoate (4.4 mg, 0.0143 mmol) were added. After another 1 h an additional portion of 2,5-dioxopyrrolidin-1-yl 6-(2,5-dioxo-2,5-dihydro-1H-pyrrol-1-yl)hexanoate (8 mg, 0.0259 mmol) was added and the mixture kept at −20° C. overnight. After 15 h the mixture was warmed to r.t. and an additional portion of 2,5-dioxopyrrolidin-1-yl 6-(2,5-dioxo-2,5-dihydro-1H-pyrrol-1-yl)hexanoate (4.4 mg, 0.0143 mmol) added. After another 1 h an additional portion of 2,5-dioxopyrrolidin-1-yl 6-(2,5-dioxo-2,5-dihydro-1H-pyrrol-1-yl)hexanoate (7.5 mg, 0.0243 mmol) was added. After 1 h hexanes:EtOAc 95:5 (25 mL) were added followed by DCM (5 mL) and the mixture was stirred for 20 min. Over this period a solid precipitated out of solution. The mixture was left to settle and the solvents then decanted. Hexanes:DCM 95:5 were then added, the suspension stirred, left to settle and the solvents decanted and the solid dried. Purification by preparative HPLC (column: Synergi-MAX RP 4µ, 21.20×250 mm; flow rate: 13 mL/min; mobile phase: solvent A: H$_2$O/TFA pH 2.47, solvent B: MeCN/H$_2$O 90:10; method: isocratic, solvent A:solvent B 35:65, 35 min; wavelength: 254 nm, 330 nm) gave N—((S)-1-((S)-1-(4-(((S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yloxy)methyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide 55 (13.7 mg, 17%, HPLC purity: 92.5%) as a pale yellow powder. $^1$H NMR δ (400 MHz, DMSO-d$_6$) 10.35 (s, 1H), 10.02 (s, 1H), 8.19 (s, 1H), 8.15 (d, J=8.3 Hz, 1H), 8.08 (d, J=8.1 Hz, 2H), 8.02 (s, 1H), 7.86 (s, 1H), 7.81-7.77 (m, 2H), 7.66 (d, J=8.5 Hz, 2H), 7.57-7.53 (m, 1H), 7.50-7.47 (m, 3H), 7.40-7.36 (m, 1H), 7.33-7.30 (m, 1H), 6.99 (s, 2H), 5.97 (t, J=5.5 Hz, 1H), 5.40 (br s, 2H), 5.21 (s, 2H), 4.42-4.32 (m, 3H), 4.22-4.14 (m, 4H), 4.03-3.98 (m, 2H), 3.87-3.77 (m, 2H), 3.34 (t, J=7.0 Hz, 2H), 3.07-3.05 (m, 2H), 2.76-2.59 (m, 4H), 2.22-2.08 (m, 2H), 2.02-1.92 (m, 3H), 1.74-1.57 (m, 2H), 1.51-1.33 (m, 6H), 1.23-1.14 (m, 3H), 0.85 (d, J=6.7 Hz, 3H), 0.82 (d, J=6.8 Hz, 3H). HRMS m/z 1115.4170 [(M−H)$^+$ calcd for C$_{59}$H$_{65}$Cl$_2$N$_8$O$_{10}$ 1115.4206].

Example 6 N—((S)-1-((S)-1-(4-(((S)-1-(chloromethyl)-3-(6-((S)-7-methoxy-5-oxo-2,3,5,11a-tetrahydro-1H-benzo[e]pyrrolo[1,2-a][1,4]diazepin-8-yloxy)hexanoyl)-2,3-dihydro-1H-benzo[e]indol-5-yloxy)methyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide 56

(S)-tert-Butyl 8-(6-((S)-1-(chloromethyl)-5-(4-nitrobenzyloxy)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate 54g (829 mg, 1.00 mmol) was reduced (Zn/NH$_4$Cl) to corresponding aniline (by the method reported for the synthesis of 54h above) and dissolved in dry DMA (3 mL). To this solution was added a mixture formed by stirring (S)-2-(((9H-fluoren-9-yl)methoxy)carbonylamino)-5-ureidopentanoic acid (Fmoc-L-citrulline, 1.19 g, 3.00 mmol) and 2-ethoxy-1-ethoxycarbonyl-1,2-dihydroquinoline EEDQ (0.99g, 4.00 mmol) in dry DMA (4 mL) at r.t. for 40 min. The final reaction mixture was stirred at r.t. and under a nitrogen atmosphere for 19 h. The mixture was poured into water and stirred at r.t. for 5 h. The solid was collected, washed with water several times, dried, and purified by a silica column chromatography (DCM-MeOH gradient from 0-5%) to give (S)-tert-butyl 8-(6-((S)-5-(4-((S)-2-(((9H-fluoren-9-yl)methoxy)carbonylamino)-5-ureidopentanamido)benzyloxy)-1-(chloromethyl)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate 56a (0.91 g, 77%) as a pure beige solid, mp 172° C.; $^1$H NMR [(CD$_3$)$_2$SO] δ 10.10 (s, 1H), 8.22-8.11 (m, 2H), 7.94-7.62 (m, 8H), 7.59-7.46 (m, 3H), 7.46-7.27 (m, 5H), 7.04 (s, 1H), 6.69 (s, 1H), 6.39 (br s, 1H), 5.99 (t, J=5.6 Hz, 1H), 5.51-5.32 (m, 3H), 5.22 (s, 2H), 4.42-3.90 (m, 10H), 3.88-3.75 (m, 1H), 3.79 (s, 3H), 3.53-3.18 (m, 3H), 3.15-2.87 (m, 2H), 2.66-2.44 (m, 2H, partially obscured by DMSO peak), 2.11-1.20 (m, 14H), 1.31 (s, 9H). Anal. (C$_{65}$H$_{72}$ClN$_7$O$_{12}$·½H$_2$O) Calc: C, 65.73; H, 6.20; N, 8.26. Found: C, 65.64; H, 6.19; N, 8.27.

To a stirred solution of N-Fmoc 56a (0.91 g, 0.77 mmol) in dry DMA (9 mL) at 0° C. under a nitrogen atmosphere was added a solution of piperidine in DMA (1.0 mmol per mL solution) (3.85 mL, 3.85 mmol). After addition, the mixture was stirred further at this temperature for 2 h and then poured into a mixture of ethyl acetate-petroleum ether (1:10) (150 mL) and stirred at 0° C. for 30 min. The solvent was decanted from the insoluble material and discarded. The wash step was repeated with more ethyl acetate-petroleum ether (1:3) (2×150 mL) at r.t. The solid was collected, washed with ethyl acetate-petroleum ether (1:3), and dried to give (S)-tert-butyl 8-(6-((S)-5-(4-((S)-2-amino-5-ureidopentanamido)benzyloxy)-1-(chloromethyl)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate 56b as a colorless solid (0.73 g, 99%); mp 223° C. (dec.); $^1$H NMR [(CD$_3$)$_2$SO] δ 10.60-9.30 (br s, 3H), 8.24-8.12 (m, 2H), 7.84 (d, J=8.2 Hz, 1H), 7.70 (d, J=8.5 Hz, 2H), 7.54 (br t, J=7.5 Hz, 1H), 7.50 (d, J=8.5 Hz, 2H), 7.39 (br t, J=7.6 Hz, 1H), 7.04 (s, 1H), 6.69 (s, 1H), 6.39 (br s, 1H), 5.93 (t, J=5.7 Hz, 1H), 5.47-5.28 (m, 3H), 5.21 (s, 2H), 4.36 (t, J=10.8 Hz, 1H), 4.28-4.13 (m, 2H), 4.10-3.92 (m, 3H), 3.90-3.77 (m, 1H), 3.79 (s, 3H), 3.54-3.20 (m, 3H, partially obscured by water peak), 3.06-2.89 (m, 2H), 2.70-2.49 (m, 3H, partially obscured by DMSO peak), 2.10-1.25 (m, 14H), 1.31 (s, 9H). Anal. (C$_{50}$H$_{62}$ClN$_7$O$_{10}$·¾H$_2$O) Calc: C, 61.91; H, 6.60; N, 10.11. Found: C, 62.05; H, 6.96; N, 10.08.

A mixture of amine 56b (0.73 g, 0.763 mmol) and (S)-2,5-dioxopyrrolidin-1-yl 2-(((9H-fluoren-9-yl)methoxy)carbonylamino)-3-methylbutanoate (Fmoc-Val-Osu, 0.50 g, 1.15 mmol) in dry DMA (7 mL) was stirred at r.t. and under a nitrogen atmosphere for 18 h. Ethyl acetate-petroleum ether (1:2) (100 mL) was added and the mixture was stirred at r.t. for 30 min. Solvents were decanted from the insoluble material and the wash step was repeated with more ethyl acetate-petroleum ether (1:1) (2×100 mL). The colorless solid was dried to give (S)-tert-butyl 8-(6-((S)-5-(4-((S)-2-((S)-2-(((9H-fluoren-9-yl)methoxy)carbonylamino)-3-methylbutanamido)-5-ureidopentanamido)benzyloxy)-1-(chloromethyl)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate 56c (0.89 g, 91%); mp 191° C. (dec.); $^1$H NMR [(CD$_3$)$_2$SO] δ 10.11 (s, 1H), 8.22-8.08 (m, 3H), 7.92-7.81 (m, 3H), 7.74 (t, J=7.4 Hz, 2H), 7.65 (d, J=8.4 Hz, 2H), 7.54 (br t, J=7.2 Hz, 1H), 7.48 (d, J=8.4 Hz, 2H), 7.46-7.35 (m, 4H), 7.32 (br t, J=7.4 Hz, 2H), 7.04 (s, 1H), 6.69 (s, 1H), 6.39 (br s, 1H), 5.97 (t, 1H), 5.47-5.34 (m, 3H), 5.21 (s, 2H), 4.53-4.13 (m, 7H), 4.10-3.75 (m, 5H), 3.79 (s, 3H), 3.53-3.20 (m, 3H, partially obscured by water peak), 3.10-2.87 (m, 2H), 2.69-2.45 (m, 2H, partially obscured by DMSO peak), 2.10-1.25 (m, 15H), 1.31 (s, 9H), 0.88 (d, J=6.8 Hz, 3H), 0.85 (d, J=6.7 Hz, 3H). Anal. (C$_{70}$H$_{81}$ClN$_8$O$_{13}$·¾H$_2$O) Calc: C, 65.10; H, 6.44; N, 8.68. Found: C, 64.85; H, 6.48; N, 8.67.

To a stirred solution of N-Fmoc compound 56c (0.89 g, 0.70 mmol) in dry DMA (6 mL) at 0° C. under a nitrogen atmosphere was added a solution of piperidine in DMA (1.0 mmol per mL solution) (3.48 mL, 3.48 mmol). After addition, the mixture was stirred further at this temperature for 1.5 h. A mixture of ethyl acetate-petroleum ether (1:2) (90 mL) was added and the mixture was stirred at 0° C. for 10 min. The solvent layer was decanted from the insoluble material and discarded. The wash step was repeated with more ethyl acetate-petroleum ether (1:2) (2×90 mL) at r.t. The colorless solid left behind was dried to give (S)-tert-butyl 8-(6-((S)-5-(4-((S)-2-((S)-2-amino-3-methylbutanamido)-5-ureidopentanamido)benzyloxy)-1-(chloromethyl)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate 56d (0.68 g, 93%); mp 225° C. (dec.); $^1$H NMR [(CD$_3$)$_2$SO] δ 10.16 (s, exchangeable with D$_2$O, 1H), 8.23-8.07 (m, 3H, reduced to 2H after D$_2$O), 7.84 (d, J=8.2 Hz, 1H), 7.65 (d, J=8.5 Hz, 2H), 7.59-7.45 (m, 3H), 7.37 (br t, J=7.5 Hz, 1H), 7.04 (s, 1H), 6.69 (s, 1H), 6.38 (br s, exchangeable with D$_2$O, 1H), 5.96 (t, J=5.8 Hz, exchangeable with D$_2$O, 1H), 5.45-5.30 (m, 3H, reduced to 1H as a d after D$_2$O, J 9.6 Hz), 5.21 (s, 2H), 4.41 (br s, became dd after D$_2$O, J=8.4, 5.4 Hz, 1H), 4.36 (br t, J=10.7 Hz, 1H), 4.26-4.13 (m, 2H), 4.10-3.91 (m, 3H), 3.88-3.76 (m, 1H), 3.79 (s, 3H), 3.53-3.43 (m, 1H), 3.41-3.20 (m, 2H), 3.09-2.88 (m, 3H), 2.70-2.50 (m, 2H, partially obscured by DMSO peak), 2.10-1.20 (m, 15H), 1.31 (s, 9H), 0.88 (d, J=6.9 Hz, 3H), 0.79 (d, J=6.8 Hz, 3H), 2H not observed. Anal. (C$_{55}$H$_{71}$ClN$_8$O$_{11}$·H$_2$O) Calc: C, 61.53; H, 6.85; N, 10.44. Found: C, 61.39; H, 7.11; N, 10.15.

A mixture of amine 56d (0.68 g, 0.64 mmol) and 2,5-dioxopyrrolidin-1-yl 6-(2,5-dioxo-2,5-dihydro-1H-pyrrol-1-yl)hexanoate (maleimido-Osu, 0.50 g, 1.61 mmol) in dry DMA (6 mL) was stirred at 0° C. under a nitrogen atmosphere for 1 h. A mixture of ethyl acetate-petroleum ether (1:2) (90 mL) was added and the mixture was stirred at 0° C. for 15 min. The solvent layer was decanted from the insoluble material and discarded. The wash step was repeated with more ethyl acetate-petroleum ether (1:1) (90 mL) and then pure ethyl acetate (50 mL) at r.t. The beige solid left behind was dried to give (S)-tert-butyl 8-(6-((S)-1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate 52 (0.72 g, 90%); HPLC: 96.7% pure; mp 210° C. (dec.); $^1$H NMR [(CD$_3$)$_2$SO] δ 10.03 (s, exchangeable with D$_2$O, 1H), 8.23-8.11 (m, 2H), 8.09 (d, J=7.3 Hz, exchangeable with D$_2$O, 1H), 7.85 (d, J=8.5 Hz, 1H), 7.80 (d, J=8.3 Hz, exchangeable with D$_2$O, 1H), 7.66 (d, J=8.6 Hz, 2H), 7.59-7.44 (m, 3H), 7.38 (br t, J=7.6 Hz, 1H), 7.04 (s, 1H), 6.99 (s, 2H), 6.69 (s, 1H), 6.38 (br s, exchangeable with D$_2$O, 1H), 5.99 (t, J=5.5 Hz, exchangeable with D$_2$O, 1H), 5.49-5.34 (m, 3H, reduced to 1H as d after D$_2$O, J 9.5 Hz), 5.20 (s, 2H), 4.44-4.30 (m, 2H), 4.26-4.13 (m, 3H), 4.10-3.91 (m, 3H), 3.88-3.76 (m, 1H), 3.79 (s, 3H), 3.53-3.44 (m, 1H), 3.41-3.20 (m, partially obscured by water peak, 4H), 3.09-2.88 (m, 2H), 2.66-2.42 (m, partially obscured by DMSO peak, 2H), 2.25-1.24 (m, 21H), 1.31 (s, 9H), 1.24-1.11 (m, 2H), 0.86 (d, J=6.8 Hz, 3H), 0.82 (d, J=6.7 Hz, 3H). Anal. ($C_{55}H_{71}ClN_8O_{11}·H_2O$) Calc: C, 61.53; H, 6.85; N, 10.44. Found: C, 61.39; H, 7.11; N, 10.15.

To a stirred solution of N-$^t$Boc derivative 52 (125 mg, 0.10 mmol) in DCM (10 mL) at −10 to −12° C. (bath temperature) was added dropwise over 10 min a solution of 2.5% water in TFA (10 mL). After addition the mixture was stirred further at this temperature for 3 h. Cold (−25° C.) ethyl acetate-petroleum ether (1:10) (300 mL) was added, followed by slow addition at −10° C. (bath temperature) of a saturated aqueous solution of NaHCO$_3$ to give pH 6-7. The organic layer was removed and the wash step was repeated with more ethyl acetate-petroleum ether (1:1) (300 mL). The solid was collected, washed successively with water and ethyl acetate several times, and dried to give the crude product as a pale yellow solid (102 mg). This was purified by preparative HPLC [Genentech] to give N—((S)-1-((S)-1-(4-(((S)-1-(chloromethyl)-3-(6-((S)-7-methoxy-5-oxo-2,3,5,11a-tetrahydro-1H-benzo[e]pyrrolo[1,2-a][1,4]diazepin-8-yloxy)hexanoyl)-2,3-dihydro-1H-benzo[e]indol-5-yloxy)methyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide 56 (4.1 mg, 3.6%); HRMS (ESI) m/z calc. for $C_{60}H_{72}ClN_9NaO_1$: 1152.4932. found: 1152.4906 [MNa$^+$]. Calc. for $C_{60}H_{73}ClN_9O_{11}$: 1130.5113. found: 1130.5077 [MH$^+$].

Example 7 (S)-1-(chloromethyl)-3-(5-((S)-1-(chloromethyl)-5-(phosphonooxy)-1H-benzo[e]indol-3(2H)-yl)-5-oxopentanoyl)-2,3-dihydro-1H-benzo[e]indol-5-yl 2-(6-(2,5-dioxo-2,5-dihydro-1H-pyrrol-1-yl)-N-methylhexanamido)ethyl(methyl)carbamate 57

At room temperature to a solution of (S)-tert-Butyl 1-(chloromethyl)-5-hydroxy-1H-benzo[e]indole-3(2H)-carboxylate 51a (2.00 g, 5.99 mmol) in DMF (5 mL) was added benzyl bromide (7.13 mL, 59.90 mmol), potassium iodide KI (50 mg, 0.30 mmol) and potassium carbonate K$_2$CO$_3$ (4.14 g, 30.00 mmol). See FIG. 9. The mixture was stirred for 2 h and then diluted with ethyl acetate. The precipitate was filtered off. The filtrate was redistributed between ethyl acetate and water. The aqueous phase was extracted with ethyl acetate three times. The combined organic extracts were washed with water and brine, dried over anhydrous Na$_2$SO$_4$, and filtered through celite. The solvent was removed by rotary evaporator and the excess benzyl bromide was pumped off. The resultant residue was purified by column chromatography using a mixture of ethyl acetate and petroleum ether (v/v 1:10) as eluent to give (S)-tert-butyl 5-(benzyloxy)-1-(chloromethyl)-1H-benzo[e]indole-3(2H)-carboxylate 57a as a white solid (1.97 g, 78%); mp 186-188° C. $^1$H NMR (CDCl$_3$) δ 8.29 (d, J=8.3 Hz, 1H), 7.86 (br s, 1H), 7.65 (d, J=8.29 Hz, 1H), 7.55-7.49 (m, 3H), 7.45-7.41 (m, 2H), 7.38-7.31 (m, 2H), 5.26 (s, 2H), 4.26 (br s, 1H), 4.13 (t, J=10.8 Hz, 1H), 4.00-3.92 (m, 2H), 3.44 (t, J=10.5 Hz, 1H), 1.61 (s, 9H) ppm. LRMS (APCI) found m/z 424.8 (M+H). $C_{25}H_{27}ClNO_3$ requires 424.2. (Boger D., Ishizakilb T., Kitos P. and Suntornwat O., (1990) *J. Org. Chem.*, 55, 5823-5832.)

Further elution with a mixture of ethyl acetate and petroleum ether (v/v 1:1) gave the cyclopropyl product shown in FIG. 9 as a yellow oil (345 mg, 19%). (Lajiness J. and Boger D., (2011) *J. Org. Chem.*, 76, 583-587.)

To a solution of 57a (1.60 g, 3.77 mmol) in DCM (15 mL) cooled in an ice bath was added 4N HCl in dioxane (40 mL). The mixture was allowed to warm up to room temperature and stirred for 3 h. All volatile components were pumped off to give (S)-5-(benzyloxy)-1-(chloromethyl)-2,3-dihydro-1H-benzo[e]indole 57b as a hydrochloride salt. The salt was dissolved in THF (15 mL) and cooled down in an ice bath. Glutaric anhydride (646 mg, 5.66 mmol), DMAP (46 mg, 0.38 mmol) and pyridine (5 mL) were added and the resultant mixture was stirred for 4 h at room temperature. After all the volatile components were pumped off, the residue was dissolved in dilute aq NaHCO$_3$ and washed 3 times with ethyl acetate. The aqueous phase was acidified using 1N HCl to a pH of 2 and extracted with ethyl acetate three times. The combined ethyl acetate extracts were washed with water and brine, dried over anhydrous Na$_2$SO$_4$, and filtered through a silica gel pad washing with a mixture of MeOH and ethyl acetate (v/v 1:10). The solvent was removed to give (S)-5-(5-(benzyloxy)-1-(chloromethyl)-1H-benzo[e]indol-3(2H)-yl)-5-oxopentanoic acid 57c as an off-white solid (978 mg, 59%).

At −10° C., to a solution of 57c (978 mg, 2.23 mmol) in THF (20 mL) was added 25% aqueous ammonium formate (20 mL) followed by Pd—C catalyst (10%, wet, 500 mg) and the mixture was stirred at −10° C. for 7 h. More Pd—C catalyst (500 mg) was added and the mixture was stirred at the same temperature overnight. The catalyst was filtered off through celite and the celite was washed with THF. The THF was pumped off from the filtrate and the remaining aqueous solution was extracted with ethyl acetate three times. The combined extracts were washed with water and brine, dried over anhydrous Na$_2$SO$_4$ and filtered. Removal of solvent gave (S)-5-(1-(chloromethyl)-5-hydroxy-1H-benzo[e]indol-3(2H)-yl)-5-oxopentanoic acid 53h as an off-white solid (487 mg, 63%); $^1$H NMR (DMSO) δ 12.08 (br s, 1H), 10.35 (br s, 1H), 8.08 (d, J=8.0 Hz, 1H), 7.98 (s, 1H), 7.77 (d, J=8.3 Hz, 1H), 7.50-7.46 (m, 1H), 7.33-7.29 (m, 1H), 4.30 (t, J=10.5 Hz, 1H), 4.14-4.12 (m, 2H), 3.98 (dd, J=2.8, 10.9 Hz, 1H), 3.78 (dd, J=7.8, 10.8 Hz, 1H), 2.63-2.54 (m, 2H), 2.34 (t, J=7.4 Hz, 2H), 1.99-1.83 (m, 2H) ppm. LRMS (APCI) found m/z 348.6 (M+H). $C_{18}H_{19}ClNO_4$ requires 348.1.

To a solution of 53h (500 mg, 1.44 mmol) in THF (15 mL) was added tetrazole (3% in acetonitrile, 51 mL, 17.25 mmol) followed by di-tert-butyl-N,N-diisopropyl phosphoramidite (5.73 mL, 17.25 mmol). The mixture was stirred at room temperature overnight then cooled in an ice bath and H$_2$O$_2$ (30% aqueous solution, 3.53 mL, 34.5 mmol) was added dropwise. The resultant mixture was allowed to warm up to room temperature and stirred for 5 h. The reaction was quenched by the addition of 10% aqueous sodium sulphite with cooling in an ice bath. Organic volatiles were removed by rotary evaporator to give an aqueous phase containing suspended oil. Petroleum ether was added and the mixture was stirred for half an hour. The precipitate which formed was collected by filtration, washed with water and petroleum ether, and dried under vacuum to give (S)-5-(1-(chloromethyl)-5-(di-tert-butoxyphosphoryloxy)-1H-benzo[e]indol-3(2H)-yl)-5-oxopentanoic acid 57d (660 mg, 85%) as an off-white foam; $^1$H NMR (DMSO) δ 12.07 (br s, 1H), 8.56 (s, 1H), 8.04 (d, J=8.2 Hz, 1H), 7.93 (d, J=8.4 Hz, 1H), 7.60-7.56 (m, 1H), 7.50-7.46 (m, 1H), 4.38 (t, J=9.8 Hz, 1H), 4.32-4.26 (m, 1H), 4.20-4.18 (m, 1H), 4.02 (dd, J=2.9, 11.0 Hz, 1H), 3.90 (dd, J=7.1, 11.0 Hz, 1H), 2.67-2.53 (m, 2H), 2.34 (t, J=7.4 Hz, 2H), 1.87-1.78 (m, 2H), 1.481 and 1.476 (2×s, 18H) ppm. $^{31}$P NMR (DMSO) δ −15.46 ppm. HRMS (ESI) found m/z 562.1719 (M+Na). $C_{26}H_{35}ClNNaO_7P$ requires 562.1732.

To a suspension of 6-(2,5-dioxo-2,5-dihydro-1H-pyrrol-1-yl)hexanoic acid (1.00 g, 4.73 mmol) in DCM (20 mL)

cooled in an ice bath was added a drop of DMF and then oxalyl chloride (2.03 mL, 23.67 mmol) dropwise. See FIG. 10. The mixture was allowed to warm up to room temperature and stirred overnight giving a dark brown solution. All volatile components were removed by rotary evaporator and then high vacuum pump. The resultant residue was dissolved in DCM (5 mL) and the solvent was removed by rotary evaporator and then high vacuum pump. The above dissolving and removal procedure was repeated once more to give crude 6-maleimidocaproyl chloride as dark brown oil. To a solution of tert-butyl methyl(2-(methylamino)ethyl)carbamate (891 mg, 4.73 mmol) in DCM (5 mL) cooled in an ice bath was added dropwise a solution of the above-made 6-maleimidocaproyl chloride in DCM (20 mL). The resultant mixture was allowed to warm up to room temperature and stirred overnight. The DCM was removed and the residue was dissolved in ethyl acetate. The solution was washed with aqueous NaHCO$_3$, cold aqueous 5% citric acid, and brine, then dried over anhydrous Na$_2$SO$_4$, and filtered through a silica gel pad washing with ethyl acetate. Solvent was removed to give tert-butyl 2-(6-(2,5-dioxo-2,5-dihydro-1H-pyrrol-1-yl)-N-methylhexanamido)ethyl(methyl)carbamate 57e as brown oil (1.33 g, 74%); $^1$H NMR (DMSO) (mixture of rotamers) δ 7.006 & 7.005 (2×s, 1H), 3.39-3.36 (m, 4H), 3.29-3.25 (m, 2H), 2.92-2.75 (m, 6H, 2NMe), 2.21 (t, J=7.38 Hz, 2H), 1.50-1.44 (m, 4H), 1.37 (s, 9H), 1.24-1.16 (m, 2H) ppm. HRMS (ESI) found m/z 382.2338 (M+H). C$_{19}$H$_{32}$N$_3$O$_5$ requires 382.2336.

To a solution of 57e (274 mg, 0.72 mmol) in DCM (5 mL) cooled in an ice bath was added TFA (5 mL) dropwise. The mixture was stirred at the same temperature for 2 h before all volatile components were removed by rotary evaporator and then high vacuum pump. The resultant residue, 6-(2,5-dioxo-2,5-dihydro-1H-pyrrol-1-yl)-N-methyl-N-(2-(methylamino)ethyl)hexanamide trifluoroacetate 57f, was used as it was.

At room temperature, 51a (200 mg, 0.60 mmol) was dissolved in DCM (5 mL) and DIPEA (0.3 mL, 1.72 mmol) was added followed by 4-nitrophenyl chloroformate (145 mg, 0.72 mmol) to form (S)-tert-butyl 1-(chloromethyl)-5-((4-nitrophenoxy)carbonyloxy)-1H-benzo[e]indole-3(2H)-carboxylate 57g. After the mixture was stirred for 5 h, a solution of the crude 57f in DCM (5 mL) and DIPEA (0.7 mL, 4.02 mmol) was added to give a bright yellow solution, which was stirred overnight. All volatile components were removed. The residue was dissolved in ethyl acetate and washed with aqueous 5% ammonia and brine. The crude material obtained was further purified by column chromatography using a mixture of ethyl acetate, DCM, and petroleum ether (v/v/v 1:2:1), followed by a mixture of ethyl acetate and DCM (v/v 1:2) as eluent to give (S)-tert-butyl 1-(chloromethyl)-5-((2-(6-(2,5-dioxo-2,5-dihydro-1H-pyrrol-1-yl)-N-methylhexanamido)ethyl)(methyl)carbamoyloxy)-1H-benzo[e]indole-3(2H)-carboxylate 57h (223 mg, 58%) as an off-white solid; mp 53-56° C. $^1$H NMR (CDCl$_3$) (mixture of rotamers) δ 8.04 (br s, 1H), 7.86-7.78 (m, 1H), 7.72-7.68 (m, 1H), 7.53-7.48 (m, 1H), 7.40-7.34 (m, 1H), 6.67 (s, 2H), 4.25 (br s, 1H), 4.46-4.10 (m, 1H), 4.06-3.98 (m, 1H), 3.92-3.72 (apparent d, J=11.2 Hz, 1H), 3.72-3.42 (m, 7H), 3.28, 3.10, 3.09, 2.99 (4×s, 6H, 2NMe), 2.38-2.21 (m, 2H), 1.67-1.54 (m, 4H), 1.57 (s, 9H), 1.33-1.25 (m, 2H) ppm. HRMS (ESI) found m/z 641.2728 (M+H). C$_{33}$H$_{42}$ClN$_4$O$_7$ requires 641.2737.

To a solution of 57h (110 mg, 0.17 mmol) in DCM (2 mL) cooled in an ice bath was added TFA (2 mL) dropwise. The mixture was stirred at the same temperature for 2 h and then all volatile components were removed. The resultant residue was redistributed between ethyl acetate and cold dilute aqueous NaHCO$_3$. The aqueous phase was extracted with ethyl acetate three times. The combined organic extracts were washed with water followed by brine, dried over anhydrous Na$_2$SO$_4$, and filtered through celite. The solvent was removed to give (S)-1-(chloromethyl)-2,3-dihydro-1H-benzo[e]indol-5-yl 2-(6-(2,5-dioxo-2,5-dihydro-1H-pyrrol-1-yl)-N-methylhexanamido)ethyl(methyl)carbamate 57i as a yellow solid (86 mg, 92%), which was used as it was without further purification; $^1$H NMR (CDCl$_3$) (mixture of rotamers) δ 7.76 (d, J=8.4 Hz, 1H), 7.63-7.59 (m, 1H), 7.48-7.41 (m, 1H), 7.25-7.20 (m, 1H), 6.79 (s, 1H), 6.68 (s, 2H), 4.01-3.94 (m, 1H), 3.88-3.78 (m, 3H), 3.74-3.68 (m, 2H), 3.62-3.47 (m, 5H), 3.28, 3.10, 3.06, 3.00 (4×s, 6H, 2NMe), 2.38-2.21 (m, 2H), 1.69-1.50 (m, 4H), 1.33-1.25 (m, 2H) ppm. HRMS (ESI) found m/z 541.2217 (M+H). C$_{28}$H$_{34}$ClN$_4$O$_5$ requires 541.2212.

To a solution of 57i (83 mg, 0.15 mmol) in DMA (3 mL) cooled in an ice bath was added (S)-5-(1-(chloromethyl)-5-(di-tert-butoxyphosphoryloxy)-1H-benzo[e]indol-3 (2H)-yl)-5-oxopentanoic acid 57d (99 mg, 0.18 mmol) followed by EDCI hydrochloride (88 mg, 0.46 mmol) and then p-toluenesulfonic acid (2.6 mg, 0.015 mmol). See FIG. 11. The mixture was allowed to warm up to room temperature and stirred overnight. The mixture was redistributed between ethyl acetate and cold dilute aqueous NaHCO$_3$. The aqueous phase was extracted with ethyl acetate three times. The combined organic extracts were washed with water followed by brine, dried over anhydrous Na$_2$SO$_4$, and filtered through celite. The solvent was removed and the resultant residue was triturated with petroleum ether. The solid obtained was re-precipitated from DCM and isopropanol to give (S)-1-(chloromethyl)-3-(5-((S)-1-(chloromethyl)-5-(di-tert-butoxyphosphoryloxy)-1H-benzo[e]indol-3 (2H)-yl)-5-oxopentanoyl)-2,3-dihydro-1H-benzo[e]indol-5-yl 2-(6-(2,5-dioxo-2,5-dihydro-1H-pyrrol-1-yl)-N-methylhexanamido)ethyl(methyl)carbamate 57j as a yellow solid (116 mg, 71%); mp 81° C. (dec.). $^1$H NMR (CDCl$_3$) (mixture of rotamers) δ 8.63 (s, 1H), 8.36 (s, 1H), 8.23 (d, J=8.5 Hz, 1H), 7.89-7.82 (m, 1H), 7.72-7.67 (m, 2H), 7.54-7.50 (m, 2H), 7.43-7.39 (m, 2H), 6.66 (s, 2H), 4.34-4.25 (m, 4H), 4.10-4.05 (m, 2H), 3.98-3.93 (m, 2H), 3.72-3.69 (m, 2H), 3.50-3.46 (m, 5H), 3.28, 3.10, 3.09, 2.99 (4×s, 6H, 2NMe), 2.79-2.73 (m, 2H), 2.70-2.62 (m, 2H), 2.38-2.32 (m, 1H), 2.27-2.20 (m, 3H), 1.67-1.54 (m, 3H), 1.56 (s, 9H), 1.55 (s, 9H), 1.33-1.25 (m, 4H) ppm. $^{31}$P NMR (CDCl$_3$) δ −15.71 ppm. HRMS (ESI) found m/z 1084.3755 (M+Na). C$_{54}$H$_{66}$Cl$_2$N$_5$NaO$_{11}$P requires 1084.3766.

To a solution of 57j (55 mg, 0.052 mmol) in DCM (1 mL) cooled in an ice bath was added TFA (1 mL) dropwise. The mixture was stirred at the same temperature for 1.5 h and then all volatile components were removed. The resultant residue was re-precipitated from DCM and ethyl acetate to give (S)-1-(chloromethyl)-3-(5-((S)-1-(chloromethyl)-5-(phosphonooxy)-1H-benzo[e]indol-3(2H)-yl)-5-oxopentanoyl)-2,3-dihydro-1H-benzo[e]indol-5-yl 2-(6-(2,5-dioxo-2,5-dihydro-1H-pyrrol-1-yl)-N-methylhexanamido)ethyl (methyl)carbamate 57 as a grey solid (33 mg, 67%, HPLC purity: 89%); mp 191-194° C. (dec.). $^1$H NMR (DMSO) (mixture of rotamers) δ 8.49 (s, 1H), 8.23-8.21 (m, 1H), 8.10 (d, J=8.4 Hz, 1H), 7.95-7.76 (m, 3H), 7.59-7.53 (m, 2H), 7.45-7.39 (m, 2H), 6.97, 6.96, 6.94, 6.90 (4×s, 2H in total, maleimidyl group), 4.34-4.21 (m, 4H), 4.06-4.01 (m, 2H), 3.95-3.85 (m, 2H), 3.71-3.61 (m, 2H), 3.54-3.30 (m, 5H), 3.23, 3.18, 3.04, 3.00, 2.97, 2.95, 2.89, 2.85 (8×s, 6H in total, 2NMe), 2.37-2.28 (m, 2H), 2.19 (d, J=7.4 Hz, 1H), 2.00-1.95 (m, 2H), 1.50-1.40 (m, 5H), 1.25-1.15 (m, 5H) ppm.

$^{31}$P NMR (DMSO) δ −5.79 ppm. HRMS (ESI) found m/z 972.2488 (M+Na). C$_{46}$H$_{50}$Cl$_2$N$_5$NaO$_{11}$P requires 972.2514.

Example 8 (S)-1-(chloromethyl)-3-(5-((S)-1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-1H-benzo[e]indol-3(2H)-yl)-5-oxopentanoyl)-2,3-dihydro-1H-benzo[e]indol-5-yl 4-methylpiperazine-1-carboxylate 58

A mixture of (S)-tert-butyl 1-(chloromethyl)-5-hydroxy-1H-benzo[e]indole-3(2H)-carboxylate 51a (3.338 g, 10 mmol), 4-methylpiperazine-1-carbonyl chloride hydrochloride (5.98 g, 30 mmol), Et$_3$N (3.5 g, 35 mmol) and DMAP (1.34 g, 11 mmol) in CH$_2$Cl$_2$ (80 mL) was stirred at room temperature for 2 days. See FIG. 12. The mixture was washed with water and the solvent was dried and removed under vacuum, to give (S)-tert-butyl 1-(chloromethyl)-5-(4-methylpiperazine-1-carbonyloxy)-1H-benzo[e]indole-3(2H)-carboxylate 58a (Boger D. L. et al, Synthesis, (1999), 1505-1509) in quantitative yield: mp 98° C.; $^1$H NMR (CDCl$_3$) δ 8.11 (br, 1H), 7.84 (d, J=8.4 Hz, 1H), 7.70 (d, J=8.4 Hz, 1H), 7.50 (ddd, J=8.2, 6.9, 1.1 Hz, 1H), 7.37 (ddd, J=8.1, 6.9, 1.0 Hz, 1H), 4.34-4.20 (m, 1H), 4.17-4.10 (m, 1H), 4.01-3.98 (m, 1H), 3.94 (dd, J=9.6, 2.4 Hz, 1H), 3.87-3.80 (br, 2H), 3.68-3.60 (br, 2H), 3.47 (t, J=10.8 Hz, 1H), 2.57-2.48 (m, 4H), 2.83 (s, 3H), 1.58 (s, 9H); MS (APCI+) m/z 461.2 MH$^+$. Anal. Calcd for C$_{24}$H$_{30}$ClN$_3$O$_4$: C, 62.7; H, 6.6; N, 9.1. Found: C, 62.5; H, 6.8; N, 9.2%.

A solution of 58a (2.30 g, 5 mmol) in CH$_2$Cl$_2$ (50 mL) was treated with excess trifluoroacetic acid (TFA) at 0° C. for 4 h, and the mixture was neutralized with cold aq. NH$_3$. Dilution with hexanes resulted in the precipitation of a solid which was collected by filtration, washed with water and hexane, and dried to give (S)-1-(chloromethyl)-2,3-dihydro-1H-benzo[e]indol-5-yl 4-methylpiperazine-1-carboxylate 58b (1.60 g, 89%): mp 144-147° C.; $^1$H NMR (CDCl$_3$) δ 7.69 (d, J=8.4 Hz, 1H), 7.63 (d, J=8.4 Hz, 1H), 7.45 (ddd, J=8.3, 6.9, 1.2 Hz, 1H), 7.25 (ddd, J=8.4, 6.8, 1.2 Hz, 1H), 6.82 (s, 1H), 5.30 (s, 1H), 4.17-4.05 (m, 2H), 4.03-3.96 (m, 2H), 3.89-3.77 (m, 4H), 3.54 (t, J=10.9 Hz, 1H), 3.20-2.90 (m, 4H), 2.76 (s, 3H). Anal. Calcd for C$_{19}$H$_{22}$ClN$_3$O$_2$: C, 63.4; H, 6.2; N, 11.7. Found: C, 63.2; H, 6.2; N, 11.5%.

A solution 55a (4.689 g, 10 mmol) in dioxane (30 mL) was treated with HCl (4M in dioxane, 10 mL) and the mixture was stirred overnight at room temperature. Ammonium hydroxide was added, the solvent was removed to give (S)-1-(chloromethyl)-5-(4-nitrobenzyloxy)-2,3-dihydro-1H-benzo[e]indole 54f which was mixed with glutaric anhydride (3.4 g, 30 mmol) in CH$_2$Cl$_2$ (50 mL). After cooling to 0° C., Et$_3$N (5.05 g, 50 mmol) was added and the mixture was allowed to warm slowly and was stirred overnight at room temperature. Dilute HCl was added to give a solid which was collected by filtration, washed with water and CH$_2$Cl$_2$, and dried to give (S)-5-(1-(chloromethyl)-5-(4-nitrobenzyloxy)-1H-benzo[e]indol-3(2H)-yl)-5-oxopentanoic acid 58c (2.95 g, 61%): $^1$H NMR (DMSO-d$_6$) δ 12.07 (br s, 1H), 8.30 (br d, J=8.8 Hz, 2H), 8.24 (d, J=8.1 Hz, 1H), 8.17 (s, 1H), 7.89-7.85 (m, 3H), 7.57 (ddd, J=8.2, 6.9, 1.1 Hz, 1H), 7.43 (ddd, J=8.1, 7.1, 1.0 Hz, 1H), 5.46 (s, 2H), 4.34 (t, J=9.7 Hz, 1H), 4.25-4.13 (m, 2H), 4.01 (dd, J=11.0, 2.8 Hz, 1H), 3.85 (dd, J=10.9, 7.4 Hz, 1H), 2.66-2.57 (m, 1H), 2.55-2.46 (m, 1H), 2.35 (t, J=7.3 Hz, 2H), 1.87-1.79 (m, 2H).

A mixture of 58b (1.33 g, 3.7 mmol) and 58c (1.63 g, 3.38 mmol) in DMA (25 mL) with 1-(3-dimethylaminopropyl)-3-ethylcarbodiimide hydrochloride (EDCI.HCl, 3.26 g, 17.0 mmol) was stirred at room temperature overnight. The mixture was diluted with aq. NaHCO$_3$ and the resulting precipitate was washed successively with water and methanol, and dried. Chromatography on silica, eluting firstly with EtOAc/MeOH 9:1, and then EtOAc/MeOH 4:1 gave (S)-1-(chloromethyl)-3-(5-((S)-1-(chloromethyl)-5-(4-nitrobenzyloxy)-1H-benzo[e]indol-3(2H)-yl)-5-oxopentanoyl)-2,3-dihydro-1H-benzo[e]indol-5-yl 4-methylpiperazine-1-carboxylate 58d (0.98 g, 35%): $^1$H NMR (CDCl$_3$) δ 8.35 (s, 1H), 8.33-8.27 (m, 3H), 8.17 (s, 1H), 7.85 (d, J=8.3 Hz, 1H), 7.73-7.68 (m, 4H), 7.58-7.49 (m, 2H), 7.45-7.38 (m, 2H), 5.33 (q, J=13.0 Hz, 2H), 4.39-4.27 (m, 4H), 4.14-4.06 (m, 2H), 4.01-3.95 (m, 2H), 3.83-3.77 (m, 2H), 3.64-3.59 (m, 2H), 3.48 (dt, J=10.5, 7.3 Hz, 2H), 2.85-2.65 (m, 4H), 2.55-2.47 (m, 4H), 2.38 (s, 3H), 2.28-2.21 (m, 2H).

A suspension of 58d (0.41 g, 5 mmol) in a mixture of THF (35 mL), MeOH (15 mL), and water (5 mL) at 0° C. was treated with aluminum amalgam (2 g) and the stirred mixture was allowed to warm to room temperature over 3 h. After dilution with MeOH the mixture was filtered through celite and the filtrate was evaporated to dryness to give (S)-3-(5-((S)-5-(4-aminobenzyloxy)-1-(chloromethyl)-1H-benzo[e]indol-3(2H)-yl)-5-oxopentanoyl)-1-(chloromethyl)-2,3-dihydro-1H-benzo[e]indol-5-yl 4-methylpiperazine-1-carboxylate 58e (0.31 g, 78%) which was used directly in the next step: $^1$H NMR (CDCl$_3$) δ 8.37 (s, 1H), 8.26 (d, J=8.2 Hz, 1H), 8.18 (s, 1H), 7.86 (d, J=8.3 Hz, 1H), 7.67 (d, J=8.3 Hz, 1H), 7.60 (d, J=8.3 Hz, 1H), 7.49-7.43 (m, 2H), 7.39 (br t, J=7.6 Hz, 1H), 7.34-7.26 (m, 3H), 6.68 (d, J=8.3 Hz, 2H), 5.10 (q, J=10.9 Hz, 2H), 4.32-4.15 (m, 4H), 4.07-3.97 (m, 2H), 3.94-3.90 (m, 2H), 3.86-3.79 (m, 2H), 3.66-3.60 (m, 2H), 3.50-3.40 (m, 2H), 2.77-2.58 (m, 4H), 2.56-2.48 (m, 4H), 2.27 (s, 3H), 2.22-2.14 (m, 2H).

A mixture of 2-ethoxy-1-ethoxycarbonyl-1,2-dihydroquinoline (EEDQ, 0.58 g, 2.3 mmol) and (S)-2-(((9H-fluoren-9-yl)methoxy)carbonylamino)-5-ureidopentanoic acid (Fmoc-L-citrulline, 0.69 g, 1.7 mmol) was stirred in dry DMA (10 mL) under nitrogen for 10 min until all solid was dissolved. See FIG. 13. Crude 58e (0.31 g, 0.39 mmol) was added and the stirring was continued overnight. The mixture was diluted with EtOAc and water was added to precipitate the product, which was collected by filtration, and triturated with boiling MeOH to give crude (S)-3-(5-((S)-5-(4-((S)-2-(((9H-fluoren-9-yl)methoxy)carbonylamino)-5-ureidopentanamido)benzyloxy)-1-(chloromethyl)-1H-benzo[e]indol-3(2H)-yl)-5-oxopentanoyl)-1-(chloromethyl)-2,3-dihydro-1H-benzo[e]indol-5-yl 4-methylpiperazine-1-carboxylate 58f (0.62 g, >100%), which was treated with piperidine (50 mg, 0.59 mmol) in dry DMF (20 mL) at room temperature for 30 min. Dilution with EtOAc, hexanes and water gave a precipitate which was collected by filtration and washed with hexanes and water, to give crude (S)-3-(5-((S)-5-(4-((S)-2-amino-5-ureidopentanamido)benzyloxy)-1-(chloromethyl)-1H-benzo[e]indol-3(2H)-yl)-5-oxopentanoyl)-1-(chloromethyl)-2,3-dihydro-1H-benzo[e]indol-5-yl 4-methylpiperazine-1-carboxylate 58g (0.33 g, 89%, 85% purity by HPLC) which was treated with 1.5 equivalents of Fmoc-Va-OSu (N-α-Fmoc-L-valine N-hydroxysuccinimide ester, 0.23 g, 0.53 mmol) in dry DMA (10 mL) overnight. Dilution with EtOAc and water gave a solid which was collected by filtration and dried, to give crude (S)-3-(5-((S)-5-(4-((S)-2-(((9H-fluoren-9-yl)methoxy)carbonylamino)-3-methylbutanamido)-5-ureidopentanamido)benzyloxy)-1-(chloromethyl)-1H-benzo[e]indol-3(2H)-yl)-5-oxopentanoyl)-1-(chloromethyl)-2,3-dihydro-1H-benzo[e]indol-5-yl 4-methylpiperazine-1-carboxylate 58h (0.38 g, 85%): ¹H NMR (DMSO-d₆) δ 10.11 (s, 1H), 8.24-8.11 (m, 3H), 7.96 (d, J=8.4 Hz, 1H), 7.90-7.80 (m, 4H), 7.74 (t, J=7.4 Hz, 2H), 7.65 (d, J=8.4 Hz, 2H), 7.61-7.53 (m, 2H), 7.50-7.36 (m, 6H), 7.32 (t, J=7.5 Hz, 2H), 5.97 (t, J=5.4 Hz, 1H), 5.40 (s, 2H), 5.20 (s, 2H), 4.44-4.19 (m, 9H), 4.08-3.81 (m, 5H), 3.74-3.70 (br, 2H), 3.50-3.42 (br, 2H), 3.07-2.89 (m, 2H), 2.77-2.55 (m, 4H), 2.52-2.36 (m, 4H), 2.25 (s, 3H), 2.03-1.94 (m, 3H), 1.76-1.53 (m, 2H), 1.49-1.30 (m, 2H), 0.87 (dd, J=11.2, 6.8 Hz, 6H).

Crude 58h (0.38 g, 0.3 mmol) was reacted with piperidine in DMA at room temperature for 1 h and the mixture was diluted with EtOAc and water, to give a solid which was collected and dried to give (S)-3-(5-((S)-5-(4-((S)-2-((S)-2-amino-3-methylbutanamido)-5-ureidopentanamido)benzyloxy)-1-(chloromethyl)-1H-benzo[e]indol-3(2H)-yl)-5-oxopentanoyl)-1-(chloromethyl)-2,3-dihydro-1H-benzo[e]indol-5-yl 4-methylpiperazine-1-carboxylate 58i (0.23 g, 73%, 83% purity by HPLC): ¹H NMR (CDCl₃) δ 9.34 (br, 1H), 8.35 (br s, 1H), 8.28 (d, J=8.1 Hz, 1H), 8.14 (s, 1H), 8.02 (s, 1H), 7.86 (d, J=8.2 Hz, 1H), 7.75 (d, J=7.5 Hz, 1H), 7.70 (d, J=7.6 Hz, 1H), 7.65-7.60 (m, 2H), 7.54-7.47 (m, 2H), 7.46-7.33 (m, 4H), 7.29 (td, J=7.4, 1.3 Hz, 1H), 5.20 (br s, 2H), 5.17-5.09 (m, 1H), 4.82-4.73 (m, 1H), 4.59-4.50 (m, 1H), 4.33-4.15 (m. 3H), 4.07-4.01 (m, 1H), 3.98-3.90 (m, 2H), 3.86-3.76 (m, 3H), 3.65-3.57 (m, 2H), 3.55-3.39 (m, 3H), 3.25 (br s, 1H), 2.81-2.60 (m, 3H), 2.59-2.41 (m, 6H), 2.37 (s, 3H), 2.27-2.16 (m, 3H), 1.55-1.48 (m, 2H), 0.98 (d, J=6.7 Hz, 3H), 0.83 (d, J=6.6 Hz, 3H).

A mixture of crude 58i (0.105 g, 0.1 mmol) and 2,5-dioxopyrrolidin-1-yl 6-(2,5-dioxo-2,5-dihydro-1H-pyrrol-1-yl)hexanoate (62 mg, 0.2 mmol) in dry DMF (10 mL) was stirred overnight at room temperature and the mixture was diluted with EtOAc and water, to give a solid which was collected and dried to give crude material (70 mg, 71% purity by HPLC) which was purified by prep-HPLC to give (S)-1-(chloromethyl)-3-(5-((S)-1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-1H-benzo[e]indol-3(2H)-yl)-5-oxopentanoyl)-2,3-dihydro-1H-benzo[e]indol-5-yl 4-methylpiperazine-1-carboxylate 58. MS m/z 1243.4 [(M+H)⁺ calcd for C₆₅H₇₆Cl₂N₁₀O₁₁ 1243.5].

Example 9 (S)-1-(chloromethyl)-3-(5-((S)-1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-1H-benzo[e]indol-3(2H)-yl)-5-oxopentanoyl)-2,3-dihydro-1H-benzo[e]indol-5-yl dihydrogen phosphate 59

To a solution of (S)-tert-butyl 5-(4-((S)-2-((S)-2-(((9H-fluoren-9-yl)methoxy)carbonylamino)-3-methylbutanamido)-5-ureidopentanamido)benzyloxy)-1-(chloromethyl)-1H-benzo[e]indole-3(2H)-carboxylate 55e (1.00 g, 1.09 mmol) in DMF (10 mL) was added piperidine (1.08 mL, 10.90 mmol). See FIG. 14. The mixture was stirred at room temperature for 2 h and then all the volatile components were pumped off. The resultant residue was triturated with ether to give (S)-tert-butyl 5-(4-((S)-2-((S)-2-amino-3-methylbutanamido)-5-ureidopentanamido)benzyloxy)-1-(chloromethyl)-1H-benzo[e]indole-3(2H)-carboxylate 59a as a white solid (700 mg, 92%). ¹H NMR (DMSO) δ 10.17 (s, 1H), 8.17 (d, J=8.0 Hz, 1H), 8.12 (d, J=8.4 Hz, 1H), 7.82 (d, J=8.4 Hz, 1H), 7.66 (d, J=8.6 Hz, 2H), 7.55-7.49 (m, 3H), 7.37-7.33 (m, 2H), 5.98 (t, J=5.7 Hz, 1H), 5.41 (s, 2H), 5.22 (s, 2H), 4.51-4.48 (m, 1H), 4.19-3.98 (m, 4H), 3.84-3.80 (m, 1H), 3.08-2.90 (m, 3H), 1.99-1.91 (m, 2H), 1.75-1.65 (m, 2H), 1.55 (s, 9H), 1.49-1.33 (m, 2H), 0.89 (d, J=6.8 Hz, 3H), 0.80 (d, J=6.8 Hz, 3H) ppm.

A mixture of 59a (688 mg, 0.99 mmol), 2,5-dioxopyrrolidin-1-yl 6-(2,5-dioxo-2,5-dihydro-1H-pyrrol-1-yl)hexanoate (SuOMC, 320 mg, 1.04 mmol), and DIPEA (190 μL, 1.09 mmol) in DMSO (10 mL) was stirred at room temperature overnight. All the volatile components were pumped off. The resultant residue was triturated with ethyl acetate to give (S)-tert-butyl 1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-1H-benzo[e]indole-3(2H)-carboxylate 59b as an off-white solid (832 mg, 95%). ¹H NMR (DMSO) δ 10.03 (s, 1H), 8.13-8.08 (m, 2H), 7.83-7.79 (m, 2H), 7.66 (d, J=8.4 Hz, 2H), 7.55-7.48 (m, 3H), 7.35 (t, J=7.5 Hz, 1H), 6.99 (s, 2H), 5.97 (t, J=5.4 Hz, 1H), 5.41 (s, 2H), 5.21 (s, 2H), 4.43-4.38 (m, 1H), 4.22-3.98 (m, 4H), 3.84-3.80 (m, 1H), 3.38-3.33 (m, 3H), 3.08-2.90 (m, 2H), 2.24-2.06 (m, 2H), 2.01-1.91 (m, 1H), 1.74-1.14 (m, 10H), 1.55 (s, 9H), 0.86 (d, J=6.8 Hz, 3H), 0.83 (d, J=6.7 Hz, 3H) ppm. HRMS (ESI) found m/z 910.3897 (M+Na). C₄₆H₅₈ClN₇NaO₉ requires 910.3877.

To a suspension of 59b (100 mg, 0.11 mmol) in DCM (2 mL) cooled in an ice bath was added TFA (2 mL). The mixture was stirred in the ice bath for 3 h. All the volatile components were pumped off. The resultant residue was dissolved in THF and redistributed between ethyl acetate and cold 5% aqueous ammonia. The aqueous phase was extracted with ethyl acetate three times. The combined organic extracts were washed with water and brine, dried over anhydrous Na₂SO₄, filtered through celite and the solvent was removed to give N—((S)-1-((S)-1-(4-(((S)-1-(chloromethyl)-2,3-dihydro-1H-benzo[e]indol-5-yloxy)methyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide 59c as a greenish-brown solid (80 mg, 90%), which was used directly. ¹H NMR (DMSO) δ 10.02 (s, 1H), 8.09-8.07 (m, 1H), 7.99 (d, J=8.3 Hz, 1H), 7.80 (d, J=8.5 Hz, 1H), 7.65 (d, J=8.3 Hz, 2H), 7.56 (d, J=8.3 Hz, 1H), 7.45 (d, J=8.4 Hz, 2H), 7.38 (t, J=7.1 Hz, 1H), 7.09 (t, J=7.4 Hz, 1H), 6.99 (s, 2H), 5.97 (br s, 1H), 5.41 (s, 2H), 5.16 (s, 2H), 4.46-4.35 (m, 1H), 4.21-4.17 (m, 1H), 3.96-3.87 (m, 1H), 3.84-3.80 (m, 1H), 3.70-3.65 (m, 1H), 3.60-3.49 (m, 1H), 3.38-3.33 (m, 3H), 3.06-2.92 (m, 2H), 2.22-2.08 (m, 2H), 2.02-1.92 (m, 1H), 1.75-1.14 (m, 10H), 0.86 (d, J=6.7 Hz, 3H), 0.82 (d, J=6.7 Hz, 3H) ppm. HRMS (ESI) found m/z 810.3332 (M+Na). C₄₁H₅₀ClN₇NaO₇ requires 810.3352.

At room temperature, to a solution of 59c (75 mg, 0.095 mmol) and (S)-5-(1-(chloromethyl)-5-(di-tert-butoxyphosphoryloxy)-1H-benzo[e]indol-3(2H)-yl)-5-oxopentanoic acid 57d (62 mg, 0.11 mmol) in DMA (3 mL) was added EDCI hydrochloride (40 mg, 0.21 mmol) and then para-toluenesulfonic acid (1.6 mg, 0.0095 mmol). After the mixture was stirred for 5 h, more EDCI hydrochloride (35 mg, 0.18 mmol) was added and the mixture was stirred overnight. All the volatile components were pumped off. The resultant residue was dissolved in THF and redistributed between ethyl acetate and cold dilute aqueous NaHCO₃. The aqueous phase was extracted with ethyl acetate three times. The combined organic extracts were washed with water and brine, dried over anhydrous Na₂SO₄, filtered through celite and the solvent was removed to give di-tert-butyl (S)-1-(chloromethyl)-3-(5-((S)-1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-

1H-benzo[e]indol-3(2H)-yl)-5-oxopentanoyl)-2,3-dihydro-1H-benzo[e]indol-5-yl phosphate 59d as a brown solid (104 mg, 83%), which was used directly. $^1$H NMR (DMSO) δ 10.03 (s, 1H), 8.60 (s, 1H), 8.19-7.38 (m, 14H), 6.87 (s, 2H), 5.97 (br s, 1H), 5.40 (s, 2H), 5.20 (br s, 2H), 4.45-3.82 (m, 10H), 3.38-3.33 (m, 3H), 3.07-2.90 (m, 2H), 2.75-2.50 (m, 2H), 2.20-2.08 (m, 4H), 2.02-1.92 (m, 2H), 1.75-1.10 (m, 12H), 1.48 (s, 18H), 0.86-0.82 (m, 6H) ppm. $^{31}$P NMR (DMSO) δ −15.46 ppm. HRMS (ESI) found m/z 1331.5071 (M+Na). $C_{67}H_{83}Cl_2N_8NaO_{13}P$ requires 1331.5086.

To a suspension of 59d (95 mg, 0.073 mmol) in DCM (2 mL) cooled in an ice bath was added TFA (1 mL). The mixture was stirred in the ice bath for 1.5 h. All the volatile components were pumped off. The resultant residue was triturated with ethyl acetate to give a bluish grey solid (77 mg, 90%), which was further purified by preparative HPLC (column: Synergi-Max RP 4μ, 250×21.20 mm; mobile phase: A/B=30:70 (A: $H_2O$-TFA pH 2.56, B: 90% acetonitrile in water); flow rate 13 mL/min) to give (S)-1-(chloromethyl)-3-(5-((S)-1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-1H-benzo[e]indol-3(2H)-yl)-5-oxopentanoyl)-2,3-dihydro-1H-benzo[e]indol-5-yl dihydrogen phosphate 59 as an off-white solid (5 mg, HPLC purity 97%). $^1$H NMR (DMSO) δ 10.04 (s, 1H), 8.49 (s, 1H), 8.19-8.09 (m, 4H), 7.87-7.81 (m, 2H), 7.66 (d, J=8.5 Hz, 2H), 7.56-7.48 (m, 4H), 7.40-7.36 (m, 2H), 6.98 (s, 2H), 6.01 (br s, 1H), 5.43 (br s, 2H), 5.22 (s, 2H), 4.42-3.34 (m, 2H), 4.25-4.12 (m, 4H), 4.03-3.98 (m, 2H), 3.88-3.81 (m, 2H), 3.38-3.33 (m, 3H), 3.10-2.90 (m, 2H), 2.75-2.55 (m, 4H), 2.20-2.08 (m, 2H), 2.00-1.92 (m, 2H), 1.75-1.10 (m, 12H), 0.88-0.81 (m, 6H) ppm. $^{31}$P NMR (DMSO) δ −5.60 ppm. HRMS (ESI) found m/z 1219.3794 (M+Na). $C_{59}H_{67}Cl_2N_8NaO_{13}P$ requires 1219.3834

Example 10 N—((S)-1-((S)-1-(4-(((S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yloxy)methyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide 60

(S)-1-(Chloromethyl)-3-(5-((S)-1-(chloromethyl)-5-(4-((S)-2-((S)-2-(6-(2,5-dioxo-2,5-dihydro-1H-pyrrol-1-yl)hexanamido)-3-methylbutanamido)-5-ureidopentanamido)benzyloxy)-1H-benzo[e]indol-3(2H)-yl)-5-oxopentanoyl)-2,3-dihydro-1H-benzo[e]indol-5-yl dihydrogen phosphate 59 was enzymatically dephosphorylated to give 60.

Example 11 2-(pyridin-2-yldisulfanyl)ethyl (S)-1-(chloromethyl)-3-(5-((S)-1-(chloromethyl)-5-(phosphonooxy)-1H-benzo[e]indol-3(2H)-yl)-5-oxopentanoyl)-2,3-dihydro-1H-benzo[e]indol-5-ylcarbamate 61

A solution of triphosgene (136 mg, 0.458 mmol) in dry DCM (10 mL) was added to a mixture of (S)-tert-butyl 5-amino-1-(chloromethyl)-1H-benzo[e]indol-3 (2H)-carboxylate 61a (150 mg, 0.451 mmol) and DMAP (386 mg, 3.16 mmol) in dry DCM (30 mL) at r.t. See FIG. 15. After 45 min a solution of 2-(pyridin-2-yldisulfanyl)ethanol (Chem. Eur. J. (2006) 12:3655-3671) (350 mg, 1.87 mmol) in dry DCM (10 mL) was added and the reaction mixture was stirred overnight. After 20 h the mixture was diluted with MeOH (30 mL) and the solvents removed under vacuum. Purification by column chromatography on silica gel using hexanes:DCM 100:0 to 0:100, then DCM:EtOAc 100:0 to 95:5 gave a mixture of compounds 61b and starting material 2-(pyridin-2-yldisulfanyl)ethanol (389 mg). This mixture was used in the next step. A solution of TBDMSCl (262 mg, 1.74 mmol) in DMF (1.5 mL) was added to a stirred mixture of product 61b, 2-(pyridin-2-yldisulfanyl) ethanol, and imidazole (118 mg, 1.74 mmol) in DMF (4 mL) at 0° C. The mixture was warmed to r.t., stirred for 45 min and then diluted with EtOAc and $H_2O$. The layers were separated and the organic layer was washed with $H_2O$ (3×), dried ($Na_2SO_4$) and solvent removed under vacuum. Purification by column chromatography on silica gel using hexanes:DCM 50:50 to 0:100, then DCM:EtOAc 98:2 to 94:6 gave (S)-tert-butyl 1-(chloromethyl)-5-((2-(pyridin-2-yldisulfanyl)ethoxy)carbonylamino)-1H-benzo[e]indole-3 (2H)-carboxylate 61b (190 mg, 77% over two steps from 61a) as a pale yellow foamy solid. $^1$H NMR δ (400 MHz, $CDCl_3$) 8.49 (br s, 1H), 8.48-8.47 (m, 1H), 7.84 (d, J=8.4 Hz, 1H), 7.71 (t, J=7.0 Hz, 2H), 7.63 (t, J=7.3 Hz, 1H), 7.54-7.50 (m, 1H), 7.40 (ddd, J=8.2, 6.8, 1.1 Hz, 1H), 7.09 (ddd, J=7.3, 4.9, 1.0 Hz, 1H), 6.93 (br s, 1H), 4.48 (t, J=6.3 Hz, 2H), 4.31-4.27 (m, 1H), 4.15-4.10 (m, 1H), 4.04-3.98 (m, 1H), 3.91 (dd, J=11.1, 2.4 Hz, 1H), 3.45 (t, J=10.7 Hz, 1H), 3.13 (t, J=6.3 Hz, 2H), 1.60 (s, 9H).

TFA (4.8 mL) was added slowly to a solution of 61b (180 mg, 0.330 mmol) in DCM (9.5 mL) at 0° C. and the mixture stirred at this temperature for 1 h. The reaction mixture was then diluted with DCM and $H_2O$ and neutralized with saturated aqueous $NaHCO_3$ until pH 7-8. The layers were separated and the organic layer washed with $H_2O$ (1×), dried ($Na_2SO_4$) and solvent removed under vacuum to give (S)-2-(pyridin-2-yldisulfanyl)ethyl 1-(chloromethyl)-2,3-dihydro-1H-benzo[e]indol-5-ylcarbamate 61c (113 mg, 77%) as a yellow solid which was used in the next step without purification. $^1$H NMR δ (400 MHz, DMSO-$d_6$) 9.52 (s, 1H), 8.48-8.46 (m, 1H), 7.88 (d, J=8.4 Hz, 1H), 7.83-7.78 (m, 2H), 7.64 (d, J=8.2 Hz, 1H), 7.39 (ddd, J=8.1, 6.9, 1.0 Hz, 1H), 7.25 (ddd, J=6.5, 4.8, 2.2 Hz, 1H), 7.14 (ddd, J=8.2, 6.8, 1.0 Hz, 1H), 7.09 (s, 1H), 5.94 (br s, 1H), 4.33 (t, J=6.2 Hz, 2H), 4.02-3.96 (m, 1H), 3.85 (dd, J=10.8, 3.5 Hz, 1H), 3.70 (t, J=9.3 Hz, 1H), 3.63-3.55 (m, 2H), 3.18 (t, J=6.1 Hz, 2H).

A solution of (S)-5-(1-(chloromethyl)-5-(di-tert-butoxyphosphoryloxy)-1H-benzo[e]indol-3(2H)-yl)-5-oxopentanoic acid 57d (135 mg, 0.250 mmol) in DMA (6 mL) was added to a mixture of 61c (110 mg, 0.247 mmol) and EDCI.HCl (116 mg, 0.605 mmol) at r.t., under nitrogen and mixture stirred overnight. After 18.5 h an additional solution of 57d (40 mg, 0.0741 mmol) in DMA (0.5 mL) and solid EDCI.HCl (28.4 mg, 0.148 mmol) were added and the mixture stirred at r.t, under nitrogen. After another 6 h an additional portion of 57d (7 mg, 0.0130 mmol) in DMA (0.5 mL) and solid EDCI.HCl (24 mg, 0.125 mmol) were added and the mixture stirred for a further 2 days and 16.5 h. The mixture was then diluted with $H_2O$ and a solid precipitated out. The solid was collected by filtration, washed with $H_2O$, saturated aqueous $NaHCO_3$, $H_2O$ and hexanes. The solid was dissolved in EtOAc, the solution was washed with saturated aqueous $NaHCO_3$ (3×) and $H_2O$ (1×) and then dried ($Na_2SO_4$) and solvent removed under vacuum. The solid was then re-dissolved in DCM and washed with more saturated aqueous $NaHCO_3$ (3×), dried ($Na_2SO_4$) and solvent removed under vacuum. The solid was then triturated with hexanes:EtOAc 95:5 to 90:10 to give 2-(pyridin-2-yldisulfanyl)ethyl (S)-1-(chloromethyl)-3-(5-((S)-1-(chloromethyl)-5-(di-tert-butoxyphosphoryloxy)-1H-benzo[e]indol-3(2H)-yl)-5-oxopentanoyl)-2,3-dihydro-1H-benzo[e]

indol-5-ylcarbamate 61d (117 mg, HPLC purity: 86.1%) as a beige solid, which was used in the next step without further purification. HRMS m/z 989.2289 [(M+Na)$^+$ calcd for C$_{47}$H$_{53}$Cl$_2$N$_4$NaO$_8$PS$_2$ 989.2312].

TFA (1 mL) was added dropwise to a stirred solution of 61d in DCM (2 mL) at 0° C. and the mixture stirred at this temperature for 70 min. The solvents were then removed under vacuum at 25° C. The resulting black residue was dissolved in DCM and the solution diluted with EtOAc. The DCM was removed under vacuum to give a suspension in EtOAc. The solid was collected by filtration, triturated with EtOAc and hexanes and dried to give a green solid. This was further purified by preparative HPLC (column: Synergi-MAX RP 4μ, 21.20×250 mm; flow rate: 12 mL/min; mobile phase: solvent A: H$_2$O/TFA pH 2.6, solvent B: MeCN/H$_2$O 90:10; method: gradient, solvent A:solvent B 60:40 to 2:98, 35 min; wavelength: 254 nm, 330 nm) to give 61, 16 mg, 8% over two steps from 61c, HPLC purity: 97.2%). $^1$H NMR δ (400 MHz, DMSO-d$_6$) 9.69 (s, 1H), 8.57-8.46 (m, 3H), 8.09 (d, J=8.3 Hz, 1H), 8.01 (d, J=8.5 Hz, 1H), 7.91 (dd, J=8.3, 2.4 Hz, 2H), 7.82 (d, J=3.3 Hz, 2H), 7.59-7.52 (m, 2H), 7.47-7.40 (m, 2H), 7.27-7.23 (m, 1H), 4.42-4.22 (m, 8H), 4.06-4.01 (m, 2H), 3.90 (td, J=11.2, 7.4 Hz, 2H), 3.19 (t, J=6.0 Hz, 2H), 2.77-2.59 (m, 4H), 2.01-1.94 (m, 2H). 2 protons not observed. $^{31}$P NMR δ (400 MHz, DMSO-d$_6$) −6.01. HRMS m/z 877.1053 [(M+Na)$^+$ calcd for C$_{39}$H$_{37}$Cl$_2$N$_4$NaO$_8$PS$_2$ 877.1060]. [α]$_D^{24}$=−42.3° (c=0.213, DMSO).

Example 12 2-(pyridin-2-yldisulfanyl)propyl (S)-1-(chloromethyl)-3-(5-((S)-1-(chloromethyl)-5-(phosphonooxy)-1H-benzo[e]indol-3(2H)-yl)-5-oxo-pentanoyl)-2,3-dihydro-1H-benzo[e]indol-5-ylcarbamate 62

Triethylamine, Et$_3$N (0.92 mL, 6.62 mmol) and triflic anhydride (1.03 mL, 6.11 mmol) were added to a stirred solution of 51a (1.70 g, 5.09 mmol) in DCM (160 mL) at 0° C. See FIG. 16. The reaction was stirred at 0° C. for 20 min, then diluted with H$_2$O, layers separated and the aqueous layer extracted with DCM (1×). The combined organic layers were dried (Na$_2$SO$_4$) and solvent removed under vacuum. Purification by column chromatography on silica gel using hexanes:EtOAc 100:0 to 95:5 gave (S)-tert-butyl 1-(chloromethyl)-5-(trifluoromethylsulfonyloxy)-1H-benzo[e]indole-3(2H)-carboxylate 62a (2.20 g, 93%) as a beige foamy solid. $^1$H NMR δ (400 MHz, CDCl$_3$) 8.30 (br s, 1H), 8.03 (d, J=8.5 Hz, 1H), 7.76 (d, J=8.4 Hz, 1H), 7.62-7.59 (m, 1H), 7.53-7.49 (m, 1H), 4.32 (br s, 1H), 4.21-4.15 (m, 1H), 4.09-4.03 (m, 1H), 3.92 (dd, J=11.2, 2.8 Hz, 1H), 3.54-3.49 (m, 1H), 1.61 (s, 9H).

A solution of 62a (2.15 g, 4.61 mmol) in dry THF (60 mL) was added to a mixture of Cs$_2$CO$_3$ (2.10 g, 6.44 mmol), BINAP (430 mg, 0.690 mmol) and Pd(OAc)$_2$ (155 mg, 0.690 mmol) in a sealed tube, under nitrogen. Diphenylmethanimine (1.0 mL, 5.98 mmol) was then added to the reaction mixture and nitrogen bubbled through the mixture for 10 min. The sealed tube was heated at 60-65° C. for 4 days. The reaction mixture was then cooled to r.t., diluted with DCM, filtered through celite, the celite plug washed with DCM until there was no more color in the washings and the filtrate evaporated under vacuum. Purification of the residue by column chromatography on silica gel using hexanes:DCM 100:0 to 50:50 gave (S)-tert-butyl 1-(chloromethyl)-5-(diphenylmethyleneamino)-1H-benzo[e]indole-3 (2H)-carboxylate 53f (2.09 g, 91%) as a yellow, foamy solid. $^1$H NMR δ (400 MHz, DMSO-d$_6$) 7.85 (d, J=8.4 Hz, 1H), 7.80 (d, J=8.4 Hz, 1H), 7.75 (d, J=7.3 Hz, 2H), 7.61-7.57 (m, 1H), 7.54-7.49 (m, 3H), 7.37-7.33 (m, 1H), 7.30-7.23 (m, 3H), 7.06 (d, J=6.7 Hz, 2H), 4.14-4.02 (m, 2H), 3.99-3.94 (m, 2H), 3.77 (dd, J=10.8, 7.4 Hz, 1H), 1.46 (s, 9H), 1H not observed. HRMS m/z 497.1984 [(M+H)$^+$ calcd for C$_{31}$H$_{30}$ClN$_2$O$_2$ 497.1990]. [α]$_D^{28}$=−101.5° (c=0.995, DCM).

Glacial acetic acid, HOAc (65 mL) was added to a stirred solution of 53f (1.30 g, 2.62 mmol) in THF and H$_2$O (195 mL/98 mL) at r.t. and the mixture stirred overnight. After 18 h the reaction mixture was concentrated under vacuum to remove most of the THF, without heating above 30° C. The mixture was then diluted with EtOAc (200 mL), the organic layer was separated, washed with saturated aqueous NaHCO$_3$ (4×, until washings were pH 8), dried (Na$_2$SO$_4$) and the solvent was removed under vacuum. Purification of the residue by column chromatography on silica gel using hexanes:EtOAc 100:0 to 90:10 gave (S)-tert-butyl 5-amino-1-(chloromethyl)-1H-benzo[e]indole-3(2H)-carboxylate 61a (503 mg, 58%). $^1$H NMR δ (400 MHz, DMSO-d$_6$) 8.01 (d, J=8.4 Hz, 1H), 7.64 (d, J=8.0 Hz, 1H), 7.40 (ddd, J=8.1, 6.8, 0.9 Hz, 1H), 7.36 (br s, 1H), 7.20 (ddd, J=8.1, 6.8, 1.1 Hz, 1H), 5.91 (s, 2H), 4.11-3.91 (m, 4H), 3.66 (dd, J=10.6, 8.2 Hz, 1H), 1.53 (s, 9H).

A solution of 2-mercaptopropanoic acid (3.02 g, 28.5 mmol) in dry THF (10 mL) was added dropwise to a stirred suspension of LiAlH$_4$ (1.29 g, 34.0 mmol) in dry THF (40 mL) at 0° C. The reaction mixture was warmed to r.t. and stirred for 3 h. The mixture was then cooled to 0° C. and quenched with H$_2$O (5 mL) and 5% aqueous NaOH solution (3 mL). The mixture was stirred at 0° C. for 20 min, filtered through celite, the celite plug washed with Et$_2$O (3×), the combined organics dried (Na$_2$SO$_4$), filtered and solvent removed to give 2-mercaptopropan-1-ol (944 mg) which was used in the next step without purification. A solution of 1,2-di(pyridin-2-yl)disulfane (*Bioorg. Med. Chem. Lett.* (2011) 21:4985-4988.) (470 mg, 5.10 mmol) in MeOH (7 mL) was added to a solution of 2-mercaptopropan-1-ol in MeOH (4 mL) at r.t. and the mixture stirred overnight. After 17.5 h the solvent was removed under vacuum. Purification by column chromatography on alumina (neutral) using hexanes:DCM 50:50 to 0:100, then DCM:EtOAc 99:1 to 75:25 gave 2-(pyridin-2-yldisulfanyl)propan-1-ol (528 mg, 18% over two steps from 2-mercaptopropanoic acid) as a yellow oil. $^1$H NMR δ (400 MHz, CDCl$_3$) 8.50 (ddd, J=5.0, 1.8, 0.9 Hz, 1H), 7.57 (ddd, J=8.0, 7.4, 1.8 Hz, 1H), 7.39 (td, J=8.1, 1.0 Hz, 1H), 7.15 (ddd, J=7.4, 5.0, 1.1 Hz, 1H), 5.93 (dd, J=8.8, 5.8 Hz, 1H), 3.68 (ddd, J=12.5, 8.8, 3.8 Hz, 1H), 3.40 (ddd, J=12.4, 7.8, 5.8 Hz, 1H), 3.14-3.06 (m, 1H), 1.31 (d, J=6.9 Hz, 3H).

A solution of triphosgene (127 mg, 0.428 mmol) in dry DCM (10 mL) was added slowly to a mixture of 61a (250 mg, 0.751 mmol) and DMAP (551 mg, 4.51 mmol) in dry DCM (40 mL) at r.t. A yellow solid precipitated immediately. After 30 min a solution of 2-(pyridin-2-yldisulfanyl)propan-1-ol (420 mg, 2.09 mmol) in dry DCM (6 mL) was added and the precipitate dissolved. The reaction mixture was left stirring overnight. After 18 h 1M NaOH (30 mL) was added and the mixture stirred. The layers were then separated and the organic layer dried (Na$_2$SO$_4$), diluted with MeOH (15 mL) and absorbed onto silica gel. The product was eluted using hexanes:DCM 100:0 to 50:50 to 0:100, then DCM:EtOAc 99:1 to 92:8. The material was then chromatographed again on silica gel using hexanes:DCM 100:0 to 50:50 to 0:100, then DCM:EtOAc 98:2 to 95:5. This gave a mixture of 62b and 2-(pyridin-2-yldisulfanyl)propan-1-ol (385 mg). This mixture was used in the next step. A solution of TBDMSCl (81 mg, 0.535 mmol) in DMF (1 mL) was added to a stirred mixture of 62b and 2-(pyridin-2-yldisulfanyl)propan-1-ol, and imidazole (36 mg, 0.535 mmol) in DMF (2 mL) at 0° C. The mixture was warmed to r.t., stirred for 50 min and then diluted with EtOAc and H$_2$O. The mixture was well stirred, the layers separated and the organic layer washed with H$_2$O (3×), dried (Na$_2$SO$_4$) and solvent removed under vacuum. Purification by column chromatography on silica gel hexanes:DCM 50:50 to 0:100, then DCM:EtOAc 95:5 gave (1S)-tert-butyl 1-(chloromethyl)-5-((2-(pyridin-2-yldisulfanyl)propoxy)carbonylamino)-1H-benzo[e]indole-3(2H)-carboxylate 62b (295 mg, 70% over two steps from compound 61a) as a pale yellow foamy solid. $^1$H NMR δ (400 MHz, CDCl$_3$) 8.49 (br s, 1H), 8.46 (ddd, J=4.8, 1.7, 0.8 Hz, 1H), 7.86 (d, J=8.4 Hz, 1H), 7.75-7.73 (m, 2H), 7.64-7.60 (m, 1H), 7.54 (ddd, J=8.1, 6.9, 1.0 Hz, 1H), 7.42 (ddd, J=8.2, 6.8, 1.1 Hz, 1H), 7.08 (ddd, J=7.4, 4.9, 0.8 Hz, 1H), 6.97 (br s, 1H), 4.37-4.28 (m, 3H), 4.17-4.11 (m, 1H), 4.05-3.99 (m, 1H), 3.92 (dd, J=11.1, 2.5 Hz, 1H), 3.47 (t, J=10.7 Hz, 1H), 3.38-3.30 (m, 1H), 1.62 (s, 9H), 1.41 (d, J=6.9 Hz, 3H). HRMS m/z 582.1265 [(M+Na)$^+$ calcd for C$_{27}$H$_{30}$ClN$_3$NaO$_4$S$_2$ 582.1258]

TFA (7 mL) was added slowly to a solution of 62b (285 mg, 509 mmol) in DCM (14 mL) at 0° C. and the mixture stirred at this temperature for 1 h. The reaction mixture was then diluted with DCM and H$_2$O and neutralized with saturated aqueous NaHCO$_3$ until pH 7. The layers were separated and the organic layer washed with H$_2$O (1×), dried (Na$_2$SO$_4$) and solvent removed under vacuum to give 2-(pyridin-2-yldisulfanyl)propyl (S)-1-(chloromethyl)-2,3-dihydro-1H-benzo[e]indol-5-ylcarbamate 62c (220 mg, 94%) as a yellow solid which was used in the next step without purification. $^1$H NMR δ (400 MHz, DMSO-d$_6$) 9.52 (s, 1H), 8.45 (ddd, J=4.8, 1.7, 0.8 Hz, 1H), 7.88 (d, J=8.5 Hz, 1H), 7.85-7.83 (m, 1H), 7.79-7.75 (m, 1H), 7.64 (d, J=8.2 Hz, 1H), 7.39 (ddd, J=8.1, 6.8, 1.0 Hz, 1H), 7.23 (ddd, J=7.3, 4.8, 1.0 Hz, 1H), 7.15 (ddd, J=8.1, 6.8, 1.0 Hz, 1H), 7.08 (s, 1H), 5.93 (br s, 1H), 4.24-4.13 (m, 2H), 4.02-3.96 (m, 1H), 3.85 (dd, J=10.8, 3.5 Hz, 1H), 3.70 (t, J=9.3 Hz, 1H), 3.63-3.55 (m, 2H), 3.43-3.36 (m, 1H), 1.34 (d, J=6.9 Hz, 3H).

A solution of (S)-5-(1-(chloromethyl)-5-(di-tert-butoxyphosphoryloxy)-1H-benzo[e]indol-3(2H)-yl)-5-oxopentanoic acid 57d (365 mg, 0.676 mmol) in DMA (10 mL) was added to a mixture of 62c (215 mg, 0.467 mmol) and EDCI.HCl (268 mg, 1.40 mmol) at r.t. TsOH was added (16 mg, 0.0929 mmol) and the mixture stirred overnight, under nitrogen (and over 3A molecular sieves). After 27.5 h the mixture was diluted with EtOAc and H$_2$O, well shaken and the layers separated. The organic layer was washed with saturated aqueous NaHCO$_3$ (3×), brine (1×), dried (Na$_2$SO$_4$) and solvent removed under vacuum. The resulting residue was dissolved in DCM and diluted with hexanes until a solid precipitated out of solution. The solvents were removed under vacuum and the solid was triturated with hexanes: EtOAc 95:5 to give 2-(pyridin-2-yldisulfanyl)propyl (S)-1-(chloromethyl)-3-(5-((S)-1-(chloromethyl)-5-(di-tert-butoxyphosphoryloxy)-1H-benzo[e]indol-3(2H)-yl)-5-oxopentanoyl)-2,3-dihydro-1H-benzo[e]indol-5-ylcarbamate 62d (372 mg) as a tan solid, which was used in the next step without further purification. HRMS m/z 1003.2445 [(M+Na)$^+$ calcd for C$_{48}$H$_{55}$Cl$_2$N$_4$NaO$_8$PS$_2$ 1003.2468].

TFA (3.5 mL) was added slowly to a stirred solution of 62d (prepared as above) in DCM (7 mL) at 0° C. The mixture was stirred at this temperature for 1 h. The solvents were then removed under vacuum at 25° C. The resulting dark green residue was dissolved in DCM and the solution diluted with EtOAc causing a solid to precipitate out of solution. The solvents were removed under vacuum at 30° C. and the residue again dissolved in DCM and diluted with EtOAc. The DCM was removed under vacuum to give a suspension in EtOAc. The solid was collected by filtration and the solid then washed with EtOAc and hexanes and dried to give a green solid. This was further purified by preparative HPLC (column: Synergi-MAX RP 4μ, 21.20× 250 mm; flow rate: 12 mL/min; mobile phase: solvent A: H$_2$O/ammonium formate buffer pH 3.5, solvent B: MeCN/H$_2$O 90:10; method: gradient, solvent A:solvent B 25:75 to 0:100 over 19 min) to give 2-(pyridin-2-yldisulfanyl)propyl (S)-1-(chloromethyl)-3-(5-((S)-1-(chloromethyl)-5-(phosphonooxy)-1H-benzo[e]indol-3(2H)-yl)-5-oxopentanoyl)-2,3-dihydro-1H-benzo[e]indol-5-ylcarbamate 62, 78 mg, 19% over two steps from 62c, HPLC purity: 87.4%) as a cream powder. $^1$H NMR δ (400 MHz, DMSO-d$_6$) 9.69 (s, 1H), 8.56 (s, 1H), 8.48 (s, 1H), 8.44 (d, J=4.5 Hz, 1H), 8.15 (d, J=8.3 Hz, 1H), 8.00 (d, J=8.5 Hz, 1H), 7.90 (d, J=8.4 Hz, 1H), 7.85-7.76 (m, 3H), 7.55-7.48 (m, 2H), 7.44-7.40 (m, 1H), 7.36-7.32 (m, 1H), 7.24-7.21 (m, 1H), 4.41-4.14 (m, 8H), 4.05-3.99 (m, 2H), 3.91 (dd, J=10.8, 7.2 Hz, 1H), 3.85-3.81 (m, 1H), 3.37-3.28 (m, 1H), 2.74-2.57 (m, 4H), 1.98-1.95 (m, 2H), 1.34 (d, J=6.7 Hz, 3H), 2 protons not observed. $^{31}$P NMR δ (400 MHz, DMSO-d$_6$) −5.09. HRMS m/z 891.1221 [(M+Na)$^+$ calcd for C$_{40}$H$_{39}$Cl$_2$N$_4$NaO$_8$PS$_2$ 891.1216]

Example 13 (S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-yl 2-(6-(2,5-dioxo-2,5-dihydro-1H-pyrrol-1-yl)-N-methylhexanamido)ethyl(methyl)carbamate 63

(S)-1-(Chloromethyl)-3-(5-((S)-1-(chloromethyl)-5-(phosphonooxy)-1H-benzo[e]indol-3(2H)-yl)-5-oxopentanoyl)-2,3-dihydro-1H-benzo[e]indol-5-yl 2-(6-(2,5-dioxo-2,5-dihydro-1H-pyrrol-1-yl)-N-methylhexanamido)ethyl (methyl)carbamate 57 was enzymatically dephosphorylated to give 63.

Example 14 2-(pyridin-2-yldisulfanyl)ethyl (S)-1-(chloromethyl)-3-(5-((S)-1-(chloromethyl)-5-hydroxy-1H-benzo[e]indol-3(2H)-yl)-5-oxopentanoyl)-2,3-dihydro-1H-benzo[e]indol-5-ylcarbamate 64

2-(Pyridin-2-yldisulfanyl)ethyl (S)-1-(chloromethyl)-3-(5-((S)-1-(chloromethyl)-5-(phosphonooxy)-1H-benzo[e] indol-3(2H)-yl)-5-oxopentanoyl)-2,3-dihydro-1H-benzo[e] indol-5-ylcarbamate 61 was enzymatically dephosphorylated to give 64.

Example 15 (11aS)-4-((S)-6-amino-2-((S)-2-(6-(2,5-dioxo-2,5-dihydro-1H-pyrrol-1-yl)hexanamido)-3-methylbutanamido)hexanamido)benzyl 8-(6-((S)-1-(chloromethyl)-5-(4-methylpiperazine-1-carbonyloxy)-1H-benzo[e]indol-3 (2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate 65

To a stirred solution of (S)-2,2,2-trichloroethyl 6-(5-(tert-butoxycarbonylamino)-4-(2-(hydroxymethyl)pyrrolidine-1-carbonyl)-2-methoxyphenoxy)hexanoate 54c (1.66 g, 2.71 mmol) in dry DCM (10 mL) at r.t. was added acetic anhydride (1.29 mL, 13.6 mmol) and triethylamine (2.27 mL, 16.3 mmol). See FIG. 17. The reaction mixture was stirred for a further 4 h. Dry MeOH (1.5 mL) was added and the mixture was stirred for 30 min. Ethyl acetate (200 mL) was added and the ethyl acetate layer was separated and then washed with water several times. The ethyl acetate solution was dried (MgSO$_4$) and evaporated to give (S)-2,2,2-trichloroethyl 6-(4-(2-(acetoxymethyl)pyrrolidine-1-carbonyl)-5-(tert-butoxycarbonylamino)-2-methoxyphenoxy)hexanoate 65a (1.8 g, 100%) as a pale yellow glue; $^1$H NMR [(CD$_3$)$_2$SO] δ 8.82 (br s, 1H), 7.27 (s, 1H), 6.86 (s, 1H), 4.89 (s, 2H), 4.39-4.20 (m, 3H), 3.93 (t, J=6.4 Hz, 2H), 3.74 (s, 3H), 3.50-3.33 (m, 2H), 2.10-1.94 (m, 4H), 1.92-1.61 (m, 7H), 1.53-1.42 (m, 2H), 1.43 (s, 9H), 2H obscured by DMSO peak. HRMS (ESI) m/z calc. for C$_{28}$H$_{39}$Cl$_3$N$_2$NaO$_9$: 675.1613. found: 675.1603 [MNa$^+$]. Calc. for C$_{28}$H$_{40}$Cl$_3$N$_2$O$_9$: 653.1794. found: 653.1778 [MH$^+$].

To a stirred solution of 65a (1.76 g, 2.69 mmol) in a mixture of acetone (30 mL), water (20 mL), and THF (12 mL) under nitrogen was added Zn (7.06 g, 108 mmol) and NH$_4$Cl (11.6 g, 216 mmol). The mixture was stirred at r.t. for 23 h. Ethyl acetate (100 mL) was added and the mixture was stirred for 15 min. The organic layer was decanted. The extraction was repeated with more ethyl acetate (2×100 mL). The combined organic solution was washed with water (2×100 mL), dried (MgSO$_4$), filtered through celite and evaporated to give (S)-6-(4-(2-(acetoxymethyl)pyrrolidine-1-carbonyl)-5-(tert-butoxycarbonylamino)-2-methoxyphenoxy)hexanoic acid 65b (1.36 g, 96%) as a sticky colorless foam; $^1$H NMR [(CD$_3$)$_2$SO] δ 11.49 (very br s, 1H), 8.83 (s, 1H), 7.27 (s, 1H), 6.86 (br s, 1H), 4.39-4.02 (m, 3H), 3.93 (t, J=6.4 Hz, 2H), 3.74 (s, 3H), 3.51-3.33 (m, 2H, partially obscured by water peak), 2.21 (t, J=7.1 Hz, 2H), 2.11-1.93 (m, 4H), 1.90-1.66 (m, 5H), 1.62-1.50 (m, 2H), 1.50-1.35 (m, 2H), 1.43 (s, 9H). Anal. (C$_{26}$H$_{38}$N$_2$O$_9$.) Calc: C, 59.76; H, 7.33; N, 5.36. Found: C, 59.66; H, 7.49; N, 5.29.

To a stirred solution of 65b (0.87 g, 2.41 mmol) and (S)-1-(chloromethyl)-2,3-dihydro-1H-benzo[e]indol-5-yl 4-methylpiperazine-1-carboxylate 58b (1.26 g, 2.41 mmol) in dry DMA (5 mL) at 0° C. under a nitrogen atmosphere was added 4M HCl in p-dioxane (1.21 mL, 4.82 mmol), followed by EDCI.HCl (1.39 g, 7.23 mmol), and anhydrous TsOH (83 mg, 0.48 mmol). The reaction mixture was stirred at 0° C. under nitrogen for 21 hours then partitioned between ethyl acetate (500 mL) and water (500 mL). The ethyl acetate layer was separated and the aqueous layer was further extracted with more ethyl acetate (200 mL). The combined ethyl acetate extracts were washed successively with water (200 mL), saturated NaHCO$_3$ solution (2×200 mL) and water (200 mL). The ethyl acetate layer was dried and evaporated to give (S)-3-(6-(4-((S)-2-(acetoxymethyl)pyrrolidine-1-carbonyl)-5-(tert-butoxycarbonylamino)-2-methoxyphenoxy)hexanoyl)-1-(chloromethyl)-2,3-dihydro-1H-benzo[e]indol-5-yl 4-methylpiperazine-1-carboxylate 65c (1.66 g, 80%) as a beige solid-foam; mp 84-87° C.; $^1$H NMR [(CD$_3$)$_2$SO] δ 8.84 (br s, 1H), 8.21 (s, 1H), 7.95 (d, J=8.3 Hz, 1H), 7.81 (d, J=8.3 Hz, 1H), 7.58 (br t, J=7.7, 1H), 7.46 (br t, J=8.1 Hz, 1H), 7.29 (s, 1H), 6.86 (s, 1H), 4.40 (t, J=10.0 Hz, 1H), 4.36-3.86 (m, 10H), 3.83-3.74 (m, 1H), 3.73 (s, 3H), 3.54-3.36 (m, 4H), 2.67-2.34 (m, 6H, partially obscured by DMSO peak), 2.26 (s, 3H), 2.02 (br s, 3H), 1.93-1.62 (m, 8H), 1.60-1.47 (m, 2H), 1.42 (s, 9H). Anal. (C$_{45}$H$_{58}$ClN$_5$O$_{10}$.1½H$_2$O) Calc: C, 60.63; H, 6.90; N, 7.86. Found: C, 60.39; H, 6.66; N, 8.08.

To a stirred solution of 65c (2.17 g, 2.51 mmol) in DCM (20 mL) at 0° C. under a nitrogen atmosphere was added TFA (20 mL). After addition, the mixture was stirred further at this temperature for 2.5 h. The mixture was poured into a cold (0° C.) mixture of NaHCO$_3$ (50 g), water (700 mL), and DCM (500 mL) and stirred for 15 min. (pH ca. 8). The DCM layer was separated and washed with more aqueous NaHCO$_3$ (200 mL) and water (200 mL) and then dried (MgSO$_4$). The solvent was evaporated to give (S)-3-(6-(4-((S)-2-(acetoxymethyl)pyrrolidine-1-carbonyl)-5-amino-2-methoxyphenoxy)hexanoyl)-1-(chloromethyl)-2,3-dihydro-1H-benzo[e]indol-5-yl 4-methylpiperazine-1-carboxylate 65d as a pale brown solid-foam (1.76 g, 92%); mp 62° C.; $^1$H NMR [(CD$_3$)$_2$SO] δ 8.21 (s, 1H), 7.95 (d, J=8.3 Hz, 1H), 7.81 (d, J=8.3 Hz, 1H), 7.57 (br t, J=7.6 Hz, 1H), 7.46 (br t, J=7.2 Hz, 1H), 6.67 (s, 1H), 6.37 (s, 1H), 5.09 (s, 2H), 4.41 (t, J=9.7 Hz, 1H), 4.36-4.20 (m, 3H), 4.17-4.00 (m, 3H), 3.97-3.86 (m, 3H), 3.81-3.70 (m, 2H), 3.63 (s, 3H), 3.54-3.32 (m, 5H), 2.66-2.34 (m, 6H, partially obscured by DMSO peak), 2.26 (s, 3H), 2.08-1.96 (m, 1H), 2.10 (s, 3H), 1.93-1.63 (m, 7H), 1.57-1.45 (m, 2H). Anal. (C$_{40}$H$_{50}$ClN$_5$O$_8$.½H$_2$O) Calc: C, 62.13; H, 6.65; N, 9.06. Found: C, 62.12; H, 6.76; N, 8.77.

A mixture of (S)-2-(allyloxycarbonylamino)-6-(tert-butoxycarbonylamino)hexanoic acid 65e (3.30 g, 10.0 mmol) and EEDQ (3.71 g, 15.0 mmol) in dry DMA (10 mL) was stirred at r.t. under nitrogen for 15 min. See FIG. 18. To this preformed mixture was added a solution of 4-((tert-butyldimethylsilyloxy)methyl)aniline (prepared from the corresponding p-nitrobenzyl alcohol and TBDMSCl in DMF; followed by reduction using Zn/NH$_4$Cl) (2.37 g, 10.0 mmol) in dry DMA (3 mL). The final reaction mixture was stirred further at r.t. under a nitrogen atmosphere for 23 h. The mixture was partitioned between ethyl acetate (500 mL) and water (500 mL). The ethyl acetate layer was separated and washed successively with saturated NaHCO$_3$ (2×300 mL) and water (300 mL) and then dried (MgSO$_4$). Evaporation of the solvent gave an orange oil which was purified by a silica column chromatography (petroleum ether-ethyl acetate gradient from 10-35%) to afford the TBDMS-protected lysine 65f (4.87 g, 89%) as a sticky beige solid-foam; $^1$H NMR [(CD$_3$)$_2$SO] δ 9.97 (s, 1H), 7.55 (d, J=8.50 Hz, 2H), 7.44 (d, J=7.8 Hz, 1H), 7.21 (d, J=8.5 Hz, 2H), 6.75 (t, J=5.3 Hz, 1H), 5.99-5.82 (m, 1H), 5.28 (br d, J=17.2 Hz, 1H), 5.17 (br d, J=10.5 Hz, 1H), 4.64 (s, 2H), 4.46 (d, J=5.2 Hz, 2H), 4.12-4.02 (m, 1H), 2.93-2.83 (m, 2H), 1.70-1.52 (m, 2H), 1.46-1.20 (m, 4H), 1.35 (s, 9H), 0.89 (s, 9H), 0.06 (s, 6H). HRMS (ESI) m/z calc. for C$_{28}$H$_{47}$N$_3$NaO$_6$Si: 572.3126. found: 572.3136 [MNa$^+$].

To a stirred solution of 65f (4.81 g, 8.75 mmol) in THF (30 mL) at r.t. was added a 1M solution of tetrabutylammonium fluoride in THF (17.5 mL, 17.5 mmol). After addition, the mixture was stirred at this temperature for a further 2.5 h. Aqueous NH$_4$Cl (300 mL) was added and product was extracted into ethyl acetate (500 mL). The ethyl acetate was washed with water (2×100 mL) and dried (MgSO$_4$). The solvent was evaporated to give benzyl alcohol lysine 65g (3.81 g, 100%) as a beige solid; mp 101-103° C.; $^1$H NMR [(CD$_3$)$_2$SO] δ 9.94 (s, 1H), 7.52 (d, J=8.4 Hz, 2H), 7.44 (d, J=7.8 Hz, 1H), 7.23 (d, J=8.4 Hz, 2H), 6.76 (t, J=5.4 Hz, 1H), 5.97-5.84 (m, 1H), 5.29 (br d, J=17.2 Hz, 1H), 5.17 (br d, J=10.4 Hz, 1H), 5.08 (t, J=5.7 Hz, 1H), 4.47 (d, J=5.3 Hz, 2H), 4.43 (d, J=5.7 Hz, 2H), 4.13-4.03 (m, 1H), 2.96-2.82 (m, 2H), 1.72-1.52 (m, 2H), 1.46-1.20 (m, 4H), 1.36 (s, 9H). HRMS (ESI) m/z calc. for C$_{22}$H$_{33}$N$_3$NaO$_6$: 458.2262. found: 458.2272 [MNa$^+$]; calc. for C$_{22}$H$_{33}$N$_3$KO$_6$: 474.2001. found: 474.1998 [MK$^+$].

To a stirred solution of 65d (764 mg, 1.00 mmol) and DMAP (367 mg, 3.00 mmol) in dry DCM (15 mL) at r.t. under nitrogen was added a solution of diphosgene in dry DCM (0.05 mmol per mL, 12 mL, 0.60 mmol) and the mixture was stirred for a further 20 min. See FIG. 19. To this mixture was added a solution of 65g (3.97 g, 9.13 mmol) in dry DCM (80 mL). The final reaction mixture was stirred further at r.t. under a nitrogen atmosphere for 48 h. The mixture was partitioned between ethyl acetate (500 mL) and water (300 mL). The ethyl acetate layer was separated and the aqueous layer was further extracted with ethyl acetate (2×200 mL). The combined ethyl acetate solution was washed with more water (2×200 mL) and dried ($MgSO_4$). Evaporation of the solvent at 30° C. (bath temperature) gave an orange oil which was purified by silica column chromatography (ethyl acetate-MeOH=10:1) to afford (S)-3-(6-(4-((S)-2-(acetoxymethyl)pyrrolidine-1-carbonyl)-5-((4-((S)-2-(allyloxycarbonylamino)-6-(tert-butoxycarbonylamino) hexanamido)benzyloxy)carbonylamino)-2-methoxyphenoxy)hexanoyl)-1-(chloromethyl)-2,3-dihydro-1H-benzo[e]indol-5-yl 4-methylpiperazine-1-carboxylate 65h (1.04 g, 85%) as a pale orange solid; mp 90-93° C.; $^1$H NMR [$(CD_3)_2SO$] δ 10.04 (s, 1H), 9.10 (br s, 1H), 8.21 (s, 1H), 7.95 (d, J=8.3 Hz, 1H), 7.81 (d, J=8.3 Hz, 1H), 7.63-7.53 (m, 3H), 7.51-7.42 (m, 2H), 7.32 (d, J=8.5 Hz, 2H), 7.21 (br s, 1H), 6.85 (br s, 1H), 6.79-6.72 (m, 1H), 5.97-5.83 (m, 1H), 5.29 (br d, J=17.2 Hz, 1H), 5.17 (br d, J=10.4 Hz, 1H), 5.08-4.96 (m, 2H), 4.52-4.37 (m, 3H), 4.37-3.85 (m, 10H), 3.83-3.66 (m, 2H), 3.74 (s, 3H), 3.54-3.41 (m, 2H), 3.41-3.23 (m, 2H, partially obscured by water peak), 2.95-2.83 (m, 2H), 2.66-2.34 (m, 6H, partially obscured by DMSO peak), 2.25 (s, 3H), 2.07-1.92 (m, 4H), 1.87-1.45 (m, 11H), 1.45-1.20 (m, 4H), 1.35 (s, 9H). HRMS (ESI) m/z calc. for $C_{63}H_{82}ClN_8O_{15}$: 1225.5583. found: 1225.5557 [$MH^+$]; calc. for $C_{63}H_{81}ClN_8NaO_{15}$: 1247.5402. found: 1247.5401 [$MNa^+$]; calc. for $C_{63}H_{81}ClKN_8O_{15}$: 1263.5142. found: 1263.5141 [$MK^+$].

A mixture of 65h (1.01 g, 0.824 mmol) and $K_2CO_3$ (1.14 g, 8.24 mmol) in DCM (20 mL) and MeOH (10 mL) was stirred at r.t. for 1 hour and 40 min. The mixture was diluted with DCM (200 mL) and stirred with ice-water (200 mL) for 10 min. The DCM layer was separated and the aqueous layer was further extracted with DCM (2×100 mL). The combined DCM solution was washed with more water (200 mL) and dried ($MgSO_4$). Evaporation of solvent at 25° C. (bath temperature) gave (S)-3-(6-(5-((4-((S)-2-(allyloxycarbonylamino)-6-(tert-butoxycarbonylamino)hexanamido)benzyloxy)carbonylamino)-4-((S)-2-(hydroxymethyl)pyrrolidine-1-carbonyl)-2-methoxyphenoxy)hexanoyl)-1-(chloromethyl)-2,3-dihydro-1H-benzo[e]indol-5-yl 4-methylpiperazine-1-carboxylate 65i (0.94 g, 96%) as a beige solid; mp 104-107° C.; $^1$H NMR [$(CD_3)_2SO$] δ 10.04 (s, 1H), 9.17 (br s, 1H), 8.21 (s, 1H), 7.95 (d, J=8.4 Hz, 1H), 7.80 (d, J=8.3 Hz, 1H), 7.63-7.53 (m, 3H), 7.51-7.42 (m, 2H), 7.38-7.21 (m, 3H), 6.93 (s, 1H), 5.32 (t, J=5.4 Hz, 1H), 5.98-5.83 (m, 1H), 5.30 (br d, J=17.2 Hz, 1H), 5.17 (br d, J=11.7 Hz, 1H), 5.03 (s, 2H), 4.73 (t, J=5.7 Hz, 1H), 4.52-4.36 (m, 3H), 4.36-4.17 (m, 2H), 4.17-3.85 (m, 6H), 3.83-3.66 (m, 2H), 3.73 (s, 3H), 3.61-3.40 (m, 4H), 3.40-3.20 (m, 2H, partially obscured by water peak), 2.94-2.83 (m, 2H), 2.67-2.34 (m, 6H, partially obscured by DMSO peak), 2.25 (s, 3H), 1.96-1.45 (m, 12H), 1.45-1.20 (m, 4H), 1.35 (s, 9H). HRMS (ESI) m/z calc. for $C_{61}H_{80}ClN_8O_{14}$: 1183.5477. found: 1183.5445 [$MH^+$]; calc. for $C_{61}H_{79}ClN_8NaO_{14}$: 1205.5296. found: 1205.5256 [$MNa^+$]; calc. for $C_{61}H_{79}ClKN_8O_{14}$: 1221.5036. found: 1221.5026 [$MK^+$].

To a stirred solution of 65i (0.92 g, 0.78 mmol) in dry DCM (20 mL) at 0° C. was added Dess-Martin periodinane (DMP, 1,1,1-triacetoxy-1,1-dihydro-1,2-benziodoxol-3(1H)-one, CAS Reg. No. 87413-09-0, 492 mg, 1.16 mmol) portionwise (over 8 min). After addition was complete the reaction mixture was stirred further at 0° C. for 2 h, then at r.t. for 45 h. The mixture was diluted with DCM (100 mL) and stirred with 10% $Na_2S_2O_3$ (100 mL) at r.t. for 10 min. The resulting mixture was partitioned between DCM (400 mL) and saturated $NaHCO_3$ solution (400 mL). The DCM layer was separated and the aqueous layer was further extracted with DCM (2×100 mL). The combined DCM solution was further washed with saturated $NaHCO_3$ solution (200 mL) and water (200 mL) and then dried ($MgSO_4$). Evaporation of solvent at 25° C. (bath temperature) gave a pale brown solid which was purified by $SiO_2$ column chromatography (DCM-ethyl acetate-MeOH=15:15:1, gradient to 15:15:3) to give (S)-4-((S)-2-(allyloxycarbonylamino)-6-(tert-butoxycarbonylamino)hexanamido)benzyl 8-(6-((S)-1-(chloromethyl)-5-(4-methylpiperazine-1-carbonyloxy)-1H-benzo[e]indol-3 (2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate 65j (0.64g, 70%) as a pale yellow solid; mp 137° C. (dec.); $^1$H NMR [$(CD_3)_2SO$] δ 10.02 (s, 1H), 8.21 (s, 1H), 7.95 (d, J=8.4 Hz, 1H), 7.80 (d, J=8.3 Hz, 1H), 7.65-7.38 (m, 5H), 7.18 (d, J=7.0 Hz, 2H), 7.03 (s, 1H), 6.82-6.63 (m, 2H), 6.49 (poorly resolved d, J=4.7 Hz, exchangeable with $D_2O$, 1H), 5.96-5.82 (m, 1H), 5.46 (poorly resolved dd, J=9.8, 4.7 Hz, became a d after $D_2O$, J=10.1 Hz, 1H), 5.27 (br d, J=17.1 Hz, 1H), 5.21-5.10 (m, 2H), 4.81 (br d, J=12.3 Hz, 1H), 4.51-4.17 (m, 5H), 4.13-3.84 (m, 4H), 3.84-3.67 (m, 2H), 3.77 (s, 3H), 3.55-3.20 (m, 6H, partially obscured by water peak), 2.66-2.30 (m, 6H, partially obscured by DMSO peak), 2.26 (s, 3H), 2.10-1.20 (m, 16H), 1.35 (s, 9H). HRMS (ESI) m/z calc. for $C_{61}H_{78}ClN_8O_{14}$:1181.5321. found: 1181.5286 [$MH^+$]; calc. for $C_{61}H_{77}ClN_8NaO_{14}$: 1203.5140. found: 1203.5130 [$MNa^+$]; calc. for $C_{61}H_{77}ClKN_8O_{14}$: 1219.4879. found: 1219.4861 [$MK^+$].

To a stirred solution of 65j (623 mg, 0.53 mmol) in dry DCM (15 mL) at 0° C. under a nitrogen atmosphere was added pyrrolidine (0.86 mL, 10.5 mmol), followed by $Pd(Ph_3P)_4$ (30 mg, 9.8% Pd). After addition the reaction mixture was stirred further at r.t. for 5 h. The mixture was diluted with petroleum ether (100 mL) and stirred at r.t. for 30 min. The solvents were decanted from the insoluble material and the wash step was repeated with DCM-petroleum ether (1:10) (100 mL). The sticky solid left behind was dissolved in DCM (200 mL) and washed with water (3×100 mL), then dried ($MgSO_4$), and passed through a short $SiO_2$ column to remove base-line material. The required compound was eluted using a DCM-MeOH gradient (from 2 to 5%). Evaporation of the solvent at 25° C. (bath temperature) gave a pale yellow solid-foam (472 mg, 82%) which was used directly in the next step. This crude amine was treated with Fmoc-val-Osu (N-α-Fmoc-L-valine N-hydroxysuccinimide ester, 550 mg, 1.26 mmol) in dry DMA (8 mL) at r.t. under a nitrogen atmosphere and the mixture was stirred for 5 h. Ethyl acetate-petroleum ether (1:10, 100 mL) was added and the mixture was stirred at r.t. for 20 min. The solvent was decanted from the insoluble material and the wash step was repeated with more ethyl acetate-petroleum ether (1:10, 2×50 mL). The sticky solid left behind was dried and purified by $SiO_2$ column chromatography (DCM-ethyl acetate-MeOH=20:10:3) to give (S)-4-((S)-2-((S)-2-(((9H-fluoren-9-yl)methoxy)carbonylamino)-3-methylbutanamido)-6-(tert-butoxycarbonylamino)hexanamido)benzyl 8-(6-((S)-1-(chloromethyl)-5-(4-methylpiperazine-1-carbonyloxy)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate 65k (246 mg, 47%) as a colorless solid; mp 143° C. (dec.); $^1$H NMR [(CD$_3$)$_2$SO] δ 10.03 (s, exchangeable with D$_2$O, 1H), 8.21 (s, 1H), 8.05 (br d, J=7.5 Hz, exchangeable with D$_2$O, 1H), 7.95 (d, J=8.5 Hz, 1H), 7.87 (d, J=7.4 Hz, 2H), 7.81 (d, J=8.3 Hz, 1H), 7.72 (t, J=7.0 Hz, 2H), 7.62-7.25 (m, 10H), reduced to 9H after D$_2$O), 7.18 (poorly resolved d, J=5.8 Hz, 2H), 7.04 (s, 1H), 6.70 (br s, 2H, reduced to 1H after D$_2$O), 6.50 (br s, exchangeable with D$_2$O, 1H), 5.53-5.40 (m, became a d after D$_2$O, J=9.9 Hz, 1H), 5.15 (br d, J=12.4 Hz, 1H), 4.82 (br d, J=12.3 Hz, 1H), 4.46-4.16 (m, 7H), 4.07-3.85 (m, 4H), 3.83-3.67 (m, 2H), 3.76 (s, 3H), 3.56-3.23 (m, 5H, partially obscured by water peak), 2.93-2.79 (m, 2H), 2.64-2.32 (m, 6H, partially obscured by DMSO peak), 2.25 (s, 3H), 2.09-1.20 (m, 17H), 1.35 (s, 9H), 0.87 (d, J=7.0 Hz, 3H), 0.83 (d, J=6.8 Hz, 3H). HRMS (ESI) m/z calc. for C$_{77}$H$_{93}$ClN$_9$O$_{15}$:1418.6474. found: 1418.6420 [MH$^+$]; calc. for C$_{77}$H$_{92}$ClN$_9$NaO$_{15}$: 1440.6294. found: 1440.6231 [MNa$^+$]; calc. for C$_{77}$H$_{92}$ClKN$_9$O$_{15}$: 1456.6033. found: 1456.6021 [MK$^+$].

To a stirred solution of 65k (224 mg, 0.158 mmol) in dry DMA (2 mL) at 0° C. under a nitrogen atmosphere was added a solution of piperidine in N,N-dimethylacetamide (DMA, 1.0 mmol per mL, 1.58 mL, 1.58 mmol). See FIG. 20. After addition the mixture was stirred at this temperature for a further 1 h and 45 min. A mixture of ethyl acetate-petroleum ether (1:5, 50 mL) was added and the mixture stirred at 0° C. for 20 min. The solvent layer was decanted from the insoluble material and discarded. The wash step was repeated with more ethyl acetate-petroleum ether (1:5, 2×30 mL) at r.t. The pale yellow solid left behind was dried to give (S)-4-((S)-2-((S)-2-amino-3-methylbutanamido)-6-(tert-butoxycarbonylamino)hexanamido)benzyl 8-(6-((S)-1-(chloromethyl)-5-(4-methylpiperazine-1-carbonyloxy)-1H-benzo[e]indol-3 (2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate 65l (173 mg, 99%); mp 74° C. (dec.); $^1$H NMR [(CD$_3$)$_2$SO] δ 10.09 (s, exchangeable with D$_2$O, 1H), 8.21 (s, 1H), 8.08 (br s, exchangeable with D$_2$O, 1H), 7.96 (d, J=8.4 Hz, 1H), 7.81 (d, J=8.2 Hz, 1H), 7.66-7.42 (m, 4H), 7.19 (poorly resolved d, J=7.5 Hz, 2H), 7.04 (s, 1H), 6.71 (br s, 2H, reduced to 1H after D$_2$O), 6.49 (br s, exchangeable with D$_2$O, 1H), 5.52-5.40 (m, became a d after D$_2$O, J=10.6 Hz, 1H), 5.16 (br d, J=12.1 Hz, 1H), 4.81 (br d, J=11.7 Hz, 1H), 4.49-4.18 (m, 4H), 4.10-3.85 (m, 3H), 3.85-3.67 (m, 2H), 3.77 (s, 3H), 3.59-3.22 (m, 5H, partially obscured by water peak), 3.03-2.97 (m, became a d after D$_2$O, J=4.8 Hz, 1H), 2.91-2.81 (m, 2H), 2.71-2.33 (m, 7H, partially obscured by DMSO peak), 2.25 (s, 3H), 2.11-1.20 (m, 17H), 1.34 (s, 9H), 0.86 (d, J=6.5 Hz, 3H), 0.76 (d, J=6.7 Hz, 3H), 2H not observed. HRMS (ESI) m/z calc. for C$_{62}$H$_{83}$ClN$_9$O$_{13}$:1196.5793. found: 1196.5804 [MH$^+$]; calc. for C$_{62}$H$_{82}$ClN$_9$NaO$_{13}$: 1218.5613. found: 1218.5612 [MNa$^+$]; calc. for C$_{62}$H$_{82}$ClKN$_9$O$_{13}$: 1234.5352. found: 1234.5359 [MK$^+$].

A mixture of 65l (173 mg, 0.158 mmol) and 2,5-dioxopyrrolidin-1-yl 6-(2,5-dioxo-2,5-dihydro-1H-pyrrol-1-yl)hexanoate (maleimido-Osu, 122 mg, 0.395 mmol) in dry DMA (2 mL) was stirred at 0° C. under a nitrogen atmosphere for 1 h 45 min. A mixture of ethyl acetate-petroleum ether (1:5, 50 mL) was added and the resulting mixture stirred at 0° C. for 15 min. The solvent layer was decanted from the insoluble material and discarded. The wash step was repeated with more ethyl acetate-petroleum ether (1:5, 2×30 mL) at r.t. The solid left behind was dried and purified by silica column chromatography (DCM:ethyl acetate: MeOH=20:10:3) to give (S)-4-((S)-6-(tert-butoxycarbonylamino)-2-((S)-2-(6-(2,5-dioxo-2,5-dihydro-1H-pyrrol-1-yl)hexanamido)-3-methylbutanamido)hexanamido)benzyl 8-(6-((S)-1-(chloromethyl)-5-(4-methylpiperazine-1-carbonyloxy)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate 65m (152 mg, 69%) as a pale yellow solid; HPLC: 90.6% pure; mp 120° C.; $^1$H NMR [(CD$_3$)$_2$SO] δ 9.95 (s, exchangeable with D$_2$O, 1H), 8.21 (s, 1H), 8.01 (d, J 7.4 Hz, exchangeable with D$_2$O, 1H), 7.95 (d, J=8.4 Hz, 1H), 7.85-7.73 (m, 2H, reduced to 1H after D$_2$O exchange), 7.63-7.50 (m, 3H), 7.46 (t, J=7.7 Hz, 1H), 7.17 (poorly resolved d, J=8.4 Hz, 2H), 7.04 (s, 1H), 6.98 (s, 2H), 6.81-6.66 (m, 2H, reduced to 1H after D$_2$O exchange), 6.49 (poorly resolved d, J=5.3 Hz, exchangeable with D$_2$O, 1H), 5.51-5.41 (m, became a d after D$_2$O, J=9.9 Hz, 1H), 5.15 (d, J=12.6 Hz, 1H), 4.81 (br d, J=11.3 Hz, 1H), 4.41 (t, J=9.7 Hz, 1H), 4.37-4.27 (m, 2H), 4.27-4.13 (m, 2H), 4.10-3.85 (m, 3H), 3.85-3.63 (m, 2H), 3.77 (s, 3H), 3.60-3.21 (m, 8H, partially obscured by water peak, 1H), 2.92-2.81 (m, 2H), 2.67-2.33 (m, 6H, partially obscured by DMSO peak), 2.26 (s, 3H), 2.23-1.11 (m, 25H), 1.30 (s, 9H), 0.84 (d, J=6.8 Hz, 3H), 0.81 (d, J=6.7 Hz, 3H). HRMS (ESI) m/z calc. for C$_{72}$H$_{94}$ClN$_{10}$O$_{16}$:1389.6532. found: 1389.6478 [MH$^+$]; calc. for C$_{72}$H$_{94}$ClN$_{10}$NaO$_{16}$: 706.3212. found: 706.3244 [MH$^+$Na$^+$]; calc. for C$_{72}$H$_{93}$ClN$_{10}$Na$_2$O$_{16}$: 717.3122. found: 717.3121 [MNa$^+$Na$^+$].

To a stirred solution of 65m (32.2 mg, 0.023 mmol) in DCM (0.4 mL) at 0° C. (bath temperature) under nitrogen was added TFA (0.8 mL), followed by a solution of 2% water in TFA (0.8 mL). After addition the mixture was stirred at this temperature for a further 8 h. Ethyl acetate-petroleum ether (1:5, 25 mL) was added and the mixture was stirred at 0° C. for 15 min. The precipitated solid was collected, washed with ethyl acetate-petroleum ether (1:5, 2×30 ml), and dried to give a crude product (30 mg) which was purified by preparative HPLC [SynergiMaxRP column; water-TFA (pH=2.56; 95% to 55%)/10% H$_2$O in CH$_3$CN (5% to 45%); flow rate: 12 mL/min] to give (S)-4-((S)-6-amino-2-((S)-2-(6-(2,5-dioxo-2,5-dihydro-1H-pyrrol-1-yl)hexanamido)-3-methylbutanamido)hexanamido)benzyl 8-(6-((S)-1-(chloromethyl)-5-(4-methylpiperazine-1-carbonyloxy)-1H-benzo[e]indol-3(2H)-yl)-6-oxohexyloxy)-11-hydroxy-7-methoxy-5-oxo-2,3,11,11a-tetrahydro-1H-benzo[e]pyrrolo[1,2-a][1,4]diazepine-10(5H)-carboxylate 65 as the bis-trifluoroacetate salt (22.2 mg, 64%) as a glassy solid; HPLC: 97.1% pure; mp 114° C.; [α]$_D$+43.6° (c 0.275, MeOH); $^1$H NMR [(CD$_3$)$_2$SO] δ 9.97 (s, 1H), 9.90 (br s, 1H), 8.73 (br s, 2H), 8.27 (s, 1H), 8.09 (d, J=7.6 Hz, 1H), 8.04-7.93 (m, 2H), 7.89 (d, J=8.4 Hz, 1H), 7.82 (d, J=7.9 Hz, 1H), 7.74-7.50 (m, 5H), 7.46 (br t, J=7.6 Hz, 1H), 7.22 (m, 2H), 7.04 (s, 1H), 7.00 (s, 2H), 6.75 (s, 1H), 6.51 (br s, 1H), 5.52-5.40 (m, 1H), 5.18-5.04 (m, 1H), 4.94-4.82 (m, 1H), 4.48-3.70 (m, 14H), 3.43-3.20 (m, 4H, partially obscured by water peak), 3.17-3.05 (m, 3H), 2.89 (s, 3H), 2.82-2.70 (m, 2H), 2.66-2.48 (m, 2H, partially obscured by DMSO peak), 2.25-1.08 (m, 25H), 0.91-0.77 (m, 6H), 2H not observed. HRMS (ESI) m/z calc. for C$_{67}$H$_{86}$ClN$_{10}$O$_{14}$:1289.6008. found: 1289.5975 [MH$^+$]; calc. for C$_{67}$H$_{85}$ClN$_{10}$NaO$_{14}$: 1311.5827. found: 1311.5772 [MNa$^+$]; calc. for C$_{67}$H$_{85}$ClN$_{10}$Na$_2$O$_{14}$: 667.2860. found: 667.2874 [MNa$^+$Na$^+$]; calc. for C$_{67}$H$_{86}$ClN$_{10}$NaO$_{14}$:656.2950. found: 656.2963 [MH$^+$Na$^+$]; calc. for C$_{67}$H$_{87}$ClN$_{10}$O$_{14}$: 645.3040. found: 645.3052 [MH$^+$H$^+$].

Example 16 N-(3-(2,5-bis((E)-3-((S)-1-(chloromethyl)-5-phosphonoxy-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide 66

To a solution of (S)-tert-butyl 5-(benzyloxy)-1-(chloromethyl)-1H-benzo[e]indole-3(2H)-carboxylate 57a, prepared from 51a in Example 7 (1.595 g, 3.76 mmol) in DCM (15 mL) cooled in an ice bath was added 4N HCl in dioxane (40 mL). See FIG. 21. The mixture was allowed to warm up to room temperature and stirred for 2 h. All volatile components were pumped off. The resultant residue was redistributed between ethyl acetate and cold aqueous 5% ammonia. The aqueous phase was extracted with ethyl acetate three times. The combined organic extracts were washed with water followed by brine, dried over anhydrous $Na_2SO_4$, and filtered through celite. The solvent was removed to give (S)-5-(benzyloxy)-1-(chloromethyl)-2,3-dihydro-1H-benzo[e]indole 57b as a brown gum, which was used directly; $^1$H NMR (DMSO) δ 8.04 (d, J=8.2 Hz, 1H), 7.61 (d, J=8.3 Hz, 1H), 7.53 (d, J=7.2 Hz, 2H), 7.45-7.34 (m, 4H), 7.14 (t, J=7.3 Hz, 1H), 6.60 (s, 1H), 5.24 (s, 2H), 3.96-3.92 (m, 1H), 3.84 (dd, J=3.4, 10.7 Hz, 1H), 3.70 (t, J=9.3 Hz, 1H), 3.60 (dd, J=2.4, 10.0 Hz, 1H), 3.55 (t, J=10.3 Hz, 1H) ppm. HRMS (ESI) found m/z 324.1150 (M+H). $C_{20}H_{19}ClNO$ requires 324.1150.

Intermediate 57b was cooled in an ice bath and pyridine (15 mL) was added, followed by trifluoroacetic anhydride (3.14 mL, 22.57 mmol). The resultant mixture was stirred for 10 min and ice was added. The mixture was redistributed between ethyl acetate and water. The aqueous phase was extracted with ethyl acetate three times. The combined organic extracts were washed with water followed by brine, dried over anhydrous $Na_2SO_4$, and filtered through celite. The solvent was removed and the resultant residue was purified by column chromatography using a mixture of ethyl acetate and petroleum ether (v/v 1:10) as eluent to give (S)-1-(5-(benzyloxy)-1-(chloromethyl)-1H-benzo[e]indol-3(2H)-yl)-2,2,2-trifluoroethanone 66a as a white solid (1.11 g, 70%); mp 167-170° C. $^1$H NMR (CDCl$_3$) δ 8.37 (d, J=8.3 Hz, 1H), 8.05 (s, 1H), 7.72 (d, J=8.2 Hz, 1H), 7.61-7.54 (m, 3H), 7.49-7.42 (m, 3H), 7.39-7.35 (m, 3H), 5.30 (AB q, J=11.7, 15.7 Hz, 2H), 4.63-4.59 (m, 1H), 4.43-4.38 (m, 1H), 4.15-4.09 (m, 1H), 3.97-3.93 (m, 1H), 3.49 (dd, J=9.9, 11.3 Hz, 1H) ppm. HRMS (ESI) found m/z 442.0799 (M+Na). $C_{22}H_{17}ClF_3NNaO_2$ requires 442.0795.

At −10° C., to a solution of 66a (1.10 g, 2.62 mmol) in THF (20 mL) was added 25% aqueous ammonium formate (20 mL) followed by Pd—C catalyst (10%, wet, 550 mg) and the mixture was stirred for 2 h before more Pd—C catalyst (550 mg) was added. The resultant mixture was stirred at −10° C. overnight and the catalyst was filtered off through celite. THF was removed from the filtrate and the residue was redistributed between ethyl acetate and water. The aqueous phase was extracted with ethyl acetate three times. The combined organic extracts were washed with water followed by brine, dried over anhydrous $Na_2SO_4$, and filtered through celite. The solvent was removed and the resultant residue was purified by column chromatography using a mixture of ethyl acetate and petroleum ether (v/v 1:5) as eluent to give (S)-1-(1-(chloromethyl)-5-hydroxy-1H-benzo[e]indol-3(2H)-yl)-2,2,2-trifluoroethanone 66b as an off-white solid (758 mg, 88%); mp 209-212° C. $^1$H NMR (CDCl$_3$) δ 8.33 (d, J=8.2 Hz, 1H), 8.10 (s, 1H), 7.85 (s, 1H), 7.64 (d, J=8.2 Hz, 1H), 7.60-7.56 (m, 1H), 7.51-7.47 (m, 1H), 4.60-4.56 (m, 1H), 4.41-4.36 (m, 1H), 4.00-3.95 (m, 1H), 3.93-3.90 (m, 1H), 3.44 (dd, J=9.8, 11.3 Hz, 1H) ppm. HRMS (ESI) found m/z 352.0331 (M+Na). $C_{15}H_{11}ClF_3NNaO_2$ requires 352.0323.

To a solution of 66b (250 mg, 0.76 mmol) in THF (15 mL) was added tetrazole (3% in acetonitrile, 13.5 mL, 4.55 mmol) followed by di-tert-butyl-N,N-di-isopropyl phosphoramidite (1.51 mL, 4.55 mmol). The mixture was stirred at room temperature overnight then cooled in an ice bath and $H_2O_2$(30% aqueous solution, 0.78 mL, 7.58 mmol) was added dropwise. The resultant mixture was allowed to warm up to room temperature and stirred for 5 h. The reaction was quenched by the addition of 10% aqueous sodium sulphite with cooling in an ice bath. Organic volatiles were removed by rotary evaporator. The resultant mixture was redistributed between ethyl acetate and water. The aqueous phase was extracted with ethyl acetate three times. The combined organic extracts were washed with water followed by brine, dried over anhydrous $Na_2SO_4$, and filtered through celite. The solvent was removed and the resultant residue was purified by Florisil® (US Silica) column chromatography using gradient mixtures of ethyl acetate and petroleum ether (v/v 1:6 to 1:3) as eluent to give (S)-di-tert-butyl 1-(chloromethyl)-3-(2,2,2-trifluoroacetyl)-2,3-dihydro-1H-benzo[e]indol-5-yl phosphate 66c as colorless oil (367 mg, 93%); $^1$H NMR (DMSO) δ 8.44 (d, J=1.0 Hz, 1H), 8.11 (d, J=8.1 Hz, 1H), 8.06 (d, J=8.2 Hz, 1H), 7.69-7.65 (m, 1H), 7.63-7.59 (m, 1H), 4.61-4.56 (m, 1H), 4.46-4.41 (m, 1H), 4.15-4.12 (m, 1H), 4.06-4.00 (m, 1H), 1.50 (s, 9H), 1.48 (s, 9H) ppm. $^{31}$P NMR (DMSO) δ −15.54 ppm. HRMS (ESI) found m/z 544.1236 (M+Na). $C_{23}H_{28}ClF_3NNaO_5P$ requires 544.1238.

To a solution of 66c (239 mg, 0.46 mmol) in MeOH (2 mL) cooled in an ice bath was added $CsCO_3$ (298 mg, 0.92 mmol) and several drops of water. The mixture was stirred in the ice bath for 1 h and then redistributed between ethyl acetate and water. The aqueous phase was extracted with ethyl acetate three times. The combined organic extracts were washed with water and brine, dried over anhydrous $Na_2SO_4$, filtered through celite, and the solvent was removed. The resultant residue was dissolved in ethyl acetate and filtered through a pad of Florisil® (US Silica) column chromatography to give (S)-di-tert-butyl 1-(chloromethyl)-2,3-dihydro-1H-benzo[e]indol-5-yl phosphate 66d as an off-white gum (183 mg, 94%) which was used directly without further purification; $^1$H NMR (DMSO) δ 8.08 (d, J=8.4 Hz, 1H), 7.58 (d, J=8.3 Hz, 1H), 7.46-7.42 (m, 1H), 7.25-7.21 (m, 1H), 7.13 (d, J=0.8 Hz, 1H), 4.00-3.93 (m, 1H), 3.87-3.78 (m, 2H), 3.54-3.42 (m, 2H), 1.50 (s, 9H), 1.49 (s, 9H) ppm. $^{31}$P NMR (DMSO) δ −15.58 ppm. HRMS (ESI) found m/z 426.1587 (M+H). $C_{21}H_{30}ClNO_4P$ requires 426.1595.

2,5-Dibromonitrobenzene (5.0 g, 17.8 mmol) and t-butyl acrylate (7.75 mL, 53.40 mmol) were dissolved in triethylamine (50 mL). See FIG. 22. The flask was flushed by bubbling nitrogen gas through the solution, then tri-p-tolyl phosphine (433 mg, 1.42 mmol) and palladium acetate (80 mg, 0.36 mmol) were added under nitrogen flow. The mixture was stirred at reflux overnight under nitrogen. Triethylamine was pumped off. The resultant residue was dissolved in ethyl acetate and filtered through a pad of silica gel. The filtrate was concentrated and loaded on a chromatography column. A mixture of ethyl acetate and petroleum ether (1:10) was used as eluent to give (2E,2'E)-tert-butyl 3,3'-(2-nitro-1,4-phenylene)diacrylate 66e as a white solid (5.85 g, 88%); mp 123-124° C. $^1$H NMR (CDCl$_3$) δ 8.14 (d, J=1.7 Hz, 1H), 7.99 (d, J=15.8 Hz, 1H), 7.74 (dd, J=1.7, 8.2 Hz, 1H), 7.66 (d, J=8.1 Hz, 1H), 7.58 (d, J=16.0 Hz, 1H), 6.50 (d, J=16.0 Hz, 1H), 6.36 (d, J=15.8 Hz, 1H), 1.58 (s, 9H), 1.56 (s, 9H) ppm. HRMS (ESI) found m/z 398.1574 (M+Na). $C_{20}H_{25}NNaO_6$ requires 398.1574.

To a solution of 66e (5.85 g, 15.58 mmol) in acetone (40 mL) cooled in an ice bath was added zinc powder (8.15 g, 125.0 mmol), followed by a solution of $NH_4Cl$ (3.33 g, 62.30 mmol) in water (20 mL). The mixture was stirred at room temperature for 1 h. More zinc powder (4.00 g) and more NH₄Cl (1.7 g) in water (10 mL) were added. After 1 h, ethyl acetate (100 mL) was added and the upper clear solution was collected by decanting. The wash and decanting steps were repeated two more times. The combined organic solution was washed with water followed by brine, dried over anhydrous Na₂SO₄, and filtered through a pad of silica gel. The solvent was removed to give (2E,2'E)-tert-butyl 3,3'-(2-amino-1,4-phenylene)diacrylate 66f as a yellow gum (5.46 g, 100%); mp 73-75° C. ¹H NMR (CDCl₃) δ 7.68 (d, J=15.8 Hz, 1H), 7.46 (d, J=16.0 Hz, 1H), 7.37 (d, J=8.1 Hz, 1H), 6.92 (dd, J=1.5, 8.1 Hz, 1H), 6.81 (d, J=1.4 Hz, 1H), 6.33 (d, J=16.0 Hz, 1H), 6.31 (d, J=15.8 Hz, 1H), 3.99 (br s, 2H), 1.53 (s, 9H), 1.51 (s, 9H) ppm. HRMS (ESI) found m/z 368.1830 (M+Na). C₂₀H₂₇NNaO₄ requires 368.1832.

A mixture of 66f (2.73 g, 7.90 mmol), 3-(((9H-fluoren-9-yl)methoxy)carbonylamino)propanoic acid (Fmoc-beta-alanine, 3.69 g, 11.85 mmol), EDCI hydrochloride (7.58 g, 39.50 mmol) and p-toluenesulfonic acid (136 mg, 0.79 mmol) in DMA (25 mL) was stirred at room temperature overnight. The mixture was redistributed between ethyl acetate and water. The aqueous phase was extracted with ethyl acetate three times. The combined organic extracts were washed with water followed by brine, dried over anhydrous Na₂SO₄, and filtered through celite. The solvent was removed to give (2E,2'E)-tert-butyl 3,3'-(2-(3-(((9H-fluoren-9-yl)methoxy)carbonylamino)propanamido)-1,4-phenylene)diacrylate 66g as a white solid (4.89 g, 97%); mp 102-105° C. ¹H NMR (CDCl₃) δ 7.87 (s, 1H), 7.70-7.66 (m, 2H), 7.62-7.52 (m, 4H), 7.44 (br s, 1H), 7.38-7.34 (m, 3H), 7.29-7.25 (m, 2H), 6.41 (d, J=16.0 Hz, 1H), 6.34 (d, J=15.7 Hz, 1H), 4.42 (br s, 2H), 4.19 (t, J=6.4 Hz, 1H), 3.59 (br s, 2H), 2.67 (br s, 2H), 1.53 (s, 9H), 1.51 (s, 9H) ppm. HRMS (ESI) found m/z 661.2878 (M+Na). C₃₈H₄₂N₂NaO₇ requires 661.2884.

To a solution of 66g (530 mg, 0.83 mmol) in DCM (4 mL) cooled in an ice bath was added TFA (1 mL, 12.98 mmol). The mixture was allowed to warm up to room temperature and stirred overnight to give a white suspension. Ethyl acetate was added to precipitate out more solid, which was collected by filtration and washed with ethyl acetate and petroleum ether, to give (2E,2'E)-3,3'-(2-(3-(((9H-fluoren-9-yl)methoxy)carbonylamino)propanamido)-1,4-phenylene)diacrylic acid 66h as a white solid (404 mg, 92%). mp 282° C. (dec.). ¹H NMR (DMSO) δ 12.46 (br s, 1H), 9.92 (s, 1H), 7.89-7.84 (m, 3H), 7.74-7.68 (m, 4H), 7.58-7.54 (m, 2H), 7.44-7.38 (m, 3H), 7.31-7.28 (m, 2H), 6.54 (dd, J=3.2, 16.0 Hz, 2H), 4.30 (d, J=6.5 Hz, 2H), 4.22 (t, J=6.8 Hz, 1H), 3.30 (br s, 2H), 2.83-2.79 (m, 2H) ppm. HRMS (ESI) found m/z 549.1643 (M+Na). C₃₀H₂₆N₂NaO₇ requires 549.1632.

A mixture of 66d (178 mg, crude, ca. 0.42 mmol), 66h (55 mg, 0.10 mmol), EDCI hydrochloride (160 mg, 0.84 mmol) and p-toluenesulfonic acid (1.8 mg, 0.01 mmol) in DMA (2 mL) was stirred at room temperature overnight. The mixture was redistributed between ethyl acetate and cold dilute aqueous NaHCO₃. The aqueous phase was extracted with ethyl acetate three times. The combined organic extracts were washed with water followed by brine, dried over anhydrous Na₂SO₄, and filtered through celite. The solvent was removed and the residue was further purified by Florisil® (US Silica) column chromatography using gradient mixtures of MeOH and ethyl acetate (v/v 0.25-5%) to give (9H-fluoren-9-yl)methyl 3-(2,5-bis((E)-3-((S)-1-(chloromethyl)-5-(di-tert-butoxyphosphoryloxy)-1H-benzo[e]indol-3(2H)-yl)-3-oxoprop-1-enyl)phenylamino)-3-oxopropylcarbamate 66i as a yellow solid (62 mg, 44%); ¹H NMR (DMSO) δ 10.04 (s, 1H), 8.67 (s, 2H), 8.11-8.05 (m, 3H), 7.97 (d, J=8.2 Hz, 2H), 7.88-7.82 (m, 4H), 7.78 (d, J=8.4 Hz, 1H), 7.73-7.67 (m, 3H), 7.63-7.58 (m, 2H), 7.53-7.47 (m, 3H), 7.38 (t, J=7.4 Hz, 2H), 7.30-7.24 (m, 4H), 4.60-4.50 (m, 4H), 4.42-4.35 (m, 2H), 4.30 (d, J=6.7 Hz, 2H), 4.22 (t, J=6.6 Hz, 1H), 4.06-3.93 (m, 4H), 3.40-3.33 (m, 2H), 2.63-2.59 (m, 2H), 1.50 (2×s, 18H), 1.47 (2×s, 18H) ppm. ³¹P NMR (DMSO) δ −15.45 ppm. HRMS (ESI) found m/z 1341.4677 (M+H). C₇₂H₈₁Cl₂N₄O₁₃P₂ requires 1341.4647.

To a solution of 66i (60 mg, 0.045 mmol) in DMF (1 mL) was added piperidine (44 μL, 0.45 mmol). The mixture was stirred at room temperature for 3 h then all the volatile components were pumped off. The resultant residue was triturated with a mixture of ether and petroleum ether (v/v 1:1) to give free amine 66j as a white solid (44 mg, 96%). ¹H NMR (DMSO) δ 8.68 (s, 2H), 8.11-8.05 (m, 3H), 7.98 (d, J=8.4 Hz, 2H), 7.91-7.86 (m, 2H), 7.78-7.85 (m, 1H), 7.70 (d, J=15.3 Hz, 1H), 7.63-7.58 (m, 2H), 7.51 (t, J=7.9 Hz, 2H), 7.26 (d, J=15.3 Hz, 2H), 4.66-4.52 (m, 4H), 4.44-4.35 (m, 2H), 4.07-3.95 (m, 4H), 2.95 (t, J=6.5 Hz, 2H), 2.56-2.50 (m, 2H), 1.50-1.49 (m, 36H) ppm. ³¹P NMR (DMSO) δ −15.42, 15.45 ppm. HRMS (ESI) found m/z 1119.3981 (M+H). C₅₇H₇₁Cl₂N₄O₁₁P₂ requires 1119.3966.

A mixture of 66j (40 mg, 0.036 mmol), 2,5-dioxopyrrolidin-1-yl 6-(2,5-dioxo-2,5-dihydro-1H-pyrrol-1-yl)hexanoate (SuOMC, 12 mg, 0.037 mmol), and DIPEA (6.8 μL, 0.039 mmol) in DMSO (1 mL) was stirred at room temperature overnight before all the volatile components were pumped off. The resultant residue was triturated with ether to give bis (di-tert-butylphosphate)N-(3-(2,5-bis((E)-3-((S)-1-(chloromethyl)-5-hydroxy-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide 66k as a yellow solid (32 mg, 67%). ¹H NMR (DMSO) δ 10.02 (s, 1H), 8.67 (s, 2H), 8.11-8.05 (m, 3H), 7.98-7.92 (m, 3H), 7.85-7.75 (m, 2H), 7.70 (d, J=15.3 Hz, 1H), 7.63-7.58 (m, 2H), 7.51 (t, J=7.9 Hz, 2H), 7.26 (dd, J=4.4, 15.4 Hz, 2H), 6.96 (s, 2H), 4.66-4.52 (m, 4H), 4.44-4.35 (m, 2H), 4.07-3.95 (m, 4H), 3.45-3.30 (m, 4H), 2.52-2.50 (m, 2H), 2.08 (t, J=7.2 Hz, 2H), 1.50-1.40 (m, 40H), 1.33-1.25 (m, 2H) ppm. ³¹P NMR (DMSO) δ −15.42, 15.45 ppm. HRMS (ESI) found m/z 1334.4515 (M+Na). C₆₇H₈₁Cl₂N₅NaO₁₄P₂ requires 1334.4525.

To a solution of 66k (30 mg, 0.02 mmol) in DCM (1 mL) cooled in an ice bath was added TFA (1 mL, 12.98 mmol). The mixture was allowed to warm up to room temperature and stirred for 3 h. All the volatile components were pumped off and the resultant residue was triturated with ethyl acetate to give N-(3-(2,5-bis((E)-3-((S)-1-(chloromethyl)-5-phosphonoxy-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide 66 as a yellow solid (20 mg, 80%, HPLC purity 95%); ¹H NMR (DMSO) δ 10.01 (s, 1H), 8.59 (s, 2H), 8.16-8.08 (m, 3H), 7.97-7.90 (m, 3H), 7.88-7.73 (m, 2H), 7.69 (d, J=14.5 Hz, 1H), 7.61-7.55 (m, 2H), 7.46 (t, J=7.3 Hz, 2H), 7.29-7.24 (d, J=14.0 Hz, 2H), 6.97 (s, 2H), 4.62-4.52 (m, 3H), 4.40-4.30 (m, 3H), 4.05-3.90 (m, 4H), 3.43-3.37 (m, 2H), 3.24-3.18 (m, 2H), 2.61-2.55 (m, 2H), 2.08 (br s, 2H), 1.54-1.44 (m, 4H), 1.27-1.15 (m, 2H) ppm. ³¹P NMR (DMSO) δ −5.81 ppm. HRMS (ESI negative) found m/z 1086.2067 (M−H). C₅₁H₄₈Cl₂N₅O₁₄P₂ requires 1086.2056.

Example 17 N-(3-(2,5-bis((E)-3-((S)-1-(chloromethyl)-5-hydroxy-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide 67

To a solution of (2E,2'E)-tert-butyl 3,3'-(2-(3-(((9H-fluoren-9-yl)methoxy)carbonylamino)propanamido)-1,4-phenylene)diacrylate 66g (4.89 g, 7.66 mmol) in DCM (30 mL) was added piperidine (4.5 mL, 45.50 mmol). See FIG. 23. The mixture was stirred at room temperature for 5 h before all the volatile components were removed by rotary evaporator. Column chromatography using ethyl acetate as eluent followed by a mixture of TEA, MeOH, and ethyl acetate (v/v 1:10:100) gave (2E,2'E)-tert-butyl 3,3'-(2-(3-aminopropanamido)-1,4-phenylene)diacrylate 67a as a white solid (2.33 g, 73%). mp 62-63° C. $^1$H NMR (CDCl$_3$) δ 11.04 (s, 1H), 8.32 (d, J=1.4 Hz, 1H), 7.91 (d, J=15.7 Hz, 1H), 7.55 (d, J=16.1 Hz, 1H), 7.54 (d, J=8.0 Hz, 1H), 7.24 (dd, J=1.5, 8.2 Hz, 1H), 6.42 (d, J=16.0 Hz, 1H), 6.34 (d, J=15.7 Hz, 1H), 3.18 (d, J=5.6 Hz, 2H), 2.52 (t, J=5.6 Hz, 2H), 1.53 (s, 18H) ppm. HRMS (ESI) found m/z 417.2394 (M+H). $C_{23}H_{33}N_2O_5$ requires 417.2384.

A mixture of 67a (1.00 g, 2.40 mmol), 2,5-dioxopyrrolidin-1-yl 6-(2,5-dioxo-2,5-dihydro-1H-pyrrol-1-yl)hexanoate (SuOMC, 740 mg, 2.40 mmol), and DIPEA (460 μL, 2.64 mmol) in DMF (10 mL) was stirred at room temperature overnight. All the volatile components were pumped off. The resultant residue was purified by column chromatography using a mixture of ethyl acetate and petroleum ether (v/v 2:1) as eluent, followed by ethyl acetate alone, to give (2E,2'E)-tert-butyl 3,3'-(2-(3-(6-(2,5-dioxo-2,5-dihydro-1H-pyrrol-1-yl)hexanamido)propanamido)-1,4-phenylene)diacrylate 67b as a white solid (1.00 g, 68%). mp 69-72° C. $^1$H NMR (CDCl$_3$) δ 7.95 (s, 1H), 7.73 (s, 1H), 7.65 (d, J=15.9 Hz, 1H), 7.61 (d, J=8.2 Hz, 1H), 7.53 (d, J=16.0 Hz, 1H), 7.37 (d, J=8.2 Hz, 1H), 6.69 (br s, 1H), 6.64 (s, 2H), 6.39 (d, J=16.0 Hz, 1H), 6.38 (d, J=15.8 Hz, 1H), 3.68-3.63 (m, 2H), 3.43 (d, J=7.0 Hz, 2H), 2.69 (d, J=5.5 Hz, 2H), 2.21 (t, J=7.3 Hz, 2H), 1.67-1.50 (m, 4H), 1.53 (s, 9H), 1.52 (s, 9H), 1.31-1.24 (m, 2H) ppm. HRMS (ESI) found m/z 632.2931 (M+Na). $C_{33}H_{43}N_3NaO_8$ requires 632.2942.

To a solution of 67b (500 mg, 0.82 mmol) in DCM (4 mL) cooled in an ice bath was added TFA (2 mL) dropwise. The mixture was allowed to warm up to room temperature and stirred for 4 h. After all volatile components were pumped off, the resultant residue was triturated with ethyl acetate to give (2E,2'E)-3,3'-(2-(3-(6-(2,5-dioxo-2,5-dihydro-1H-pyrrol-1-yl)hexanamido)propanamido)-1,4-phenylene)diacrylic acid 67c as a white solid (380 mg, 93%). mp 257-261° C. $^1$H NMR (DMSO) δ 12.47 (s, 2H), 9.90 (s, 1H), 7.89-7.83 (m, 2H), 7.71-7.67 (m, 2H), 7.57-7.53 (m, 2H), 6.99 (s, 2H), 6.53 (d, J=15.9 Hz, 2H), 3.36-3.30 (m, 4H), 2.54-2.50 (m, 2H), 2.06 (t, J=7.3 Hz, 2H), 1.52-1.42 (m, 4H), 1.22-1.17 (m, 2H) ppm. HRMS (ESI) found m/z 520.1683 (M+Na). $C_{25}H_{27}N_3NaO_8$ requires 520.1690.

To a solution of (S)-tert-Butyl 1-(chloromethyl)-5-hydroxy-1H-benzo[e]indole-3(2H)-carboxylate 51a (298 mg, 0.89 mmol) in DCM (5 mL) cooled in an ice bath was added 4N HCl in dioxane (10 mL). The mixture was allowed to warm up to room temperature and stirred for 3 h. All volatile components were pumped off to give (S)-1-(chloromethyl)-2,3-dihydro-1H-benzo[e]indol-5-ol 67d as a hydrochloride salt to which was added 67c (185 mg, 0.37 mmol), EDCI hydrochloride (428 mg, 2.23 mmol), p-toluenesulfonic acid (6 mg, 0.037 mmol) and DMA (5 mL). After the mixture was stirred at room temperature for 6 h, more EDCI hydrochloride (285 mg, 1.49 mmol) and toluenesulfonic acid (6 mg, 0.037 mmol) were added. The mixture was stirred overnight and then redistributed between ethyl acetate and water. The aqueous phase was extracted with ethyl acetate three times. The combined organic extracts were washed with water followed by brine, dried over anhydrous Na$_2$SO$_4$, and filtered through celite. The solvent was removed and the resultant residue was further purified by column chromatography using gradient mixtures of MeOH and ethyl acetate (v/v 1-15%) as eluent to give 67 as a yellow solid (160 mg, 46%, HPLC purity 96%); mp 230-234° C. (dec). $^1$H NMR (DMSO) δ 10.43 (s, 1H), 10.40 (s, 1H), 10.00 (s, 1H), 8.14-8.08 (m, 5H), 7.95 (br s, 1H), 7.83-7.75 (m, 5H), 7.68 (d, J=15.2 Hz, 1H), 7.52 (t, J=7.4 Hz, 2H), 7.35 (t, J=7.6 Hz, 2H), 7.28-7.23 (dd, J=5.2, 15.2 Hz, 2H), 6.95 (s, 2H), 4.58-4.45 (m, 4H), 4.29-4.20 (m, 2H), 4.04-3.97 (m, 2H), 3.88-3.80 (m, 2H), 3.43-3.37 (m, 2H), 3.23 (d, J=6.9 Hz, 2H), 2.60-2.56 (m, 2H), 2.09 (d, J=7.1 Hz, 2H), 1.50-1.40 (m, 2H), 1.40-1.30 (m, 2H), 1.24-1.14 (m, 2H) ppm. HRMS (ESI) found m/z 950.2672 (M+Na). $C_{51}H_{47}Cl_2N_5NaO_8$ requires 950.2694.

Example 18 (S)-1-(chloromethyl)-3-((E)-3-(4-((E)-3-((S)-1-(chloromethyl)-5-hydroxy-1H-benzo[e]indol-3(2H)-yl)-3-oxoprop-1-enyl)-2-(3-(6-(2,5-dioxo-2,5-dihydro-H-pyrrol-1-yl)hexanamido)propanamido)phenyl)acryloyl)-2,3-dihydro-1H-benzo[e]indol-5-yl dihydrogen phosphate 68

To a solution of (S)-di-tert-butyl 1-(chloromethyl)-3-(2,2,2-trifluoroacetyl)-2,3-dihydro-1H-benzo[e]indol-5-yl phosphate 66c (125 mg, 0.24 mmol) in MeOH (1 mL) cooled in an ice bath was added CsCO$_3$ (298 mg, 0.92 mmol) and several drops of water. The mixture was stirred in an ice bath for 1 h and then redistributed between ethyl acetate and water. The aqueous phase was extracted with ethyl acetate three times. The combined organic extracts were washed with water and brine, dried over anhydrous Na$_2$SO$_4$, filtered through celite, and the solvent was removed. The resultant residue was dissolved in ethyl acetate and filtered through a pad of Florisil® (US Silica). Solvent removal gave (S)-di-tert-butyl 1-(chloromethyl)-2,3-dihydro-1H-benzo[e]indol-5-yl phosphate 66d as an off-white gum, which was used directly without further purification.

To a solution of (S)-tert-Butyl 1-(chloromethyl)-5-hydroxy-1H-benzo[e]indole-3(2H)-carboxylate 51a (80 mg, 0.24 mmol) in DCM (2 mL) cooled in an ice bath was added of 4N HCl in dioxane (4 mL). The mixture was allowed to warm up to room temperature and stirred for 2 h. All volatile components were pumped off and (S)-1-(chloromethyl)-2,3-dihydro-1H-benzo[e]indol-5-ol 67d was used directly.

To a solution of 66d and 67d (each prepared as above) in DMA (2 mL) cooled in a salt-ice bath (−10° C.), (2E,2'E)-3,3'-(2-(3-(6-(2,5-dioxo-2,5-dihydro-1H-pyrrol-1-yl)hexanamido)propanamido)-1,4-phenylene)diacrylic acid 67c (119 mg, 0.24 mmol) was added followed by EDCI hydrochloride (276 mg, 1.44 mmol) and p-toluenesulfonic acid (4 mg, 0.024 mmol). The mixture was allowed to warm up to room temperature, stirred overnight, and then poured on ice. The resultant precipitate was collected by filtration, washed with water, and dried under vacuum. Purification by Florisil® (US Silica) chromatography column using gradient mixtures of MeOH and DCM (v/v 2-10%) gave a yellow solid (50 mg), which was identified by LC-MS as a mixture of di-tert-butyl ((S)-1-(chloromethyl)-3-((E)-3-(4-((E)-3-((S)-1-(chloromethyl)-5-hydroxy-1H-benzo[e]indol-3(2H)-yl)-3-oxoprop-1-en-1-yl)-2-(3-(6-(2,5-dihydro-1H-pyrrol-1-yl)hexanamido)propanamido)phenyl)acryloyl)-2,3-dihydro-1H-benzo[e]indol-5-yl) phosphate 68a and di-tert-butyl ((S)-1-(chloromethyl)-3-((E)-3-(4-((E)-3-((S)-1-(chloromethyl)-5-hydroxy-1H-benzo[e]indol-3(2H)-yl)-3-oxoprop-1-en-1-yl)-3-(3-(6-(2,5-dioxo-2,5-dihydro-1H-pyrrol-1-yl)hexanamido)propanamido)phenyl)acryloyl)-2,3-dihydro-1H-benzo[e]indol-5-yl) phosphate 68b (20% and 23% respectively by HPLC), 67 (44% by HPLC), and 66

(8% by HPLC). The mixture was further purified by preparative HPLC (Column: Synergi-Max® RP 4μ, 250×21.20 mm; Mobile phase: A/B=from 25% to 0% (A: ammonium formate pH 3.45, B: 90% acetonitrile in water); flow rate 12 mL/min, gradient method; wave length: 254 nm, 325 nm) to give a mixture of 68a and 68b as a yellow solid (18 mg, 8%). HRMS (ESI) found m/z 1142.3577 (M+Na). $C_{59}H_{64}Cl_2N_5NaO_{11}P$ requires 1142.3609.

To a solution of 68a and 68b (17 mg, 0.015 mmol) in DCM (0.5 mL) cooled in an ice bath was added TFA (0.5 mL) dropwise. The mixture was allowed to warm up to room temperature and stirred for 3 h. All volatile components were pumped off. The resultant residue was triturated with ethyl acetate to give a mixture of (S)-1-(chloromethyl)-3-((E)-3-(4-((E)-3-((S)-1-(chloromethyl)-5-hydroxy-1H-benzo[e]indol-3(2H)-yl)-3-oxoprop-1-enyl)-2-(3-(6-(2,5-dioxo-2,5-dihydro-1H-pyrrol-1-yl)hexanamido)propanamido)phenyl)acryloyl)-2,3-dihydro-1H-benzo[e]indol-5-yl dihydrogen phosphate 68 and phosphate regioisomer, (S)-1-(chloromethyl)-3-((E)-3-(4-((E)-3-((S)-1-(chloromethyl)-5-hydroxy-1H-benzo[e]indol-3(2H)-yl)-3-oxoprop-1-enyl)-3-(3-(6-(2,5-dioxo-2,5-dihydro-1H-pyrrol-1-yl)hexanamido)propanamido)phenyl)acryloyl)-2,3-dihydro-1H-benzo[e]indol-5-yl dihydrogen phosphate 68c as an orange solid (11 mg, 72%, HPLC purity: 95%, ratio of isomers 1:1). $^1H$ NMR (DMSO) δ 10.45 (s, 1H), 10.01 (s, 1H), 8.58 (s, 1H), 8.15-7.23 (m, 17H), 6.95 (s, 2H), 4.60-3.80 (m, 10H), 3.43-3.37 (m, 2H), 3.27-3.18 (m, 2H), 2.60-2.50 (m, 2H), 2.10-2.00 (m, 2H), 1.55-1.35 (m, 4H), 1.20-1.10 (m, 2H) ppm. $^{31}P$ NMR (DMSO) δ −5.81 ppm. HRMS (ESI negative) found m/z 1006.2394 (M−H). $C_{51}H_{47}Cl_2N_5O_{11}P$ requires 1006.2392.

Figure 37:
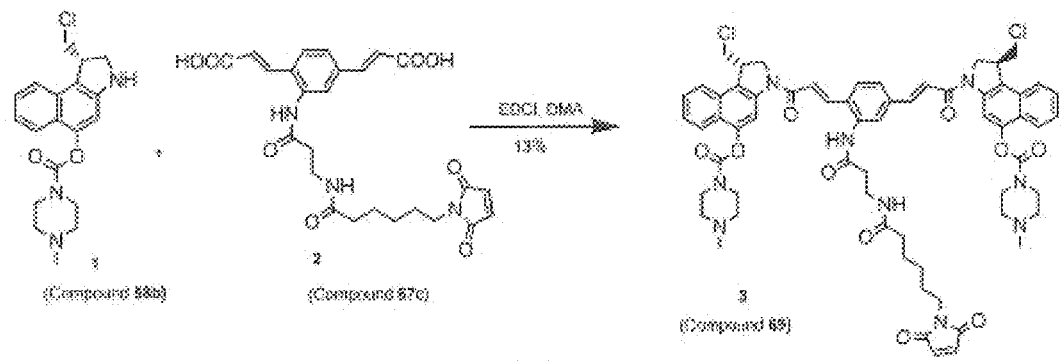
FIG. 37 shows the synthesis of N-(3-(2,5-bis((E)-3-((S)-1-(chloromethyl)-5-(4-methylpiperazine-1-carbonyloxy)-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide (Compound No. 69, Table 4).

Example 23 N-(3-(2,5-bis((E)-3-((S)-1-(chloromethyl)-5-(4-methylpiperazine-1-carbonyloxy)-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide (Compound No. 69, Table 4, FIG. 37)

To 192 mg (0.53 mmol) of 1 (freshly made by the procedure mentioned above) in DMA (2 mL) was added 2 (100 mg, 0.20 mmol), EDCI hydrochloride (231 mg, 1.21 mmol) and toluenesulfonic acid (3.5 mg, 0.020 mmol). The mixture was stirred overnight and then poured into a mixture of aqueous ammonia and ice. The resulting precipitate was collected by filtration, washed with water, dried and purified by silica gel column chromatography. Gradient mixtures of MeOH and DCM (v/v 1-15%) were used as eluent to provide N-(3-(2,5-bis((E)-3-((S)-1-(chloromethyl)-5-(4-methylpiperazine-1-carbonyloxy)-1H-benzo[e]indol-3(2H)-yl)-3-oxoprop-1-enyl)phenylamino)-3-oxopropyl)-6-(2,5-dioxo-2,5-dihydro-1H-pyrrol-1-yl)hexanamide as a yellow solid (30 mg, 13%, HPLC purity 96%). mp 268° C. (dec.) $^1H$ NMR (CDCl$_3$) δ 8.60 (s, 1H), 8.46 (s, 1H), 8.42 (s, 1H), 7.87-7.84 (m, 3H), 7.75-7.60 (m, 5H), 7.40-7.33 (m, 5H), 7.22 (br s, 1H), 6.77 (t, J=15.3 Hz, 2H), 6.56 (s, 2H), 4.46-4.40 (m, 2H), 4.30-4.25 (m, 2H), 4.11-4.00 (m, 2H), 3.95-3.90 (m, 7H), 3.68 (apparent s, 6H), 3.53-3.46 (m, 3H), 3.38 (t, J=7.0 Hz, 2H), 2.73 (apparent s, 2H), 2.59-2.55 (m, 8H), 2.42 (s, 6H), 2.28 (t, J=7.0 Hz, 2H), 1.56-1.49 (m, 2H), 1.31-1.23 (m, 2H) ppm. HRMS (ESI) found m/z 1180.4416 (M+H). $C_{63}H_{68}Cl_2N_9O_{10}$ requires 1180.4416.

Figure 38:
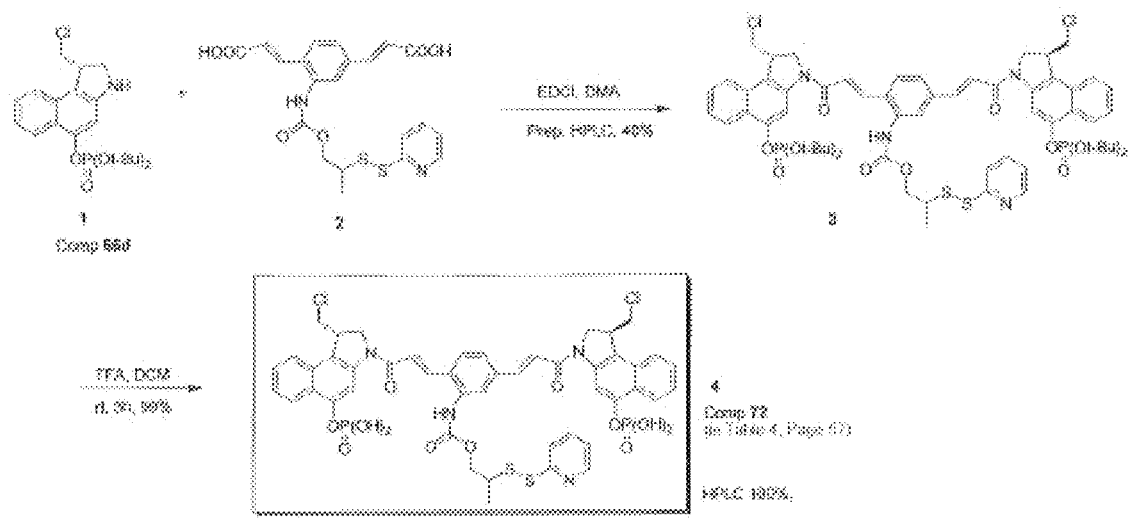

Example 24 2-(pyridin-2-yldisulfanyl)propyl 2,5-bis((E)-3-((S)-1-(chloromethyl)-5-(phosphonooxy)-1H-benzo[e]indol-3(2H)-yl)-3-oxoprop-1-enyl)phenylcarbamate (Table 4, Compound No. 72, FIG. 38)

To 207 mg (0.49 mmol) of 1 (freshly made by the procedure mentioned above) was added 2 (70 mg, 0.15 mmol), EDCI hydrochloride (233 mg, 1.22 mmol), toluenesulfonic acid (3 mg, 0.015 mmol) and DMA (0.5 mL). After the mixture was stirred overnight, most of the DMA was removed under vacuum and the residue was redistributed between ethyl acetate and water. The aqueous phase was extracted with ethyl acetate three times. The combined organic extracts were washed with water followed by brine, dried over anhydrous $Na_2SO_4$, and filtered through a pad of Celite. The solvent was removed and the resultant residue was dissolved in the minimum DCM and precipitated by adding heptane to give crude product (156 mg), which was further purified by preparative HPLC (Column: Synergi-Max RP 4μ, 250×21.20 mm; Mobile phase: A/B=from 10% to 1% (A: ammonium formate pH 3.45, B: 90% acetonitrile in water); flow rate 12 mL/min, gradient method; wavelength: 254 nm, 325 nm) to give 3 (78 mg, 40%) as a yellow solid. $^1H$ NMR (DMSO) δ 9.67 (s, 1H), 8.67 (s, 2H), 8.43 (d, J=4.5 Hz, 1H), 8.11-8.06 (m, 3H), 7.97 (apparent d, J=8.5 Hz, 2H), 7.92 (d, J=15.3 Hz, 1H), 7.84-7.76 (m, 3H), 7.70 (d, J=15.3 Hz, 2H), 7.61 (t, J=7.6 Hz, 2H), 7.51 (t, J=7.7 Hz, 2H), 7.28 (d, J=15.3 Hz, 1H), 7.27 (d, J=15.3 Hz, 1H), 7.23-7.19 (m, 1H), 4.62-4.53 (m, 4H), 4.43-4.37 (m, 2H), 4.23-4.13 (m, 2H), 4.05-3.95 (m, 4H), 3.42-3.37 (m, 1H), 1.51 (s, 9H), 1.50 (s, 9H), 1.49 (s, 9H), 1.48 (s, 9H), 1.34 (d, J=6.5 Hz, 3H) ppm. $^{31}P$ NMR (DMSO) δ −15.46 (s) and −15.48 (s) ppm. HRMS (ESI) found m/z 1297.3471 (M+Na). $C_{63}H_{74}Cl_2N_4NaO_{12}P_2S_2$ requires 1297.3489.

To a solution of 3 (60 mg, 0.047 mmol) in DCM (2 mL) cooled in an ice bath was added TFA (1 mL, 6.49 mmol). The mixture was allowed to warm up to room temperature and stirred for 3 h. All the volatile components were pumped off and the resultant residue was triturated with ethyl acetate to give 4 as a yellow solid (49 mg, 99%, HPLC purity 100%); $^1H$ NMR (DMSO) δ 9.65 (s, 1H), 8.59 (s, 2H), 8.46-8.44 (m, 1H), 8.15-8.08 (m, 3H), 7.96-7.90 (m, 3H), 7.82-7.70 (m, 3H), 7.70 (d, J=15.6 Hz, 1H), 7.59 (t, J=6.8 Hz, 2H), 7.48 (t, J=7.5 Hz, 2H), 7.31-7.22 (m, 3H), 5.75 (s, 1H), 4.64-4.53 (m, 4H), 4.40-4.33 (m, 3H), 4.25-4.15 (m, 3H), 4.06-3.93 (m, 3H), 1.35-1.32 (m, 3H) ppm. $^{31}P$ NMR (DMSO) δ −5.95 (s) ppm. HRMS (ESI) found m/z 1073.0949 (M+Na). $C_{47}H_{42}Cl_2N_4NaO_{12}P_2S_2$ requires 1073.0985.

Figure 39:
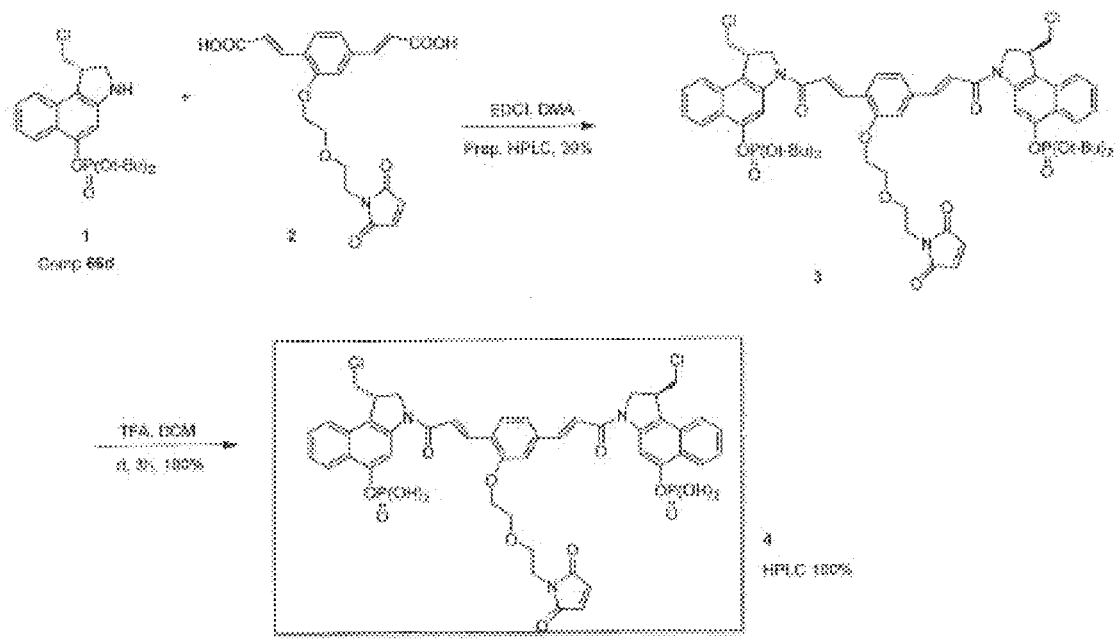
FIG. 39 shows the synthesis of [(1S)-1-(chloromethyl)-3-[(E)-3-[4-[(E)-3-[(1S)-1-(chloromethyl)-5-phosphonooxy-1,2-dihydrobenzo[e]indol-3-yl]-3-oxo-prop-1-enyl]-2-[2-[2-(2,5-dioxopyrrol-1-yl)ethoxy]ethoxy]phenyl]prop-2-enoyl]-1,2-dihydrobenzo[e]indol-5-yl]dihydrogen phosphate (Compound No. 78, Table 4, FIG. 39).

Example 25 [(1S)-1-(chloromethyl)-3-[(E)-3-[4-[(E)-3-[(1S)-1-(chloromethyl)-5-phosphonooxy-1,2-dihydrobenzo[e]indol-3-yl]-3-oxo-prop-1-enyl]-2-[2-[2-(2,5-dioxopyrrol-1-yl)ethoxy]ethoxy]phenyl]prop-2-enoyl]-1,2-dihydrobenzo[e]indol-5-yl] dihydrogen phosphate (Compound No. 78, Table 4, FIG. 39)

Intermediate 3

To 76 mg (0.18 mmol) of 1 (freshly made by the procedure mention above) was added 2 (18 mg, 0.045 mmol), EDCI hydrochloride (69 mg, 0.36 mmol), toluenesulfonic acid (0.8 mg, 0.005 mmol) and DMA (0.25 mL). After the mixture was stirred overnight, most of DMA was removed under vacuum and the residue was redistributed between ethyl acetate and water. The aqueous phase was extracted with ethyl acetate three times. The combined organic extracts were washed with water followed by brine, dried over anhydrous $Na_2SO_4$, and filtered through a pad of Celite. The solvent was removed and the resultant residue was dissolved in the minimum DCM and precipitated by adding heptane to give crude product (54 mg), which was further purified by preparative HPLC (Column: Synergi-Max RP 4μ, 250×21.20 mm; Mobile phase: A/B=from 20% to 1% (A: ammonium formate pH 3.45, B: 90% acetonitrile in water); flow rate 12 mL/min, gradient method; wavelength: 254 nm, 325 nm) to give 3 (17 mg, 30%) as a yellow solid.

¹H NMR (CDCl₃) δ 8.72 (br s, 2H), 8.23 (d, J=8.4 Hz, 2H), 7.96 (d, J=15.2 Hz, 1H), 7.83 (d, J=15.3 Hz, 1H), 7.71 (d, J=8.2 Hz, 2H), 7.54-7.50 (m, 3H), 7.42-7.39 (m, 2H), 7.26-7.12 (m, 3H), 6.95-6.88 (m, 1H), 6.67 (s, 2H), 4.57-4.52 (m, 2H), 4.47-4.38 (m, 2H), 4.28-4.24 (m, 2H), 4.16-4.09 (m, 2H), 4.00-3.94 (m, 4H), 3.78 (apparent s, 4H), 3.55-0.348 (m, 2H), 1.57 (s, 36H) ppm. ³¹P NMR (CDCl₃) δ −15.64 (s) ppm. HRMS (ESI) found m/z 1238.3862 (M+Na). $C_{62}H_{73}Cl_2N_3NaO_{14}P_2$ requires 1238.3837.

To a solution of 3 (16 mg, 0.013 mmol) in DCM (1 mL) cooled in an ice bath was added TFA (0.5 mL, 3.24 mmol). The mixture was allowed to warm up to room temperature and stirred for 3 h. All the volatile components were pumped off and the resultant residue was triturated with ethyl acetate to give Compound 78 as a yellow solid (13 mg, 100%, HPLC purity 100%). ¹H NMR (DMSO) δ 8.60 (s, 2H), 8.12 (d, J=8.4 Hz, 2H), 7.95-7.87 (m, 4H), 7.72 (d, J=15.1 Hz, 1H), 7.61-7.57 (m, 2H), 7.53-7.45 (m, 4H), 7.38-7.32 (m, 2H), 6.97 (s, 2H), 4.60-4.48 (m, 4H), 4.30-4.28 (m, 4H), 4.08-3.88 (m, 6H), 3.68-3.58 (m, 4H). ³¹P NMR (DMSO) δ −5.94 (s) ppm. HRMS (ESI) found m/z 1014.1301 (M+Na). $C_{46}H_{41}Cl_2N_3NaO_{14}P_2$ requires 1014.1333.

Figure 40:
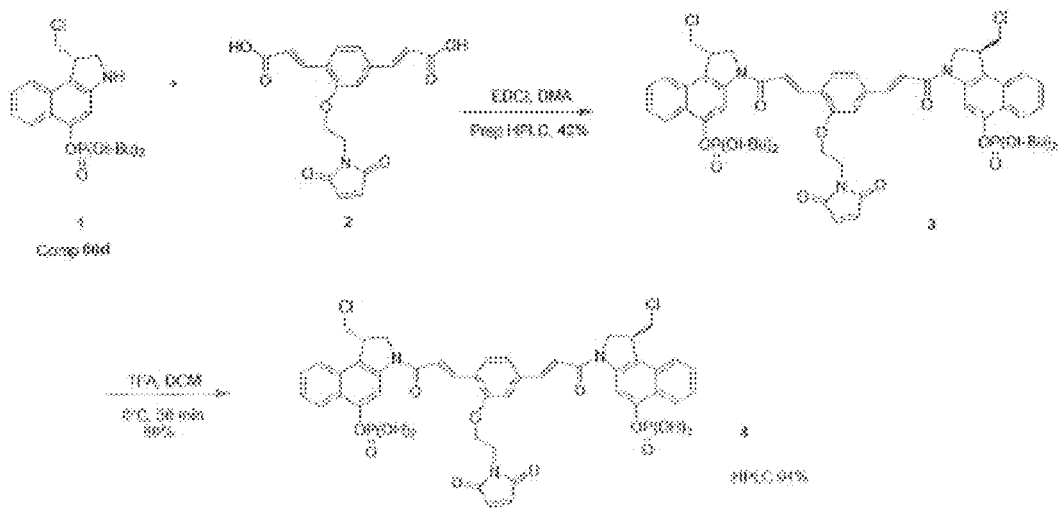
FIG. 40 shows the synthesis of [(1S)-1-(chloromethyl)-3-[(E)-3-[4-[(E)-3-[(1S)-1-(chloromethyl)-5-phosphonooxy-1,2-dihydrobenzo[e]indol-3-yl]-3-oxo-prop-1-enyl]-2-[2-(2,5-dioxopyrrol-1-yl)ethoxy]phenyl]prop-2-enoyl]-1,2-dihydrobenzo[e]indol-5-yl]dihydrogen phosphate (Compound No. 79, Table 4, FIG. 40).

Example 26 [(1S)-1-(chloromethyl)-3-[(E)-3-[4-[(E)-3-(1S)-1-(chloromethyl)-5-phosphonooxy-1,2-dihydrobenzo[e]indol-3-yl-3-oxo-prop-1-enyl]-2-[2-(2,5-dioxopyrrol-1-yl)ethoxy]phenyl]prop-2-enoyl]-1,2-dihydrobenzo[e]indol-5-yl] dihydrogen phosphate (Compound No. 79, Table 4, FIG. 40)

Intermediate 3

To 52 mg (0.12 mmol) of 1 (freshly made by the procedure mentioned above) was added 2 (11 mg, 0.031 mmol), EDCI hydrochloride (35 mg, 0.18 mmol), toluenesulfonic acid (0.5 mg, 0.003 mmol) and DMA (0.25 mL). After the mixture was stirred overnight, most of the DMA was removed under vacuum and the residue was redistributed between ethyl acetate and water. The aqueous phase was extracted with ethyl acetate three times. The combined organic extracts were washed with water followed by brine, dried over anhydrous $Na_2SO_4$, and filtered through a pad of Celite. The solvent was removed and the resultant residue was dissolved in the minimum DCM and precipitated by adding heptane to give crude product (71 mg), which was further purified by preparative HPLC (Column: Synergi-Max RP 4μ, 250×21.20 mm; Mobile phase: A/B=from 20% to 1% (A: ammonium formate pH 3.45, B: 90% acetonitrile in water); flow rate 12 mL/min, gradient method; wavelength: 254 nm, 300 nm) to give 3 (15 mg, 42%) as a yellow solid. ¹H NMR (CDCl₃) δ 8.71 (br s, 2H), 8.25 (d, J=8.4 Hz, 2H), 7.95 (d, J=15.5 Hz, 1H), 7.83 (d, J=15.3 Hz, 1H), 7.72 (d, J=8.2 Hz, 2H), 7.60-7.52 (m, 3H), 7.46-7.40 (m, 2H), 7.28-7.20 (m, 2H), 7.13-6.99 (m, 2H), 6.78 (s, 2H), 4.64-4.60 (m, 2H), 4.51-4.45 (m, 2H), 4.38-4.32 (m, 2H), 4.15-4.05 (m, 4H), 4.00-3.95 (m, 2H), 3.57-3.49 (m, 2H), 1.58 (s, 36H) ppm. ³¹P NMR (CDCl₃) δ −15.67 (s) ppm. HRMS (ESI) found m/z 1194.3606 (M+Na). $C_{60}H_{69}Cl_2N_3NaO_{13}P_2$ requires 1194.3575.

Compound No. 79

To a solution of 3 (13 mg, 0.011 mmol) in DCM (0.5 mL) cooled in an ice bath was added TFA (0.2 mL, 1.30 mmol). The mixture was allowed to warm up to room temperature and stirred for 0.5 h. Diethyl ether was added to give a precipitate, which was filtered off and washed with ethyl acetate to give 4 (Compound No. 79) as a yellow solid (8.4 mg, 80%, HPLC purity 90%). ¹H NMR (DMSO) δ 8.59 (s, 2H), 8.13 (d, J=8.3 Hz, 2H), 7.97-7.82 (m, 4H), 7.71 (d, J=15.1 Hz, 1H), 7.60-7.52 (m, 3H), 7.49-7.44 (m, 3H), 7.35-7.24 (m, 2H), 7.08 (s, 2H), 4.65-4.50 (m, 4H), 4.40-4.30 (m, 4H), 4.05-3.90 (m, 6H). ³¹P NMR (DMSO) δ −5.81 (s) ppm. HRMS (ESI) found m/z 970.1036 (M+Na). $C_{44}H_{37}Cl_2N_3NaO_3P_2$ requires 970.1071.

Figure 41:
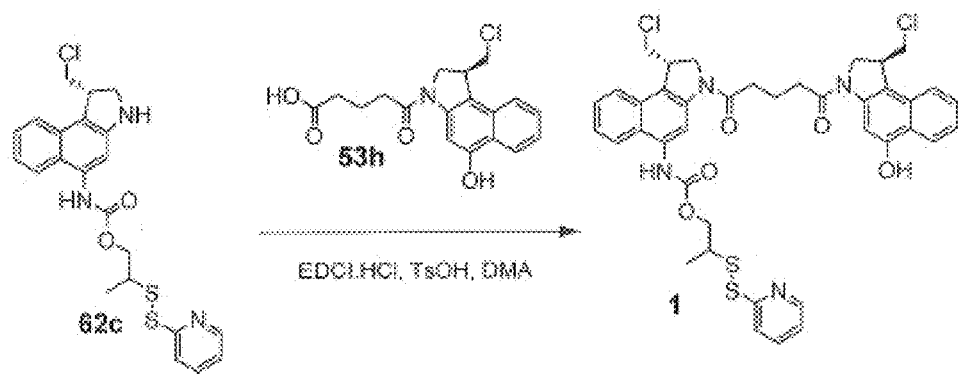
FIG. 41 shows the synthesis of 2-(2-pyridyldisulfanyl)propyl N-[1-(chloromethyl)-3-[5-[1-(chloromethyl)-5-hydroxy-1,2-dihydrobenzo[e]indol-3-yl]-5-oxo-pentanoyl]-1,2-dihydrobenzo[e]indol-5-yl]carbamate (Compound No. 80, Table 4, FIG. 41).

Example 27 2-(2-pyridyldisulfanyl)propyl N-[1-(chloromethyl)-3-[5-[1-(chloromethyl)-5-hydroxy-1,2-dihydrobenzo[e]indol-3-yl]-5-oxo-pentanoy]-1,2-dihydrobenzo[e]indol-5-yl]carbamate (Compound No. 80, Table 4, FIG. 41)

A mixture of 62c (31.0 mg, 0.0674 mmol, freshly made by the procedure mentioned above), 53h (23.0 mg, 0.0674 mmol, freshly made by the procedure mentioned above), EDCI.HCl (38.7 mg, 0.202 mmol) and TsOH (2.3 mg, 0.0135 mmol) in dry DMA (2 mL) was stirred at r.t. overnight, under nitrogen. After 18 h the reaction mixture was diluted with EtOAc and $H_2O$ and well mixed. The layers were separated and the organic layer washed with $H_2O$ (3×), dried ($Na_2SO_4$) and solvent removed under vacuum. The crude product was purified by column chromatography on silica gel using DCM:MeOH 100:0 to 98:2, followed by trituration with diisopropyl ether to give compound 1 (Compound No. 80, 26.0 mg, 49%, HPLC purity: 95.2%) as a cream solid. ¹H NMR δ (400 MHz, DMSO-d₆) 10.36 (s, 1H), 9.69 (s, 1H), 8.56 (s, 1H), 8.44 (d, J=4.3 Hz, 1H), 8.08 (d, J=8.0 Hz, 1H), 8.02-8.00 (m, 2H), 7.92 (d, J=8.3 Hz, 1H), 7.85-7.77 (m, 3H), 7.57-7.53 (m, 1H), 7.51-7.47 (m, 1H), 7.45-7.41 (m, 1H), 7.34-7.30 (m, 1H), 7.24-7.21 (m, 1H), 4.42-4.29 (m, 3H), 4.25-4.13 (m, 5H), 4.05-3.97 (m, 2H), 3.91 (dd, J=11, 7.2 Hz, 1H), 3.79 (dd, J=11, 8.3 Hz, 1H), 3.43-3.36 (m, 1H), 2.77-2.56 (m, 4H), 2.01-1.93 (m, 2H), 1.34 (d, J=6.7 Hz, 3H). HRMS m/z 811.1542 [(M+Na)⁺ calcd for $C_{40}H_{38}Cl_2N_4NaO_5S_2$ 811.1553].

Examples 28

Figure 42:
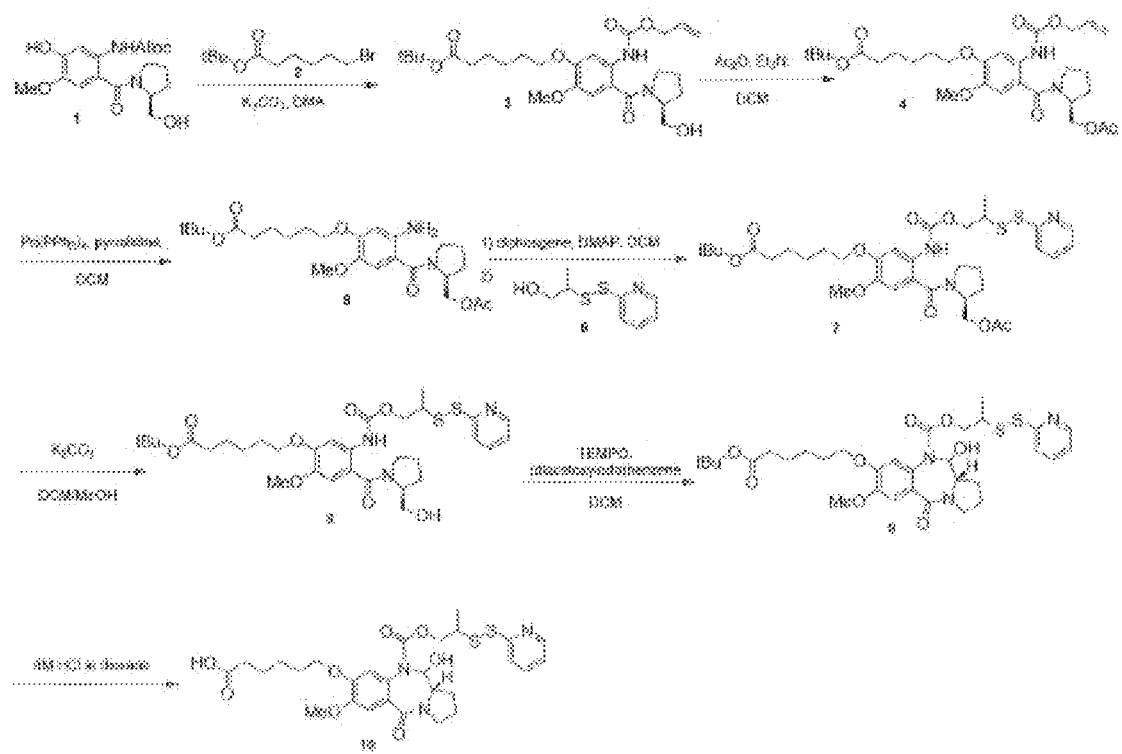
FIG. 42-43 show the synthesis of 2-(2-pyridyldisulfanyl)propyl 3-[6-[1-(chloromethyl)-5-(4-methylpiperazine-1-carbonyl)oxy-1,2-dihydrobenzo[e]indol-3-yl]-6-oxo-hexoxy]-6-hydroxy-2-methoxy-11-oxo-6a,7,8,9-tetrahydro-6H-pyrrolo[2,1-c][1,4]benzodiazepine-5-carboxylate, 2-(2-pyridyldisulfanyl)propyl 3-[6-[1-(chloromethyl)-5-phosphonooxy-1,2-dihydrobenzo[e]indol-3-yl]-6-oxo-hexoxy]-6-hydroxy-2-methoxy-11-oxo-6a,7,8,9-tetrahydro- 6H-pyrrolo[2,1-c][1,4]benzodiazepine-5-carboxylate, and 2-(2-pyridyldisulfanyl)propyl 3-[6-[1-(chloromethyl)-5-hydroxy-1,2-dihydrobenzo[e]indol-3-yl]-6-oxo-hexoxy]-6-hydroxy-2-methoxy-11-oxo-6a,7,8,9-tetrahydro-6H-pyrrolo [2,1-c][1,4]benzodiazepine-5-carboxylate (Compound No. 81-83, Table 4, FIG. 42-43).
Figure 43:
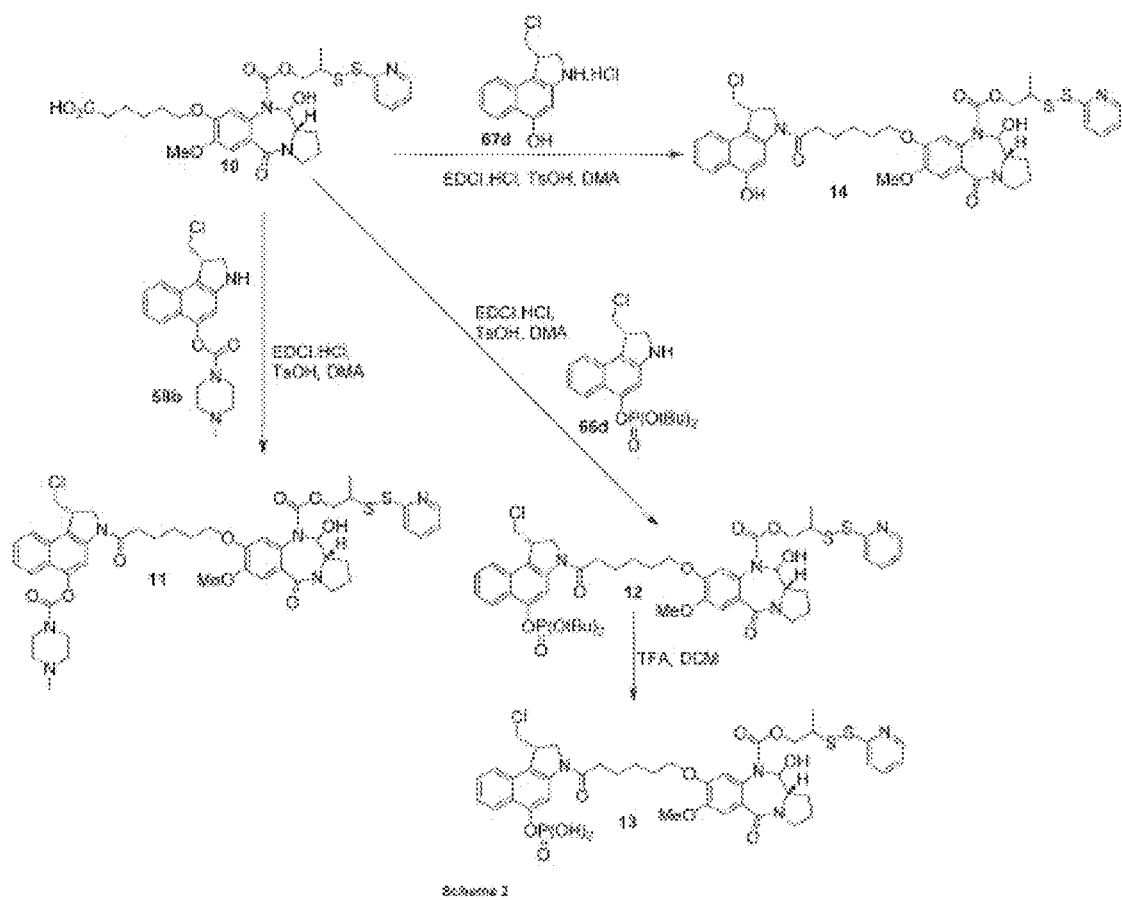

2-(2-pyridyldisulfanyl)propyl 3-[6-[1-(chloromethyl)-5-(4-methylpiperazine-1-carbonyl)oxy-1,2-dihydrobenzo[e]indol-3-yl]-6-oxo-hexoxy]-6-hydroxy-2-methoxy-11-oxo-6a,7,8,9-tetrahydro-6H-pyrrolo[2,1-c][1,4]benzodiazepine-5-carboxylate, 2-(2-pyridyldisulfanyl)propyl 3-[6-[1-(chloromethyl)-5-phosphonooxy-1,2-dihydrobenzo[e]indol-3-yl]-6-oxo-hexoxy]-6-hydroxy-2-methoxy-11-oxo-6a,7,8,9-tetrahydro-6H-pyrrolo[2,1-c][1,4]benzodiazepine-5-carboxylate, and 2-(2-pyridyldisulfanyl)propyl 3-[6-[1-(chloromethyl)-5-hydroxy-1,2-dihydrobenzo[e]indol-3-yl]-6-oxo-hexoxy]-6-hydroxy-2-methoxy-11-oxo-6a,7,8,9-tetrahydro-6H-pyrrolo[2,1-c][1,4]benzodiazepine-5-carboxylate (Compound No. 81-83, Table 4, FIG. 42-43)

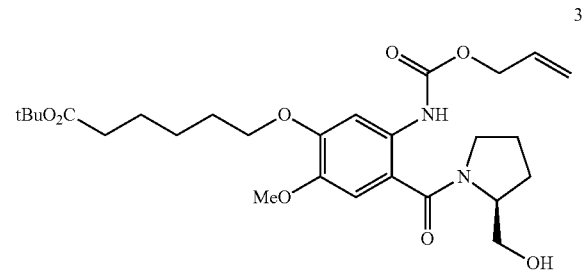 [SMILES: C=CCOC(=O)Nc1cc(OCCCCCC(=O)OC(C)(C)C)c(OC)cc1C(=O)N1CCC[C@H]1CO]

3

A mixture of 1 (1.40 g, 4.00 mmol, prepared following literature procedure: *J. Med. Chem.* 2003, 46, 2132-2151), 2 (1.31 g, 5.22 mmol, prepared following literature procedure: WO2004065491 A1) and $K_2CO_3$ (829 mg, 6.00 mmol) in dry DMA (15 mL) was stirred at r.t. for 43 h. The mixture was then diluted with EtOAc and $H_2O$, well mixed and the layers separated. The organic layer was washed with $H_2O$ (3×), brine (1×) and dried ($Na_2SO_4$) and the solvent removed under vacuum. The crude product was purified by column chromatography on silica gel using EtOAc:Hex 50:50 to 67:33 to 100:0 to give compound 3 (1.74 g, 84%) as a yellow oil. $^1H$ NMR δ (400 MHz, $CDCl_3$) 8.77 (br s, 1H), 7.79 (s, 1H), 6.82 (s, 1H), 6.02-5.92 (m, 1H), 5.36 (dq, J=17.2, 1.5 Hz, 1H), 5.26 (dq, J=10.4, 1.2 Hz, 1H), 4.69-4.60 (m, 2H), 4.47-4.39 (m, 1H), 4.28 (br s, 1H), 4.09-4.05 (m, 2H), 3.83 (s, 3H), 3.90-3.80 (m, 1H), 3.74-3.70 (m, 1H), 3.65-3.59 (m, 1H), 3.54-3.47 (m, 1H), 2.25 (t, J=7.4 Hz, 2H), 2.20-2.15 (m, 1H), 1.93-1.84 (m, 3H), 1.81-1.72 (m, 1H), 1.70-1.63 (m, 3H), 1.53-1.47 (m, 2H), 1.44 (s, 9H). HRMS m/z 543.2666 [(M+Na)$^+$ calcd for $C_{27}H_{40}N_2NaO_8$ 543.2677].

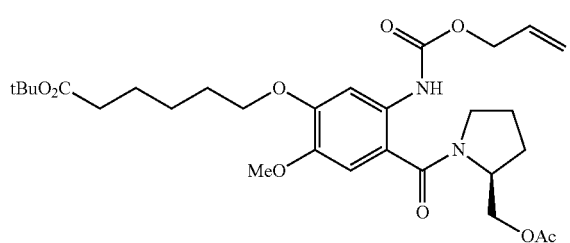

4

Et$_3$N (1.32 mL, 9.47 mmol) was added to a solution of 3 (821 mg, 1.58 mmol) in dry DCM (6 mL) at r.t. Acetic anhydride (0.75 mL, 7.93 mmol) was then added and the mixture stirred at r.t. for 4.5 h. The reaction mixture was cooled to 0° C. and dry MeOH (1 mL) added and the mixture stirred at 0° C. for 15 mins. EtOAc (120 mL) was then added and the mixture washed with $H_2O$ (2×), brine (1×), dried ($Na_2SO_4$) and solvent removed under vacuum to give compound 4 (891 mg, quantitative) which was used in the next step without purification. $^1H$ NMR δ (400 MHz, $CDCl_3$) 8.88 (br s, 1H), 7.82 (s, 1H), 6.81 (s, 1H), 6.01-5.91 (m, 1H), 5.36 (dq, J=17.2, 1.5 Hz, 1H), 5.25 (dq, J=10.4, 1.3 Hz, 1H), 4.65-4.62 (m, 2H), 4.61-4.54 (m, 1H), 4.32-4.22 (m, 2H), 4.09-4.06 (m, 2H), 3.83 (s, 3H), 3.55-3.47 (m, 2H), 2.26-2.23 (m, 2H), 2.18-2.12 (m, 1H), 2.07 (s, 3H), 1.97-1.77 (m, 5H), 1.70-1.63 (m, 2H), 1.54-1.47 (m, 2H), 1.44 (s, 9H). HRMS m/z 585.2774 [(M+Na)$^+$ calcd for $C_{29}H_{42}N_2NaO_9$ 585.2783].

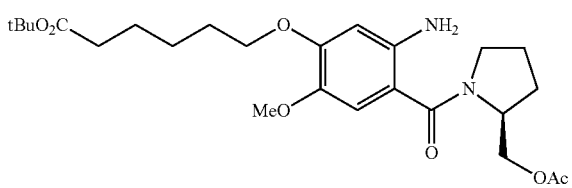

5

Pyrrolidine (1.6 mL, 19.2 mmol) was added to a solution of 4 (1.06 g, 1.88 mmol) in dry DCM (20 mL) at r.t. Pd(PPh$_3$)$_4$(109 mg, 0.0943 mmol) was then added and the reaction mixture stirred at r.t. for 40 mins. The reaction mixture was washed with 0.25 M HCl solution (2×75 mL), dried (Na$_2$SO$_4$) and solvent removed under vacuum. The crude product was purified by column chromatography on silica gel using EtOAc:Hex 50:50 to 100:0 to give compound 5 (726 mg, 81%) as a yellow oil. $^1H$ NMR δ (400 MHz, DMSO-d$_6$) 6.67 (s, 1H), 6.35 (s, 1H), 5.08 (s, 2H), 4.35-4.30 (m, 1H), 4.13-4.06 (m, 2H), 3.87 (t, J=6.4 Hz, 2H), 3.63 (s, 3H), 3.50-3.44 (m, 1H), 3.42-3.35 (m, 1H), 2.21 (t, J=7.2 Hz, 2H), 2.07-2.00 (m, 1H), 2.01 (s, 3H), 1.89-1.82 (m, 1H), 1.77-1.67 (m, 4H), 1.59-1.51 (m, 2H), 1.44-1.36 (m, 2H), 1.39 (s, 9H). HRMS m/z 501.2573 [(M+Na)$^+$ calcd for $C_{25}H_{38}N_2NaO_7$ 501.2571].

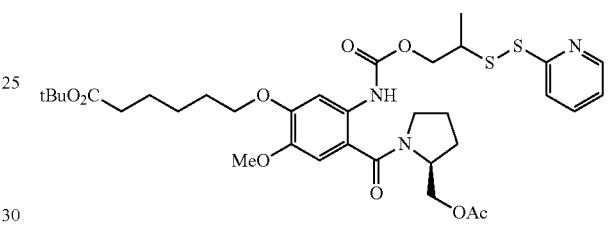

7

Diphosgene (0.22 mL, 1.82 mmol) was added to a mixture of 5 (726 mg, 1.52 mmol) and DMAP (557 mg, 4.56 mmol) in dry DCM (25 mL) at r.t. under nitrogen. After 30 mins a solution of 6 (2.60 g, 12.9 mmol; freshly made by the procedure mentioned above—no number previously assigned to alcohol) in dry DCM (25 mL) was added and the mixture stirred at r.t. overnight. After 18 h the reaction mixture was washed with H$_2$O (1×), dried (Na$_2$SO$_4$) and solvent removed under vacuum. The crude product was purified by column chromatography on silica gel using DCM:EtOAc 100:0 to 95:5 to 94:6 until excess 6 eluted and then EtOAc:Hex 70:30 to give compound 7 (920 mg, 86%) as a pale yellow oil. $^1H$ NMR δ (400 MHz, DMSO-d$_6$) 9.16 (br s, 1H), 8.45-8.43 (m, 1H), 7.83-7.78 (m, 2H), 7.25-7.21 (m, 1H), 7.15 (d, J=2.8 Hz, 1H), 6.87 (s, 1H), 4.29 (br s, 1H), 4.17-3.99 (m, 4H), 3.92 (t, J=6.4 Hz, 2H), 3.75 (s, 3H), 3.42-3.30 (m, 3H), 2.20 (t, J=7.2 Hz, 2H), 2.06-1.95 (m, 4H), 1.83 (br s, 1H), 1.77-1.68 (m, 4H), 1.58-1.49 (m, 2H), 1.43-1.36 (m, 2H), 1.39 (s, 9H), 1.29 (d, J=6.8 Hz, 3H). HRMS m/z 706.2832 [(M+H)$^+$ calcd for $C_{34}H_{48}N_3O_9S_2$ 706.2826].

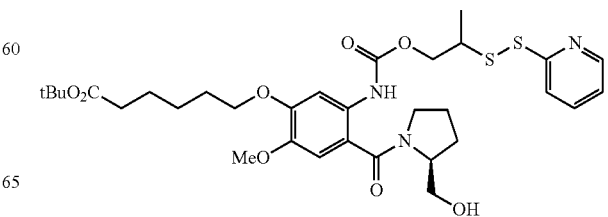

8

A mixture of 7 (949 mg, 1.34 mmol) and K$_2$CO$_3$ (1.85 g, 13.4 mmol) in DCM-MeOH (34 mL/17 mL) was stirred at r.t. for 45 mins. The mixture was diluted with DCM, poured into ice H$_2$O (200 mL), well mixed and the layers separated. The aqueous layer was extracted with DCM (1×), the combined organic layers were dried (Na$_2$SO$_4$) and solvent removed under vacuum. The crude product was purified by column chromatography on silica gel using DCM:EtOAc 100:0 to 50:50 to give compound 8 (808 mg, 91%) as a pale yellow oil. $^1$H NMR δ (400 MHz, DMSO-d$_6$) 9.20 (br s, 1H), 8.44 (d, J=4.7 Hz, 1H), 7.81-7.80 (m, 2H), 7.25-7.20 (m, 2H), 6.94 (s, 1H), 4.75 (t, J=5.6 Hz, 1H), 4.17-3.99 (m, 3H), 3.92 (t, J=6.4 Hz, 2H), 3.74 (s, 3H), 3.60-3.46 (m, 2H), 3.37-3.20 (m, 3H), 2.20 (t, J=7.2 Hz, 2H), 1.93-1.76 (m, 3H), 1.75-1.68 (m, 3H), 1.58-1.51 (m, 2H), 1.44-1.36 (m, 2H), 1.39 (s, 9H), 1.29 (d, J=6.9 Hz, 3H). HRMS m/z 664.2721 [(M+H)$^+$ calcd for C$_{32}$H$_{46}$N$_3$O$_8$S$_2$ 664.2724].

9

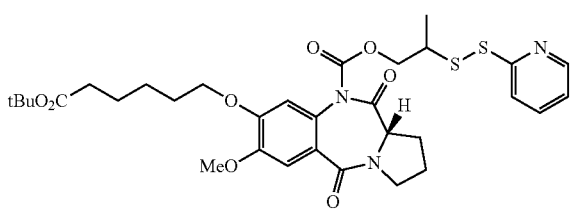

7.10 (s, 1H), 6.96 and 6.91 (2s, 1H), 6.55 (t, J=5.9 Hz, 1H), 5.46 (dd, J=8.9, 6.1 Hz, 1H), 4.31-4.21 (m, 1H), 4.02-3.84 (m, 3H), 3.80 and 3.79 (2s, 3H), 3.52-3.46 (m, 1H), 3.40-3.18 (m, 3H), 2.19-2.13 (m, 2H), 2.09-2.00 (m, 1H), 1.96-1.85 (m, 3H), 1.70-1.67 (m, 2H), 1.56-1.45 (m, 2H), 1.40-1.34 (m, 2H), 1.38 and 1.37 (2s, 9H), 1.15-1.10 (m, 3H). HRMS m/z 662.2592 [(M+H)$^+$ calcd for C$_{32}$H$_{44}$N$_3$O$_8$S$_2$ 662.2564].

10

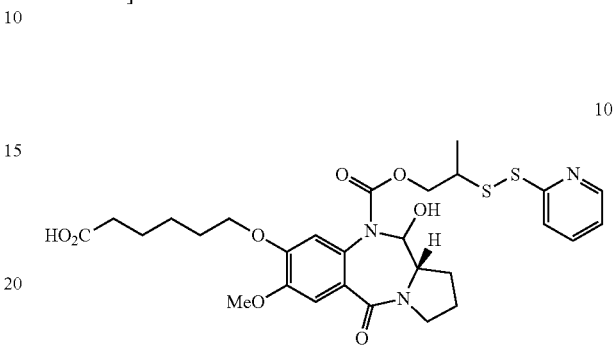

A mixture of 9 (254 mg, 0.384 mmol) and 4 M HCl in dioxane (11 mL) was stirred at r.t. for 1 h 15 mins. The solvent was removed under vacuum at 25-30° C. to give compound 10 (162 mg, 70%) which was used in the next step without purification.

11

(Diacetoxyiodo)benzene (259 mg, 0.804 mmol) was added to a mixture of 8 (349 mg, 0.526 mmol) and TEMPO (82.2 mg, 0.526 mmol) in dry DCM (10 mL) at r.t. and the reaction mixture stirred overnight. After 24 h the mixture was diluted with DCM and saturated aqueous Na$_2$S$_2$O$_3$ and well mixed. The layers were separated and the organic layer was washed with saturated aqueous Na$_2$S$_2$O$_3$ (1×), saturated aqueous NaHCO$_3$ (1×), dried (Na$_2$SO$_4$) and solvent removed under vacuum. The crude product was purified by column chromatography on silica gel using EtOAc:Hex 70:30 to 100:0 to give compound 9 (248 mg, 71%) as a white foam. $^1$H NMR δ (400 MHz, DMSO-d$_6$) 8.45-8.43 (m, 1H), 7.79-7.69 (m, 1H), 7.51-7.48 (m, 1H), 7.24-7.20 (m, 1H), A mixture of 10 (161 mg, 0.266 mmol), 58b (195 mg, 0.542 mmol, freshly made by the procedure mentioned above), EDCI.HCl (253 mg, 1.32 mmol) and TsOH (19.5 mg, 0.113 mmol) in dry DMA (5 mL) was stirred at r.t. overnight, under nitrogen. After 23 h the reaction mixture was diluted with EtOAc and saturated aqueous NaHCO$_3$ and well mixed. The layers were separated and the aqueous layer extracted with EtOAc (1×). The combined organic layers were washed with H$_2$O (1×), brine (1×), dried (Na$_2$SO$_4$) and solvent removed under vacuum. The crude product was purified by column chromatography on silica gel using DCM:MeOH 100:0 to 93:7 and the material recolumned using DCM:MeOH 99:1 to 94:6 to give 11 (Compound No.

81, 118 mg, 47%, HPLC purity: 98.0%) as a pale yellow foam. $^1$H NMR δ (400 MHz, DMSO-$d_6$) 8.43-8.41 (m, 1H), 8.22 (s, 1H), 7.96 (d, J=8.4 Hz, 1H), 7.83 (d, J=8.4 Hz, 1H), 7.73-7.66 (m, 1H), 7.61-7.56 (m, 1H), 7.51-7.45 (m, 2H), 7.22-7.17 (m, 1H), 7.10 (s, 1H), 6.97 and 6.92 (2s, 1H), 6.56 (t, J=6.0 Hz, 1H), 5.46 (dd, J=9.1, 6.2 Hz, 1H), 4.42-4.20 (m, 4H), 4.05-3.76 (m, 7H), 3.80 and 3.79 (2s, 3H), 3.52-3.47 (m, 1H), 3.38-3.11 (m, 4H), 2.09-1.99 (m, 1H), 1.94-1.88 (m, 3H), 1.77-1.74 (m, 2H), 1.65-1.62 (m, 2H), 1.48-1.42 (m, 2H), 1.35-1.23 (m, 1H), 1.15-1.10 (m, 3H), 9H partially obscured by DMSO. HRMS m/z 969.3070 [(M+Na)$^+$ calcd for $C_{47}H_{55}ClN_6NaO_9S_2$ 969.3053].

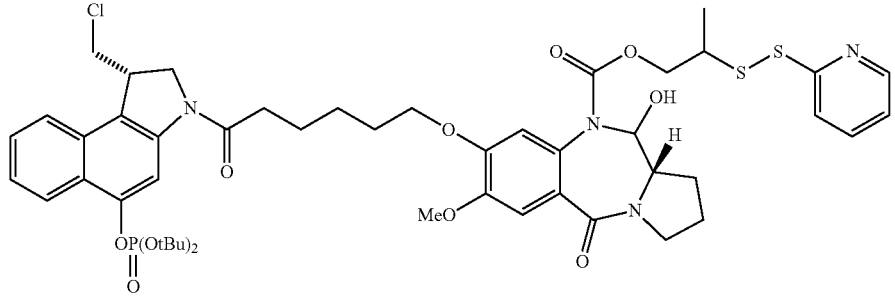

12

A mixture of 10 (162 mg, 0.267 mmol), 66d (178 mg, 0.418 mmol, freshly made by the procedure mentioned above), EDCI.HCl (184 mg, 0.960 mmol) and TsOH (11 mg, 0.0639 mmol) in dry DMA (5 mL) was stirred at r.t. overnight, under nitrogen. After 18.5 h the reaction mixture was diluted with EtOAc and H$_2$O and well mixed. The layers were separated and the organic layer washed with saturated aqueous NaHCO$_3$ (1×), H$_2$O (1×), brine (1×), dried (Na$_2$SO$_4$) and solvent removed under vacuum. The crude product was purified by column chromatography on silica gel using EtOAc:MeOH 100:0 to 95:5 to give a yellow residue. This was further purified by preparative HPLC (column: Synergi-MAX RP 4μ, 21.20×250 mm; flow rate: 12 mL/min; mobile phase: solvent A: H$_2$O/ammonium formate buffer pH 3.45, solvent B: MeCN/H$_2$O 90:10; method: gradient, solvent A:solvent B 90:10 to 10:90 to 0:100 over 30 min) to give compound 12 (89.3 mg, 33%, HPLC purity: 99.5%) as a white foam. $^1$H NMR δ (400 MHz, DMSO-$d_6$) 8.56 (s, 1H), 8.43-8.41 (m, 1H), 8.04 (d, J=8.2 Hz, 1H), 7.92 (d, J=8.4 Hz, 1H), 7.73-7.67 (m, 1H), 7.60-7.56 (m, 1H), 7.51-7.45 (m, 2H), 7.22-7.17 (m, 1H), 7.10 (s, 1H), 6.98 and 6.92 (2s, 1H), 6.55 (t, J=5.6 Hz, 1H), 5.47-5.44 (m, 1H), 4.40-4.36 (m, 1H), 4.30-4.19 (m, 3H), 4.04-3.86 (m, 4H), 3.86-3.75 (m, 1H), 3.80 and 3.79 (2s, 3H), 3.52-3.46 (m, 1H), 3.38-3.22 (m, 3H), 3.21-3.15 (m, 1H), 2.09-1.99 (m, 1H), 1.94-1.85 (m, 3H), 1.78-1.74 (m, 2H), 1.69-1.60 (m, 2H), 1.55-1.40 (m, 2H), 1.47 and 1.47 (2s, 18H), 1.28-1.23 (m, 1H), 1.15-1.10 (m, 3H). HRMS m/z 1035.3162 [(M+Na)$^+$ calcd for $C_{49}H_{62}ClN_4NaO_{11}PS_2$ 1035.3175].

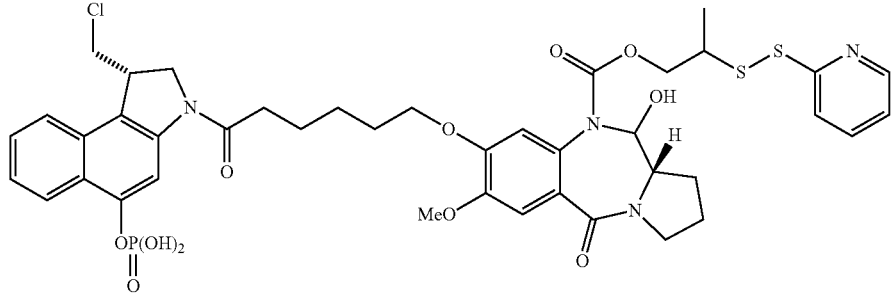

13

A mixture of 12 (84.0 mg, 0.0829 mmol) and TFA (1 mL) in dry DCM (2 mL) was stirred at r.t. for 40 mins. The solvent was then removed under vacuum at 25° C. to give a green residue. The residue was dissolved in DCM, the solution diluted with EtOAc and the DCM removed under vacuum to give a white solid and the remaining solvent decanted. This process was repeated and the resulting solid was triturated with EtOAc and dried to give compound 13 (Compound No. 82, 43.8 mg, 59%, HPLC purity: 93.8%) as a white solid. $^1$H NMR δ (400 MHz, DMSO-$d_6$) 8.47 (s, 1H), 8.44-8.42 (m, 1H), 8.08 (d, J=8.3 Hz, 1H), 7.90 (d, J=8.3 Hz, 1H), 7.74-7.68 (m, 1H), 7.58-7.54 (m, 1H), 7.51-7.48 (m, 1H), 7.47-7.43 (m, 1H), 7.22-7.18 (m, 1H), 7.10 (s, 1H), 6.98 and 6.93 (2s, 1H), 5.46 (d, J=9.5 Hz, 1H), 4.39-4.18 (m, 4H), 4.04-3.95 (m, 3H), 3.90-3.85 (m, 1H), 3.84-3.76 (m, 1H), 3.80 and 3.80 (2s, 3H), 3.52-3.47 (m, 1H), 3.40-3.27 (m, 3H), 3.21-3.15 (m, 1H), 2.10-2.02 (m, 1H), 1.94-1.88 (m, 3H), 1.78-1.74 (m, 2H), 1.69-1.60 (m, 2H), 1.48-1.42 (m, 2H), 1.35-1.23 (m, 1H), 1.16-1.10 (m, 3H), 3H not observed. HRMS m/z 923.1938 [(M+Na)$^+$ calcd for $C_{41}H_{46}ClN_4NaO_{11}PS_2$ 923.1923].

Figure 44:
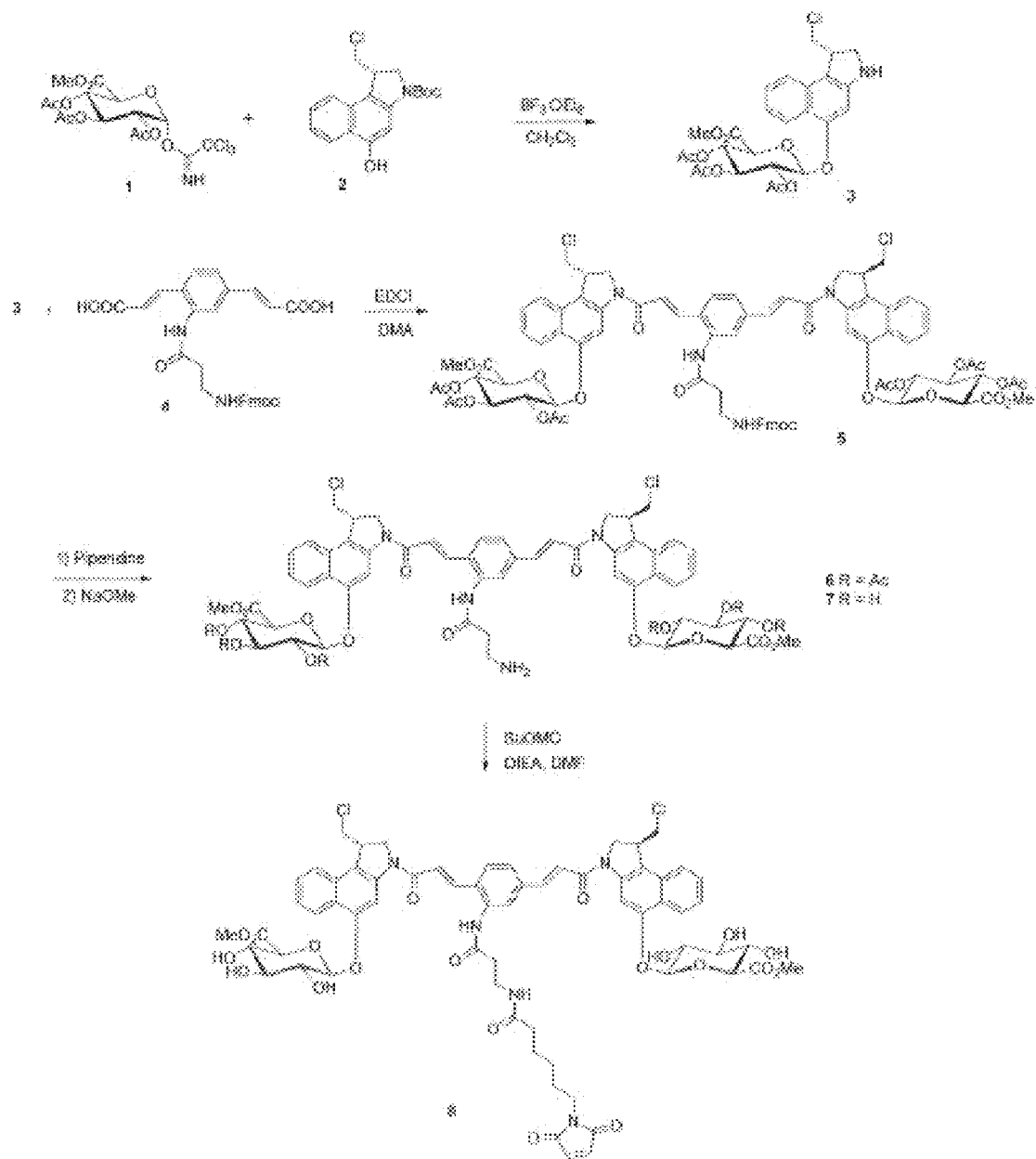
FIG. 44 shows the synthesis of (1S)-1-(chloromethyl)-3-((2E)-3-{4-((1E)-3-{(1S)-1-(chloromethyl)-5-[(6-methyl-β-D-glucopyranuronosyl)oxy]-1,2-dihydro-3H-benzo[e]indol-3-yl}-3-oxo-1-propenyl)-2-[(3-{[6-(2,5-dioxo-2,5-dihydro-1H-pyrrol-1-yl) hexanoyl]amino}propanoyl) amino]phenyl}-2-propenoyl)-1,2-dihydro-3H-benzo[e] indol-5-yl methyl 3-D-glucopyranosiduronate (Compound No. 84, Table 4, FIG. 44).

Example 29 (1S)-1-(chloromethyl)-3-((2E)-3-{4-((1E)-3-{(1S)-1-(chloromethyl)-5-[(6-methyl-β-D-glucopranuronosyl)oxy]-1,2-dihydro-3H-benzo[e]indol-3-yl}-3-oxo-1-propenyl)-2-[(3-{[6-(2,5-dioxo-2,5-dihydro-1H-pyrrol-1-yl) hexanoyl] amino}propanoyl)amino]phenyl}-2-propenoyl)-1,2-dihydro-3H-benzo[e]indol-5-yl methyl β-D-glucopyranosiduronate (Compound No. 84, Table 4, FIG. 44)

Trichloroacetimidate (1) was prepared according to literature procedures: L. Lázár, E. Mező, M. Herczeg, A. Lipták, S. Antus, A. Borbás, *Tetrahedron* 2012, 68, 7386-7399; L. Tietze, H. Schuster, K. Schmuck, I. Schuberth, F. Alves, *Bioorg. & Med. Chem.* 2008, 16, 6312-6318.

A suspension of trichloroacetimidate (1) (360 mg, 0.75 mmol), phenol-CBI (2, compound 51a in first patent filing) (200 mg, 0.60 mmol) and activated molecular sieves 4 Å (1 g) in anhydrous CH$_2$Cl$_2$ (20 mL) was stirred at RT for 1 h. The mixture was cooled to −10° C., then BF$_3$.OEt$_2$ (40 μl, 0.3 mmol) was added dropwise. The temperature was kept between −10° C. and −5° C. for 1 h, it was then stirred at 0° C. for 30 min. BF$_3$—OEt$_2$ (0.24 mL, 1.8 mmol) was sub-

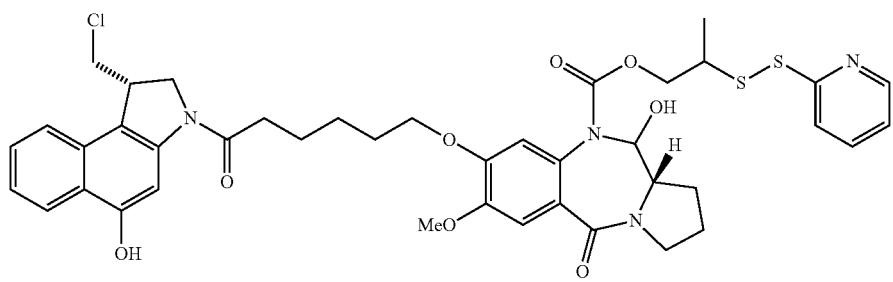

14

A mixture of 10 (45.0 mg, 0.0743 mmol), 67d (24.3 mg, 0.0899 mmol, freshly made by the procedure mentioned above), EDCI.HCl (42.7 mg, 0.223 mmol) and TsOH (3 mg, 0.0174 mmol) in dry DMA (3 mL) was stirred at r.t. under nitrogen for 5 h. Additional portions of 67d (24.3 mg, 0.0899 mmol) and EDCI.HCl (16.0 mg, 0.0835 mmol) were added to the mixture and the reaction stirred at r.t. overnight. After 22 h the reaction mixture was diluted with EtOAc and washed with H$_2$O (2×), brine (1×), dried (Na$_2$SO$_4$) and solvent removed under vacuum. The crude product was purified by column chromatography on silica gel using EtOAc to give a green powder. This was further purified carrying out column chromatography on silica gel using EtOAc a second time to give compound 14 (Compound No. 83, 8.3 mg, 13.5%, HPLC purity: 81.2%) as a beige solid. $^1$H NMR δ (400 MHz, DMSO-$d_6$) 10.33 (s, 1H), 8.43-8.42 (m, 1H), 8.07 (d, J=8.1 Hz, 1H), 7.98 (s, 1H), 7.77 (d, J=8.4 Hz, 1H), 7.74-7.67 (m, 1H), 7.50-7.46 (m, 2H), 7.33-7.29 (m, 1H), 7.24-7.18 (m, 1H), 7.10 (s, 1H), 6.98 and 6.92 (2s, 1H), 6.56 (t, J=6.0 Hz, 1H), 5.47-5.44 (m, 1H), 4.33-4.21 (m, 2H), 4.15-4.13 (m, 2H), 4.05-3.93 (m, 3H), 3.90-3.75 (m, 2H), 3.80 and 3.79 (2s, 3H), 3.52-3.47 (m, 1H), 3.38-3.13 (m, 4H), 2.10-1.99 (m, 1H), 1.94-1.89 (m, 3H), 1.77-1.74 (m, 2H), 1.66-1.62 (m, 2H), 1.52-1.41 (m, 2H), 1.32-1.24 (m, 1H), 1.15-1.10 (m, 3H). HRMS m/z 843.2258 [(M+Na)$^+$ calcd for $C_{41}H_{45}ClN_4NaO_8S_2$ 843.2260].

sequently added dropwise at 0° C., the temperature allowed to raise to RT and it was stirred for 2 h. The suspension was then filtered over celite and the solvent evaporated to give crude CBI-Glucuronide (3) which was used in the next step without further purification. A solution of amine (3) and bis-acid (4, compound 66h in first patent filing) (126 mg, 0.24 mmol) in anhydrous DMA (4 mL) was cooled to 0° C. pTsOH (17 mg, 0.096 mmol) and EDCI-HCl (276 mg, 1.44 mmol) were then added, the temperature was allowed to raise to RT and it was stirred for 16 h. The solvent was removed under reduced pressure and the residue purified by column chromatography (SiO$_2$, CH$_2$Cl$_2$/MeOH 0-2%) then (SiO$_2$, CH$_2$Cl$_2$/MeOH 1-2%) to give (1S)-1-(chloromethyl)-3-((2E)-3-{4-((1E)-3-{(1S)-1-(chloromethyl)-5-[(2,3,4-tri-O-acetyl-6-methyl-β-D-glucopyranuronosyl)oxy]-1,2-dihydro-3H-benzo[e]indol-3-yl}-3-oxo-1-propenyl)-2-[(3-{[[(9H-fluoren-9-ylmethoxy)carbonyl]amino}propanoyl)amino]phenyl}-2-propenoyl)-1,2-dihydro-3H-benzo[e]indol-5-yl methyl 2,3,4-tri-O-acetyl-β-D-glucopyranosiduronate (5) (127 mg, 27%) as a yellow solid. $^1$H NMR (300 MHz, [(CD$_3$)$_2$SO]) δ 10.04 (s, 1H, NH), 8.38 (br s, 2H), 8.11 (d, J=8.1 Hz, 1H), 7.97 (d, J=8.5 Hz, 2H), 7.93 (d, J=8.2 Hz, 2H), 7.83-7.88 (m, 4H), 7.78 (d, J=7.6 Hz, 1H), 7.68-7.72 (m, 3H), 7.59 (t, J=7.5 Hz, 2H), 7.45-7.48 (m, 3H), 7.38 (t, J=7.4 Hz, 2H), 7.25-7.29 (m, 4H), 5.85 (d, J=7.7 Hz, 1H), 5.83 (d, J=7.8 Hz, 1H), 5.62-5.65 (m, 2H), 5.32 (t, J=8.7 Hz, 2H), 5.14 (t, J=9.6 Hz, 2H), 4.78 (t, J=8.2 Hz, 2H), 4.55 (m, 4H), 4.31-4.38 (m, 4H), 4.22 (t, J=6.9 Hz, 1H), 4.01-4.03 (m, 2H), 3.91-3.96 (m, 2H), 3.65 (s, 3H), 3.63 (s, 3H), 3.36-3.38 (m, 2H), 2.59-2.64 (m, 2H), 1.98-2.03 (m, 18H); LC-MS (ESI) Calcd for $C_{82}H_{79}Cl_2N_4O_{25}$ (M+H)$^+$ m/z 1591.4. found m/z 1591.4; Calcd for $C_{82}H_{78}Cl_2N_4O_{25}Na$ (M+Na)$^+$ m/z 1613.4. found m/z 1613.4.

A solution of derivative (5) (110 mg, 0.07 mmol) and piperidine (468 μL, 0.7 mmol) in anhydrous DMF (5 mL) was stirred at RT for 30 min. The solvent was removed under reduced pressure at RT and the residue was triturated with cold Et$_2$O, to give crude (1S)-3-{(2E)-3-[2-[(3-aminopropanoyl)amino]-4-((1E)-3-{(1S)-1-(chloromethyl)-5-[(2,3,4-tri-O-acetyl-6-methyl-3-D-glucopyranuronosyl)oxy]-1,2-dihydro-3H-benzo[e]indol-3-yl}-3-oxo-1-propenyl) phenyl]-2-propenoyl}-1-(chloromethyl)-1,2-dihydro-3H-benzo[e]indol-5-yl methyl 2,3,4-tri-O-acetyl-β-D-glucopyranosiduronate (6) (86 mg, 90%) which was used in the next step without further purification. $^1$H NMR (300 MHz, [(CD$_3$)$_2$SO] δ 8.38 (br s, 2H), 8.10 (d, J=8.4 Hz, 1H), 7.98 (d, J=8.4 Hz, 2H), 7.94 (d, J=8.4 Hz, 2H), 7.90 (s, 1H), 7.88 (d, J=15.1 Hz, 1H), 7.76 (d, J=7.6 Hz, 1H), 7.70 (d, J=15.1 Hz, 1H), 7.59 (t, J=7.9 Hz, 2H), 7.47 (t, J=7.9 Hz, 2H), 7.27 (dd, J=3.4, 15.3 Hz, 2H), 5.85 (d, J=7.8 Hz, 1H), 5.84 (d, J=7.8 Hz, 1H), 5.63-5.68 (m, 2H), 5.32 (dd, J=7.8, 9.6 Hz, 2H), 5.14 (dt, J=1.5, 9.6 Hz, 2H), 4.79 (d, J=9.6 Hz, 2H), 4.56-4.60 (m, 4H), 4.29-4.41 (m, 2H), 4.02-4.04 (m, 2H), 3.92-3.97 (m, 2H), 3.67 (s, 6H), 2.93 (t, J=6.4 Hz, 2H), 2.03-2.04 (m, 18H), 2H under DMSO peak, NH and NH$_2$ not observed.

To a stirred solution of amine (6) (110 mg, 0.08 mmol) in a (1:1) mixture of MeOH/CH$_2$Cl$_2$ (10 mL) was added dropwise a solution of NaOMe (8.7 mg, 0.16 mmol) in MeOH (1 mL) at 0° C., and the reaction mixture was stirred at 0° C. for 2 h. AcOH (8 drops) was then added and the solvent was removed under reduced pressure at RT and dried under high vacuum to give (1S)-3-{(2E)-3-[2-[(3-aminopropanoyl)amino]-4-((1E)-3-{(1S)-1-(chloromethyl)-5-[(6-methyl-3-D-glucopyranuronosyl)oxy]-1,2-dihydro-3H-benzo[e]indol-3-yl}-3-oxo-1-propenyl)phenyl]-2-propenoyl}-1-(chloromethyl)-1,2-dihydro-3H-benzo[e]indol-5-yl methyl β-D-glucopyranosiduronate (7) a an orange solid which was used in the next step without further purification. To a stirred solution of amine (7) and N-succinimidyl 6-maleimidohexanoate (24 mg, 0.077 mmol) in anhydrous DMF (5 mL) was added DIEA (78 μL, 0.1 mmol) and the mixture was stirred at RT overnight. The solvent was then removed under reduced pressure at RT and the residue was purified by column chromatography (SiO$_2$, EtOAc/MeOH 10-20%) then twice (SiO$_2$, EtOAc/MeOH 15%) to give (1S)-1-(chloromethyl)-3-((2E)-3-{4-((1E)-3-{(1S)-1-(chloromethyl)-5-[(6-methyl-3-D-glucopyranuronosyl) oxy]-1,2-dihydro-3H-benzo[e]indol-3-yl}-3-oxo-1-propenyl)-2-[(3-{[6-(2,5-dioxo-2,5-dihydro-1H-pyrrol-1-yl) hexanoyl]amino}propanoyl)amino]phenyl}-2-propenoyl)-1,2-dihydro-3H-benzo[e]indol-5-yl methyl 3-D-glucopyranosiduronate 8 (Compound No. 84) (31 mg, 34%) as a yellow solid. HPLC purity 95.9%; $^1$H NMR (300 MHz, [(CD$_3$)$_2$SO] δ 10.01 (s, 1H), 8.32 (s, 2H), 8.31 (d, J=8.6 Hz, 2H), 8.09 (d, J=8.2 Hz, 1H), 7.89-7.95 (m, 3H), 7.84 (t, J=7.6 Hz, 2H), 7.77 (d, J=8.0 Hz, 1H), 7.70 (d, J=15.1 Hz, 1H), 7.58 (t, J=7.9 Hz, 2H), 7.43 (t, J=8.0 Hz, 2H), 7.27 (d, J=15.6 Hz, 2H), 6.96 (s, 2H), 5.67 (d, J=5.3 Hz, 1H), 5.66 (d, J=5.3 Hz, 1H), 5.45 (d, J=5.6 Hz, 2H), 5.35 (d, J=4.6 Hz, 2H), 5.16 (d, J=7.5 Hz, 2H), 4.52-4.62 (m, 4H), 4.33 (br s, 2H), 3.99-4.04 (m, 4H), 3.93 (m, J=7.4, 10.5 Hz, 2H), 3.68 (s, 3H), 3.67 (s, 3H), 3.37-3.48 (m, 8H), 2.57-2.61 (m, 2H), 2.09 (t, J=7.3 Hz, 2H), 1.41-1.54 (m, 4H), 1.14-1.23 (m, 4H); HRMS (ESI) Calcd for $C_{65}H_{67}Cl_2N_5NaO_{20}$ (M+Na$^+$) m/z 1330.3649. found m/z 1330.3600.

Figure 45:
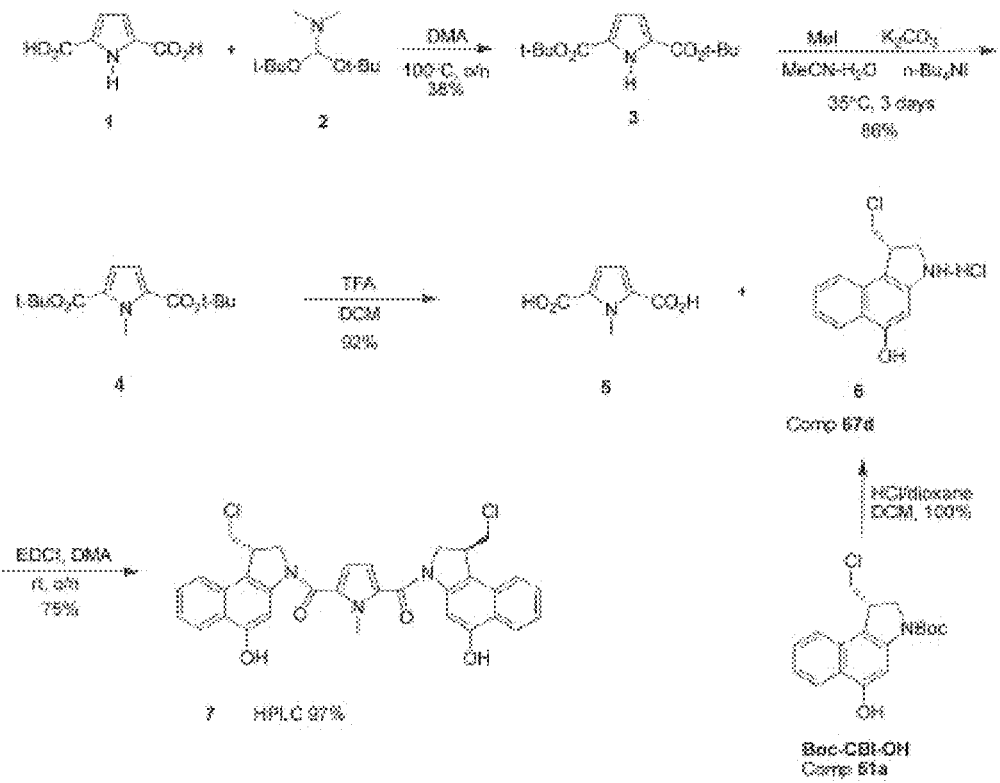
FIG. 45 shows the synthesis of (S)-(1-methyl-1H-pyrrole-2,5-diyl)bis(((S)-1-(chloromethyl)-5-hydroxy-1H-benzo[e] indol-3(2H)-yl)methanone) (Compound No. 15, table 1, FIG. 45).

Example 30 (S)-(1-methyl-1H-pyrrole-2,5-diyl)bis (((S)-1-(chloromethyl)-5-hydroxy-1H-benzo[e]indol-3(2H)-yl)methanone) (Compound No. 15, table 1, FIG. 45)

A mixture of 1 (500 mg, 3.22 mmol) and N,N-Dimethylformamide di-tert-butyl acetal (2, 5.24 g, 25.77 mmol) in NMP (10 mL) was heated up to 100° C. and stirred overnight. Most volatile components were removed under reduced pressure and the resultant residue was redistributed between ethyl acetate and water. The aqueous phase was extracted with ethyl acetate three times. The combined organic extracts were washed with water followed by brine, dried over anhydrous Na$_2$SO$_4$, and filtered through a pad of silica gel. The solvent was removed and 3 was obtained as a pale crystalline solid (331 mg, 38%); $^1$H NMR (DMSO) δ 12.26 (s, 1H), 6.68 (d, J=2.0 Hz, 2H), 1.51 (s, 18H) ppm. HRMS (ESI) found m/z 290.1362 (M+Na). $C_{14}H_{21}NNaO_4$ requires 290.1363.

A mixture of 3 (50 mg, 0.18 mmol), K$_2$CO$_3$ (52 mg, 0.37 mmol), MeI (0.12 mL, 1.87 mmol) and tetrabutylamonium iodide (3.5 mg, 0.0094 mmol) in MeCN (1 mL) and water (0.01 mL) was heated at 35-40° C. and stirred for 3 days. The reaction mixture was redistributed between ethyl acetate and water. The aqueous phase was extracted with ethyl acetate three times. The combined organic extracts were washed with water followed by brine, dried over anhydrous Na$_2$SO$_4$, and filtered through a pad of silica gel. The solvent was removed and 4 was obtained as a pale oil, which became a colourless crystalline solid in hours (45 mg, 86%); $^1$H NMR (CDCl$_3$) δ 6.77 (s, 2H), 4.21 (s, 3H), 1.56 (s, 18H) ppm. HRMS (ESI) found m/z 304.1512 (M+Na). $C_{15}H_{23}NNaO_4$ requires 304.1519.

To a solution of 4 (45 mg, 0.16 mmol) in DCM (1 mL) at room temperature was added TFA (0.5 mL, 6.49 mmol). The mixture was stirred for 3 h to give a pink solution. All volatile components were pumped off and the resultant residue was triturated with petroleum ether to give 5 as a pink solid (25 mg, 93%). $^1$H NMR (DMSO) δ 12.81 (s, 2H), 6.80 (s, 2H), 4.15 (s, 3H) ppm. HRMS (ESI negative) found m/z 168.0306 (M–H). $C_7H_6NO_4$ requires 168.0302.

To a solution of Boc-CBI-OH (Comp 51a, 130 mg, 0.39 mmol) in DCM (2 mL) at room temperature was added 4N HCl in dioxane (2 mL). The mixture was stirred for 2.5 h. All volatile components were pumped off and the resultant residue (6) was used directly as it was.

A mixture of 6 (made above), 5 (22 mg, 0.13 mmol), EDCI hydrochloride (150 mg, 0.78 mmol) and toluenesulfonic acid (2.2 mg, 0.013 mmol) in DMA (2 mL) was stirred at room temperature overnight. Most of the solvent was pumped off and the resultant residue was redistributed between ethyl acetate and water. The aqueous phase was extracted with ethyl acetate three times. The combined organic extracts were washed with water followed by brine, dried over anhydrous Na$_2$SO$_4$, and filtered through a pad of Celite. The solvent was removed and the resultant residue was purified by silica gel column chromatography using a mixture of MeOH and DCM (v/v 2%) as eluent to give 7 (Compound No. 15, Table 1) as an off-white solid (60 mg, 77%). $^1$H NMR (DMSO) δ 10.43 (s, 2H), 8.12 (d, J=8.3 Hz, 2H), 7.83 (d, J=8.3 Hz, 2H), 7.73 (br s, 2H), 7.52 (dd, J=1.0, 8.0 Hz, 2H), 7.37 (dd, J=0.4, 8.0 Hz, 2H), 6.77 (s, 2H), 4.62-4.57 (m, 2H), 4.31-4.27 (m, 2H), 4.10-4.07 (m, 2H), 4.02-4.00 (m, 2H), 3.88-3.85 (m, 5H) ppm. HRMS (ESI) found m/z 622.1255 (M+Na). $C_{33}H_{27}Cl_2N_3NaO_4$ requires 622.1271.

Figure 46:
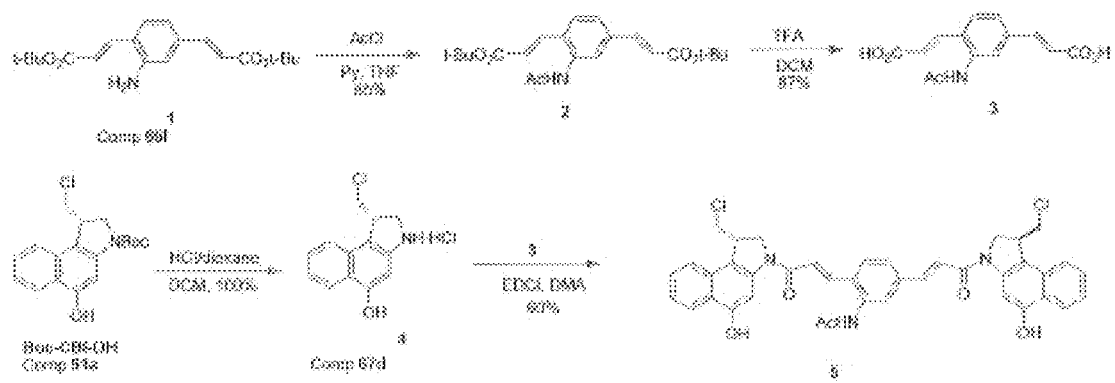
FIG. 46 shows the synthesis of N-(2,5-bis((E)-3-((S)-1-(chloromethyl)-5-hydroxy-1H-benzo[e]indol-3(2H)-yl)-3-oxoprop-1-enyl)phenyl)acetamide (Compound No. 16, Table 1, FIG. 46).

Example 31 N-(2,5-bis((E)-3-((S)-1-(chloromethyl)-5-hydroxy-1H-benzo[e]indol-3(2H)-yl)-3-oxoprop-1-enyl)phenyl)acetamide (Compound No. 16, Table 1, FIG. 46)

To a solution of 1 (66f, 500 mg, 1.45 mmol) in THF (5 mL) and pyridine (5 mL) in an ice bath was added acetyl chloride (0.50 mL, 7.03 mmol). The mixture was allowed to warm up to room temperature and stirred overnight. All volatile components were pumped off and the resultant residue was redistributed between ethyl acetate and aqueous sodium bicarbonate. The aqueous phase was extracted with ethyl acetate three times. The combined organic extracts were washed with water followed by brine, dried over anhydrous $Na_2SO_4$, and filtered through a pad of Celite. The solvent was removed and the resultant residue was purified by silica gel column chromatography using a mixture of ethyl acetate and petroleum ether (v/v 1:2) as eluent to give 2 as an off-white solid (475 mg, 85%); $^1$H NMR (CDCl$_3$) δ 8.00 (s, 1H), 7.70 (d, J=15.8 Hz, 1H), 7.55-7.51 (m, 2H), 7.31 (apparent d, J=8.6 Hz, 2H), 6.40 (d, J=16.0 Hz, 1H), 6.37 (d, J=15.8 Hz, 1H), 2.25 (s, 3H), 1.54 (s, 9H), 1.53 (s, 9H) ppm. HRMS (ESI) found m/z 410.1921 (M+Na). $C_{22}H_{29}NNaO_5$ requires 410.1938.

To a solution of 2 (470 mg, 1.21 mmol) in DCM (5 mL) at room temperature was added TFA (2.5 mL, 32.40 mmol). The mixture was stirred for 3 h to give a white suspension. More DCM was added to precipitate out more solid, which was collected by filtration and washed with ethyl acetate and petroleum ether. 3 was obtained as a white solid (290 mg, 87%). $^1$H NMR (DMSO) δ 12.40 (br s, 2H), 9.89 (s, 1H), 7.85 (d, J=8.3 Hz, 1H), 7.70 (apparent d, J=16.0 Hz, 2H), 7.57-7.53 (m, 2H), 6.54 (d, J=15.9 Hz, 1H), 6.53 (d, J=16.0 Hz, 1H), 2.09 (s, 3H) ppm. HRMS (ESI) found m/z 298.0672 (M+Na). $C_{14}H_{13}NNaO_5$ requires 298.0686.

To a solution of Boc-CBI-OH (Comp 51a, 291 mg, 0.87 mmol) in DCM (3 mL) at room temperature was added 4N HCl in dioxane (3 mL). The mixture was stirred for 2.5 h. All volatile components were pumped off and the resultant residue (4) was used directly as it was.

A mixture of 4 (made above), 3 (80 mg, 0.29 mmol), EDCI hydrochloride (334 mg, 1.74 mmol) and toluenesulfonic acid (5 mg, 0.029 mmol) in DMA (3 mL) was stirred at room temperature overnight. All the volatile components were pumped off and the resultant residue was triturated with methanol several times to give crude product (123 mg), which was dissolved in THF and precipitated by the addition of MeOH to give 5 (Compound No. 16, Table 1) as a yellow solid (96 mg, 47%, HPLC purity 97%); $^1$H NMR (DMSO) δ 10.43 (s, 2H), 9.97 (s, 1H), 8.12-8.07 (m, 5H), 7.85-7.81 (m, 4H), 7.74 (apparent d, J=6.7 Hz, 1H), 7.68 (d, J=15.4 Hz, 1H), 7.73 (t, J=7.4 Hz, 2H), 7.35 (t, J=7.5 Hz, 2H), 7.26 (dd, J=3.2, 15.3 Hz, 2H), 4.58-4.46 (m, 4H), 4.28-4.22 (m, 2H), 4.05-3.98 (m, 2H), 3.88-3.82 (m, 2H), 2.15 (s, 3H) ppm. HRMS (ESI) found m/z 728.1662 (M+Na). $C_{40}H_{33}Cl_2N_3NaO_5$ requires 728.1689.

Figure 47:
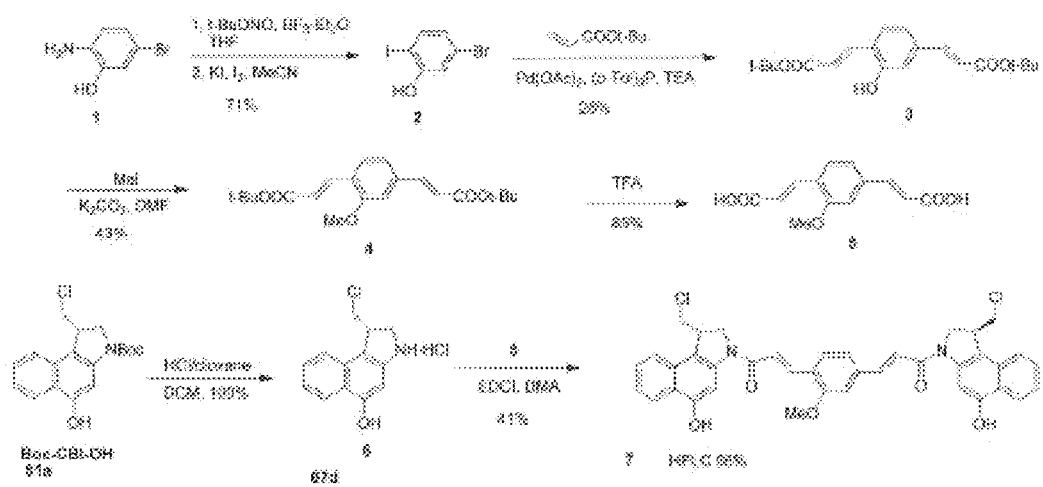
FIG. 47 shows the synthesis of (S,2E,2'E)-3,3'-(2-methoxy-1,4-phenylene)bis(1-((S)-1-(chloromethyl)-5-hydroxy-1H-benzo[e]indol-3(2H)-yl)prop-2-en-1-one) (Compound No. 17, Table 1, FIG. 47).

Example 32 (S,2E,2'E)-3,3'-(2-methoxy-1,4-phenylene)bis(1-((S)-1-(chloromethyl)-5-hydroxy-1H-benzo[e]indol-3(2H)-yl)prop-2-en-1-one) (Compound No. 17, Table 1, FIG. 47)

To a solution of 1 (2.50 g, 13.30 mmol) in dry THF (12 mL) at −30 to −40° C. in a dry ice-MeCN bath was added boron trifluoride diethyl etherate (BF$_3$.Et$_2$O, 4.92 mL, 39.90 mmol) dropwise under N$_2$. After the mixture was stirred at −30° C. for 10 min, $^t$BuONO (2.39 mL, 19.94 mmol) was added dropwise. The reaction mixture was allowed to warm up to room temperature and stirred for 1.5 h to give a suspension. Petroleum ether (50 mL) was added to give more precipitate. The supernatant was removed by decantation and the solid left was washed with petroleum ether to afford a white solid. This solid was dissolved in dry MeCN (20 mL) and cooled in an ice bath. KI (11.00 g, 66.26 mmol) and I$_2$ (6.00 g, 23.64 mmol) were added. The reaction mixture was stirred at room temperature for 4 h before saturated Na$_2$S$_2$O$_3$ solution (50 mL) was added to quench the reaction. The mixture was extracted with ethyl acetate three times. The combined organic extracts were washed with water followed by brine, dried over anhydrous Na$_2$SO$_4$, and filtered through a pad of Celite. The solvent was removed and the resultant residue was purified by silica gel column chromatography using a mixture of ethyl acetate and petroleum ether (v/v 1:9) as eluent to give 2 as a pale solid (2.83 g, 71%); $^1$H NMR (CDCl$_3$) δ 7.50 (d, J=8.5 Hz, 1H), 7.16 (d, J=2.2 Hz, 1H), 6.84 (dd, J=2.2, 8.5 Hz, 1H), 5.39 (s, 1H) ppm.

A mixture of 2 (500 mg, 1.67 mmol), tert-butyl acrylate (0.728 mL, 5.02 mmol), palladium (II) acetate (7.5 mg, 0.033 mmol) and tri-ortho-tolyl phosphine (41 mg, 0.13 mmol) in redistilled triethylamine (5 mL) was heated at reflux overnight under N$_2$ to give a dark grey suspension. All volatile components were pumped off. The resultant residue was dissolved in ethyl acetate and the precipitate was filtered off. The filtrate was evaporated and the residue obtained was purified by column chromatography using a mixture of ethyl acetate and petroleum ether (v/v 1:6) as eluent to give 3 (160 mg, 28%) as an off-white solid. $^1$H NMR (DMSO) δ 10.43 (s, 1H), 7.75 (d, J=16.4 Hz, 1H), 7.63 (d, J=8.4 Hz, 1H), 7.45 (d, J=16.0 Hz, 1H), 7.18 (d, J=8.0 Hz, 1H), 7.07 (d, J=0.8 Hz, 1H), 6.56 (d, J=16.4 Hz, 1H), 6.41 (d, J=15.6 Hz, 1H), 1.483 (s, 9H), 1.478 (s, 9H) ppm. HRMS (ESI) found m/z 369.1687 (M+Na). $C_{20}H_{26}NaO_5$ requires 369.1672.

To a solution of 3 (160 mg, 0.46 mmol) in DMF (2 mL) was added K$_2$CO$_3$ (254 mg, 1.84 mmol) and MeI (0.28 mL, 4.50 mmol). The mixture was stirred at room temperature overnight and the precipitate was filtered off. The resultant filtrate was washed with water followed by brine, dried over anhydrous Na$_2$SO$_4$, and filtered through a pad of Celite. The solvent was removed and the resultant residue was purified by silica gel column chromatography using a mixture of ethyl acetate and petroleum ether (v/v 1:10) as eluent to give 4 as a colourless oil (72 mg, 43%); $^1$H NMR (CDCl$_3$) δ 7.87 (d, J=16.2 Hz, 1H), 7.54 (d, J=15.9 Hz, 1H), 7.49 (d, J=8.0 Hz, 1H), 7.10 (dd, J=1.3, 8.0 Hz, 1H), 7.00 (d, J=1.2 Hz, 1H), 6.47 (d, J=16.1 Hz, 1H), 6.38 (d, J=15.9 Hz, 1H), 3.91 (s, 3H), 1.539 (s, 9H), 1.533 (s, 9H) ppm. HRMS (ESI) found m/z 383.1838 (M+Na). $C_{21}H_{28}NaO_5$ requires 383.1829.

To a solution of 4 (70 mg, 0.19 mmol) in DCM (2 mL) at room temperature was added TFA (1 mL, 12.98 mmol). The mixture was stirred for 2.5 h to give a white suspension. All volatile components were pumped off and the resultant residue was triturated with DCM and ethyl acetate to give 5 as a white solid (41 mg, 85%). $^1$H NMR (DMSO) δ 12.41 (br s, 2H), 7.80 (d, J=16.2 Hz, 1H), 7.72 (d, J=8.0 Hz, 1H), 7.58 (d, J=16.0 Hz, 1H), 7.41 (d, J=1.2 Hz, 1H), 7.30 (dd, J=1.0, 8.1 Hz, 1H), 6.47 (d, J=16.0 Hz, 1H), 6.38 (d, J=16.1 Hz, 1H), 3.92 (s, 3H) ppm. HRMS (ESI) found m/z 271.0573 (M+Na). $C_{13}H_{12}NaO_5$ requires 271.0577.

To a solution of Boc-CBI-OH (Comp 51a, 161 mg, 0.48 mmol) in DCM (2 mL) at room temperature was added 4N HCl in dioxane (2 mL). The mixture was stirred for 2.5 h. All volatile components were pumped off and the resultant residue (6) was used directly as it was.

A mixture of 6 (made above), 5 (40 mg, 0.16 mmol), EDCI hydrochloride (185 mg, 0.97 mmol) and toluenesulfonic acid (2.8 mg, 0.016 mmol) in DMA (1 mL) was stirred at room temperature overnight. All the volatile components were pumped off and the resultant residue was triturated with methanol to give a yellow solid, which was dissolved in THF and precipitated by the addition of methanol to afford 7 (Compound No. 17, Table 1) as a yellow solid (45 mg, 41%, HPLC purity 98%); $^1$H NMR (DMSO) δ 10.43 (s, 2H), 8.12-8.10 (m, 4H), 8.00-7.95 (m, 2H), 7.85-7.80 (m, 2H), 7.72 (d, J=15.4 Hz, 1H), 7.54-7.50 (m, 4H), 7.37-7.26 (m, 4H), 4.57-4.45 (m, 4H), 4.28-4.22 (m, 2H), 4.00-3.99 (m, 5H), 3.90-3.83 (m, 2H) ppm. HRMS (ESI) found m/z 701.1596 (M+Na). $C_{39}H_{32}Cl_2N_2NaO_5$ requires 701.1580.

Figure 48:
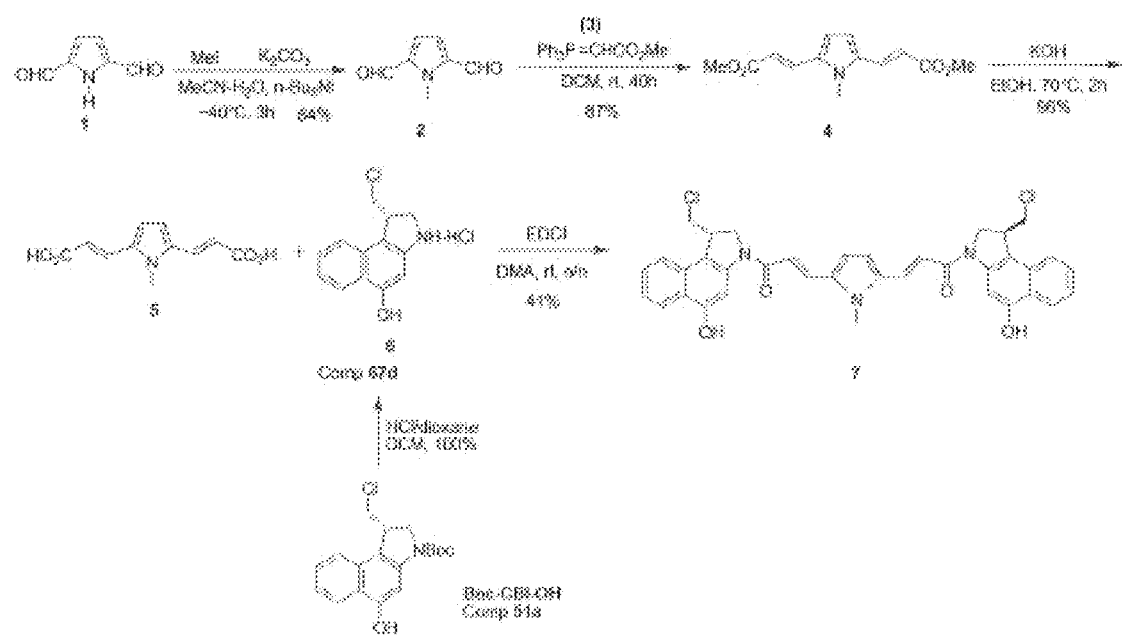
FIG. 48 shows the synthesis of (S,2E,2'E)-3,3'-(1-methyl-1H-pyrrole-2,5-diyl)bis(1-((S)-1-(chloromethyl)-5-hydroxy-1H-benzo[e]indol-3(2H)-yl)prop-2-en-1-one) (Compound No. 18 Table 1, FIG. 48).

Example 33 (S,2E,2'E)-3,3'-(1-methyl-1H-pyrrole-2,5-diyl)bis(1-((S)-1-(chloromethyl)-5-hydroxy-1H-benzo[e]indol-3(2H)-yl)prop-2-en-1-one) (Compound No. 18 Table 1, FIG. 48)

1 was prepared using a literature method (Ref. *Russ J Org Chem,* 2007, 43, 855-860.)

2

A mixture of 1 (50 mg, 0.41 mmol), $K_2CO_3$ (112 mg, 0.81 mmol), MeI (0.25 mL, 4.06 mmol) and tetrabutylamonium iodide (7.5 mg, 0.020 mmol) in MeCN (2 mL) and water (0.02 mL) was heated at 40° C. and stirred for 3 h. Most volatile components were removed under reduced pressure and the resultant residue was redistributed between ethyl acetate and water. The aqueous phase was extracted with ethyl acetate three times. The combined organic extracts were washed with water followed by brine, dried over anhydrous $Na_2SO_4$, and filtered through a pad of silica gel. The solvent was removed and 2 was obtained as a white solid (47 mg, 84%); with $^1$H NMR spectrum identical to that reported (Ref. C. E. Loader, G. H. Barnett and H. J. Anderson, *Can. J. Chem.*, 1982, 60, 383.)

4

A mixture of 2 (40 mg, 0.29 mmol) and methyl (triphenylphosphoranylidene)acetate (3, 400 mg, 1.20 mmol) in DCM (3 mL) was stirred for two days to give a yellow solution. The mixture was purified by silica gel column chromatography using gradient mixtures of ethyl acetate and petroleum ether (v/v=1:5, 1:4 and 1:3) as eluent to give 4 as a yellow solid (63 mg, 87%); $^1$H NMR (CDCl$_3$) δ 7.61 (d, J=15.6 Hz, 2H), 6.70 (s, 2H), 6.26 (d, J=15.6 Hz, 2H), 3.79 (s, 6H), 3.73 (s, 3H) ppm. HRMS (ESI) found m/z 272.0898 (M+Na). $C_{13}H_{15}NNaO_4$ requires 272.0893.

5

A mixture of 4 (60 mg, 0.24 mmol) and KOH (100 mg, 1.78 mmol) in EtOH (2 mL) and THF (1 mL) was stirred at 70° C. for 2h. The mixture was evaporated under reduced pressure to dryness. The resultant residue was dissolved in water and acidified with 1N HCl till pH 5 to give a yellow precipitate, which was collected by filtration, and then washed with water and petroleum ether to give 5 as a yellow solid (51 mg, 96%); $^1$H NMR (DMSO) δ 12.20 (s, 2H), 7.54 (d, J=15.6 Hz, 2H), 6.89 (s, 2H), 6.30 (d, J=15.6 Hz, 2H), 3.70 (s, 3H) ppm. HRMS (ESI) found m/z 244.0590 (M+Na). $C_{11}H_{11}NNaO_4$ requires 244.0580.

7

To a solution of Boc-CBI-OH (Comp 51a, 200 mg, 0.60 mmol) in DCM (2 mL) at room temperature was added 4N HCl in dioxane (10 mL). The mixture was stirred for 2 h. All volatile components were pumped off and the resultant residue (6, comp 67d) was used directly as it was.

A mixture of 6 (made above), 5 (49 mg, 0.22 mmol), EDCI hydrochloride (255 mg, 1.33 mmol) and toluenesulfonic acid (3.8 mg, 0.022 mmol) in DMA (2 mL) was stirred at room temperature overnight. The solvent was removed and the resultant residue was purified by silica gel column chromatography using a mixture of MeOH and ethyl acetate (v/v 3%) and the crude product was triturated with ethyl acetate to give 7 as an orange solid (60 mg, 41%, HPLC 100%); $^1$H NMR (DMSO) δ 10.41 (s, 2H), 8.11 (d, J=8.2 Hz, 4H), 7.81 (d, J=8.3 Hz, 2H), 7.70 (d, J=14.9 Hz, 2H), 7.50 (t, J=7.4 Hz, 2H), 7.33 (t, J=7.5 Hz, 2H), 7.12 (s, 2H), 7.01 (d, J=14.9 Hz, 2H), 4.49-4.42 (m, 4H), 4.24-4.19 (m, 2H), 4.01-3.97 (m, 2H), 3.85-3.82 (m, 5H) ppm. HRMS (ESI negative) found m/z 650.1600 (M−H). $C_{37}H_{30}Cl_2N_3O_4$ requires 650.1619.

Figure 49:
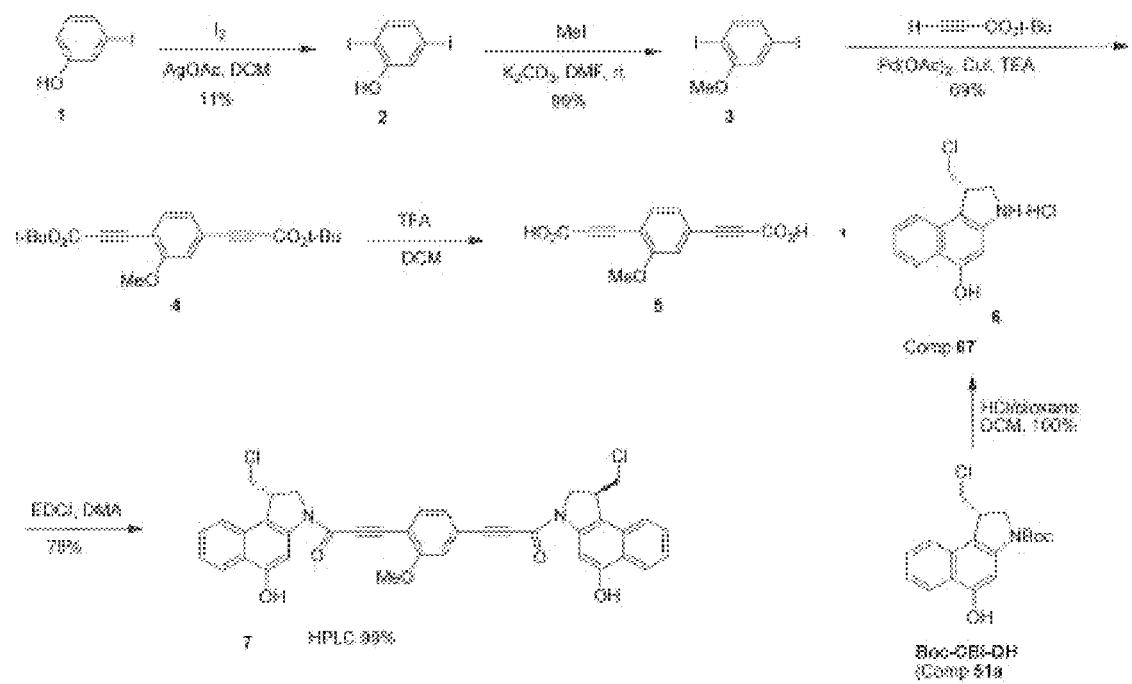
FIG. 49 shows the synthesis of (S)-3,3'-(2-methoxy-1,4-phenylene)bis(1-((S)-1-(chloromethyl)-5-hydroxy-1H-benzo[e]indol-3(2H)-yl)prop-2-yn-1-one) (Compound 19, table 1, FIG. 49).

Example 34 (S)-3,3'-(2-methoxy-1,4-phenylene)bis(1-((S)-1-(chloromethyl)-5-hydroxy-1H-benzo[e]indol-3(2H)-yl)prop-2-yn-1-one) (Compound 19, table 1, FIG. 49)

2

Compound 2 was synthesised by a modified procedure based on that described in US2007/49758. To a suspension of 1 (5.50 g, 25.00 mmol) and silver (I) acetate (6.26 g, 37.5 mmol) in DCM (100 mL) was added dropwise a solution of iodine (6.98 g, 27.50 mmol) in DCM (150 mL). The resulting mixture was stirred overnight at room temperature, and then filtered through a pad of Celite. The filtrate was evaporated and the resultant residue was purified by silica gel column chromatography using a mixture of ethyl acetate and petroleum ether (v/v 1:10) as eluent to give 2 as a white solid (966 mg, 11%); mp 97-99° C. $^1$H NMR (CDCl$_3$) δ 7.342 (d, J=8.3 Hz, 1H), 7.339 (d, J=2.0 Hz, 1H), 7.00 (dd, J=2.0, 8.3 Hz, 1H), 5.32 (s, 1H) ppm. $^{13}$C NMR (CDCl$_3$, 100.6 MHz) δ 155.70, 139.46 (CH), 131.80 (CH), 124.44 (CH), 94.65, 85.52 ppm.

3

To a solution of 2 (270 mg, 0.78 mmol) in DMF (4 mL) was added $K_2CO_3$ (162 mg, 1.17 mmol) and MeI (0.24 mL, 3.90 mmol). The mixture was stirred at room temperature for 2 h. The mixture was filtered through a pad of silica gel and the filtrate was evaporated to give 3 as a colourless oil (277 mg, 99%); $^1$H NMR (CDCl$_3$) δ 7.45 (d, J=8.1 Hz, 1H), 7.09 (d, J=1.8 Hz, 1H), 7.04 (dd, J=1.8, 8.1 Hz, 1H), 3.87 (s, 3H) ppm.

4

A mixture of 3 (274 mg, 0.76 mmol), tert-butyl propiolate (0.314 mL, 2.28 mmol), copper (I) iodide (5.8 mg, 0.030 mmol), palladium (II) acetate (3.4 mg, 0.015 mmol) and triphenyl phosphine (12 mg, 0.046 mmol) in redistilled triethylamine (5 mL) was heated at 60° C. overnight under $N_2$ to give a dark-coloured suspension. All volatile components were pumped off. The resultant residue was stirred with DCM and the precipitate was filtered off. The filtrate was evaporated and the residue obtained was purified by silica gel column chromatography using a mixture of DCM and petroleum ether (v/v=1:1) as eluent to give 4 (195 mg, 72%) as an off-white solid. $^1$H NMR (CDCl$_3$) δ 7.48 (d, J=7.9 Hz, 1H), 7.13 (d, J=7.9 Hz, 1H), 7.06 (s, 1H), 3.89 (s, 3H), 1.545 (s, 9H) and 1.514 (s, 9H) ppm. HRMS (ESI) found m/z 379.1510 (M+Na). $C_{21}H_{24}NaO_5$ requires 379.1516.

5

To a solution of 4 (100 mg, 0.28 mmol) in DCM (2 mL) at room temperature was added TFA (1 mL, 12.98 mmol). The mixture was stirred for 2.5 h to give a white suspension. All volatile components were pumped off and the resultant residue was triturated with a mixture of DCM and petroleum ether (v/v=1:1) to give 5 as a white solid (66 mg, 96%). $^1$H NMR (DMSO) δ 13.92 (br s, 2H), 7.61 (d, J=7.9 Hz, 1H), 7.37 (apparent s, 1H), 7.25 (dd, J=1.1, 7.9 Hz, 1H), 3.90 (s, 3H) ppm.

7

To a solution of Boc-CBI-OH (Comp 51a, 267 mg, 0.80 mmol) in DCM (3 mL) at room temperature was added 4N HCl in dioxane (3 mL). The mixture was stirred for 2.5 h. All volatile components were pumped off and the resultant residue (6) was used directly as it was.

A mixture of 6 (made above), 5 (65 mg, 0.27 mmol), EDCI hydrochloride (306 mg, 1.60 mmol) and toluenesulfonic acid (4.6 mg, 0.027 mmol) in DMA (1 mL) was stirred at room temperature overnight. All the volatile components were pumped off and the resultant residue was triturated with methanol to give a yellow solid, which was dissolved in THF and precipitated by the addition of methanol to afford 7 as a yellow solid (140 mg, 78%, HPLC purity 99%); $^1$H NMR (DMSO) δ 10.52 (s, 2H), 8.12 (d, J=8.4 Hz, 2H), 7.90-7.85 (m, 4H), 7.76 (d, J=7.9 Hz, 1H), 7.56-7.50 (m, 3H), 7.41-7.37 (m, 3H), 4.63-4.49 (m, 4H), 4.29-4.21 (m, 2H), 4.09-4.06 (m, 2H), 4.01 (s, 3H), 3.99-3.94 (m, 1H), 3.91-3.86 (m, 1H) ppm. HRMS (ESI) found m/z 697.1267 (M+Na). $C_{39}H_{28}Cl_2N_2NaO_5$ requires 697.1267.

Example 19 Preparation of Cysteine Engineered Antibodies for Conjugation by Reduction and Reoxidation Under certain conditions, the cysteine engineered antibodies may be made reactive for conjugation with linker-drug intermediates of the invention, such as those in Table 4, by treatment with a reducing agent such as DTT (Cleland's reagent, dithiothreitol) or TCEP (tris(2-carboxyethyl) phosphine hydrochloride; Getz et al (1999) Anal. Biochem. Vol 273:73-80; Soltec Ventures, Beverly, Mass.). Full length, cysteine engineered monoclonal antibodies (ThioMabs) expressed in CHO cells (Gomez et al (2010) Biotechnology and Bioeng. 105(4):748-760; Gomez et al (2010) Biotechnol. Prog. 26:1438-1445) were reduced, for example with about a 50 fold excess of DTT overnight at room temperature to reduce disulfide bonds which may form between the newly introduced cysteine residues and the cysteine present in the culture media.

Light chain amino acids are numbered according to Kabat (Kabat et al., Sequences of proteins of immunological interest, (1991) 5th Ed., US Dept of Health and Human Service, National Institutes of Health, Bethesda, Md.). Heavy chain amino acids are numbered according to the EU numbering system (Edelman et al (1969) Proc. Natl. Acad. of Sci. 63(1):78-85), except where noted as the Kabat system. Single letter amino acid abbreviations are used.

Full length, cysteine engineered monoclonal antibodies (ThioMabs) expressed in CHO cells bear cysteine adducts (cystines) or glutathionylated on the engineered cysteines due to cell culture conditions. To liberate the reactive thiol groups of the engineered cysteines, the ThioMabs are dissolved in 500 mM sodium borate and 500 mM sodium chloride at about pH 8.0 and reduced with about a 50-100 fold excess of 1 mM TCEP (tris(2-carboxyethyl)phosphine hydrochloride (Getz et al (1999) Anal. Biochem. Vol 273: 73-80; Soltec Ventures, Beverly, Mass.) for about 1-2 hrs at 37° C. Alternatively, DTT can be used as reducing agent. The formation of inter-chain disulfide bonds was monitored either by non-reducing SDS-PAGE or by denaturing reverse phase HPLC PLRP column chromatography. The reduced ThioMab is diluted and loaded onto a HiTrap SP FF column in 10 mM sodium acetate, pH 5, and eluted with PBS containing 0.3M sodium chloride, or 50 mM Tris-Cl, pH 7.5 containing 150 mM sodium chloride.

Disulfide bonds were reestablished between cysteine residues present in the parent Mab by carrying out reoxidation. The eluted reduced ThioMab is treated with 15× or 2 mM dehydroascorbic acid (dhAA) at pH 7 for 3 hours or for 3 hrs in 50 mM Tris-Cl, pH 7.5, or with 2 mM aqueous copper sulfate ($CuSO_4$) at room temperature overnight. Other oxidants, i.e. oxidizing agents, and oxidizing conditions, which are known in the art may be used. Ambient air oxidation may also be effective. This mild, partial reoxidation step forms intrachain disulfides efficiently with high fidelity. The buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm.

Liquid chromatography/Mass Spectrometric Analysis was performed on a TSQ Quantum Triple Quadrupole™ mass spectrometer with extended mass range (Thermo Electron, San Jose Calif.). Samples were chromatographed on a PRLP-S®, 1000 A, microbore column (50 mm×2.1 mm, Polymer Laboratories, Shropshire, UK) heated to 75° C. A linear gradient from 30-40% B (solvent A: 0.05% TFA in water, solvent B: 0.04% TFA in acetonitrile) was used and the eluent was directly ionized using the electrospray source. Data were collected by the Xcalibur® data system and deconvolution was performed using ProMass® (Novatia, LLC, New Jersey). Prior to LC/MS analysis, antibodies or drug conjugates (50 micrograms) were treated with PNGase F (2 units/ml; PROzyme, San Leandro, Calif.) for 2 hours at 37° C. to remove N-linked carbohydrates.

Hydrophobic Interaction Chromatography (HIC) samples were injected onto a Butyl HIC NPR column (2.5 micron particle size, 4.6 mm×3.5 cm) (Tosoh Bioscience) and eluted with a linear gradient from 0 to 70% B at 0.8 ml/min (A: 1.5 M ammonium sulfate in 50 mM potassium phosphate, pH 7, B: 50 mM potassium phosphate pH 7, 20% isopropanol). An Agilent 1100 series HPLC system equipped with a multi wavelength detector and Chemstation software was used to resolve and quantitate antibody species with different ratios of drugs per antibody.

Example 20 Conjugation of Linker-Drug Intermediates to Antibodies

After the reduction and reoxidation procedures of Example 19, the antibody is dissolved in PBS (phosphate buffered saline) buffer and chilled on ice. An excess, from about 1.5 molar to 20 equivalents of a linker-drug intermediate, including but not limited to 51-68 in Table 4, with a thiol-reactive functional group such as maleimido or bromoacetamide, is dissolved in DMSO, diluted in acetonitrile and water, and added to the chilled reduced, reoxidized antibody in PBS. After about one hour, an excess of maleimide is added to quench the reaction and cap any unreacted antibody thiol groups. The conjugation mixture may be loaded and eluted through a HiTrap SP FF column to remove excess drug-linker intermediate and other impurities. The reaction mixture is concentrated by centrifugal ultrafiltration and the cysteine engineered antibody drug conjugate is purified and desalted by elution through G25 resin in PBS, filtered through 0.2 µm filters under sterile conditions, and frozen for storage.

By the procedure above, cysteine engineered, antibody drug conjugates 101-133 of Table 3 were prepared.

Example 21 In Vitro Cell Proliferation Assay

Efficacy of ADC was measured by a cell proliferation assay employing the following protocol (CELLTITER GLO™ Luminescent Cell Viability Assay, Promega Corp. Technical Bulletin TB288; Mendoza et al (2002) Cancer Res. 62:5485-5488):
1. An aliquot of 100 μl of cell culture containing about $10^4$ cells (SKBR-3, BT474, MCF7 or MDA-MB-468) in medium was deposited in each well of a 96-well, opaque-walled plate.
2. Control wells were prepared containing medium and without cells.
3. ADC was added to the experimental wells and incubated for 3-5 days.
4. The plates were equilibrated to room temperature for approximately 30 minutes.
5. A volume of CELLTITER GLO™ Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.

Data are plotted as the mean of luminescence for each set of replicates, with standard deviation error bars. The protocol is a modification of the CELLTITER GLO™ Luminescent Cell
Media: SK-BR-3 grow in 50/50/10% FBS/glutamine/250 g/mL G-418 OVCAR-3 grow in RPMI/20% FBS/glutamine Example 22 Tumor Growth Inhibition, In Vivo Efficacy in High Expressing HER2 Transgenic Explant Mice and Other Tumor Models Tumors were established and allowed to grow to 150-200 $mm^3$ in volume (as measured using calipers) before a single treatment on day 0. Tumor volume was measured using calipers according to the formula: $V (mm^3)=0.5A \times B^2$, where A and B are the long and short diameters, respectively. Mice were euthanized before tumor volume reached 3000 $mm^3$ or when tumors showed signs of impending ulceration. Data collected from each experimental group (10 mice per group) were expressed as mean±SE.

The Fo5 mouse mammary tumor model was employed to evaluate the in vivo efficacy of antibody-drug conjugates of the invention after single dose intravenous injections, and as described previously (Phillips G D L, Li G M, Dugger D L, et al. Targeting HER2-Positive Breast Cancer with Trastuzumab-DM1, an Antibody-Cytotoxic Drug Conjugate. (2008) Cancer Res. 68:9280-90), incorporated by reference herein. Anti-Her2 ADC were tested with the Fo5 model, a transgenic mouse model in which the human HER2 gene is over-expressed in mammary epithelium under transcriptional regulation of the murine mammary tumor virus promoter (MMTV-HER2) as shown in FIGS. 31 and 32. The HER2 over-expression causes spontaneous development of a mammary tumor. The mammary tumor of one of these founder animals (founder #5 [Fo5]) has been propagated in subsequent generations of FVB mice by serial transplantation of tumor fragments (~2×2 mm in size). All studies were conducted in accordance with the Guide for the Care and Use of Laboratory Animals. Each antibody-drug conjugate (single dose) was dosed in nine animals intravenously at the start of the study, and 14 days post-transplant. Initial tumor size was about 200 $mm^3$ volume. Measurements of tumor growth inhibition over time by antibody-drug conjugates of the invention and controls are shown in FIGS. 31-34.

The OVCAR-3 mammary fat pad transplant efficacy model was employed as described (Chen et al. (2007) Cancer Res 67:4924-4932), evaluating tumor volume after a single intravenous dose and using tumors excised from a mouse bearing an intraperitoneal tumor, then serially passaged into the mammary fat pads of recipient mice (FIG. 33).

The efficacy of the anti-Napi2B antibody-drug conjugates (ADCs) was investigated in a mouse xenograft model of Igrov-1 (human ovarian cancer).

Figure 36:
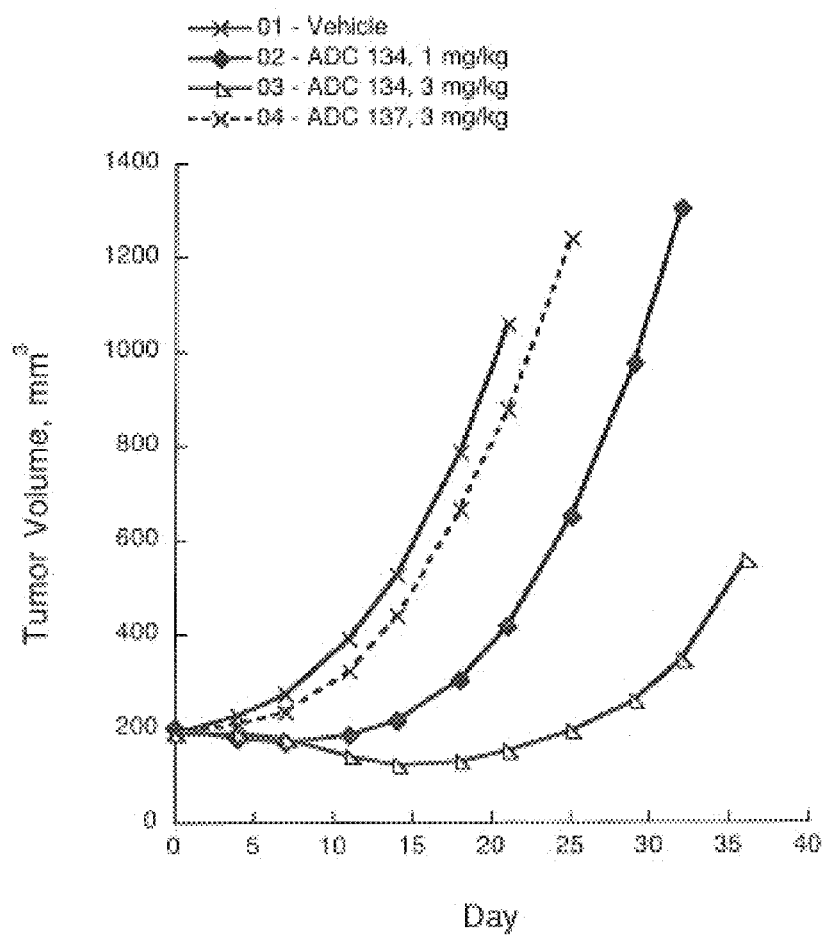
FIG. 36 shows efficacy of ADC134 in SCID-beige mice with Igrov-1 human ovarian tumors. ADC134 demonstrated dose-dependent inhibition of tumor growth compared with vehicle group. The non-targeting control ADC137 had no effect on tumor growth.

Female C.B-17 SCID-beige mice (Charles River Laboratories; San Diego, Calif.) were each inoculated in the thoracic mammary fat pad area with 5 million Igrov-1 cells. When the xenograft tumors reached an average tumor volume of 100-300 mm3 (referred to as Day 0), animals were randomized into groups of 7-10 mice each and received a single intravenous injection of the ADCs. Tumors and body weights of mice were measured 1-2 times a week throughout the study. Mice were promptly euthanized when body weight loss was >20% of their starting weight. All animals were euthanized before tumors reached 3000 mm3 or showed signs of impending ulceration. The anti-Napi2B antibody-drug conjugate (ADC 134) demonstrated dose-dependent inhibition of tumor growth compared with vehicle group. The non-targeting control (ADC 137) had no effect on tumor growth (FIG. 36).

The efficacy of the anti-CD33 antibody-drug conjugates (ADCs) was investigated in a mouse xenograft model of HL-60 or EOL-1 (human acute myeloid leukemia). The HL-60 cell line was obtained from ATCC (American Type Culture Collection; Manassas, Va.) and EOL-1 cell line was originated from DSMZ (German Collection of Microorganisms and Cell Cultures; Braunschweig, Germany).

Female C.B-17 SCID mice (Charles River Laboratories; Hollister, Calif.) were each inoculated subcutaneously in the flank area with five million cells of HL-60 or EOL-1. When the xenograft tumors reached an average tumor volume of 100-300 mm3 (referred to as Day 0), animals were randomized into groups of 7-10 mice each and received a single intravenous injection of the ADCs. Approximately 4 hours prior to administration of ADCs, animals were dosed intraperitoneally with excess amount (30 mg/kg) of anti-gD control antibody to block possible nonspecific antibody binding sites on the tumor cells. Tumors and body weights of mice were measured 1-2 times a week throughout the study. Mice were promptly euthanized when body weight loss was >20% of their starting weight. All animals were euthanized before tumors reached 3000 mm3 or showed signs of impending ulceration.

Although the foregoing invention has been described in some detail by way of illustration and example for purposes of clarity of understanding, the descriptions and examples should not be construed as limiting the scope of the invention. All patents, patent applications, and references cited throughout the specification are expressly incorporated by reference.

We claim:

1. An antibody-drug conjugate compound having the formula:

Ab-(L-D)$_p$ wherein:
Ab is an anti-Napi2b antibody;
L is a linker having the formula:

-Str-(Pep)$_m$-(Sp)$_n$- where Str is a stretcher unit covalently attached to the anti-Napi2b antibody; Pep is an optional peptide unit of two to twelve amino acid residues, Sp is an optional spacer unit covalently attached to a dimer drug moiety, and m and n are independently selected from 0 and 1;
p is an integer from 1 to 8;
D is the dimer drug moiety having the formula:

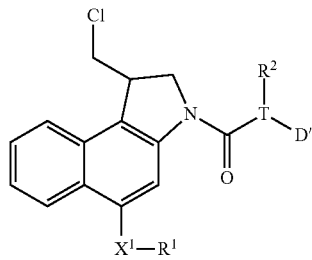

where
R$^1$ is selected from H, P(O)$_3$H$_2$, C(O)NR$^a$R$^b$, or a bond to L;
R$^2$ is selected from H, P(O)$_3$H$_2$, C(O)NR$^a$R$^b$, or a bond to L;
R$^a$ and R$^b$ are independently selected from H and C$_1$-C$_6$ alkyl optionally substituted with one or more F, or R$^a$ and R$^b$ form a five or six membered heterocyclyl group;
T is a tether group selected from C$_3$-C$_{12}$ alkylene, Y, (C$_1$-C$_6$ alkylene)-Y-(C$_1$-C$_6$ alkylene), (C$_1$-C$_6$ alkylene)-Y-(C$_1$-C$_6$ alkylene)-Y-(C$_1$-C$_6$ alkylene), (C$_2$-C$_6$ alkenylene)-Y-(C$_2$-C$_6$ alkenylene), and (C$_2$-C$_6$ alkynylene)-Y-(C$_2$-C$_6$ alkynylene);
where Y is independently selected from O, S, NR$^1$, aryl, and heteroaryl;

where alkylene, alkenylene, aryl, and heteroaryl are independently and optionally substituted with F, OH, O(C$_1$-C$_6$ alkyl), NH$_2$, NHCH$_3$, N(CH$_3$)$_2$, OP(O)$_3$H$_2$, and C$_1$-C$_6$ alkyl, where alkyl is optionally substituted with one or more F;
or alkylene, alkenylene, aryl, and heteroaryl are independently and optionally substituted with a bond to L;
D' is the drug moiety having the formula:

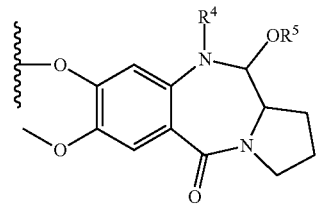

where the wavy line indicates the site of attachment to T;
X$^1$ is selected from O and NR$^3$, where R$^3$ is selected from H and C$_1$-C$_6$ optionally substituted with one or more F;
R$^4$ is H, CO$_2$R, or a bond to L, where R is C$_1$-C$_6$ alkyl or benzyl; and
R$^5$ is H or C$_1$-C$_6$ alkyl; and
the anti-Napi2b antibody comprises three light chain hypervariable regions (HVR-L1, HVR-L2 and HVR-L3) and three heavy chain hypervariable regions (HVR-H1, HVR-H2 and HVR-H3) wherein:
HVR-L1 comprises the amino acid sequence of SEQ ID NO:75;
HVR-L2 comprises the amino acid sequence of SEQ ID NO:76;
HVR-L3 comprises the amino acid sequence of SEQ ID NO:77;
HVR-H1 comprises the amino acid sequence of SEQ ID NO:78;
HVR-H2 comprises the amino acid sequence of SEQ ID NO:79; and
HVR-H3 comprises the amino acid sequence of SEQ ID NO:80 or
the anti-Napi2b antibody comprises a light chain hypervariable region comprising the amino acid sequence of SEQ ID NO:81 or a heavy chain variable region comprising the amino acid sequence of SEQ ID NO:82.

2. The antibody-drug conjugate compound of claim 1 wherein Str has the formula:

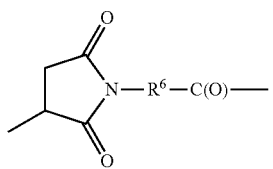

wherein $R^6$ is selected from the group consisting of $C_1$-$C_{10}$ alkylene, $C_3$-$C_8$ carbocyclyl, O-($C_1$-$C_8$ alkyl), arylene, $C_1$-$C_{10}$ alkylene-arylene, arylene-$C_1$-$C_{10}$ alkylene, $C_1$-$C_{10}$ alkylene-($C_3$-$C_8$ carbocyclyl), ($C_3$-$C_8$ carbocyclyl)-$C_1$-$C_{10}$ alkylene, $C_3$-$C_8$ heterocyclyl, $C_1$-$C_{10}$ alkylene-($C_3$-$C_8$ heterocyclyl), ($C_3$-$C_8$ heterocyclyl)-$C_1$-$C_{10}$ alkylene, $C_1$-$C_{10}$ alkylene-C(O)N($R^8$)—$C_2$-$C_6$ alkylene-N($R^8$), N($R^8$)—($C_2$-$C_6$ alkylene), and $(CH_2CH_2O)_r$—$CH_2$: where $R^8$ is H or $C_1$-$C_6$ alkyl, and r is an integer ranging from 1 to 10.

3. The antibody-drug conjugate compound of claim 2 wherein $R^6$ is $(CH_2)_5$.

4. The antibody-drug conjugate compound of claim 1 wherein m is 0 and n is 0.

5. The antibody-drug conjugate compound of claim 1 wherein m is 0 and n is 1.

6. The antibody-drug conjugate compound of claim 1 wherein Str has the formula:

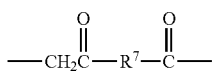

wherein $R^7$ is selected from $C_1$-$C_{10}$ alkylene, $C_1$-$C_{10}$ alkylene-O, N($R^8$)—($C_2$-$C_6$ alkylene)-N($R^8$), N($R^8$)—($C_2$-$C_6$ alkylene), and $(CH_2CH_2O)_r$—$CH_2$; where $R^8$ is H or $C_1$-$C_6$ alkyl, and r is an integer ranging from 1 to 10.

7. The antibody-drug conjugate compound of claim 1 wherein Str has the formula:

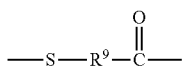

wherein $R^7$ is selected from $C_1$-$C_{10}$ alkylene, $C_1$-$C_{10}$ alkylene-O, ($C_2$-$C_6$ alkylene)-N($R^8$), and $(CH_2CH_2O)_r$—$CH_2$; where $R^8$ is H or $C_1$-$C_6$ alkyl, and r is an integer ranging from 1 to 10.

8. The antibody-drug conjugate compound of claim 7 wherein L forms a disulfide bond with a cysteine amino acid of the antibody, and $R^9$ is $C_2$-$C_6$ alkylene-O where alkylene is optionally substituted with F, OH, O($C_1$-$C_6$ alkyl), $NH_2$, $NHCH_3$, $N(CH_3)_2$, $OP(O)_3H_2$, and $C_1$-$C_6$ alkyl, where alkyl is optionally substituted with one or more F.

9. The antibody-drug conjugate compound of claim 1 wherein m is 1 and n is 1.

10. The antibody-drug conjugate compound of claim 1 wherein m is 1 and Pep comprises two to twelve amino acid residues independently selected from glycine, alanine, phenylalanine, lysine, arginine, valine, and citrulline.

11. The antibody-drug conjugate compound of claim 10 wherein Pep is valine-citrulline.

12. The antibody-drug conjugate compound of claim 1 wherein n is 1 and Sp comprises para-aminobenzyl or para-aminobenzyloxycarbonyl.

13. The antibody-drug conjugate compound of claim 9 having the formula:

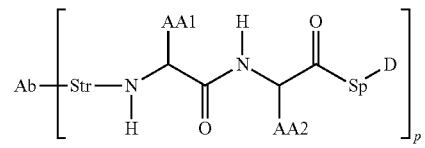

where AA1 and AA2 are independently selected from an amino acid side chain; p is an integer from 1 to 8.

14. The antibody-drug conjugate compound of claim 13 wherein the amino acid side chain is independently selected from H, —$CH_3$, —$CH_2(C_6H_5)$, —$CH_2CH_2CH_2CH_2NH_2$, —$CH_2CH_2CH_2NHC(NH)NH_2$, —$CHCH(CH_3)CH_3$, and —$CH_2CH_2CH_2NHC(O)NH_2$.

15. The antibody-drug conjugate compound of claim 13 having the formula:

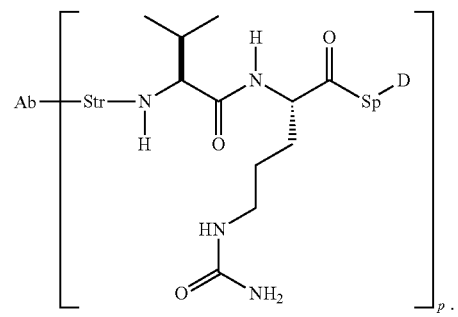

16. The antibody-drug conjugate compound of claim 13 having the formula:

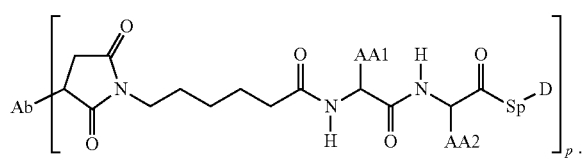

17. The antibody-drug conjugate compound of claim 15 having the formula:

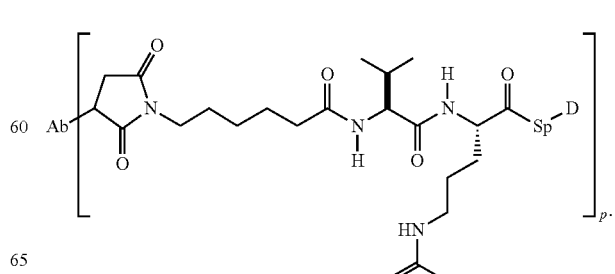

18. The antibody-drug conjugate compound of claim 16 having the formula:
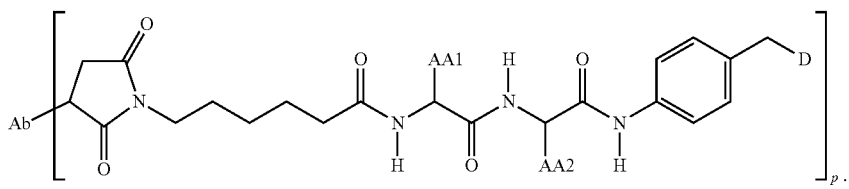
19. The antibody-drug conjugate compound of claim 18 having the formula:
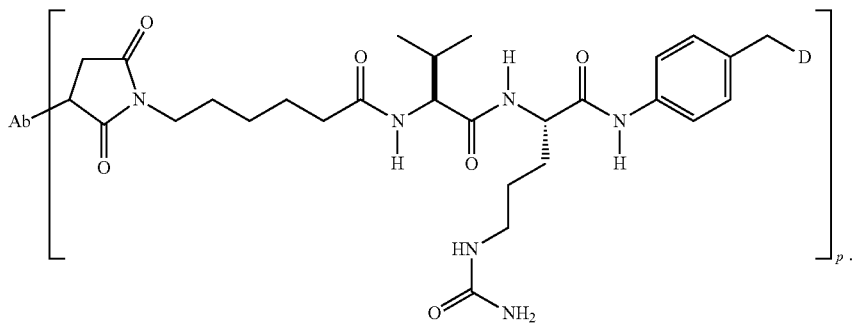
20. The antibody-drug conjugate compound of claim 16 having the formula:
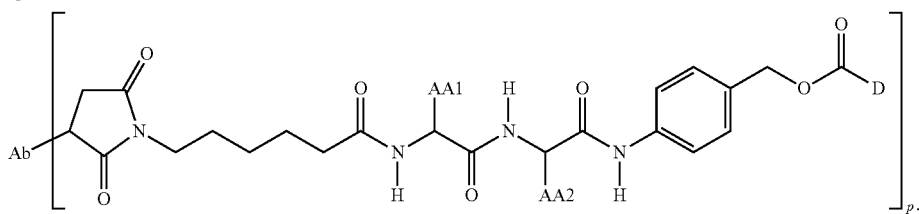
21. The antibody-drug conjugate compound of claim 20 having the formula:
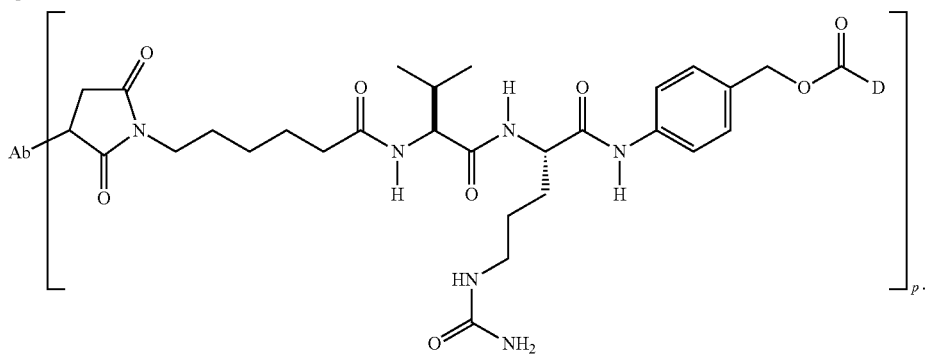
22. The antibody-drug conjugate compound of claim 16 having the formula:
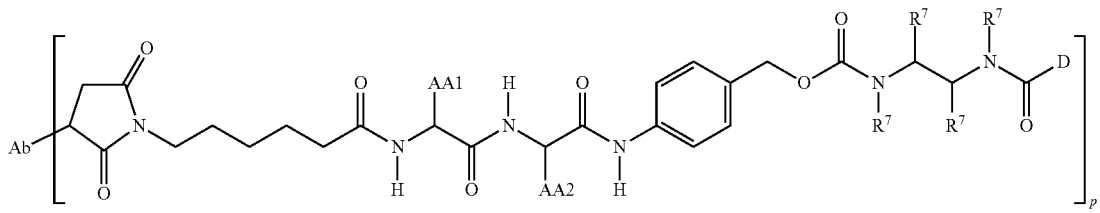

where $R^7$ is independently selected from H and $C_1$-$C_{12}$ alkyl.

23. The antibody-drug conjugate compound of claim 1 where $R^a$ and $R^b$ form a five or six membered heterocyclyl group selected from N-methylpiperazinyl, morpholinyl, piperidyl, and pyrrolidinyl.

24. The antibody-drug conjugate compound of claim 1 where T is $C_3$-$C_5$ alkylene.

25. The antibody-drug conjugate compound of claim 24 where T is selected from $(CH_2)_3$, $(CH_2)_4$ and $(CH_2)_5$.

26. The antibody-drug conjugate compound of claim 1 where T is ($C_1$-$C_6$ alkylene)-Y-($C_1$-$C_6$ alkylene), where Y is phenyl substituted with a bond to L.

27. The antibody-drug conjugate compound of claim 1 where T is ($C_2$-$C_6$ alkenylene)-Y-($C_2$-$C_6$ alkenylene), where Y is phenyl substituted with a bond to L.

28. The antibody-drug conjugate compound of claim 1 where Y is selected from phenyl, pyridyl, 1-methyl-1H-benzo[d]imidazole, and [1,2,4]triazolo[1,5-a]pyridine.

29. A pharmaceutical composition comprising the antibody-drug conjugate compound of claim 1, and a pharmaceutically acceptable carrier, glidant, diluent, or excipient.

\* \* \* \* \*

UNITED STATES PATENT AND TRADEMARK OFFICE
CERTIFICATE OF CORRECTION

PATENT NO. : 10,544,215 B2
APPLICATION NO. : 15/182444
DATED : January 28, 2020
INVENTOR(S) : John A. Flygare et al.

Page 1 of 1

It is certified that error appears in the above-identified patent and that said Letters Patent is hereby corrected as shown below:

In the Claims

Column 201, Line 51, Claim 7, please delete "wherein $R^7$ is" and insert -- wherein $R^9$ is -- therefor.

Signed and Sealed this
Thirty-first Day of March, 2020

Andrei Iancu
*Director of the United States Patent and Trademark Office*

SEQUENCE LISTING

<160> NUMBER OF SEQ ID NOS: 82

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ser Ser Gln Ser Ile Val His Ser Val Gly Asn Thr Phe Leu Glu
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Val Ser Asn Arg Phe Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Phe Gln Gly Ser Gln Phe Pro Tyr Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Glu Phe Ser Arg Ser Trp Met Asn
1               5                   10

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Arg Ile Tyr Pro Gly Asp Gly Asp Thr Asn Tyr Ser Gly Lys Phe
1               5                   10                  15

Lys Gly

<210> SEQ ID NO 6
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Asp Gly Ser Ser Trp Asp Trp Tyr Phe Asp Val
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Ala Ser Asp Leu Ile His Asn Trp Leu Ala
1               5                   10

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Gly Ala Thr Ser Leu Glu Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Gln Tyr Trp Thr Thr Pro Phe Thr
1               5

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Tyr Ser Ile Thr Asn Asp Tyr Ala Trp Asn
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 11

Gly Tyr Ile Ser Tyr Ser Gly Tyr Thr Thr Tyr Asn Pro Ser Leu Lys
1               5                   10                  15

Ser

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Arg Trp Thr Ser Gly Leu Asp Tyr
1               5

<210> SEQ ID NO 13
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Ser Tyr Ser Gly Tyr Thr Thr Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Thr Ser Gly Leu Asp Tyr Trp Gly Gln Gly Thr Leu Val
            100                 105                 110

Thr Val Ser Ser
        115

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Trp Thr Thr Pro Phe
                 85                  90                  95

Thr Phe Gly Gln Gly Thr Lys Val Glu Ile Lys Arg
            100                 105
```

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Glu Val Gln Leu Cys Glu Ser Gly Gly Gly
1               5                   10
```

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Leu Arg Leu Ser Cys Cys Ala Ser Gly Tyr Ser
1               5                   10
```

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Met Asn Ser Leu Arg Cys Glu Asp Thr Ala Val
1               5                   10
```

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Thr Leu Val Thr Val Cys Ser Ala Ser Thr Lys
1               5                   10
```

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Val Thr Val Ser Ser Cys Ser Thr Lys Gly Pro
1               5                   10
```

```
<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Ser Ala Ala Ser Cys Lys Gly Pro Ser Val
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Trp Tyr Val Asp Gly Cys Glu Val His Asn Ala
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Gly Phe Val Pro Cys Asp Ile Ala Val Glu
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Pro Val Leu Asp Cys Gly Asp Ser Phe Phe
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Val Gln Leu Cys Glu Ser Gly Pro Gly
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 25

Leu Ser Leu Thr Cys Cys Val Thr Gly Tyr Ser
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Asn Ser Val Thr Cys Glu Asp Thr Ala Thr
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Leu Val Thr Val Cys Ser Ala Ser Thr Lys
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Thr Val Ser Ser Cys Ser Thr Lys Gly Pro
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Ser Ala Ala Ser Cys Lys Gly Pro Ser Val
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Trp Tyr Val Asp Gly Cys Glu Val His Asn Ala
1               5                   10

<210> SEQ ID NO 31
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 31

Lys Gly Phe Val Pro Cys Asp Ile Ala Val Glu
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Pro Pro Val Leu Asp Cys Asp Gly Ser Phe Phe
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Leu Ser Ala Ser Cys Gly Asp Arg Val Thr
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Ile Lys Arg Thr Cys Ala Ala Pro Ser Val
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Val Ala Ala Pro Cys Val Phe Ile Phe Pro
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Ile Phe Pro Pro Cys Asp Glu Gln Leu Lys
1               5                   10
```

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Glu Gln Leu Lys Cys Gly Thr Ala Ser Val
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Thr Glu Gln Asp Cys Lys Asp Ser Thr Tyr
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Leu Ser Ser Pro Cys Thr Lys Ser Phe Asn
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Phe Leu Ser Val Ser Cys Gly Gly Arg Val Thr
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Glu Ile Lys Arg Thr Cys Ala Ala Pro Ser Val
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 42

Thr Val Ala Ala Pro Cys Val Phe Ile Phe Pro
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Phe Ile Phe Pro Pro Cys Asp Glu Gln Leu Lys
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Glu Gln Leu Lys Cys Gly Thr Ala Ser Val
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Val Thr Glu Gln Asp Cys Lys Asp Ser Thr Tyr
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Leu Ser Ser Pro Cys Thr Lys Ser Phe Asn
1               5                   10

<210> SEQ ID NO 47
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30
```

```
Tyr Ala Trp Asn Trp Val Arg Gln Ala Pro Gly Lys Gly Leu Glu Trp
             35                  40                  45
Val Gly Tyr Ile Ser Tyr Ser Gly Tyr Thr Thr Tyr Asn Pro Ser Leu
 50                  55                  60
Lys Ser Arg Phe Thr Ile Ser Arg Asp Thr Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Trp Thr Ser Gly Leu Asp Tyr Trp Gly Gln Gly Thr Leu Val
            100                 105                 110
Thr Val Ser Ser Cys Ser Thr Lys Gly Pro Ser Val Phe Pro Leu Ala
            115                 120                 125
Pro Ser Ser Lys Ser Thr Ser Gly Gly Thr Ala Ala Leu Gly Cys Leu
130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
            165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
            195                 200                 205
Lys Val Asp Lys Lys Val Glu Pro Lys Ser Cys Asp Lys Thr His Thr
            210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
            435                 440                 445
```

```
<210> SEQ ID NO 48
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Thr Thr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 49
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Val Gln Leu Gln Glu Ser Gly Pro Gly Leu Val Asn Pro Ser Gln
1               5                   10                  15

Ser Leu Ser Leu Thr Cys Thr Val Thr Gly Tyr Ser Ile Thr Asn Asp
            20                  25                  30

Tyr Ala Trp Asn Trp Ile Arg Gln Phe Pro Gly Asn Lys Leu Glu Trp
        35                  40                  45

Met Gly Tyr Ile Asn Tyr Ser Gly Tyr Thr Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu His Leu Asn Ser Val Thr Thr Glu Asp Thr Ala Thr Tyr Tyr Cys
```

```
                    85                  90                  95
Ala Arg Trp Asp Gly Gly Leu Thr Tyr Trp Gly Gln Gly Thr Leu Val
                100                 105                 110

Thr Val Ser Ala Cys Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 50
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50
```

Asp Ile Gln Met Thr Gln Ser Ser Ser Phe Leu Ser Val Ser Leu Gly
1               5                   10                  15

Gly Arg Val Thr Ile Thr Cys Lys Ala Ser Asp Leu Ile His Asn Trp
            20                  25                  30

Leu Ala Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
50                  55                  60

Ser Gly Ser Gly Asn Asp Tyr Thr Leu Ser Ile Ala Ser Leu Gln Thr
65                  70                  75                  80

Glu Asp Ala Ala Thr Tyr Tyr Cys Gln Gln Tyr Trp Thr Thr Pro Phe
                85                  90                  95

Thr Phe Gly Ser Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Ser Ser Gln Ser Leu Leu His Ser Asn Gly Tyr Asn Tyr Leu Asp
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Gly Val Asn Ser Val Ser
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 53

Met Gln Ala Leu Gln Thr Pro Trp Thr
1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asn His Ala Ile Ser
1               5

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Ile Ile Pro Ile Phe Gly Thr Ala Asn Tyr Ala Gln Lys Phe Gln
1               5                   10                  15

Gly

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Glu Trp Ala Asp Val Phe Asp
1               5

<210> SEQ ID NO 57
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Val Asn Ser Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
```

<210> SEQ ID NO 58
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Val Gln Ser Gly Ala Glu Val Lys Pro Gly Ser
1               5                   10                  15

Ser Val Lys Val Ser Cys Lys Ala Ser Gly Gly Ile Phe Ser Asn His
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Phe
65                  70                  75                  80

Met Glu Leu Ser Ser Leu Arg Ser Glu Asp Thr Ala Val Tyr Tyr Cys
                85                  90                  95

Ala Arg Glu Trp Ala Asp Val Phe Asp Ile Trp Gly Gln Gly Thr Met
            100                 105                 110

Val Thr Val Ser Ser
        115

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Ala Ser Gln Gly Ile Arg Asn Asp Leu Gly
1               5                   10

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Ala Ser Ser Leu Gln Ser
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Leu Gln His Asn Ser Tyr Pro Trp Thr
1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Asn Tyr Met Ser
1               5

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Ile Tyr Ser Gly Asp Ser Thr Tyr Tyr Ala Asp Ser Val Lys Gly
1               5                   10                  15

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Gly Tyr Tyr Val Ser Asp Met Val Val
1               5                   10

<210> SEQ ID NO 65
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 66
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Asn Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115
```

<210> SEQ ID NO 67
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105
```

<210> SEQ ID NO 68
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30
```

```
Tyr Met Ser Trp Val Arg Gln Ala Pro Gly Lys Gly Leu Glu Trp Val
             35                  40                  45

Ser Leu Ile Tyr Ser Gly Asp Ser Thr Tyr Tyr Ala Asp Ser Val Lys
 50                  55                  60

Gly Arg Phe Thr Ile Ser Arg Asp Ile Ser Lys Asn Thr Val Tyr Leu
 65                  70                  75                  80

Gln Met Asn Ser Leu Arg Val Glu Asp Thr Ala Val Tyr Tyr Cys Val
             85                  90                  95

Arg Asp Gly Tyr Tyr Val Ser Asp Met Val Val Trp Gly Lys Gly Thr
                100                 105                 110

Thr Val Thr Val Ser Ser
            115
```

<210> SEQ ID NO 69
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
             85                  90                  95

Thr Phe Gly Gln Gly Thr Lys Leu Glu Ile Lys
            100                 105
```

<210> SEQ ID NO 70
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

```
Glu Val Gln Leu Val Glu Ser Gly Gly Ala Leu Ile Gln Pro Gly Gly
 1               5                  10                  15

Ser Leu Arg Leu Ser Cys Val Ala Ser Gly Phe Thr Ile Ser Gly Asn
             20                  25                  30

Tyr Met Ser Trp Val Arg Gln Ala Pro Gly Lys Gly Leu Glu Trp Val
             35                  40                  45

Ser Leu Ile Tyr Ser Gly Asp Ser Thr Tyr Tyr Ala Asp Ser Val Lys
 50                  55                  60

Gly Arg Phe Ser Ile Ser Arg Asp Ile Ser Lys Asn Thr Val Tyr Leu
 65                  70                  75                  80

Gln Met Asn Ser Leu Arg Val Glu Asp Thr Ala Val Tyr Tyr Cys Val
             85                  90                  95
```

```
Arg Asp Gly Tyr Tyr Val Ser Asp Met Val Val Trp Gly Lys Gly Thr
                100                 105                 110
Thr Val Thr Val Ser Ser
        115

<210> SEQ ID NO 71
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro Trp
                85                  90                  95
Thr Phe Gly Gln Gly Thr Lys Leu Glu Ile Lys
            100                 105

<210> SEQ ID NO 72
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Glu Ser Gly Gly Ala Leu Ile Gln Pro Gly Gly
1               5                   10                  15
Ser Leu Arg Leu Ser Cys Val Ala Ser Gly Phe Thr Ile Ser Gly Asn
            20                  25                  30
Tyr Met Ser Trp Val Arg Gln Ala Pro Gly Lys Gly Leu Glu Trp Val
        35                  40                  45
Ser Leu Ile Tyr Ser Gly Asp Ser Thr Tyr Tyr Ala Asp Ser Val Lys
    50                  55                  60
Gly Arg Phe Ala Ile Ser Arg Asp Ile Ser Lys Asn Thr Val Tyr Leu
65                  70                  75                  80
Gln Met Asn Ser Leu Arg Val Glu Asp Thr Ala Val Tyr Tyr Cys Val
                85                  90                  95
Arg Asp Gly Tyr Tyr Val Ser Asp Met Val Val Trp Gly Lys Gly Thr
                100                 105                 110
Thr Val Thr Val Ser Ser
        115

<210> SEQ ID NO 73
<211> LENGTH: 7
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 73

Met Ala Glu Ala Ile Thr Tyr
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Thr Ala Phe Arg Phe Pro Asp
1               5

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Arg Ser Ser Glu Thr Leu Val His Ser Ser Gly Asn Thr Tyr Leu
1               5                   10                  15

Glu

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Arg Val Ser Asn Arg Phe Ser
                5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Phe Gln Gly Ser Phe Asn Pro Leu Thr
                5

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gly Phe Ser Phe Ser Asp Phe Ala Met Ser
                5                   10

```
<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Ala Thr Ile Gly Arg Val Ala Phe His Thr Tyr Tyr Pro Asp Ser
1               5                  10                  15

Met Lys Gly

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Ala Arg His Arg Gly Phe Asp Val Gly His Phe Asp Phe
                5                  10

<210> SEQ ID NO 81
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asp Ile Gln Met Thr Gln Ser Pro Ser Ser Leu Ser Ala Ser Val
1               5                  10                  15

Gly Asp Arg Val Thr Ile Thr Cys Arg Ser Ser Glu Thr Leu Val
                20                  25                  30

His Ser Ser Gly Asn Thr Tyr Leu Glu Trp Tyr Gln Gln Lys Pro
            35                  40                  45

Gly Lys Ala Pro Lys Leu Leu Ile Tyr Arg Val Ser Asn Arg Phe
        50                  55                  60

Ser Gly Val Pro Ser Arg Phe Ser Gly Ser Gly Ser Gly Thr Asp
65                  70                  75

Phe Thr Leu Thr Ile Ser Ser Leu Gln Pro Glu Asp Phe Ala Thr
                80                  85                  90

Tyr Tyr Cys Phe Gln Gly Ser Phe Asn Pro Leu Thr Phe Gly Gln
                95                 100                 105

Gly Thr Lys Val Glu Ile Lys Arg
        110

<210> SEQ ID NO 82
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Glu Ser Gly Gly Gly Leu Val Gln Pro Gly
1               5                  10                  15
```

```
Gly Ser Leu Arg Leu Ser Cys Ala Ala Ser Gly Phe Ser Phe Ser
            20                  25                  30

Asp Phe Ala Met Ser Trp Val Arg Gln Ala Pro Gly Lys Gly Leu
            35                  40                  45

Glu Trp Val Ala Thr Ile Gly Arg Val Ala Phe His Thr Tyr Tyr
    50                  55                  60

Pro Asp Ser Met Lys Gly Arg Phe Thr Ile Ser Arg Asp Asn Ser
65                  70                  75

Lys Asn Thr Leu Tyr Leu Gln Met Asn Ser Leu Arg Ala Glu Asp
                80                  85                  90

Thr Ala Val Tyr Tyr Cys Ala Arg His Arg Gly Phe Asp Val Gly
            95                  100                 105

His Phe Asp Phe Trp Gly Gln Gly Thr Leu Val Thr Val Ser Ser
            110                 115                 120
```